US007232899B2

(12) United States Patent
Von Seggern et al.

(10) Patent No.: US 7,232,899 B2
(45) Date of Patent: Jun. 19, 2007

(54) ADENOVIRUS VECTORS, PACKAGING CELL LINES, COMPOSITIONS, AND METHODS FOR PREPARATION AND USE

(75) Inventors: Daniel J. Von Seggern, San Diego, CA (US); Glen R. Nemerow, Encinitas, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 09/482,682

(22) Filed: Jan. 14, 2000

(65) Prior Publication Data

US 2003/0157688 A1  Aug. 21, 2003

Related U.S. Application Data

(63) Continuation-in-part of application No. 09/423,783, filed as application No. PCT/EP97/05251 on Sep. 24, 1997, now abandoned, which is a continuation-in-part of application No. 08/719,806, filed on Sep. 25, 1996, now abandoned, application No. 09/482,682, which is a continuation-in-part of application No. 09/795,292, filed on Jan. 14, 1999.

(51) Int. Cl.
  C07H 21/04    (2006.01)
  C12N 1/36     (2006.01)
  C12N 15/00    (2006.01)
  C12P 21/06    (2006.01)
  A16K 39/21    (2006.01)
(52) U.S. Cl. .................. 536/24.1; 435/240.2; 435/69.1; 435/320.1; 424/207.1; 424/93.1
(58) Field of Classification Search .................... 435/5, 435/69.3, 41.1, 456, 320.1, 23.5; 530/350; 536/23.1, 24.1
See application file for complete search history.

(56) References Cited

U.S. PATENT DOCUMENTS

| 4,356,270 | A |   | 10/1982 | Itakura .......................... 435/317 |
| 4,675,285 | A | * | 6/1987  | Clark et al. ..................... 435/6 |
| 5,149,384 | A |   | 9/1992  | Plow et al. ..................... 530/324 |
| 5,543,328 | A |   | 8/1996  | McClelland et al. ......... 435/320.1 |
| 5,559,099 | A |   | 9/1996  | Wickham et al. ............... 514/44 |
| 5,750,396 | A |   | 5/1998  | Yang et al. ................... 435/357 |
| 5,756,086 | A |   | 5/1998  | McClelland et al. ......... 424/93.2 |
| 5,770,442 | A | * | 6/1998  | Wickham et al. ........... 435/320.1 |
| 5,871,727 | A | * | 2/1999  | Curiel ....................... 424/93.2 |
| 5,919,676 | A |   | 7/1999  | Graham et al. ............. 435/172.3 |
| 5,994,106 | A |   | 11/1999 | Kovesdi et al. ............. 435/91.4 |
| 5,998,205 | A |   | 12/1999 | Hallenbeck et al. ......... 435/325 |
| 6,410,011 | B1 | * | 6/2002 | Branellec et al. ........... 424/93.2 |
| 2002/0037851 | A1 |   | 3/2002 | Fleckenstein et al. ......... 514/12 |

FOREIGN PATENT DOCUMENTS

EP    0 892 047           1/1999

| WO | WO 92/06693  | 4/1992 |
| WO |   9417832    | 8/1994 |
| WO |   9502697    | 1/1995 |
| WO | WO 95/00655  | 1/1995 |
| WO | WO 95/11984  | 5/1995 |
| WO |   9527071    | 10/1995 |
| WO | WO 95/26412  | 10/1995 |
| WO | WO 95/34671  | 12/1995 |
| WO |   9607734    | 3/1996 |
| WO | WO 96/14061  | 5/1996 |
| WO | WO 96/22378  | 7/1996 |
| WO | WO 96/39530  | 12/1996 |
| WO |   9721826    | 6/1997 |
| WO | WO 97/37220  | 10/1997 |
| WO | WO-98/13499  | * 4/1998 |
| WO | WO 98/13499  | 4/1998 |
| WO | WO 98/17783  | 4/1998 |
| WO | WO 98/44121  | 10/1998 |
| WO |   0042208    | 7/2000 |
| WO | PCT/EP01/04863 | 4/2001 |
| WO | PCT/EP01/07878 | 7/2001 |
| WO |   0183729 A2 | 11/2001 |
| WO |   0192299 A2 | 12/2001 |
| WO | PCT/US03/02295 | 1/2002 |

OTHER PUBLICATIONS

Sequence alignment of SEQ ID No. Sep. 26, 1998. ID No. V32372.
Memerow et al. in PCT application 97WO-EPO5251 corresponding to published WO 98/13499.*
Stevenson et al. 1997. Selective targeting of human cells by a chimeric adenovirus vector containing a modified fiver protein. Journal of Virology. vol. 71. No. 6, pp. 4782-4790.*
Guo et al. 1998. Apoptosis induced by adenovirus-mediated wild-type p53 expression in human pancreatic cancer cells. Chinese Journal of Pathology. vol. 27. No. 3, pp. 194-197. Abstract only.*
Logan et al. Proc. Natl. Acad. Sci. 1994; 81: 3655-3659.*
Sheay et al. Biotechniques. 1993; 15 (5): 856-862.*
Kaufman. PNAS. 1985; 82: 689-693.*
Hodges et al. Molecular Pharmacology. 1995; 48: 905-918.*
Caravokyri et al. Journal of Virology. 1995; 69 (11): 6627-6633.*
Zhang et al. "Secondary structure analysis of adenovirus tripartite leader" J. biological Chem. vol. 264 (1989), No. 18, pp. 10679-10684.*
Allison, J. et al., "Tissue-Specific and Hormonal Regulation of the Gene for Rat Prostatic Steroid-Binding Protein in Transgenic Mice," *Mol. Cell. Biol.* 9:2254-2257, American Society for Microbiology (1989).

(Continued)

*Primary Examiner*—Bruce R. Campell
*Assistant Examiner*—Bo Peng
(74) *Attorney, Agent, or Firm*—DLA Piper US LLP

(57) ABSTRACT

The present invention relates to methods for gene therapy, especially to adenovirus-based gene therapy, and related cell lines and compositions. In particular, novel nucleic acid constructs and packaging cell lines are disclosed, for use in facilitating the development of high-capacity and targeted vectors. The invention also discloses a variety of high-capacity adenovirus vectors and related compositions and kits including the disclosed cell lines and vectors. Finally, the invention discloses methods of preparing and using the disclosed vectors, cell lines and kits.

22 Claims, 23 Drawing Sheets

OTHER PUBLICATIONS

Altschul, S.F. et al., Basic Local Alignment Search Tool, *J. Mol. Biol.* 215:403-410, Academic Press Ltd. (1990).

Amalfitano, A. et al., "Improved Adenovirus Packaging Cell Lines to Support the Growth of Replication-Defective Gene-Delivery Vectors," *Proc. Natl. Acad. Sci. USA* 93:3352-3356, The National Academy of Sciences of the USA (Apr. 1996).

Armentano, D. et al., "Characterization of An Adenovirus Gene Transfer Vector Containing an E4 Deletion," *Hum. Gene Ther.* 6:1343-1353, Mary Ann Liebert, Inc. (Oct. 1995).

Arnberg, N., et al., "Fiber Genes of Adenoviruses with Tropism for the Eye and the Genital Tract," *Virology* 227:239-244, Academic Press, Inc. (Jan. 1997).

Austin, E.A. and Huber, B.E., "A First Step in the Development of Gene Therapy for Colorectal Carcinoma: Cloning, Sequencing, and Expression of *Escherichia coli* Cytosine Deaminase," *Mol. Pharmacol.* 43:380-387, ASPET (1993).

Ausubel, F.M. et al., "Synthesizing RNA," in *Current Protocols in Molecular Biology*, Suppl. 8 p. 2.11.7, John Wiley & Sons, Inc. New York (1991).

Berkner, K.L., "Development of Adenovirus Vectors for the Expression of Heterologous Genes," *BioTechniques* 6:616-629, Eaton Publishing Co. (1988).

Bett, A.J., et al., "Packaging Capacity and Stability of Human Adenovirus Type 5 Vectors," *J. Virol.* 67:5911-5921, American Society for Microbiology (1993).

Bett, A.J., et al., "An Efficient and Flexible System for Construction of Adenovirus Vectors with Insertions or Deletions in Early Regions 1 and 3," *Proc. Natl. Acad. Sci. USA* 91:8802-8806, The National Academy of Sciences of the USA (1994).

Birnboim, H.C. and Doly, J., "A rapid alkaline extraction procedure for screening recombinant plasmid DNA," *Nucl. Acids Res.* 7:1513-1523, Oxford University Press (1978).

Braun, R.E., et al., "Protamine 3'-Untranslated Sequences Regulate Temporal Translational Control and Subcellular Localization of Growth Hormone in Spermatids of Transgenic Mice," *Genes Dev.* 3:793-802, Cold Spring Harbor Laboratory Press (1989).

Brinster, R.L., et al., "Expression of a Microinjected Immunoglobulin Gene in the Spleen of Transgenic Mice," *Nature* 306:332-336, Macmillan Magazines Ltd (1983).

Brough, D.E., et al., "A Gene Transfer Vector-Cell Line System for Complete Functional Complementation of Adenovirus Early Regions E1 and E4," *J. Virol.* 70:6497-6501, American Society for Microbiology (Sep. 1996).

Brown, E.L., et al., "Chemical Synthesis and Cloning of a Tyrosine tRNA Gene," *Meth. Enzymol.* 68:109-151, Academic Press, Inc. (1979).

Bucchini, D., et al., "Pancreatic Expression of Human Insulin Gene in Transgenic Mice," *Proc. Natl. Acad. Sci. USA* 83:2511-2515, The National Academy of Sciences of the USA (1986).

Cannon, M.J., et al., "Epstein-Barr Virus Induces Aggressive Lymphoproliferative Disorders of Human B Cell Origin in SCID/hu Chimeric Mice," *J. Clin. Invest.* 85:1333-1337, The Rockefeller University Press (1990).

Carillo, H., and Lipton, D., "The Multiple Sequence Alignment Problem in Biology," *SIAM J. Applied Math* 48:1073, Society for Industrial and Applied Mathematics (1988).

Chee-Sheung, C.C. et al., "Characterization of a Temperature-Sensitive Fiber Mutant of Type 5 Adenovirus and Effect of the Mutation on Virion Assembly," *J. Virol.* 42:932-950, American Society for Microbiology (1982).

Choi, T., et al., "A Generic Intron Increases Gene Expression in Transgenic Mice," *Mol. Cell Biol.* 11:3070-3074, American Society for Microbiology (1991).

Chroboczek, J., et al., "The Sequence of Adenovirus Fiber: Similarities and Differences Between Serotypes 2 and 5," *Virology* 161:549-554, Academic Press, Inc. (1987).

Chroboczek, J., et al., "The Sequence of the Genome of Adenovirus Type 5 and Its Comparison with the Genome of Adenovirus Type 2," *Virology* 185:280-285, Academic Press, Inc. (1992).

Chroboczek,J., et al., GenBank Accession No. M73260, (Apr. 8, 1996).

Crenshaw, E.B., 3rd, et al., "Cell-Specific Expression of the Prolactin Gene in Transgenic Mice is Controlled by Synergistic Interactions Between Promoter and Enhancer Elements," *Genes Dev.* 3:959-972, Cold Spring Laboratory Press (1989).

Crystal, R.G., et al., "Administration of an Adenovirus Containing the Human CFTR cDNA to the Respiratory Tract of Individuals with Cystic Fibrosis," *Nature Genet.* 8:42-51, Macmillan Magazines Ltd (1994).

Danciger, E., et al., "Olfactory Marker Protein Gene: Its Structure and Olfactory Neuron-Specific Expression in Transgenic Mice," *Proc. Natl. Acad. Sci. USA* 86:8565-8569, The National Academy of Sciences of the USA (1989).

Devereux, J., et al., "A Comprehensive Set of Sequence Analysis Programs for the VAX," *Nucl. Acids Res.* 12:387-395, Oxford University Press (1984).

Edwards, R.H., et al., "Directed Expression of NGF to Pancreatic β Cells in Transgenic Mice Leads to Selective Hyperinnervation of the Islets," *Cell* 58:161-170, Cell Press (1989).

Falgout, B., and Ketner, G., "Characterization of Adenovirus Particles made by Deletion Mutants Lacking the Fiber Gene," *J. Virol.* 62:622-625, American Society for Microbiology (1988).

Fender, P., et al., "Adenovirus Dodecahedron, A New Vector for Human Gene Transfer," *Nature Biotechnol.* 15:52-56, Nature Publishing Co. (Jan. 1997).

Fisher, K.J., et al., "Recombinant Adenovirus Deleted of All Viral Genes for Therapy of Cystic Fibrosis," *Virology* 217:11-22, Academic Press, Inc. (Mar. 1996).

Forss-Petter, S., et al., "Neuron-Specific Enolase: Complete Structure of Rat mRNA, Multiple Transcriptional Start Sites, and Evidence Suggesting Post-Transcriptional Control," *J. Neurosci. Res.* 16:141-151, John Wiley & Sons, Inc. (1986).

Gall, J., et al., "Adenovirus Type 5 and 7 Capsid Chimera: Fiber Replacement Alters Receptor Tropism Without Affecting Primary Immune Neutralization Epitopes," *J. Virol.* 70:2116-2123, American Society for Microbiology (Apr. 1996).

Gorziglia, M. I., et al., "Elimination of Both E1 and E2 from Adenovirus Vectors Further Improves Prospects for in vivo Human Gene Therapy," *J. Virol.* 70:4173-4178, American Society for Microbiology (Jun. 1996).

Graham, F.L., et al., "Characteristics of a Human Cell Line Transformed by DNA From Human Adenovirus Type 5," *J. Gen. Virol.* 36:59-72, Society of General Microbiology (1977).

Gribskov, M., and Burgess, R.R., "Sigma Factors from *E. coli, B. subtilis*, phage SP01, and phage T4 are Homologous Proteins," *Nucl. Acids Res.* 14:6745-6763, Oxford University Press (1986).

Grosschedl, R., et al., "Introduction of a µ Immunoglobul in Gene into the Mouse Germ Line: Specific Expression in Lymphoid Cells and Synthesis of Functional Antibody," *Cell* 38:647-658, Cell Press (1984).

Haecker, S.E., et al., "In vivo Expression of Full-Length Human Dystrophin from Adenoviral Vectors Deleted of All Viral Genes," *Human Gene Ther.* 7:1907-1914, Mary Ann Liebert, Inc. (Oct. 1996).

Hardy, S., et al., "Construction of Adenovirus Vectors Through *Cre-lox* Recombination," *J. Virol.* 71:1842-1849, American Society for Microbiology (Mar. 1997).

He, T.C., et al., "A simplified system for generating recombinant adenoviruses," *Proc. Natl. Acad. Sci USA* 95:2509-2514, The National Academy of Sciences of the USA (Mar. 1998).

Henry, L.J., et al., "Characterization of the Knob Domain of the Adenovirus type 5 Fiber Protein Expressed in *Escherichia coli,*" *J. Virol.* 68:5239-5246, American Society for Microbiology (1994).

Hérissé, J., et al., "Nucleotide Sequence of Adenovirus 2 DNA Fragment Encoding for the Carboxylic Region of the Fiber Protein and the Entire E4 region," *Nucl. Acids. Res.* 9:4023-4041, Oxford University Press (1981).

Hong, J.S., and Engler, J.A., "The Amino Terminus of the Adenovirus Fiber Protein Encodes the Nuclear Localization Signal," *Virology* 185:758-767, Academic Press, Inc. (1991).

Horton, R.M., et al., "Gene Splicing by Overlap Extension: Tailor-Made Genes Using the Polymerase Chain Reaction," *BioTechniques* 8:528-535, Eaton Publishing Co. (1990).

Horwitz, M.S., "Adenoviridae and Their Replication," in *Virology*, Fields and Knipe, eds., Raven Press, NY pp. 1679-1740 (1990).

Huang, S., et al., "Upregulation of Integrins $\alpha_v\beta_3$ and $\alpha_v\beta_5$ on Human Monocytes and T Lymphocytes Facilitates Adenovirus-Mediated Gene Delivery," *J. Virol.* 69:2257-2263, American Society for Microbiology (Apr. 1995).

Huang S., et al., "Adenovirus Interaction with Distinct Integrins Mediates Separate Events in Cell Entry and Gene Delivery to Hematopoietic Cells," *J. Virol.* 70:4502-4508, American Society for Microbiology (Jul. 1996).

Huang, S., et al., "Growth Arrest of Epstein-Barr Virus Immortalized B Lymphocytes by Adenovirus-Delivered Ribozymes," *Proc. Natl. Acad. Sci. USA* 94:8156-8161, The National Academy of Sciences of the USA (Jul. 1997).

Huang, S., et al., "A Single Amino Acid in the Adenovirus Type 37 Fiber Confers Binding to Human Conjunctival Cells," *J. Virol.* 73:2798-2802, American Society for Microbiology (Apr. 1999).

Kinloch, R., et al., "Adenovirus Hexon. Sequence Comparison of Subgroup C Serotypes 2 and 5," *J. Biol. Chem.* 259:6431-6436, American Society for Biochemistry and Molecular Biology, Inc. (1984).

Knowles, M.R., et al., "A Controlled Study of Adenoviral-Vector-Mediated Gene Transfer in the Nasal Epithelium of Patients with Cystic Fibrosis," *New Engl. J. Med.* 333:823-831, Massachusetts Medial Society (Sep. 1995).

Krasnykh, V.N., et al., "Generation of Recombinant Adenovirus Vectors with Modified Fibers for Altering Viral Tropism," *J. Virol.* 70:6839-6846, American Society for Microbiology (Oct. 1996).

Lieber, A., et al., "Integrating Adenovirus-Adeno-Associated Virus Hybrid Vectors Devoid of All Viral Genes," *J. Virol.* 73:9314-9324, American Society for Microbiology (Nov. 1999).

Loeb, J.E. et al., "Enhanced Expression of Transgenes From Adeno-Associated Virus Vectors with the Woodchuck Hepatitis Virus Posttranscriptional Regulatory Element: Implications for Gene Therapy," *Hum. Gene. Ther.* 10:2295-2305, Mary Ann Liebert, Inc. (Sep. 1999).

Logan, et al., "Adenovirus Tripartite Leader Sequence Enhances Translation of mRNAs Late After Infection," *Proc. Natl. Acad. Sci. USA* 81:3655-3659, The National Academy of Sciences of the USA (1984).

Lopez, C., et al., "Efficient Production of Biologically Active Human Recombinant Proteins in Human Lymphoblastoid Cells from Integrative and Episomal Expression Vectors," *Gene* 148:285-291, Elsevier Science Publishers B.V. (1994).

Magram, J., et al., "β-globin Enhancers Target Expression of a Heterologous Gene to Erythroid Tissues of Transgenic Mice," *Mol. Cell. Biol.* 9:4581-4584, American Society for Microbiology (1989).

McVey, J.H., et al., "Characterization of the Mouse SPARC/osteonectin Gene. Intron/exon Organization and an Unusual Promoter Region," *J. Biol. Chem.* 263:11, 111-11, 116, American Society for Biochemistry and Molecular Biology, Inc. (1988).

Michael, S.L., et al., "Addition of a Short Peptide Ligand to the Adenovirus Fiber Protein," *Gene Ther.* 2:660-668, Stockton Press (Nov. 1995).

Mitani, K., et al., "Rescue, Propagation, and Partial Purification of a Helper Virus-Dependent Adenovirus Vector," *Proc. Natl. Acad. Sci. USA* 92:3854-3858, The National Academy of Sciences of the USA (Apr. 1995).

Morsy, M.A., and Caskey, C.T., "Expanded-Capacity Adenoviral Vectors—The Helper—Dependent Vectors," *Mol. Med. Today* 5:18-24, Molecular Medicine Society (Jan. 1999).

Muller, W.J., et al., "Single-Step Induction of Mammary Adenocarcinoma in Transgenic Mice Bearing the Activated *C-Neu* Oncogene," *Cell* 54:105-115, Cell Press (1988).

Narang, S.A., et al., "Improved Phosphotriester Method for the Synthesis of Gene Fragments," *Meth. Enzymol.* 68:90-98, Academic Press, Inc. (1979).

Nathans, J., et al., "Isolation and Nucleotide Sequence of the Gene Encoding Human Rhodopsin," *Proc. Natl. Acad. Sci. USA* 81:4851-4855, The National Academy of Sciences of the USA (1984).

Needleman, S.B., and Wunsch, C.D., "A General Method Applicable to the Search for Similarities in the Amino Acid Sequence of Two Proteins," *J. Mol. Biol.* 48:443-453, Academic Press, Inc. (1970).

Neumann, R., et al., "Determination of the Nucleotide Sequence for the Penton-Base Gene of Human Adenovirus Type 5," *Gene* 69:153-157, Elsevier Science Publishers B.V. (1988).

Novelli, A., et al., "Assembly of Adenovirus Type 2 Fiber Synthesized in Cell-Free Translation System," *J. Biol. Chem.* 266:9299-9303, American Society for Biochemistry and Molecular Biology, Inc. (1991).

Overbeek, P.A., et al., "Lens-Specific Expression and Developmental Regulation of the Bacterial Chloramphenicol Acetyltransferase Gene Driven by the Murine α A-Crystallin Promoter in Transgenic Mice," *Proc. Natl. Acad. Sci. USA* 82:7815-7819, The National Academy of the USA (1985).

Palmiter, R.D., et al., "Germ-Line Transformation of Mice," *Ann. Rev. Genet.* 20:465-499, Annual Reviews Inc. (1986).

Parks, R.J., et al., "A Helper Dependent Adenovirus Vector System: Removal of Helper Virus by Cre-Mediated Excision of the Viral Packaging Signal," *Proc. Natl. Acad. Sci. USA* 93:13565-13570, The National Academy of Sciences of the USA (Nov. 1996).

Pearson, W.R., and Lipman, D.J., "Improved Tools for Biological Sequence Comparison," *Proc. Natl. Acad. Sci. USA* 85:2444-2448, The National Academy of Sciences of the USA (1988).

Peschon, J.J., et al., "Expression of Mouse Protamine 1 Genes in Transgenic Mice," *Ann. New York Acad. Sci.* 564:186-197, Springer Press (1989).

Petitclerc, D., et al., "The Effect of Various Introns and Transcription Terminators on the Efficiency of Expression Vectors in Various Cultured Cell Lines and in the Mammary Gland of Transgenic Mice," *J. Biotechnol.* 40:169-178, Elsevier Science Publishers B.V. (Jun. 1995).

Pisa, P. et al., "Epstein-Barr Virus Lymphoproliferative Tumors in Severe Combined Immunodeficient Mice are Oligoclonal," *Blood* 79:173-179, W.B. Saunders (1992).

Roberts, R.J., et al., "DNA Sequences From the Adenovirus 2 Genome," *J. Biol. Chem.* 259:13968-13975, American Society for Biochemistry and Molecular Biology, Inc. (1984).

Rosenfeld, M.A., et al., "In vivo Transfer of the Human Cystic Fibrosis Transmembrane Conductance Regulator Gene to the Airway Epithelium," *Cell* 68:143-155, Cell Press (1992).

Rowe, M., et al., "Analysis of Epstein-Barr Virus Gene Expression in Lymphomas Derived from Normal Human B Cells Grafted into SCID Mice," *Curr. Topics Microbiol. Immunol.* 166:325-331, Springer-Verlag (1990).

Rusconi, S., et al., "Transmission and Expression of a Specific Pair of Rearranged Immunoglobulinμ and κ Genes in a Transgenic Mouse Line," *Nature* 314:330-334, Macmillan Magazines Ltd (1985).

Shani, M., "Tissue-Specific and Developmentally Regulated Expression of a Chimeric Actin-Globin Gene in Transgenic Mice," *Mol. Cell. Biol.* 6:2624-2631, American Society for Microbiology (1986).

Sheay, W., et al., "Downstream Insertion of the Adenovirus Tripartite Leader Sequence Enhances Expression in Universal Eukaryotic Vectors," *BioTechniques* 15:856-862, Eaton Publishing Co. (1993).

Shenk, T., "Virology," Ch. 67 in Fields et al., eds., Lippincott-Raven, Philadelphia, pp. 2111-2148 (1996; month of publication not known).

Smith, T.F. and Waterman, M.S. "Comparison of Biosequences," *Adv. Appl. Math.* 2:482-489, Academic Press, Inc. (1981).

Sorscher, E.J., et al., "Tumor Cell Bystander Killing in Colonic Carcinoma Utilizing the *Escherichia coli DeoD* Gene to Generate Toxic Purines," *Gene Ther.* 1:233-238, Stockton Press (1994).

Spector, D.J., "The Pattern of Integration of Viral DNA Sequences in the Adenovirus 5-Transformed Human Cell Line 293," *Virol.* 130:533-538, Academic Press, Inc. (1983).

Stevenson, S.C. et al., "Selective targeting of human cells by a chimeric adenovirus vector containing a modified fiber protein," *J. Virol.* 71:4782-4790, American Society for Microbiology (Jun. 1997).

Stevenson, S.C., et al., "Human Adenovirus Serotypes 3 and 5 Bind to Two Different Cellular Receptors via the Fiber Head Domain," *J. Virol.* 69:2850-2857, American Society for Microbiology (May 1995).

Storb, U., et al., "High Expression of Cloned Immunoglobulin κ Gene in Transgenic Mice is Restricted to B Lymphocytes," *Nature* 310:238-231, Macmillan Magazines Ltd (1984).

Suhadolnik R.J., et al., "Nucleoside antibiotics. I. Biochemical tools for studying the structural requirements for interaction at the catalytic and regulatory sites of ribonucleotide reductase from *Lactobacillus leichmannii*," *J. Biol. Chem.* 243:3532-3539, American Society of Biological Chemists, Inc. (1968).

Sutcliffe, J.G., "The genes for myelin," *Trends in Genet.* 3:73-76, Elsevier Science Ltd (1987).

Tatsumi, K., et al., Thyrotropin (TSH)—Gene Organization and Expression, *Nippon Rinsho* 47:2213-2220, Nippon Rinsho Co. (1989).

Thiel, J.F. ,et al., "Fluorescent Focus Assay of Viruses in Cell Monolayers in Plastic Petri Plates," *Proc. Soc. Exp. Biol. Med.* 125:892-895, Society for Experimental Biology and Medicine (1967).

Townes, T.M., et al., "Expression of Human β-Globin Genes in Transgenic Mice: Effects of a Flanking Metallothionein-Human Growth Hormone Fusion Gene," *Mol. Cell. Biol.* 5:1977-1983, American Society for Microbiology (1985).

Tremblay, Y., et al., "Pituitary-Specific Expression and Glucocorticoid Regulation of a Propiomelanocortin Fusion Gene in Transgenic Mice," *Proc. Natl. Acad. Sci. USA* 85:8890-8894, The National Academy of Sciences of the USA (1988).

Van Der Vliet, P.C., et al., "Thermolabile DNA Binding Proteins from Cells Infected with a Temperature-Sensitive Mutant of Adenovirus Defective in Viral DNA Synthesis," *J. Virol.* 15:348-354, American Society for Microbiology (1975).

Vassar, R., et al., "Tissue-Specific and Differentiation-Specific Expression of a Human K14 Keratin Gene in Transgenic Mice," *Proc. Natl. Acad. Sci. USA* 86:1563-1567, The National Academy of Sciences of the USA (1989).

von Seggern, D.J., et al., "Complementation of a fibre mutant adenovirus by packaging cell lines stably expressing the adenovirus type 5 fibre protein," *J. Gen. Virol.* 79:1461-1468, Society for General Microbiology (Jun. 1998).

von Seggeren, D.J., et al., "Adenovirus vector pseudotyping in fiber-expressing cell lines: Improved transduction of Epstein-Barr virus-transformed B cells," *J. Virol.* 74:354-362, American Society for Microbiology (Jan. 2000).

von Seggern, D.J., et al., "An Adenoviral Gene Therapy Vector Deleted for E1, E3 and Fiber: Structure and Infectivity of Fiberless Particles," *Cancer Gene Ther.* 5:S14, Abstract P-39 D, Stockton Press (Nov. 1998).

von Seggern, D.J., et al., "A helper-independent adenovirus vector with E1, E3, and fiber deleted: Structure and infectivity of fiberless particles," *J. Virol.* 73:1601-1608, American Society for Microbiology (Feb. 1999).

Wickham, T.J., et al., "Integrins $\alpha_v\beta_3$ and $\alpha_v\beta_5$ Promote Adenovirus Internalization But Not Virus Attachment," *Cell.* 73:309-319, Cell Press (1993).

Wickham, T.J., et al., "Targeted Adenovirus Gene Transfer to Endothelial and Smooth Muscle Cells by Using Bispecific Antibodies," *J. Virol.* 70:6831-6838, American Society for Microbiology (Oct. 1996).

Zabner, J., et al., "Adenovirus-Mediated Gene Transfer Transiently Corrects the Chloride Transport Defect in Nasal Epithelia of Patients with Cystic Fibrosis," *Cell* 75:207-216, Cell Press (1993).

Zufferey, R. et al., "Woodchuck hepatitis virus posttranscirptional regulatory element enhances expression of transgenes delivered by retroviral vectors," *J. Virol.* 73:2886-2892, American Society for Microbiology (Apr. 1999).

Enlish language abstract of WO 96/22378, Derwent World Patents Index Accesiion No. 1996-354535/199635.

English language abstract of WO 98/44121, Derwent World Patents Index Accession No. 1998-542706/199846.

English language abstract of EP 0 892 047, Derwent World Patents Index Accession No. 1999-083564/199908.

U.S. Appl. No. 09/562,934, filed May 1, 2000.

U.S. Appl. No. 09/847,101, filed May 1, 2000.

U.S. Appl. No. 09/586,625, filed Jun. 2, 2000.

U.S. Appl. No. 09/903,327, filed Jul. 10, 2001.

U.S. Appl. No. 60/408,931, filed Sep. 4, 2002.

U.S. Appl. No. 60/408,440, filed Sep. 4, 2002.

U.S. Appl. No. 60/408,248, filed Sep. 4, 2002.

U.S. Appl. No. 10/351,890, filed Jan. 24, 2002.

Behnam et al., "Stereotactic Delivery of a Recombinant Adenovirus into a C6 Glioma Cell Line in a Rat Brain Tumor Model", *Neurosurgery*, 35(5):910-916 (1994).

Caravokyri et al., "Constitutive Episomal Expression of Polypeptide 1X (pIX) in a 293-Based Cell Line Complements the Deficiency of pIX Mutant Adenovirus Type 5", *J. Virol.*, 69(11):6627-6633 (1995).

Certified English Translation of Tatsumi et al., "Thyroid-Stimulating Hormone (Thyrotropin) (TSH)—From Gene Structure to Expression," *Nihon Rinsho 47(10)*: 2213-2220 (1989).

Derwent# 010166087, WPI Acc. No. 1995-067340/199509, citing PCT Patent Application No. WO 9502697, "New defective recombinant adenovirus for gene therapy—contains inverted terminal repeats, encapsidation sequence and heterologous DNA, also cell lines able to complement the virus defect."

Engelhardt et al., "Direct gene transfer of human CFTR into human bronchial epithelia of xenografts with E1-deleted adenoviruses", *Nature Genetics*, 4:27-34 (1993).

Guo et al., "Apoptosis induced by adenovirus-mediated wild-type p53 expression in human pancreatic cancer cells", article in Chinese, *Clin. J. Pathol.*, 27(3):194-197 (1998).

Hallenbeck et al., "A Novel Tumor-Specific Replication-Restricted Adenoviral Vector for Gene Therapy of Hepatocellular Carcinoma", *Hum. Gene Ther.*, 10:1721-1733 (1999).

Harrison, Stephen C., Chapter 3, "Principles of Virus Structure", *Virol.*, 2nd. Ed., pp. 37-61 (1990).

Kay et al., "Genetically Targeted Research & Therapeutics: Antisense & Gene Therapy", *Cell. Biochem.*, 17E:207 S310 (1993).

Krougliak et al., "Development of Cell Lines Capable of Complementing E1, E4, and Protein IX Defective Adenovirus Type 5 Mutants," *Hum. Gene Ther.*, 6:1575-1586 (1995).

Legrand et al., "Fiberless recombinant adenoviruses: virus maturation and infectivity in the absence of fiber," *J. Virol.* 73(2): 907-19 (1999).

Mittal et al., "Monitoring foreign gene expression by a human adenovirus-based vector using the firefly luciferase gene as a reporter", *Virus Res.*, 28:67-90 (1993).

Mittereder et al., "Evaluation of the concentration and bioactivity of adenovirus vectors for gene therapy," *J. Virol.* 70(11): 7498-7509 (1996).

NCBI Nucleotide JO4514.

NCBI Nucleotide M73260.

NCBI Nucleotide M12411

NCBI Nucleotide M18369.

Nemerow, G,R., "Adenoviral Vectors—new insights", Elsevier Science Ltd., PII:SO966-842X (2000).

Nemerow, NIH Grant HL54352, "Alpha-V Integrins and Adenovirus Cell Entry", funding period from Jan. 20, 1995 to Dec. 31, 2003.

Rich et al., "Development and Analysis of Recombinant Adenoviruses for Gene Therapy of Cystic Fibrosis", *Hum. Gene Ther.*, 4:461-476 (1993).

Swift et al., "Tissue-Specific Expression of the Rat Pancreatic Elastase I Gene in Transgenic Mice", *Cell*, 38:630-646 (1984).

Wickham et al., "Increased in vitro and in vivo gene transfer by adenovirus vectors containing chimeric fiber proteins," *J. Virol.* 71(11): 8221-9 (1997).

Yang et al., "Cellular immunity to viral antigens limits E1-deleted adenoviruses for gene therapy", *Proc. Natl. Acad. Sci. USA*, 91:4407-4411 (1994).

Kaufman and Sharp, "Construction of a modular dihydrofolate reductase cDNA gene: Analysis of signals utilized for efficient expression", *Mol. Cell. Biol.* 2(11):1304-1319 (1982).

U.S. Appl. No. 09/795,292, filed Jan. 14, 1999.

U.S. Appl. No. 10/403,337, filed Mar. 27, 2003.

U.S. Appl. No. 60/478,008, filed Jun. 11, 2003.

U.S. Appl. No. 60/459,000, filed Mar. 28, 2003.

* cited by examiner

```
Ad2/5      M-KRARPSEDTFNPVYPYDTETGPPTVPFLTPPFVSPNGFQESPP
Ad3        MAKRARLS-TSFNPVYPYEDESSS-QHPFINPGFLSPDGFTQSPN
Ad19/37    MSKRLRVEDD-FNPVYPYGYARNQ-NIPFLTPPFVSSDGFKNFPP
Ad40 (1)   M-KRARF-EDDFNPVYPYEHYN-PLDIPFTTPPFASSNGLQEKPP
Ad40 (2)   M-KRTR-IEDDFNPVYPYDTSSTPS-IPYVAPPFVSSDGLOENPP
```

PCR analysis for fiber presence contamination of fiberless adenonovectors.

1. 100 bp ladder
2. positive control-10ng
3. positive control-1ng
4. positive control-1pg
5. positive control-1fg
6. positive control-$10^{-18}$g
7. Ad5BgF-one step preparation with soluble fiber on s.8 cell line
8. Ad5BgF-two step preparation (211B and S.8 cell lines)

ADENOVIRUS VECTORS, PACKAGING CELL LINES, COMPOSITIONS, AND METHODS FOR PREPARATION AND USE

This application is a continuation-in-part of U.S. application Ser. No. 09/423,783, filed Jun. 26, 2000, now abandoned which is the National Stage of International Application No. PCT/EP97/05251, filed Sep. 24, 1997, which is a continuation-in-part of U.S. application Ser. 08/719,806, filed Sep. 25, 1996, now abandoned. This application also is a continuation-in-part of U.S. application Ser. No. 09/795, 292, filed Jan. 14, 1999 converted to a U.S. Non-Provisional Application from U.S. Provisional Application No. 60/115, 920, filed Jan. 14, 1999.

The contents of U.S. application Ser. No. 09/423,783 and U.S. application Ser. No. 09/795,292 (converted from U.S. Provisional Application No. 60/115,920), are incorporated herein by reference.

STATEMENT AS TO RIGHTS TO INVENTIONS MADE UNDER FEDERALLY SPONSORED RESEARCH AND DEVELOPMENT

This invention was made with made with U.S. government support under N.I.H. Grant Nos. NL 54352 and EY 11431 from the National Institutes of Health. The government has certain rights in the invention.

TECHNICAL FIELD OF THE INVENTION

The present invention relates to gene therapy, especially to adenovirus-based gene therapy. In particular, novel packaging cell lines are disclosed, for use in facilitating the development of high-capacity and targeted vectors. High-capacity adenovirus vectors are also disclosed herein, as are related compositions, kits, and methods of preparation and use of the disclosed vectors, cell lines and kits.

BACKGROUND OF THE INVENTION

Enhanced transfer of DNA conjugates into cells has been achieved with adenovirus, a human DNA virus which readily infects epithelial cells (Horwitz, "Adenoviridae and Their Replication", in *Virology*, Fields and Knipe, eds., Raven Press, NY (1990) pp. 1679–1740).

Although adenovirus-mediated gene therapy represents an improved method of DNA transfer into cells, a potential limitation of this approach is that adenovirus replication results in disruption of the host cell. In addition, adenovirus also possesses oncogenic properties including the ability of one of its proteins to bind to tumor suppressor gene products. The use of so-called replication defective strains of adenovirus (which typically possess E1A and/or E1B deletions that render the virus unable to replicate in host cells) is in principle more suitable for in vivo therapy; however, the potential of co-infection of epithelial cells with wild-type strains of virus resulting in transactivation of the recombinant virus may represent a significant safety concern for in vivo applications.

Another undesirable aspect of using intact or replication-competent adenovirus as a gene transfer means is that it is an oncogenic virus whose gene products are known to interfere with the function of host cell tumor suppressor proteins as well as immune recognition molecules, such as the major histocompatibility complex (MHC). In addition, pre-existing circulating antibodies to adenovirus may significantly reduce the efficiency of in vivo gene delivery. Lastly, only a foreign gene of 6 kilobases (kb) or less can be incorporated into the intact adenovirus genome for gene transfer experiments, whereas DNA segments of greater than 12 kb can be transferred using the methods of this invention.

In order to make Ad vectors more replication-incompetent, some investigators have attempted to construct recombinant Ad-derived vectors which have nearly all of their genome deleted, except for portions known to be required for packaging of virus particles. For example, helper-dependent vectors lacking all viral ORFs but including essential cis elements (the inverted terminal repeats—ITRs—and the contiguous packaging sequence) have been constructed, but the virions package less efficiently than the helper and package as multimers part of the time, which suggests that the virus may "want" to package a fuller DNA complement (see, e.g., Fisher, et al., *Virology* 217: 11–22, 1996). Mitani et al. (*Proc. Natl. Acad. Sci. USA* 92: 3854–3858, 1995) also describe a helper-dependent Ad vector that was apparently not completely replication-defective.

Amalfitano, et al. (*Proc. Natl. Acad. Sci. USA* 93: 3352–3356, 1996) describe the construction of Ad packaging cell lines that support the growth of E1- and polymerase-deleted Ad vectors, in an effort to block the replication of Ad vectors in vivo. Similarly, Armentano, et al. (*Hum. Gene Ther.* 6: 1343–53, 1995) describes Ad vectors with most— but not all—of the E4 sequence deleted therefrom. However, since such a small amount of genetic material is deleted from the vectors, their ability to transport therapeutic sequences is rather limited. Published International App. No. WO96/14061 describes efforts to construct packaging cell lines containing nucleotide sequences encoding E1 and ORF6 of E4.

In addition to being able to incorporate large amounts of DNA into a vector, the ability to target the vectors to specific cell types will result in more efficient administration of desired therapeutics. Such targeting of adenovirus in a relatively simple system is one of the advantages of the current invention.

Thus, there is a need in the art to obtain Adenovirus vectors 1) capable of incorporating large segments of foreign DNA and capable of being targeted to specific cells, as well as to obtain cell lines which can package such adenovirus-gene deficient vector or targeted vectors. These needs, as well as others, are met by the invention.

BRIEF SUMMARY OF THE INVENTION

This invention utilizes recombinant adenovirus constructs which duplicate the cell receptor binding and DNA delivery properties of intact adenovirus virions and thus represents an improved method for gene therapy and cell targeting as well as for antisense-based antiviral therapy.

In contrast to the disadvantages of using intact adenovirus, modified adenovirus vectors requiring a helper plasmid or virus, or so-called replication-deficient adenovirus in the art, the use of recombinant adenovirus-derived vectors according to one aspect of the present invention provides certain advantages for gene delivery. First, the Ad-derived vectors of the present invention possess all of the functional properties required for gene therapy including binding to epithelial cell receptors and penetration of endocytic vesicles. Therapeutic viral vectors of the present invention may also be engineered to target the receptors of and achieve penetration of non-epithelial cells; means of engineering viral vectors to accomplish these ends are described in detail herein below.

Second, the vectors of the present invention have deletions of substantial portions of the Ad genome, which not only limits the ability of the Ad-derived vectors to "spread" to other host cells or tissues, but allows significant amounts of "foreign" (or non-native) nucleic acids to be incorporated into the viral genome without interfering with the reproduction and packaging of the viral genome. Therefore, the vectors of the present invention are ideal for use in a wide variety of therapeutic applications.

Third, while the vectors disclosed herein are safe for use as therapeutic agents in the treatment of a variety of human afflictions, some of these vectors do not require the presence of any "helpers" for propagation and packaging, largely because of the novel cell lines in which they are reproduced. Such cell lines—referred to herein as packaging cell lines—comprise yet another aspect of the invention.

To reduce the frequency of contamination with wild-type adenovirus, it is desirable to improve either the viral vector or the cell line to reduce the probability of recombination. For example, an adenovirus from a group with less homology to the group C viruses may be used to engineer recombinant viruses with little propensity for recombination with the Ad5 sequence contained in the packaging lines. The invention describes the preparation of packaging cells lines which stably expresses adenovirus proteins or polypeptides. These cell lines are useful for complementing viral vectors bearing deletions of regulatory and/or structural genes, irrespective of the serotype from which such a vector was derived.

It is also contemplated that the constructs and methods of the present invention will support the design and engineering of chimeric viral vectors which express amino acid residue sequences derived from two or more Ad serotypes. Thus, unlike methods and constructs available prior to the advent of the present disclosure, this invention allows the greatest possible flexibility in the design and preparation of useful viral vectors and cell lines which support their construction and propagation—all with a decreased risk of recombining with wild-type Ad to produce potentially-harmful recombinants.

In part, the present invention discloses a simpler, alternative means of reducing the recombination between viral and cellular sequences than those discussed in the art. One such means is to increase the size of the deletion in the recombinant virus and thereby reduce the extent of shared sequences between that virus and any Ad genes present in a packaging cell line e.g., the Ad5 genes in 293 cells, or the various Ad genes in the novel cell lines of the present invention.

Deletions of all or portions of structural genes of the adenovirus have been considered undesirable because of the anticipated deleterious effects such deletions would have on viral reproduction and packaging. Indeed, the use of "helper" viruses or plasmids has often been recommended when using Ad-derived vectors containing large deletions in structural protein sequences precisely for this reason.

Contrary to what has been suggested in the art, however, this invention discloses the preparation, propagation and use of recombinant Ad-derived vectors having deletions of all or part of various gene sequences encoding Ad structural proteins, both as away of reducing the risk of wild-type adenovirus contamination in virus preparations, as a way of allowing foreign DNA to be packaged in such vectors for a variety of diagnostic and therapeutic applications and as a way of targeting an adenovirus vector to a specific cell type.

The invention further discloses a wide variety of nucleic acid sequences and viral vectors. Thus, in one embodiment, the invention discloses a nucleic acid sequence encoding any one of the adenovirus fiber proteins mentioned in the specification, polypeptides or fragments thereof—including, without limitation, those that include deletions or other mutations; those that are chimeric; and those that have linkers, foreign amino acid residues, or other molecules attached for various purposes as disclosed herein. Nucleic acid sequences encoding various other adenovirus structural and/or regulatory proteins or polypeptides are also within the scope of the present invention.

In various embodiments, the adenovirus is a Group C adenovirus selected from serotypes 1, 2, 5 or 6; while in other embodiments, adenovirus selected from other serotypes, such as for example Ad37 (subgroup D) are useful as disclosed herein.

The invention is also directed to an isolated nucleic acid molecule comprising an adenovirus tripartite leader (TPL) nucleotide sequence, said TPL nucleotide sequence comprising (a) first and second different TPL exons or (b) first, second and third same or different TPL exons, said TPL exons selected from the group consisting of complete TPL exon 1, partial TPL exon 1, complete TPL exon 2 and complete TPL exon 3. A preferable embodiment of the invention may further comprise an intron operatively linked to the TPL, wherein said intron also contains requisite processing signals for the intron's removal. Another preferable embodiment of the invention is directed to the isolated nucleic acid molecule wherein said TPL nucleotide sequence consists essentially of complete TPL exon 1 operatively linked to complete TPL exon 2 operatively linked to complete TPL exon 3. A related embodiment may further include an intron and appropriate processing signals. Additional embodiments of the invention are directed to nucleic acid molecules contained in plasmids selected from the group; consisting of pCLF, pDV60, pDV67, pDV69, pDV80 and PDV90. Packaging cell lines and adenovirus particles containing the nucleic acids described above are also included in the invention.

The invention is further directed to methods for producing an adenovirus vector particle containing a helper-independent fiberless recombinant adenovirus vector genome comprising providing a) a packaging cell line which complements replication and packaging of said genome and b) a helper-independent fiberless recombinant adenovirus vector genome which is deficient in expressing sufficient functional fiber protein to support assembly of fiber-containing particles. The genome is introduced into the cell line. Additional embodiments of the invention may also include the following steps; a) growing the cell line produced under conditions for producing particles; and/or b) harvesting an adenovirus vector particle containing said helper-independent fiberless recombinant adenovirus vector genome. The method may also include a cell line that expresses a fiber protein and complements a fiber mutation in the vector.

The invention is also directed to an adenovirus vector packaging cell line comprising a stably integrated nucleic acid molecule as described above, an operatively-linked promoter and a nucleic acid sequence which encodes an adenovirus structural protein, wherein said TPL sequence consists essentially of a first TPL exon operatively linked to a complete second TPL exon operatively linked to a complete third TPL exon. Preferably, the cell line may have a complete or partial first TPL exon. Another embodiment of the invention comprises adenovirus structural protein, such as adenovirus fiber protein or a chimeric protein which includes an adenovirus fiber protein tail domain.

The invention is further directed to a recombinant adenovirus particle comprising a recombinant adenovirus vector genome wherein said genome:(a) does not encode or does not express sufficient adenovirus fiber protein to support packaging of a fiber-containing adenovirus particle without complementation of said fiber gene, and (b) encodes an adenovirus packaging signal and inverted terminal repeats containing adenovirus origin of replication. The invention is also directed to a helper-independent fiberless recombinant adenovirus vector genome comprising genes which (a) encode all adenovirus structural gene products but do not express sufficient adenovirus fiber protein to package a fiber-containing adenovirus particle without complementation of said fiber gene or said genome lacks at least the fibre gene and (b) encodes an exogenous protein. Either of the above embodiments may substitute a helper-dependent for a helper-independent recombinant adenovirus vector genome. In a preferable embodiment, no fiber protein is expressed. In yet another embodiment of the invention, the recombinant adenovirus particle fails to express sufficient fiber protein to allow fiber incorporation into the particle such that the particle can use the fiber pathway for infection.

The invention is further directed to a method for producing an adenovirus vector particle containing a helper-independent fiberless recombinant adenovirus vector genome, said method comprising providing a packaging cell line which complements replication and packaging of said genome and a helper-independent fiberless recombinant adenovirus vector genome which is deficient in expressing sufficient functional fiber protein to support assembly of fiber-containing particles and harvesting said particles produced by said cell line. The method may also comprise a step of coating (i.e. providing fiber protin in any way) to a particle with an adenovirus fiber protein. In a preferable embodiment the adenovirus particle comprises an exogenous protein or a modified fiber protein.

Another aspect of the invention is directed to a method for pseudotyping recombinant viral vectors comprising complementing a missing fiber gene of a helper-independent fiberless recombinant adenovirus vector genome by expressing in packaging cells a fiber gene from a different adenoviral serotype than said recombinant adenovirus vector, thereby pseudotyping said vector. An additional embodiment of the invention is directed to the method for pseudotyping recombinant viral vectors comprising: a) providing a packaging cell line for propagating a fiber gene deleted recombinant adenovirus vector, b) introducing into said cell line a helper-independent fiberless recombinant adenovirus vector genome, and c) complementing the missing fiber gene by expression in the cells of a fiber gene from a different adenoviral serotype thereby pseudotyping the vector.

The invention is further directed to a method for specifically targeting an adenovirus vector to a cell of choice comprising providing a packaging cell line for producing a fiber gene-deleted adenovirus vector and providing a helper-independent fiberless recombinant adenovirus vector genome, wherein said gene for a missing fiber protein is complemented with a gene for a desired modification for targeting the vector to a cell of choice.

The invention is further directed to a method for producing a modified adenovirus comprising providing in vitro an exogenous fiber protein to a fiberless adenovirus. Additional embodiments of the invention may provide any combination of all of the following steps such that the invention be directed to a method for producing a modified adenovirus comprising: a) providing a packaging cell line for producing a fiberless adenovirus vector, b) introducing into said cell line a helper-independent fiberless or helper-dependent fiberless recombinant adenovirus vector genome, c) growing and harvesting a fiberless adenovirus, d) maintaining the fiberless adenovirus in any suitable buffer, and e) providing exogenous fiber, wherein said fiber may be a modified fiber, to the fiberless adenovirus by adding conditioned media or a soluble fiber preparation or a fiber in any suitable buffer to a virus preparation thereby producing the modified adenovirus.

The invention is further directed to a method for producing a modified adenovirus comprising providing a packaging cell line for producing a helper-dependent fiberless adenovirus vector genome and providing a helper virus vector, wherein said cell line complements at least a deficient fiber protein gene, thereby producing the modified adenovirus. Another aspect of the invention is directed to a method for producing a modified adenovirus comprising: a) providing a packaging cell line for producing a fiberless adenovirus vector, b) introducing into said cell line a helper dependent fiberless recombinant adenovirus vector genome and a fiberless helper virus vector, c) growing and harvesting a fiberless adenovirus, and d)maintaining the fiberless adenovirus in infectious media, and e) providing exogenous fiber to the fiberless adenovirus by adding conditioned media or a soluble fiber preparation to a virus preparation thereby producing the modified adenovirus.

Additional aspects of the invention are directed to hybrid Ad/AAV vectors and to new helper-dependent vectors used with fiberless adenovirus vectors.

The invention is also directed to a method for delivering a heterologous gene to an EBV-infected B cells comprising infecting said B cells with a pseudotyped Ad5βgal.ΔF particle or other fiber-deleted adenovirus particle, said particle having a chimeric fiber with the receptor-binding knob domain of the adenovirus type 3 fiber.

The invention is also directed to an isolated nucleic acid comprising a post-transcriptional regulatory element (PRE) and a TPL. Preferably the PRE is the woodchuck hepatitis virus PRE (WPRE).

The invention is further directed to a composition for preparing a therapeutic vector, said composition comprising a plasmid comprising an adenovirus genome lacking a nucleotide sequence encoding a fiber protein or a genome that is incapable of expressing sufficient fiber to result in packaging.

Another aspect of the invention is directed to a method of delivering a heterologous gene to a human or any animal comprising providing an exogenous gene to a target cell comprising contacting said cell in vivo or ex vivo with an amount of a recombinant adenovirus particle sufficient to infect said cell.

The invention is also directed to A method for producing a gutless adenoviral vector particle comprising: a) delivering a helper adenovirus vector genome to an adenovirus vector packaging cell, wherein said helper adenovirus vector genome lacks any gene encoding adenovirus fiber protein or lacks the ability to encode sufficient adenovirus fiber protein to produce an adenoviral vector comprising fiber protein in the absence of complemetation by said packing cell and wherein said packaging cell comprises the nucleic acid molecule of claim 2 operably linked to a promoter and to an adenoviral fiber protein or to a chimeric protein that includes an adenovirus fiber protein tail domain; (b) delivering a gutless adenovirus vector genome to said packaging cell; and (c) recovering the gutless adenoviral vector particle produced by said cell.

Another aspect of the invention is directed to a helper adenovirus particle comprising an adenovirus vector genome that does not encode or does not express sufficient adenovirus fiber protein to support packaging of a fiber-containing adenovirus particle without complementation of said fiber gene, wherein said genome has a mutation in its packaging sequence that renders said genome substantially incapable of being packaged. Packaging sequence are those sequences are those sequences involved in packaging the viral particle.

The invention is further directed to a helper adenovirus particle comprising an adenovirus vector genome with recombinase sites flanking its packaging sequence, wherein said vector genome does not encode or does not express sufficient adenovirus fiber protein to support packaging of a fiber-containing adenovirus particle without complementation of said fiber gene.

The invention is also directed to an adenovirus particle comprising a gutless adenoviral vector genome and a fiberless capsid, as well as an adenovirus particle comprising a gutless adenoviral vector genome and a capsid comprising a modified fiber protein.

Another aspect of the invention is directed to a packaging cell for the production of a fiberless or fiber-modified gutless adenovirus particle comprising an adenovirus vector complementing plasmid and a nucleotide sequence encoding a recombinase, wherein said complementing plasmid comprises the nucleic acid molecule of claim 2 operably linked to a promoter and to a nucleotide sequence encoding an adenoviral fiber protein or a chimeric adenoviral fiber protein. Preferably the cell line may comprise a recombinase. In an embodiment of the invention the recombinase may be Cre.

In another embodiment of the invention, the fiber-deleted adenovirus vectors of the invention and the fiber-complementing adenovirus packaging cells of the invention are used to produce a gutless adenovirus vector particle. Such particle comprises a gutless adenoviral vector genome in an adenoviral capsid. The fiber proteins of the capsid may be wild-type fiber, or the modified fiber proteins disclosed herein. Alternatively, such particle may have a fiberless capsid as disclosed herein. Preferably, the gutless genome contains at least one heterologous gene as described herein. As used herein, the term "gutless adenoviral vector genome" means an adenoviral vector genome from which all of the viral genes have been deleted.

The invention also discloses systems or kits for use in any of the aforementioned methods. The systems or kits may contain any appropriate combination of the within-described vectors, plasmids, cell lines, virus particles and additional therapeutic agents as disclosed. Preferably, each such kit or system includes a quantity of the appropriate therapeutic substance or sequence sufficient for at least one administration, and instructions for administration and use. Thus, one system further comprises an effective amount of a therapeutic agent which enhances the therapeutic effect of the therapeutic viral vector-containing composition. Another variation discloses that the composition and the therapeutic agent are each included in a separate receptacle or container.

It will also be appreciated that any combination of the preceding elements may also be efficacious as described herein, and that all related methods are also within the scope of the present invention.

BRIEF DESCRIPTION OF THE DRAWINGS

FIG. 15 shows the incorporation of the recombinant Ad5 fiber into Ad3 particles.

FIG. 16 shows the fiber deletion in pDV44 and the genomic structures of the Ad5.βgal.ΔF and Ad5.βgal.wt vectors.

FIG. 17 shows the analysis of the viral chromosomes.

FIG. 19 shows the infectivity of Ad particles on TKP-1 monocytic cells.

DETAILED DESCRIPTION OF THE INVENTION

Figure 1:
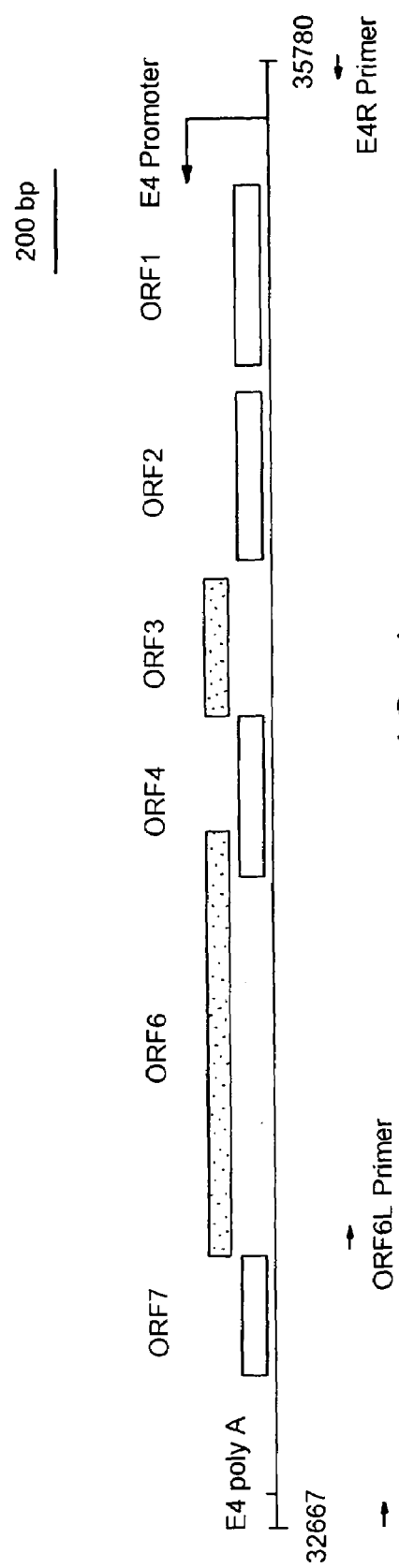
FIG. 1 is a schematic diagram of the entire adenoviral E4 transcriptional unit with the open reading frames (ORF) indicated by blocked segments along with the promoter and terminator sequences. The location of primers for amplifying specific portions of E4 are also indicated as further described in Example 1A.

To reduce the frequency of contamination with wild-type adenovirus, it is considered desirable to improve either the viral vector or the cell line to reduce the probability of recombination. For example, an adenovirus from a group with less homology to the group C viruses may be used to engineer recombinant viruses with little propensity for recombination with the Ad5 sequence in 293 cells. Similarly, an epithelial cell line—e.g. the cell line known as 293—may be used or further modified according to within-disclosed methods which stably expresses adenovirus proteins or polypeptides from Ad3 and/or proteins or polypeptides from another non-group-C or group C serotype; such a cell line would be useful to support adenovirus-derived viral vectors bearing deletions of regulatory and/or structural genes, irrespective of the serotype from which such a vector was derived.

It is also contemplated that the constructs and methods of the present invention will support the design and engineering of chimeric viral vectors which express amino acid residue sequences derived from two or more Ad serotypes. Thus, unlike methods and constructs available prior to the advent of the present disclosure, this invention allows the greatest possible flexibility in the design and preparation of useful viral vectors and cell lines which support their construction and propagation—all with a decreased risk of recombining with wild-type Ad to produce potentially-harmful recombinants.

In part, the present invention discloses a simpler, alternative means of reducing the recombination between viral and cellular sequences than those discussed in the art. One such means is to increase the size of the deletion in the recombinant virus and thereby reduce the extent of shared sequences between that virus and any Ad genes present in a packaging cell line—e.g., the Ad5 genes in 293 cells, or the various Ad genes in the novel cell lines of the present invention.

Therefore, the present invention makes it feasible to engineer and produce novel viral vectors that are able to package and deliver significantly larger foreign nucleic acid sequences for efficacious use in a variety of therapeutic applications, without endangering the subject to whom they are administered, due to their impaired ability to self-replicate in non-complementing cell lines. Due to the fact that "helper" viruses or plasmids need not be used in conjunction with many of the viral vectors of the present invention, those vectors of the present invention are also simpler to use than those previously described in the art.

I. Definitions

In order to provide a clearer understanding of the specification and claims, the following definitions are provided.

Adenoviral Vector or Ad-Derived Vector: Any adenovirus-derived plasmid, genome or virus into which a foreign DNA may be inserted or expressed. This term may also be used interchangeably with "viral vector." This "type" of vector may be utilized to carry nucleotide sequences encoding therapeutic proteins or polypeptides to specific cells or cell types in a subject in need of treatment, as described further herein below.

Amino Acid Residue: An amino acid formed upon chemical digestion (hydrolysis) of a polypeptide at its peptide linkages. The amino acid residues described herein are preferably in the "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxyl terminus of a polypeptide. In keeping with standard polypeptide nomenclature described in *J. Biol. Chem.*, 243:3552–59 (1969) and adopted at 37 C.F.R. §§ 1.821–1.822, abbreviations for amino acid residues are shown in the following Table of Correspondence:

TABLE 1

Table of Correspondence

| SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| X | Xaa | Unknown or other |

It should be noted that all amino acid residue sequences represented herein by formulae have a left to right orientation in the conventional direction of amino-terminus to carboxyl-terminus. In addition, the phrase "amino acid residue" is broadly defined to include the amino acids listed in the Table of Correspondence and modified and unusual amino acids, such as those referred to in 37 C.F.R. §§1.821–1.822, and incorporated herein by reference. Furthermore, it should be noted that a dash at the beginning or end of an amino acid residue sequence indicates a peptide bond to a further sequence of one or more amino acid residues or to an amino-terminal group such as $NH_2$ or to a carboxyl-terminal group such as COOH.

Complementing Plasmid: This term is generally used herein to describe plasmid vectors used to deliver particular nucleotide sequences into a packaging cell line, with the intent of having said sequences stably integrate into the cellular genome.

Delivery Plasmid: This term is generally used herein to describe a plasmid vector that carries or delivers nucleotide sequences in or into a cell line (e.g., a packaging cell line) for the purpose of propagating therapeutic viral vectors of the present invention.

DNA Homolog: A nucleic acid having a preselected conserved nucleotide sequence and a sequence encoding a preferred polypeptide according to the present invention, where the nucleic acid is substantial homologous to a named preferred embodiment. By the term "substantially homologous" is meant having at least 80%, preferably at least 90%, most preferably at least 95% homology therewith.

The terms "homology" and "identity" are often used interchangeably. In this regard, percent homology or identity may be determined, for example, by comparing sequence information using a GAP computer program. The GAP program utilizes the alignment method of Needleman and Wunsch (*J. Mol. Biol.* 48:443 (1970), as revised by Smith and Waterman (*Adv. Appl. Math.* 2:482 (1981). Briefly, the GAP program defines similarity as the number of aligned symbols (i.e., nucleotides or amino acids) which are similar, divided by the total number of symbols in the shorter of the two sequences. The preferred default parameters for the GAP program may include: (1) a unary comparison matrix (containing a value of 1 for identities and 0 for non-identities) and the weighted comparison matrix of Gribskov and Burgess, *Nucl. Acids Res.* 14:6745 (1986), as described by Schwartz and Dayhoff, eds., ATLAS OF PROTEIN SEQUENCE AND STRUCTURE, National Biomedical Research Foundation, pp. 353–358 (1979); (2) a penalty of 3.0 for each gap and an additional 0.10 penalty for each symbol in each gap; and (3) no penalty for end gaps.

Whether any two nucleic acid molecules have nucleotide sequences that are at least 80%, 85%, 90%, 95%, 96%, 97%, 98% or 99% "identical" can be determined using known computer algorithms such as the "FAST A" program, using for example, the default parameters as in Pearson and Lipman, *Proc. Natl. Acad. Sci. USA* 85:2444 (1988). Alternatively the BLAST function of the National Center for Biotechnology Information database may be used to determine identity In general, sequences are aligned so that the highest order match is obtained. "Identity" per se has an art-recognized meaning and can be calculated using published techniques. (See, e.g.: *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part I*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H. & Lipton, D., *SIAM J Applied Math* 48:1073 (1988)). Methods commonly employed to determine identity or similarity between two sequences include, but are not limited to, those disclosed in Guide to Huge Computers, Martin J. Bishop, ed., Academic Press, San Diego, 1994, and Carillo, H. & Lipton, D., *SIAM J Applied Math* 48:1073 (1988). Methods to determine identity and similarity are codified in computer programs.

Preferred computer program methods to determine identity and similarity between two sequences include, but are not limited to, GCG program package (Devereux, J., et al., *Nucleic Acids Research* 12(I):387 (1984)), BLASTP, BLASTN, FASTA (Atschul, S. F., et al., *J Molec Biol* 215:403 (1990)).

Therefore, as used herein, the term "identity" represents a comparison between a test and a reference polypeptide or polynucleotide. For example, a test polypeptide may be defined as any polypeptide that is 90% or more identical to a reference polypeptide. As used herein, the term at least "90% identical to" refers to percent identities from 90 to 99.99 relative to the reference polypeptides. Identity at a level of 90% or more is indicative of the fact that, assuming for exemplification purposes a test and reference polynucleotide length of 100 amino acids are compared. No more than 10% (i.e., 10 out of 100) amino acids in the test polypeptide differs from that of the reference polypeptides. Similar comparisons may be made between a test and reference polynucleotides. Such differences may be represented as point mutations randomly distributed over the entire length of an amino acid sequence or they may be clustered in one or more locations of varying length up to the maximum allowable, e.g. 10/100 amino acid difference (approximately 90% identity). Differences are defined as nucleic acid or amino acid substitutions, or deletions.

An embodiment of the invention may use polynucleotides at least 90% or 95% identical to those encoding the TPL nucleic acid sequences. A further embodiment of the invention may include those polynucleotides that encode a polypeptide of interest that are at least 95% identical when the variation in such a polynucleotide is due to more than merely degenerate changes.

Expression or Delivery Vector: Any plasmid or virus into which a foreign DNA may be inserted for expression in a suitable host cell—i.e., the protein or polypeptide encoded by the DNA is synthesized in the host cell's system. Vectors capable of directing the expression of DNA segments (genes) encoding one or more proteins are referred to herein as "expression vectors." Also included are vectors which allow cloning of cDNA (complementary DNA) from mRNAs produced using reverse transcriptase.

Foreign Gene: This term is used to identify a DNA molecule not present in the exact orientation and position as the counterpart DNA molecule found in wild-type adenovirus. It may also refer to a DNA molecule from another organism or species (i.e., exogenous) or from another Ad serotype.

Gene: A nucleic acid whose nucleotide sequence encodes an RNA or polypeptide. A gene can be either RNA or DNA. Genes may include regions preceding and following the coding region (leader and trailer) as well as intervening sequences (introns) between individual coding segments (exons).

Isolated: This term is used to indicate a nucleic acid or polypeptide sequence separated from the genetic environment from which the sequences were obtained. It may also mean altered from the natural state. For example, a polynucleotide or a polypeptide naturally present in a living animal is not "isolated," but the same polynucleotide or polypeptide separated from the coexisting materials of its natural state is "isolated", as the term is employed herein. Thus, a polypeptide or polynucleotide produced and/or contained within a recombinant host cell is considered isolated for purposes of the present invention. Also intended as an "isolated polypeptide" or an "isolated polynucleotide" are polypeptides or polynucleotides that have been purified, partially or substantially, from a recombinant host cell or from a native source.

For example, a recombinantly produced version of a compounds can be substantially purified by the one-step method described in Smith and Johnson, *Gene* 67:31–40 (1988). The terms isolated and purified are sometimes used interchangeably.

By "isolated" is meant that the DNA is free of the coding sequences of those genes that, in the naturally-occurring genome of the organism (if any) from which the DNA of the invention is derived, immediately flank the gene encoding the DNA of the invention. The isolated DNA may be single-stranded or double-stranded, and may be genomic DNA,cDNA, recombinant hybrid DNA, or synthetic DNA. It may be identical to a native DNA sequence, or may differ from such sequence by the deletion, addition, or substitution of one or more nucleotides.

Isolated or purified as it refers to preparations made from biological cells or hosts should be understood to mean any cell extract containing the indicated DNA or protein including a crude extract of the DNA or protein of interest. For example, in the case of a protein, a purified preparation can be obtained following an individual technique or a series of preparative or biochemical techniques and the DNA or protein of interest can be present at various degrees of purity in these preparations. The procedures may include for example, but are not limited to, ammonium sulfate fractionation, gel filtration, ion exchange change chromatography, affinity chromatography, density gradient centrifugation and electrophoresis.

A preparation of DNA or protein that is "pure" or "isolated" should be understood to mean a preparation free from naturally occurring materials with which such DNA or protein is normally associated in nature. "Essentially pure" should be understood to mean a "highly" purified preparation that contains at least 95% of the DNA or protein of interest.

A cell extract that contains the DNA or protein of interest should be understood to mean a homogenate preparation or cell-free preparation obtained from cells that express the protein or contain the DNA of interest. The term "cell extract" is intended to include culture media, especially spent culture media from which the cells have been removed.

Packaging Cell line: A packaging cell line is a cell line that provides a missing gene product or its equivalent.

Particle: The adenovirus (Ad) particle is relatively complex and may be resolved into various substructures. The particle is the minimal structural or functional unit of a virus. A virus can refer to a single particle, a stock of particles or a viral genome.

Penton: The terms "penton" or "penton complex" are preferentially used herein to designate a complex of penton base and fiber. The term "penton" may also be used to indicate penton base, as well as penton complex. The meaning of the term "penton" alone should be clear from the context within which it is used.

Plasmid: An autonomous self-replicating extrachromosomal circular DNA

Post-transcription Regulatory Element (PRE) is a regulatory element found in viral or cellular messenger RNA that is not spliced, i.e. intronless messages. Examples include, but are not limited to, human hepatitis virus, woodchuck hepatitits virus, the TK gene and mouse histone gene. The PRE may be placed before a polyA sequence and after a heterologous DNA sequence.

Pseudotyping: This term as generally used herein describes the production of adenoviral vectors having modified capsid protein or capsid proteins from a different serotype than the serotype of the vector itself. One example, is the production of an adenovirus 5 vector particle containing a chimeric Ad3/Ad5 fiber protein. This may be accomplished by producing the adenoviral vector in packaging cell lines expressing different fiber proteins.

Promoter: Useful promoters according to the present invention may be inducible or constitutive. Inducible promoters will initiate transcription only in the presence of an additional molecule; constitutive promoters, on the other hand, do not require the presence of any additional molecule to regulate gene expression. A regulatable or inducible promoter may also be described as a promoter wherein the rate of RNA polymerase binding and initiation is modulated by external stimuli. Such stimuli include various compounds or compositions, light, heat, stress, chemical energy sources, and the like. Inducible, suppressible and repressible promoters are considered regulatable promoters.

Receptor: Receptor is a term used herein to indicate a biologically active molecule that specifically binds to (or with) other molecules. The term "receptor protein" may be used to more specifically indicate the proteinaceous nature of a specific receptor.

Recombinant: As used herein, the term is intended to refer to any progeny formed as the result of genetic engineering. This may also be used to describe a virus formed by recombination of plasmids in a packaging cell.

Transgene or Therapeutic Nucleotide Sequence: As described and claimed herein, such a sequence includes DNA and RNA sequences encoding an RNA or polypeptide. Such sequences may be "native" or naturally-derived sequences; they may also be "non-native" or "foreign" sequences which are naturally- or recombinantly-derived. The term "transgene," which may be used interchangeably herein with the term "therapeutic nucleotide sequence," is often used to describe a heterologous or foreign (exogenous) gene that is carried by a viral vector and transduced into a host cell.

Therefore, therapeutic nucleotide sequences may also include antisense sequences or nucleotide sequences which may be transcribed into antisense sequences. Therapeutic nucleotide sequences (or transgenes) further comprise sequences which function to produce a desired effect in the cell or cell nucleus into which said therapeutic sequences are delivered. For example, a therapeutic nucleotide sequence may encode a functional protein intended for delivery into a cell which is unable to produce that functional protein.

II. Adenovirus

Fiber plays a crucial role in adenovirus infection by attaching the virus to a specific receptor on the cell surface. The fiber is an elongated protein which exists as a trimer of three identical polypeptides (polypeptide IV) of 582 amino acids in length. An adenovirus fiber consists of three domains: an N-terminal tail domain that interacts with penton base; a shaft composed of variable numbers of repeats of a 15-amino-acid segment that forms beta-sheet and beta-bends; and a knob at the C-terminus ("head domain") that contains the type-specific antigen and is responsible for binding to the cell surface receptor. The gene encoding the fiber protein from Ad2 has been expressed in human cells and has been shown to be correctly assembled into trimers, glycosylated and transported to the nucleus. (See, e.g., Hong and Engler, *Virology* 185: 758–761, 1991).

Thus, alteration of the fiber in recombinant Ad vectors can lead to alteration in gene delivery. This has great utility for a variety of gene therapy applications and is one of the objects of the present invention.

Hexon, penton and fiber capsomeres are the major components on the surface of the virion. Their constituent polypeptides, nos. II, III and IV, contain tyrosine residues that are exposed on the surface of the virion and can be labeled—e.g., by iodination of intact particles.

The 35,000+ base pair (bp) genome of adenovirus type 2 has been sequenced and the predicted amino acid sequences of the major coat proteins (hexon, fiber and penton base) have been described. (See, e.g., Neumann et al., *Gene* 69: 153–157 (1988); Herisse et al., *Nuc. Acids Res.* 9: 4023–4041 (1981); Roberts et al., *J. Biol. Chem.* 259: 13968–13975 (1984); Kinloch et al., *J. Biol. Chem.* 259: 6431–6436 (1984); and Chroboczek et al., *Virol.* 161: 549–554, 1987).

The sequence of Ad5 DNA was completed more recently; its sequence includes a total of 35,935 bp. Portions of many other adenovirus genomes have also been sequenced. It is presently understood that the upper packaging limit for adenovirus virions is about 105% of the wild-type genome length. (See, e.g., Bett, et al., *J. Virol.* 67(10): 5911–21, 1993). Thus, for Ad2 and Ad5, this would be an upper packaging limit of about 38 kb of DNA.

Adenovirus DNA also includes inverted terminal repeat sequences (ITRs) ranging in size from about 100 to 150 bp, depending on the serotype. The inverted repeats enable single strands of viral DNA to circularize by base-pairing of their terminal sequences, and the resulting base-paired "panhandle" structures required for replication of the viral DNA.

For efficient packaging, the ITRs and the packaging signal (a few hundred bp in length) comprise the "minimum requirement" for replication and packaging of a genomic nucleic acid into an adenovirus particle. Helper-dependent vectors lacking all viral ORFs but including these essential cis elements (the ITRs and contiguous packaging sequence) have been constructed, but the virions package less efficiently that the helper and package as multimers part of the time, which suggests that the virus may "want" to package a fuller DNA complement (see, e.g., Fisher, et al., *Virology* 217: 11–22, 1996).

The viral vectors of the present invention may retain their ability to express the genome packaged within—i.e., they may retain their "infectivity"—they do not act as infectious agents, however, to the extent that they cause disease in the subjects to whom they are administered for therapeutic purposes.

It is to be appreciated that Ad vectors have several distinct advantages over other viral vectors in the art. For example, recombination of such vectors is rare; there are no known associations of human malignancies with adenoviral infections despite common human infection with adenoviruses; the genome may be manipulated to accommodate foreign genes of a fairly substantial size; and host proliferation is not required for expression of adenoviral proteins.

An extension of this invention is that the Ad-derived viral vectors disclosed herein may be used to target and deliver genes into specific cells by incorporating the attachment sequence for other receptors (such as CD4) onto the fiber protein by recombinant DNA techniques, thus producing a chimeric molecule. This should result in the ability to target and deliver genes into a wide range of cell types with the advantage of evading recognition by the host's immune system. The within-disclosed delivery systems thus provide for increased flexibility in gene design to enable gene delivery into proliferating and nonproliferating cell types.

For example, U.S. Pat. Nos. 5,756,086, and 5,543,328 as well as WO95/26412 and WO 98/44121 and Krasnykh, et al. (J. Virol. 70: 6839–46, 1996), the disclosures of which are incorporated by reference herein, describe modifications that may be made to the adenovirus fiber protein. Such modifications are useful in altering the targeting mechanism and specificity of adenovirus and could readily be utilized in conjunction with the constructs of the present invention to target the novel viral vectors disclosed herein to different receptors and different cells. Moreover, modifications to fiber protein which alter its tropism may permit greater control over the localization of viral vectors in therapeutic applications.

Similarly, incorporation of various structural proteins into cell lines of the present invention, whether or not those proteins are modified, is also contemplated by the present invention. Thus, for example, modified penton base polypeptides such as those described in Wickham, et al. (J. Virol. 70: 6831–8, 1996) may have therapeutic utility when used according to the within-disclosed methods.

While some of the Examples appearing below specifically recite fiber proteins, polypeptides, and fragments thereof, it is expressly provided herein that other structural and non-structural Ad proteins and polypeptides (e.g., regulatory proteins and polypeptides) may be used as components of the various disclosed vectors and cell lines. Moreover, chimeric molecules comprised of proteins, polypeptides, and/or fragments thereof which are derived from different Ad serotypes may be used in any of the within-disclosed methods, constructs and compositions. Similarly, recombinant DNA sequences of the present invention may be prepared using nucleic acid sequences derived from different Ad serotypes, in order to design useful constructs with broad applicability, as disclosed and claimed herein.

It should also be appreciated that, while the members of Group C or Group D adenovirus—i.e., Ad serotypes 1, 2, 5, 6 or 37—are specifically recited in various examples herein, the present invention is in no way limited to those serotypes alone. In view of the fact that the adenovirus serotypes are all closely-related in structure and functionality, therapeutic viral vectors, packaging cell lines, and plasmids of the present invention may be constructed from components of any and all Ad serotypes—and the within-disclosed methods of making and using the various constructs and cell lines of the present invention apply to all of said serotypes.

The family of Adenoviridae includes many members with at least 47 known serotypes of human adenovirus (Ad1-Ad47) (Shenk, Virology, Chapter 67, in Fields et al., eds. Lippincott-Raven, Philadelphia, 1996,) as well as members of the genus Mastadenovirus including human, simian, bovine, equine, porcine, ovine, canine and opossum viruses, and members of the Aviadenovirus genus, including bird viruses, e.g. CELO. Thus it is contemplated that the disclosed inventions can be applied to any adenovirus species, and the invention need not be so limited. One of skill in the art would have knowledge of the different adenoviruses as evidenced by (Shenk, Virology, Chapter 67, in Fields et al., eds. Lippincott-Raven, Philadelphia, 1996,) which is herein incorporated by reference.

III. Packaging Cell Lines

A. Adenovirus Complentation Genetics

Figure 3:
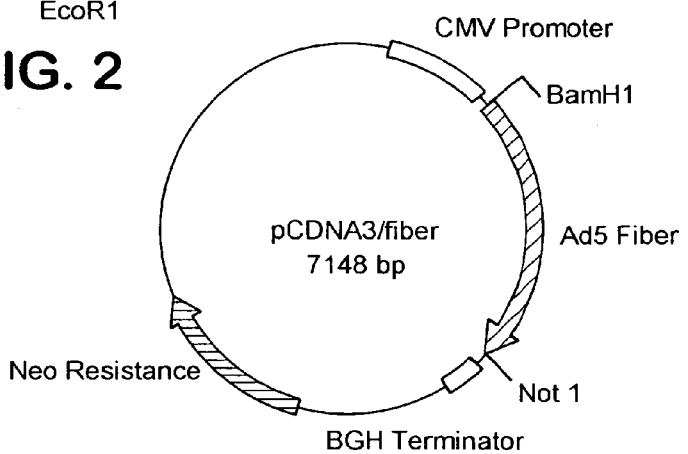
FIG. 3 is a schematic map of plasmid pCDNA3/Fiber as further described in Example 1B.

The first generation of recombinant adenoviral vectors currently available typically have a deletion in the first viral early gene region which is generally referred to as E1, which comprises the E1a and E1b regions. (These regions span genetic map units 1.30 to 9.24.) FIG. 3 in chapter 67 of Fields Virology, 3d Ed. (Fields et al. eds, Lippincott-Raven Publ., Philadelphia, 1996, p. 2116) illustrates a transcription and translation map of adenovirus type 2 (Ad2).

Deletion of the viral E1 region renders the recombinant adenovirus defective for replication and incapable of producing infectious viral particles in subsequently-infected target cells. Thus, to generate E1-deleted adenovirus genome replication and to produce virus particles requires a system of complementation which provides the missing E1 gene product. E1 complementation is typically provided by a cell line expressing E1, such as the human embryonic kidney packaging cell line, i.e. an epithelial cell line, called 293. Cell line 293 contains the E1 region of adenovirus, which provides E1 gene region products to "support" the growth of E1-deleted virus in the cell line (see, e.g., Graham et al., J. Gen. Virol. 36: 59–71, 1977). Additionally, cell lines that may be usable for production of defective adenovirus having a portion of the adenovirus E4 region have been reported (WO 96/22378). Multiply deficient adenoviral vectors and complementing cell lines have also been described (WO 95/34671, U.S. Pat. No. 5,994,106). Nevertheless, inherent problems exist concerning first-generation recombinant adenoviruses.

B. Adenovirus Particle Packaging Cell Lines

Packaging cell lines disclosed herein support viral vectors with deletions of major portions of the viral genome, without the need for helper viruses. Additionally, the invention provides novel cell lines and helper viruses for use with helper-dependent vectors.

Thus, in one embodiment of the present invention, a packaging cell line is disclosed having DNA sequences stably integrated into the cellular genome wherein the DNA sequences encode one or more adenovirus regulatory and/or structural polypeptides which complement the genes deleted or mutated in the adenovirus vector genome to be replicated and packaged.

In another embodiment, the packaging cell line expresses one or more adenovirus structural proteins, polypeptides, or fragments thereof, wherein said structural protein is selected from the group consisting of penton base, hexon, fiber, polypeptide IIIa, polypeptide V, polypeptide VI, polypeptide VII, polypeptide VIII, and biologically active fragments thereof.

In one variation, the sequences are constitutively expressed; in another, one or more sequences is under the control of a regulatable promoter. In a preferred embodiment expression is constitutive. In various preferred embodiments, the polypeptides expressed by the DNA sequences are biologically active.

In a further and preferred embodiment the packaging cell line of the present invention supports the production of a viral vector. In a preferred embodiment the viral vector is a therapeutic vector.

The present invention also discloses a packaging cell line which complements a viral vector having a deletion or mutation of a DNA sequence encoding an adenovirus structural protein, regulatory polypeptides E1A and E1B, and/or one or more of the following regulatory proteins or polypeptides: E2A, E2B, E3, E4, L4, or fragments thereof.

Various useful packaging cells are contemplated which complement adenovirus. In one aspect of the present invention, each DNA sequence is introduced into the genome of the within-disclosed cell lines via a separate complementing plasmid. In other embodiments, two or more DNA sequences were introduced into the genome via a single complementing plasmid. In one variation, the complementing plasmid comprises a DNA sequence encoding adenovirus fiber protein, polypeptide or fragment thereof. An example of a useful complementing plasmid according to the present invention is a plasmid having the characteristics of pCLF (for deposit details, see Example 3)

One embodiment discloses a packaging cell useful in the preparation of recombinant adenovirus viral vectors comprising a delivery plasmid comprising an adenovirus genome lacking a nucleotide sequence encoding fiber. In one variation, the delivery plasmid further comprises a nucleotide sequence encoding a foreign polypeptide. A preferred delivery plasmid is pDV44, pE1B gal, or pE1sp1B. In another variation, the cell further comprises a complementing plasmid containing a nucleotide sequence encoding fiber, the plasmid being stably integrated into the cellular genome of the cell.

In one embodiment, a composition comprises a cell containing first and second delivery plasmids wherein a first delivery plasmid comprises an adenovirus genome lacking a nucleotide sequence encoding fiber and incapable of directing the packaging of new viral particles in the absence of a second delivery plasmid, and a second delivery plasmid comprises an adenoviral genome capable of directing the packaging of new viral particles in the presence of the first delivery plasmid.

In another variation, the first and second delivery plasmids interact within the cell to produce a therapeutic viral vector. In yet another variation, the cell further comprises a complementing plasmid containing a nucleotide sequence encoding fiber, the plasmid being stably integrated into the cellular genome of the cell. In still another, the first or second delivery plasmid further comprises a nucleotide sequence encoding a foreign polypeptide. In various embodiments, the polypeptide is a therapeutic molecule.

Another embodiment discloses a composition as before, wherein the first delivery plasmid lacks adenovirus packaging signal sequences. In another aspect, the second delivery plasmid contains a LacZ reporter construct. In another variation, the second delivery plasmid further lacks a nucleotide sequence encoding an adenovirus regulatory protein. In one variation, the regulatory protein is E1. In one embodiment of the above-noted compositions, the complementing plasmid has the characteristics of pCLF.

In another embodiment, a composition is disclosed wherein the first delivery plasmid lacks a nucleotide sequence encoding an adenovirus structural protein and the second delivery plasmid lacks a nucleotide sequence encoding adenovirus E1 protein. In another, the first delivery plasmid lacks a nucleotide sequence encoding adenovirus E4 protein and the second delivery plasmid lacks a nucleotide sequence encoding adenovirus E1 protein. In still another, the cell contains at least one complementing plasmid encoding an adenoviral regulatory protein and a structural protein.

In one preferred variation of the present invention, a packaging cell line expresses fiber protein. In one embodiment, the fiber protein has been modified to include a non-native amino acid residue sequence which targets a specific receptor, but which does not disrupt trimer formation or transport of fiber into the nucleus. In another variation, the non-native amino acid residue sequence alters the binding specificity of the fiber for a targeted cell type. In still another embodiment, the structural protein is fiber comprising amino acid residue sequences from more than one adenovirus serotype. As disclosed herein, the nucleotide sequences encoding fiber protein or polypeptide need not be modified solely at one or both termini; fiber protein—and indeed, any of the adenovirus structural proteins, as taught herein—may be modified "internally" as well as at the termini.

In one variation, the non-native amino acid residue sequence is coupled to the carboxyl terminus of the fiber. In yet another, the non-native amino acid residue sequence further includes a linker sequence. Alternatively, the fiber protein further comprises a ligand coupled to the linker. A suitable ligand may be selected from the group consisting of ligands that specifically bind to a cell surface receptor and ligands that can be used to couple other proteins or nucleic acid molecules. Typically, any of the packaging cell lines of this invention may have a DNA sequence encoding all or part of a fiber protein—including modified or chimeric proteins—stably integrated into the genome.

In various aspects of the present invention, a packaging cell line of the present invention is derived from a procaryotic cell line; in another, it is derived from a eucaryotic cell line. While various embodiments suggest the use of mammalian cells, and more particularly, epithelial cell lines, a variety of other, non-epithelial cell lines are used in various embodiments. Thus, while various embodiments disclose the use of a cell line selected from the group consisting of 293, A549, W162, HeLa, Vero, 211, and 211A cell lines, it is understood that various other cell lines are likewise contemplated for use as disclosed herein.

IV. Therapeutic Viral Vectors and Related Systems

A. Nucleic Acid Segments

A therapeutic viral vector or composition of the present invention comprises a nucleotide sequence, nucleic acid molecule or segment as described herein. Typically, the nucleic acid molecule or molecules encodes a protein or polypeptide molecule—or a biologically active fragment thereof—which may be used for therapeutic applications. A nucleotide sequence may further comprise an enhancer element or a promoter located 3' or 5' to and controlling the expression of such a therapeutic nucleotide sequence or gene.

A subject nucleotide sequence consists of a nucleic acid molecule that comprises at least 2 different operatively linked DNA segments. The DNA can be manipulated and amplified by PCR as described herein and by using standard techniques, such as those described in *Molecular Cloning: A Laboratory Manual*, 2nd Ed., Sambrook et al., eds., Cold Spring Harbor, N.Y. (1989). Typically, to produce a nucleotide sequence of the present invention, the sequence encoding the selected polypeptide and the promoter or enhancer are operatively linked to a DNA molecule capable of autonomous replication in a cell either in vivo or in vitro. By operatively linking the enhancer element or promoter and the nucleotide sequence to the vector, the attached segments are replicated along with the vector sequences.

Thus, a recombinant DNA molecule (rDNA) of the present invention is a hybrid DNA molecule comprising at least 2 nucleotide sequences not normally found together in nature. In various preferred embodiments, one of the sequences is a sequence encoding an Ad-derived polypeptide, protein, or fragment thereof. Stated another way, a nucleotide sequence of the present invention is one that encodes an expressible protein, polypeptide or fragment thereof, and it may further include an active constitutive or regulatable (e.g. inducible) promoter sequence.

A nucleotide sequence of the present invention is optimally from about 20 base pairs to about 40,000 base pairs in length. Preferably the nucleotide sequence is from about 50 bp to about 38,000 bp in length. In various embodiments, the nucleotide sequence is of sufficient length to encode one or more adenovirus proteins or functional polypeptide portions thereof. Since individual Ad polypeptides vary in length from about 19 amino acid residues to about 967 amino acid residues, corresponding nucleotide sequences will range from about 50 bp up to about 3000 bp, depending on the number and size of individual polypeptide-encoding sequences that are "replaced" in the viral vectors by therapeutic nucleotide sequences of the present invention.

1. Tripartite Leader (TPL) Nucleic Acid Sequences

In one aspect of the invention, it has been discovered that expression of adenovirus late proteins such as the structural proteins in a packaging cell line according to the present invention is substantially improved when the expression cassette present on the complementing plasmid or in the packaging cell line's genome contains an adenovirus tripartite leader (TPL) nucleic acid sequence.

Thus, the invention contemplates a nucleic acid molecule comprising a TPL nucleotide sequence. Preferably, the TPL nucleotide sequence may be operatively linked to an intron containing RNA processing signals (such as for example, splice donor or splice acceptor sites) suitable for expression in the packaging cell line. Most preferably the intron contains a splice donor site and a splice acceptor site. Alternatively, the TPL nucleotide sequence may not comprise an intron.

In one embodiment, a subject nucleic acid molecule of this invention is isolated, i.e., separated from the genetic environment from which the component sequences were obtained. Thus, molecular cloning of fragments of a gene will produce an isolated nucleic acid, as will the chemical synthesis of an oligonucleotide to build a nucleic acid molecule.

The intron useful in the present invention is any nucleotide sequence which functions in the packaging cell line to provide RNA processing signals, as are well known in the art, including splicing signals. Introns have been well characterized from a large number of structural genes, and therefor the invention should not be considered as limited. Well characterized and preferred introns include a native intron 1 from adenovirus, such as Ad5's TPL intron 1; others include the SV40 VP intron; the rabbit beta-globin intron, and synthetic intron constructs. See, for example, Petitclerc et al., *J. Biothechnol.*, 40:169, 1995, and Choi et al., Mol. Cell. Biol., 11:3070, 1991.

The TPL nucleotide sequence comprises either (a) first and second TPL exons or (b) first, second and third TPL exons, where each TPL exon in the sequence is selected from the group consisting of complete TPL exon 1, partial TPL exon 1, complete TPL exon 2 and complete TPL exon 3. A complete exon is one which contains the complete nucleic acid sequence based on the sequence found in the wild type viral genome. Preferably the TPL exons are from Ad2, Ad3, Ad5, Ad7 and the like, however, they may come from any Ad serotype, as described herein. A preferred partial TPL exon 1 is described in the Examples. The use of a TPL with a partial exon 1 has been reported (WO98/13499).

The intron and the TPL exons can be operatively linked in a variety of configurations to provide a functional TPL nucleotide sequence, although in some embodiments of the invention, an intron may not be a part of the construct. For example, the intron can be positioned between any of TPL exons 1, 2 or 3, and the exons can be in any order of first and second, or first/second/third. The intron can also be placed preceding the first TPL exon or following the last TPL exon.

In a preferred embodiment, complete TPL exon 1 is operatively linked to complete TPL exon 2 operatively linked to complete TPL exon 3. In a preferred variation, adenovirus TPL intron 1 is positioned between complete TPL exon 1 and complete TPL exon 2. It may also be possible to use analogous translational regulators from other viral systems such as rabiesvirus.

A preferred "complete" TPL nucleic acid molecule containing complete TPL exons 1, 2 and 3 with adenovirus intron 1 inserted between exons 1 and 2 has a nucleotide sequence shown in SEQ ID NO: 32. A preferred "partial" TPL nucleic acid molecule containing partial TPL exon 1 and complete TPL exons 2 and 3 in that order has a nucleotide sequence shown in SEQ ID NO: 26. The construction of these preferred TPL nucleotide sequences is described in the Examples.

Thus, preferred expression cassettes and complementing plasmids for expressing adenovirus structural genes, particularly fiber protein, contain an adenovirus TPL nucleotide sequence as described herein. Preferred packaging cell lines containing the subject nucleic acid molecules also contain a TPL nucleotide sequence of the invention.

2. Complementing Plasmids

The invention describes in a related embodiment nucleic acid molecules and nucleotide sequences, typically in the form of DNA plasmid vectors, which are capable of expression of an adenovirus structural protein or regulatory protein. Because these expression plasmids are used to complement the defective genes of a recombinant adenovirus vector genome of this invention, the plasmids are referred to as complementing or complementation plasmids.

The complementing plasmid contains an expression cassette, a nucleotide sequence capable of expressing a protein product off the gene encoded by the nucleotide sequence. Expression cassettes are described in more detail herein, but typically contain a promoter and a structural gene operatively linked to the promoter and whose expression is controlled by the promoter. A preferred complementing plasmid further includes a TPL nucleotide sequence described herein to enhance expression of the structural gene product when used in the context of adenovirus genome replication and packaging.

In one embodiment, a complementing plasmid comprises a promoter nucleotide sequence operatively linked to a nucleotide sequence encoding an adenovirus structural polypeptide. The adenovirus structural polypeptide is selected from the group consisting of penton base; hexon; fiber; polypeptide IIIa; polypeptide V; polypeptide VI; polypeptide VII; polypeptide VIII; and biologically active fragments thereof. In another variation, a complementing plasmid further comprises a nucleotide sequence encoding a first adenovirus regulatory polypeptide, a nucleotide sequence encoding a second regulatory polypeptide, a nucleotide sequence encoding a third regulatory polypeptide; or any combination of the foregoing.

The present invention also discloses a complementing plasmid comprising a promoter nucleotide sequence operatively linked to a nucleotide sequence encoding an adenovirus structural protein, polypeptide or fragment thereof and a nucleotide sequence encoding an adenovirus regulatory protein, polypeptide or fragment thereof. In one variation, the early region polypeptide is E4; in another, the plasmid comprises pE4/Hygro. In still another variation, the early region polypeptides are E1 and E4.

In another aspect of the present invention, the complementing plasmid used to transform a cell line of the present invention further comprises a DNA sequence encoding an adenovirus regulatory protein, polypeptide or fragment thereof. In one variation, the regulatory protein is selected from the group consisting of E1A, E1B, E2A, E2B, E3, E4 and L4 (also referred to as "the 100K protein"); an exemplary complementing plasmid has the characteristics of is pE4/Hygro (for deposit details, see the Examples). In another aspect, the complementing plasmid used to transform a cell line of the present invention further comprises a DNA sequence encoding two or more of the above mentioned adenovirus regulatory proteins, polypeptides or fragments thereof.

Preferred complementing plasmids include pCLF, pDV60, pDV61, pDV67, pDV69, pDV80, pDV90 and the like plasmids described in the Examples. The nucleic acid sequence of particularly preferred complementing plasmids are shown in SEQ ID NO: 43 for pDV60, SEQ ID NO: 44 for pDV67 and SEQ ID NO: 47 for pDV69, SEQ ID NO: 64 for pDV80 and SEQ ID NO: 65 for pDV90.

3. Nucleic Acid Molecule Synthesis

A nucleic acid molecule comprising synthetic oligonucleotide sequences of the present invention can be prepared using any suitable method, such as, the phosphotriester or phosphodiester methods. See Narang et al., *Meth. Enzymol.*, 68:90, (1979); U.S. Pat. No. 4,356,270; and Brown et al., *Meth. Enzymol.*, 68:109, (1979), the disclosures of which are incorporated by reference herein.

For oligonucleotide sequences in which a family of variants is preferred, the synthesis of the family members can be conducted simultaneously in a single reaction vessel, or can be synthesized independently and later admixed in preselected molar ratios. For simultaneous synthesis, the nucleotide residues that are conserved at preselected positions of the sequence of the family member can be introduced in a chemical synthesis protocol simultaneously to the variants by the addition of a single preselected nucleotide precursor to the solid phase oligonucleotide reaction admixture when that position number of the oligonucleotide is being chemically added to the growing oligonucleotide polymer. The addition of nucleotide residues to those positions in the sequence that vary can be introduced simultaneously by the addition of amounts, preferably equimolar amounts, of multiple preselected nucleotide precursors to the solid phase oligonucleotide reaction admixture during chemical synthesis. For example, where all four possible natural nucleotides (A,T,G and C) are to be added at a preselected position, their precursors are added to the oligonucleotide synthesis reaction at that step to simultaneously form four variants.

This manner of simultaneous synthesis of a family of related oligonucleotides has been previously described for the preparation of "Degenerate Oligonucleotides" by Ausubel et al. (*Current Protocols in Molecular Biology*, Suppl. 8. p.2.11.7, John Wiley & Sons, Inc., New York, 1991), and can readily be applied to the preparation of the therapeutic oligonucleotide compositions described herein.

Nucleotide bases other than the common four nucleotides (A,T,G or C), or the RNA equivalent nucleotide uracil (U), can also be used in the present invention. For example, it is well known that inosine (I) is capable of hybridizing with A, T and G, but not C. Examples of other useful nucleotide analogs are known in the art and may be found referred to in 37 C.F.R. §1.822.

Thus, where all four common nucleotides are to occupy a single position of a family of oligonucleotides, that is, where the preselected nucleotide sequence is designed to contain oligonucleotides that can hybridize to four sequences that vary at one position, several different oligonucleotide struc tures are contemplated. The composition can contain four members, where a preselected position contains A,T,G or C. Alternatively, a composition can contain two nucleotide sequence members, where a preselected position contains I or C, and has the capacity the hybridize at that position to all four possible common nucleotides. Finally, other nucleotides may be included at the preselected position that have the capacity to hybridize in a non-destabilizing manner with more than one of the common nucleotides in a manner similar to inosine.

Similarly, larger nucleic acid molecules can be constructed in synthetic oligonucleotide pieces, and assembled by complementary hybridization and ligation, as is well known.

B. Adenovirus Expression Vector Systems

One key component of the present invention for producing gene therapy reagents comprised of recombinant adenovirus particles is the recombinant adenovirus vector genome which is encapsulated in the virus particle and which expresses exogenous genes in a gene therapy setting. Thus, the components of an recombinant adenovirus vector genome include the ability to express selected adenovirus structural genes, to express a desired exogenous protein, and to contain sufficient replication and packaging signals that the genome is packaged into a gene delivery vector particle. The preferred replication signal is an adenovirus inverted terminal repeat containing an adenovirus origin of replication, as is well known and described herein.

According to the present invention, a preferred recombinant adenovirus vector genome is "helper independent" which means the genome can replicate and be packaged without the help of a second, complementing helper virus. Instead, the complementation is provided by a packaging cell line of the present invention. Additional embodiments of the invention, however, are drawn to a vector genome referred to as "gutless" which is "helper dependent."

In a preferred embodiment, the adenovirus vector genome does not encode a functional adenovirus fiber protein. A non-functional fiber gene refers to a deletion, mutation or other modification to the adenovirus fiber gene such that the gene does not express any or insufficient adenovirus fiber protein to package a fiber-containing adenovirus particle without complementation of the fiber gene by a complementing plasmid or packaging cell line. Such a genome is referred to as a "fiberless" genome, not to be confused with a fiberless particle. Alternatively, a fiber protein may be encoded but is insufficiently expressed to result in a fiber containing particle.

Thus, the invention describes a helper-independent fiberless recombinant adenovirus vector genome comprising genes which (a) express all adenovirus structural gene products but express insufficient adenovirus fiber protein to package a fiber-containing adenovirus particle without complementation of said fiber gene, (b) express an exogenous protein, and (c) contains an adenovirus packaging signal and inverted terminal repeats containing adenovirus origin of replication.

The introduction of exogenous DNA into eucaryotic cells has become one of the most powerful tools of the molecular biologist. The term "exogenous" encompasses any therapeutic composition of this invention which is administered by the therapeutic methods of this invention. Thus, "exogenous" may also be referred to herein as "foreign," "non-native," and the like. The methods of this invention preferably require efficient delivery of the DNA into the nucleus of the recipient cell and subsequent identification of cells that are expressing the foreign DNA.

The adenovirus vector genome is propagated in the laboratory in the form of rDNA plasmids containing the genome, and upon introduction into an appropriate host, the viral genetic elements provide for viral genome replication and packaging rather than plasmid-based propagation. Exemplary methods for preparing an Ad-vector genome are described in the Examples.

A widely-used plasmid is pBR322, a vector whose nucleotide sequence and endonuclease cleavage sites are well known. Various other useful plasmid vectors are described in the Examples that follow.

A nucleic acid vector of the present invention comprises a nucleic acid (preferably DNA) molecule capable of autonomous replication in a cell and to which a DNA segment, e.g., a gene or polynucleotide, can be operatively linked so as to bring about replication of the attached segment. In the present invention, one of the nucleotide segments to be operatively linked to vector sequences encodes at least a portion of a therapeutic nucleic acid molecule—in effect, a nucleic acid sequence that encodes one or more therapeutic proteins or polypeptides, or fragments thereof.

As one of skill in the art will note, in various embodiments of the present invention, different "types" of vectors are disclosed. For example, one "type" of vector is used to deliver particular nucleotide sequences into a packaging cell line, with the intent of having said sequences stably integrate into the cellular genome; these "types" of vectors are generally identified herein as complementing plasmids. A further "type" of vector described herein carries or delivers nucleotide sequences in or into a cell line (e.g., a packaging cell line) for the purpose of propagating therapeutic viral vectors of the present invention; hence, these vectors are generally referred to herein as delivery plasmids. A third "type" of vector described herein is utilized to carry nucleotide sequences encoding therapeutic proteins or polypeptides to specific cells or cell types in a subject in need of treatment; these vectors are generally identified herein as therapeutic viral vectors or Ad-derived vectors and are in the form of a virus particle encapsulating a viral nucleic acid containing an expression cassette nucleic acid sequence for expressing the therapeutic gene.

1. Nucleic Acid Gene Expression Cassettes

In various embodiments, a peptide-coding sequence of the therapeutic gene is inserted into an expression vector and expressed; however, it is also feasible to construct an expression vector which also includes some non-coding sequences as well. Preferably, however, non-coding sequences are excluded. Alternatively, a nucleotide sequence for a soluble form of a polypeptide may be utilized. Another preferred therapeutic viral vector includes a nucleotide sequence encoding at least a portion of a therapeutic nucleotide sequence operatively linked to the expression vector for expression of the coding sequence in the therapeutic nucleotide sequence.

As used herein with regard to DNA sequences or segments, the phrase "operatively linked" generally means the sequences or segments have been covalently joined into one piece of DNA, whether in single or double stranded form.

The choice of viral vector into which a therapeutic nucleotide sequence of this invention is operatively linked depends directly, as is well known in the art, on the functional properties desired, e.g., vector replication and protein expression, and the host cell to be transformed—these being limitations inherent in the art of constructing recombinant DNA molecules. Although certain adenovirus serotypes are recited herein in the form of specific examples, it should be understood that the present invention contemplates the use of any adenovirus serotype, including hybrids and derivatives thereof. As one will observe, it is not unusual or outside the scope of the present invention to utilize nucleotide and/or amino acid residue sequences of two or more serotypes in constructs, compositions and methods of the invention.

A translatable nucleotide sequence is a linear series of nucleotides that provide an uninterrupted series of at least 8 codons that encode a polypeptide in one reading frame. Preferably, the nucleotide sequence is a DNA sequence. The vector itself may be of any suitable type, such as a viral vector (RNA or DNA), naked straight-chain or circular DNA, or a vesicle or envelope containing the nucleic acid material and any polypeptides that are to be inserted into the cell.

2. Promoters

As noted elsewhere herein, an expression nucleic acid in an Ad-derived vector of the present invention may also include a promoter sequence.

In general, promoters are DNA segments that contain a DNA sequence that controls the expression of a gene located 3' or downstream of the promoter. The promoter is the DNA sequence to which RNA polymerase specifically binds and initiates RNA synthesis (transcription) of that gene, typically located 3' of the promoter. A promoter also includes DNA sequences which direct the initiation of transcription, including those to which RNA polymerase specifically binds. If more than one nucleic acid sequence encoding a particular polypeptide or protein is included in a therapeutic viral vector or nucleotide sequence, more than one promoter or enhancer element may be included, particularly if that would enhance efficiency of expression. For purposes of the present invention, regulatable (inducible) as well as constitutive promoters may be used, either on separate vectors or on the same vector.

Both constitutive and regulatable (often called "inducible") promoters are useful in constructs and methods of the present invention. For example, some useful regulatable promoters are those of the CREB-regulated gene family and include inhibin, gonadotropin, cytochrome c, glucagon, and the like. (See, e.g., published International App. No. WO96/14061, the disclosure of which is incorporated by reference herein.)

A regulatable or inducible promoter may be described as a promoter wherein the rate of RNA polymerase binding and initiation is modulated by external stimuli. (See U.S. Pat. Nos. 5,750,396 and 5,998,205). Such stimuli include various compounds or compositions, light, heat, stress, chemical energy sources, and the like. Inducible, suppressible and repressible promoters are considered regulatable promoters.

Regulatable promoters may also include tissue-specific promoters. Tissue-specific promoters direct the expression of the gene to which they are operably linked to a specific cell type. Tissue-specific promoters cause the gene located 3' of it to be expressed predominantly, if not exclusively, in the specific cells where the promoter expressed its endogenous gene. Typically, it appears that if a tissue-specific promoter expresses the gene located 3' of it at all, then it is expressed appropriately in the correct cell types (see, e.g., Palmiter et al., *Ann. Rev. Genet.* 20: 465–499, 1986).

When a tissue-specific promoter controls the expression of a gene, that gene will be expressed in a small number of tissues or cell types rather than in substantially all tissues and cell types. Examples of tissue-specific promoters include the immunoglobulin promoter described by Brinster et al., *Nature* 306: 332–336 (1983) and Storb et al., *Nature*

310: 238–231 (1984); the elastase-I promoter described by Swift et al., *Cell* 38: 639–646 (1984); the globin promoter described by Townes et al., *Mol. Cell. Biol.* 5: 1977–1983 (1985), and Magram et al., *Mol. Cell. Biol.* 9: 4581–4584 (1989), the insulin promoter described by Bucchini et al., *PNAS USA,* 83: 2511–2515 (1986) and Edwards et al., *Cell* 58: 161 (1989); the immunoglobulin promoter described by Ruscon et al., *Nature* 314: 330–334 (1985) and Grosscheld et al., *Cell* 38: 647–658 (1984); the alpha actin promoter described by Shani, *Mol. Cell. Biol.* 6: 2624–2631 (1986); the alpha crystalline promoter described by Overbeek et al., *PNAS USA* 82: 7815–7819 (1985); the prolactin promoter described by Crenshaw et al., *Genes and Development* 3: 959–972 (1989); the propiomelanocortin promoter described by Tremblay et al., *PNAS USA* 85: 8890–8894 (1988); the beta-thyroid stimulating hormone (BTSH) promoter described by Tatsumi et al., *Nippon Rinsho* 47: 2213–2220 (1989); the mouse mammary tumor virus (MMTV) promoter described by Muller et al., *Cell* 54: 105 (1988); the albumin promoter described by Palmiter et al., *Ann. Rev. Genet.* 20: 465–499 (1986); the keratin promoter described by Vassar et al., *PNAS USA* 86: 8565–8569 (1989); the osteonectin promoter described by McVey et al., *J. Biol. Chem.* 263: 11,111–11,116 (1988); the prostate-specific promoter described by Allison et al., *Mol. Cell. Biol.* 9: 2254–2257 (1989); the opsin promoter described by Nathans et al., *PNAS USA* 81: 4851–4855 (1984); the olfactory marker protein promoter described by Danciger et al., *PNAS USA* 86: 8565–8569 (1989); the neuron-specific enolase (NSE) promoter described by Forss-Pelter et al., *J. Neurosci. Res.* 16: 141–151 (1986); the L-7 promoter described by Sutcliffe, *Trends in Genetics* 3: 73–76 (1987) and the protamine 1 promoter described Peschon et al., *Ann. New York Acad. Sci.* 564: 186–197 (1989) and Braun et al., *Genes and Development* 3: 793–802 (1989). (The disclosures of all references cited are incorporated by reference herein.)

3. Adenovirus Vectors

Although adenovirus consists of many proteins, not all adenovirus proteins are required for assembly of a recombinant adenovirus particle (vector) of this invention. Thus, deletion of the appropriate genes from a recombinant Ad vector as taught herein will thus allow the vector to accommodate even larger "foreign" DNA segments. Thus, if the sequences encoding one or more adenovirus polypeptides or proteins are supplanted by a recombinant nucleotide sequence of the present invention, the length of the recombinant sequence can conceivably extend nearly to the packaging limit of the relevant adenovirus-derived vector.

In view of the fact that preferred embodiments disclosed herein are helper-independent Ad-derived vectors, the entire wild-type Ad genome cannot be completely supplanted by recombinant nucleic acid molecules without transforming such a vector into a vector requiring "help" of some kind. However, most of the Ad-derived vectors of the present invention do not depend on a helper virus; instead, the vectors of the present invention are propagated in cell lines stably expressing proteins or polypeptides that have been removed from said vectors to allow the addition of "foreign" DNA into the vectors. In various disclosed embodiments, specific early region and structural polypeptides are deleted from the vectors of the present invention, thereby enabling the vectors to accommodate recombinant nucleic acid sequences (or cassettes) of various lengths. For example, Ad-derived vectors of the present invention may easily include 12 kb or more of foreign (or "therapeutic") DNA sequences.

Thus, adenovirus viral vectors are also disclosed which comprise nucleotide sequences encoding a packaging signal and a foreign protein or polypeptide, wherein the nucleotide sequence encoding an adenovirus structural protein has been deleted.

In one variation, the nucleotide sequence encoding the foreign protein or polypeptide is a DNA molecule up to about 3 kb in length; in another, the nucleotide sequence encoding the foreign protein or polypeptide is a DNA molecule up to about 9.5 kb in length; in still another, the nucleotide sequence encoding the foreign protein or polypeptide is a DNA molecule up to about 12.5 kb in length. Nucleotide sequences of intermediate lengths are also contemplated by the present invention, as are sequences in excess of 12.5 kb.

The invention also discloses viral vectors wherein the sequence encoding a foreign protein or polypeptide is a sequence encoding an anti-tumor agent, a tumor suppressor protein, a suicide protein, or a fragment or functional equivalent thereof. In one variation, nucleotide sequences encoding one or more regulatory proteins have also been deleted from the vector. In another, the regulatory proteins are selected from the group consisting of E1A, E1B, E2A, E2B, E3, E4, and L4 (100K protein).

A wide variety of therapeutic viral vectors are also embodiments of the present invention. In one embodiment, a therapeutic viral vector is disclosed which lacks a DNA sequence encoding fiber protein, or a portion thereof. In another variation, a therapeutic viral vector may further or alternatively comprise deletion of a DNA sequence encoding one or more regulatory proteins, polypeptides, or fragments thereof. In various embodiments, foreign DNA sequences are inserted in place of the DNA sequence encoding fiber protein in the viral vectors of the present invention. In other embodiments, the therapeutic viral vectors further comprise foreign DNA sequences inserted in place of the DNA sequences encoding one or more regulatory proteins, polypeptides, or fragments thereof, and/or one or more structural proteins, polypeptides, or fragments thereof.

The present invention further discloses a number of viral vectors. In one variation, a viral vector comprises a deletion or mutation of a DNA sequence encoding an adenovirus structural protein, polypeptide, or fragment thereof. A vector may further comprise deletion or mutation of the DNA sequences encoding regulatory polypeptides E1A and E1B; and it may still further comprise deletion or mutation of the DNA sequence encoding one or more of the following regulatory proteins or polypeptides: E2A, E2B, E3, E4, L4, or fragments thereof. In another variation, in a viral vector of the present invention, the structural protein comprises fiber. Any combination of the foregoing is also contemplated by the present invention. The viral vectors of the present invention are suitable for the preparation of pharmaceutical compositions comprising any of the therapeutic viral vectors disclosed herein—including combinations thereof—are also disclosed herein. A further use of the viral vectors of the present invention is for targeting specific cells in a cell population comprising different cell types.

Yet another variation discloses that a foreign DNA sequence encoding one or more foreign proteins, polypeptides or fragments thereof has been inserted in place of any of the deletions in the therapeutic viral vector. In one embodiment, the foreign DNA encodes a tumor-suppressor protein or a biologically active fragment thereof. In another embodiment, the foreign DNA encodes a suicide protein or a biologically active fragment thereof.

The invention further contemplates that a viral vector comprises a foreign DNA sequence encoding one or more foreign proteins, polypeptides or fragments thereof wherein said DNA sequence has been inserted in place of any structural and/or regulatory proteins (or portions thereof) that have been deleted. Thus, in one embodiment, the foreign DNA encodes a therapeutic molecule such as a tumor-suppressor protein; a suicide protein; a cystic fibrosis transmembrane conductance regulator (CFTR) protein; or a biologically active fragment of any of them.

The therapeutic (or foreign) nucleotide sequence can be a gene or gene fragment that encodes a protein or polypeptide—or a biologically active fragment thereof (See, e.g., Crystal, et al., Nature Genetics 8: 42–51 (1994); Zabner, et al., Cell 75: 207–216 (1993); Knowles, et al, NEJM 333(13): 823–831 (1995); and Rosenfeld, et al., Cell 68: 143–155 (1992), the disclosures of which are incorporated by reference herein.)

It is further contemplated that a therapeutic protein or polypeptide expressed by a therapeutic viral vector of the present invention may be used in conjunction with another therapeutic agent when appropriate—e.g., a thymidine kinase metabolite may be used in conjunction with the gene encoding thymidine kinase and its gene product—in order to be even more effective.

Alternatively, a therapeutic viral vector can include a DNA or RNA oligonucleotide sequence that exhibits therapeutic activity without needing to be translated into a polypeptide product before exerting a therapeutic effect. Examples of the latter include antisense oligonucleotides that will inhibit the transcription of deleterious genes or ribozymes that act as site-specific ribonucleases for cleaving selected mutated gene sequences. In another variation, a therapeutic nucleotide sequence of the present invention may comprise a DNA construct capable of generating therapeutic nucleotide molecules, including ribozymes and antisense DNA, in high copy numbers in target cells, as described in published PCT application No. WO 92/06693 (the disclosure of which is incorporated herein by reference). Other preferred therapeutic nucleotide sequences according to the present invention are capable of delivering HIV antisense oligonucleotides to latently-infected T cells via CD4. Similarly, delivery of Epstein-Barr Virus (EBV) EBNa-1 antisense oligonucleotides to B cells via CR2 is capable of effecting therapeutic results.

A preferred recombinant adenovirus vector genome is based on the vector described in the Examples and designated Ad5.Bgal.ΔF. This vector is a helper independent, fiberless vector genome which can host, upon insertion, an exogenous gene for expression of an exogenous or therapeutic protein. The genome of Ad5.Bgal.ΔF has a nucleotide sequence shown in SEQ ID NO: 27. A virus particle containing Ad5.Bgal.ΔF vector genome has been prepared as described in the Examples and is deposited with the ATCC as Accession No. VR-2636

The Ad5.Bgal.ΔF genome nucleic acid can be manipulated to contain any exogenous gene in place of the beta-galactosidase gene present in the construct, as described herein.

V. Construction of Therapeutic Viral Vectors for Gene Delivery

A. Adenovirus Particles

Various methods of making and using the vectors, plasmids, cell lines and other compositions and constructs of the present invention are also disclosed herein. The following methods are considered exemplary and not limiting.

Thus, in one variation, the invention discloses a method of constructing therapeutic viral vectors, comprising introducing a delivery plasmid into an Ad fiber-expressing complementing cell line, wherein the DNA sequence encoding Ad fiber protein has been deleted from the delivery plasmid. In one variation, the delivery plasmid further includes a DNA sequence encoding a foreign protein, polypeptide, or fragment thereof. In other embodiments, a combination of pDV44 and pDE1Bβgal or a similar construct such as, for example, that found in pDV44, pΔE1Bβgal or the equivalent.

A recombinant adenovirus particle may be produced with a fiber protein, or it may be produced without a fiber protein ("fiberless particle") according to the present invention. Where the particle is made without fiber, such as by passaging the fiberless viral vector genome, e.g., Ad5.Bgal.ΔF in the 293 cells, a fiberless genome is replicated and packaged in a fiberless particle. In contrast, where the fiberless genome Ad5.Bgal.ΔF is passaged in the 211B or other fiber expressing cells, a fiberless genome is replicated and packaged into a fiber-containing particle.

Recombinant adenovirus particles may be made such that they include no fiber proteins, modified fiber proteins or other exogenous proteins. They may also be produced in systems using either helper-independent or helper-dependent adenovirus recombinant genomes, i.e. with or without helper viruses.

B. Targeting of Particles to Tissues—Virus Trophism

A preferred viral vector particle in which therapeutic nucleotide compositions of this invention are present is derived from adenovirus (Ad). As taught herein, viral vector particles of this invention may be designed and constructed in such a way that they specifically target a preselected recipient cell type, depending on the nature of therapy one seeks to administer. Methods of making and using therapeutic viral vectors that target specific cells are further described in the Examples that follow.

Novel vectors, viral particles or compositions may also be designed and prepared to preferentially target cells that might not otherwise be targeted by wild-type adenovirus virions. For example, in order to target non-epithelial cells, one following the teachings of the present specification may be able to prepare a therapeutic vector particle including a nucleotide sequence encoding a foreign protein, polypeptide or other ligand directed to a non-epithelial cell or to a different receptor than that generally targeted by a particular adenovirus. Examples of useful ligands directed to specific receptors (identified in parentheses) include the V3 loop of HIV gp120 (CD4); transferrin (transferrin receptor); LDL, apolipoprotein B100, apolipoprotein E (LDL receptors); and deglycosylated proteins (asialoglycoprotein receptor). Various useful ligands which may be added to adenovirus fiber—and methods for preparing and attaching same—are set forth in U.S. Pat. Nos. 5,756,086 and 5,543,328, the disclosures of which are incorporated by reference herein.

In yet another embodiment, the non-native amino acid residue sequence is incorporated into the fiber amino acid residue sequence at a location other than one of the fiber termini. Alternatively, the non-native amino acid residue sequence alters the binding specificity of the fiber for a targeted cell type. In other embodiments, the linker sequence alters the binding specificity of the fiber for a targeted cell type. The expressed fiber may, in various embodiments, bind to a specific targeted cell type not usually targeted by adenovirus and/or may comprise amino acid residue sequences from more than one adenovirus serotype.

Useful ligands may be encoded by a foreign nucleotide sequence contained within a viral vector of the present invention, or may be linked to proteins or polypeptides, include antibodies and attachment sequences, as well as receptors themselves. For example, antibodies to cell receptor molecules such as integrins and the like, MHC Class I and Class II, asialoglycoprotein receptor, transferrin receptors, LDL receptors, CD4, and CR2 are but a few which are useful according to the present invention. It is also understood that the ligands typically bound by receptors, as well as analogs to those ligands, may be used as cellular targeting agents, as disclosed herein.

VI. Therapeutic Methods

The recombinant adenovirus vectors of the present invention, typically in the form of an adenovirus particle encapsulating a recombinant adenovirus vector genome containing an expression cassette for expressing a therapeutic gene, are particularly suited for gene therapy. Thus, various therapeutic methods are contemplated by the present invention.

For example, it has now been discovered that Ad-derived viral vectors are capable of delivering a therapeutic nucleotide sequence to a specific cell or tissue, based on the tissue tropism of the particle, thereby expanding and enhancing treatment options available in numerous conditions in which more conventional therapies are of limited efficacy. Accordingly, methods of gene therapy utilizing a recombinant adenovirus particle containing a modified fiber or chimeric fiber which targets a preselected tissue, as described herein, is within the scope of the invention. Vector particles are typically purified and then an effective amount is administered in vivo or ex vivo (in vitro) into the subject.

For in vitro or ex vivo gene transfer, administration is often accomplished by first isolating a selected cell population from a patient such as lung epithelial cells, lymphocytes and the like followed by in vitro or ex vivo gene transfer of the therapeutic compositions of this invention and the replacement of the cells into the patient. In vivo therapy is also contemplated, e.g., via the administration of therapeutic compositions of this invention by various delivery means. For example, aerosol administration and administration via subcutaneous, intravenous, intraperitoneal, intramuscular, ocular means and the like are also within the scope of the present invention.

Other gene-delivery methods are also useful in conjunction with the methods, compositions and constructs of the present invention; see, e.g., published International Application No. WO 95/11984, the disclosures of which are incorporated by reference herein.

The present invention also contemplates various methods of targeting specific cells—e.g., cells in a subject in need of diagnosis and/or treatment. As discussed herein, the present invention contemplates that the viral vectors and compositions of the present invention may be directed to specific receptors or cells, for the ultimate purpose of delivering those vectors and compositions to specific cells or cell types. The viral vectors and constructs of the present invention are particularly useful in this regard.

In general, adenovirus attachment and uptake into cells are separate but cooperative events that result from the interaction of distinct viral coat proteins with a receptor for attachment and $\alpha_v$ integrin receptors for internalization. Adenovirus attachment to the cell surface via the fiber coat proteins has been discovered to be dissociable and distinct from the subsequent step of internalization, and the present invention is able to take advantage of and function in conjunction with these differing receptors.

The invention also discloses methods of transforming a pathologic hyperproliferative mammalian cell comprising contacting the cell with any of the vectors described herein. In another embodiment, methods of infecting a mammalian target cell with a viral vector containing a preselected foreign nucleotide sequence are disclosed. One such variation comprises the following steps: (a) infecting the target cell with a viral vector of the present invention, the viral vector carrying a preselected foreign nucleotide sequence; and (b) expressing the foreign nucleotide sequence in the targeted cell.

The invention also encompasses mammalian target cells infected with a preselected foreign nucleotide sequence produced by the methods disclosed herein. In one variation, the target cells are selected from the group consisting of replicating, slow-replicating and non-replicating human cells.

Methods of treating an acquired or hereditary disease are also disclosed. One method comprises (a) administering a pharmaceutically acceptable dose of a viral vector to a target cell, wherein the vector comprises a preselected therapeutic nucleotide sequence; and (b) expressing the therapeutic sequence in the target cell for a time period sufficient to ameliorate the acquired or hereditary disease in the cell. Method of gene therapy comprising administering to a subject an effective amount of a therapeutic viral vector produced by a packaging cell line of the present invention are also disclosed.

Also contemplated by the present invention are various methods of inhibiting the proliferation of a tumor in a subject comprising administering an effective amount of a therapeutic viral vector of the present invention under suitable conditions to the subject. In one variation, the gene encodes an anti-tumor agent. In another variation, the agent is a tumor-suppressor gene. In still another embodiment, the agent is a suicide gene or a functional equivalent thereof. In another variation, the vector is administered via intra-tumoral injection.

A composition of this invention may be used prophylactically or therapeutically in vivo to disrupt HIV infection and mechanisms of action by inhibiting gene expression or activation, via delivery of antisense HIV sequences or ribozymes to T cells or monocytes. Using methods of the present invention, one may target therapeutic viral vectors as disclosed herein to specific cells and tissues, including hematopoietic cells, as infection of such cells appears to be mediated by distinct integrins to which viral vectors of the present invention may readily be targeted. (See, e.g., Huang, et al., *J. Virol.* 70: 4502–8, 1996).

Other useful therapeutic nucleotide sequences include antisense nucleotide sequences complementary to EBV EBNa-1 gene. Use of such therapeutic sequences may remediate or prevent latent infection of B cells with EBV. As discussed herein and in the Examples below, targeting and delivery may be accomplished via the use of various ligands, receptors, and other appropriate targeting agents.

Thus, in one embodiment, a therapeutic method of the present invention comprises contacting the cells of a subject infected with EBV or HIV with a therapeutically effective amount of a pharmaceutically acceptable composition comprising a therapeutic nucleotide sequence of this invention. In a related embodiment, the contacting involves introducing the therapeutic nucleotide sequence composition into cells having an EBV or HIV-mediated infection.

Methods of gene therapy are well known in the art (see, e.g., Larrick and Burck, *Gene Therapy: Application of Molecular Biology*, Elsevier Science Publ. Co., Inc., New York, N.Y. (1991); Kriegler, *Gene Transfer and Expression: A Laboratory Manual*, W. H. Freeman and Company, New York, 1990). The term "subject" should be understood to include any animal—particularly mammalian—patient, such as any murine, rat, bovine, porcine, canine, feline, equine, ursine, or human patient.

When the foreign gene carried in the vector encodes a tumor suppressor gene or another anti-tumor protein, the vector is useful to treat or reduce hyperproliferative cells in a subject, to inhibit tumor proliferation in a subject or to ameliorate a particular, related pathology.

The present invention also contemplates methods of depleting suitable samples of pathologic mammalian hyperproliferative cells contaminating hematopoietic precursors during bone marrow reconstitution via the introduction of a wild-type tumor suppressor gene into the cell preparation using a vector of this invention. As used herein, a suitable sample is defined as a heterogeneous cell preparation obtained from a patient, e.g., a mixed population of cells containing both phenotypically normal and pathogenic cells.

Administration includes—but is not limited to—the introduction of therapeutic agents of the present invention into a cell or subject via various means, including direct injection, intravenously, intraperitoneally, via intra-tumor injection, via aerosols, or topically. Therapeutic agents as disclosed herein may also be combined for administration of an effective amount of the agents with a pharmaceutically-acceptable carrier, as described herein.

As used herein, "effective amount" generally means the amount of vector particle (or proteins produced/released thereby) which achieves a positive outcome in the subject to whom the vector is administered. The total volume administered will necessarily vary depending on the mode of administration, as those of skill in the relevant art will appreciate, and dosages may vary as well.

The dose of a biologic vector (particle) is somewhat complex and may be described in terms of the concentration (in plaque-forming units per milliliter (pfu/ml)), the total dose (in pfus), or the estimated number of particles administered per cell (the estimated multiplicity of infection or MOI). Thus, if a vector is administered via infusion—say, across nasal epithelium—at a constant total volume, the respective concentration, etc. may be described as follows:

In general, when recombinant adenoviral vector particles are administered via infusion across the nasal epithelium (e.g. an area of nasal epithelium containing $2 \times 10^7$ cells,) administered amounts producing an estimated MOI (multiplicity of infection) of about 10 or greater are much more effective than lower

TABLE 2

| Concentration (pfu/ml) | Volume (ml) | Dose (pfu) | Estimated MOI |
|---|---|---|---|
| $10^7$ | 2 | $2 \times 10^7$ | 1 |
| $10^8$ | 2 | $2 \times 10^8$ | 10 |
| $10^9$ | 2 | $2 \times 10^9$ | 100 |
| $10^{10}$ | 2 | $2 \times 10^{10}$ | 1000 | dosages. (See, e.g., Knowles, et al., *New Eng. J. Med.* 333: 823–831, 1995). Similarly, when direct injection is the preferred treatment modality—e.g., direct injection of a viral vector into a tumor—doses of $1 \times 10^9$ pfu or greater are generally preferred. (See, e.g., published International App. No. WO95/11984.)

Thus, depending on the mode of administration, an effective amount administered in a single dose preferably contains from about $10^6$ to about $10^{15}$ infectious units. A typical course of treatment would be one such dose per day over a period of five days. As those of skill in the art will appreciate, an effective amount may vary depending on (1) the pathology or other condition to be treated, (2) the status and sensitivity of the patient, and (3) various other factors well known to those of skill in the art, such as the patient's tolerance to other courses of treatment that may have been applied previously. Thus, those of skill in the art may easily and precisely determine effective amounts of the agents/vectors of the present invention which may be administered to a particular patient, based on their understanding of and evaluation of such factors.

The present invention also contemplates methods of ameliorating pathologies characterized by hyperproliferative cells or genetic defects in a subject, by administering to the subject an effective amount of a vector as described herein. Such vectors preferably contain a foreign gene encoding a gene product (e.g. polypeptide or protein) having the ability to ameliorate the pathology, under suitable conditions. As used herein, the term "genetic defect" means any disease, condition or abnormality which results from inherited factors, e.g. Huntington's Disease, Tay-Sachs Disease, or Sickle Cell Disease.

The present invention further provides methods for reducing the proliferation of tumor cells in a subject by introducing into the tumor mass an effective amount of an adenoviral expression vector containing an anti-tumor gene other than a tumor suppressor gene. The anti-tumor gene can encode, for example, thymidine kinase (TK). An effective amount of a therapeutic agent is then administered to the subject; the therapeutic agent, in the presence of the anti-tumor gene, is toxic to the cell.

Using thymidine kinase as exemplary, the therapeutic agent is a thymidine kinase metabolite such as ganciclovir (GCV), 6-methoxypurine arabinonucleoside (araM), or a functional equivalent thereof. Both the thymidine kinase gene and the thymidine kinase substrate must be used concurrently in order to exert a toxic effect on the host cell. In the presence of the TK gene, GCV is phosphorylated and becomes a potent inhibitor of DNA synthesis, whereas araM is converted to the cytotoxic anabolite araATP. Thus, the precise method of action or synergism is not relevant to therapeutic efficacy; what is relevant is the fact that the concurrent use of appropriate genes and therapeutic agents may effectively ameliorate a specific disease condition.

Another useful example contemplates use of a vector of the present invention which expresses the enzyme cytosine deaminase. Such a vector could be used in conjunction with administration of the drug 5-fluorouracil (Austin and Huber, *Mol. Pharm.* 43: 380–387, 1993) or the recently-described *E. coli* Deo gene in combination with 6-methyl-purine-2'-deoxyribonucleoside (Sorscher et al., *Gene Therapy* 1: 233–238, 1994).

As with the use of the tumor suppressor genes described previously, the use of other anti-tumor genes, either alone or in combination with the appropriate therapeutic agent, provides a treatment for the uncontrolled cell growth or proliferation characteristic of tumors and malignancies. Thus, the present invention provides therapies to halt the uncontrolled cellular growth in a patient, thereby alleviating the symptoms or the disease or cachexia present in the patient. The effect of this treatment includes, but is not limited to, prolonged survival time of the patient, reduction in tumor mass or burden, apoptosis of tumor cells, or the reduction in the number of circulating tumor cells. Means of quantifying the beneficial effects of this therapy are well known to those of skill in the art.

The present invention provides a recombinant adenovirus expression vector characterized by the partial or total deletion of one or more adenoviral structural protein genes, such as the gene encoding fiber, which allows the vector to accommodate a therapeutic, foreign nucleic acid sequence encoding a functional foreign polypeptide, protein, or biologically active fragment thereof.

A therapeutic gene sequence may be introduced into a tumor mass by combining the adenoviral expression vector with a suitable pharmaceutically acceptable carrier. Introduction can be accomplished, for example, via direct injection of the recombinant Ad vector into the tumor mass.

A method of tumor-specific delivery of a tumor-suppressor gene is accomplished by contacting target tissue in a subject with an effective amount of a recombinant Ad-derived vector of this invention. In the case of anti-tumor therapy, the gene is intended to encode an anti-tumor agent, such as a functional tumor suppressor gene product or suicide gene product. The term "contacting" is intended to encompass any delivery method for the efficient transfer of the vector, such as via intra-tumoral injection.

In another example, adenovirus vectors of the present invention can be used to transfer genes to central nervous system (CNS) tumors in vivo.

The present invention also contemplates methods for determining the efficacy of the within-disclosed therapeutic compositions and methods. One such method for confirming efficacy utilizes the human/SCID (severe combined immunodeficient) mouse model of EBV-induced LPD (lymphoproliferative disease) to ascertain whether EBV-antisense therapeutic nucleotide sequences block tumor formation. (See, e.g., Pisa, et al., *Blood* 79: 173–179 (1992); Rowe, et al., *Curr. Top. Microbiol. Immunol.* 166: 325 (1990); and Cannon, et al., *J Clin. Invest.* 85: 1333–1337 (1990), the disclosures of which are incorporated by reference herein.)

Finally, the use of Ad vectors of the present invention to prepare medicaments for the treatment, therapy and/or diagnosis of various diseases is also contemplated by this invention. Moreover, other anti-tumor genes may be used in combination with the corresponding therapeutic agent to reduce the proliferation of tumor cells. Such other gene-and-therapeutic-agent combinations are known to those of skill in the art and may be applied as taught herein.

A. Therapeutic Compositions

In various alternative embodiments of the present invention, therapeutic sequences and compositions useful for practicing the therapeutic methods described herein are contemplated. Therapeutic compositions of the present invention may contain a physiologically tolerable carrier together with one or more therapeutic nucleotide sequences of this invention, dissolved or dispersed therein as an active ingredient. In a preferred embodiment, the composition is not immunogenic or otherwise able to cause undesirable side effects when administered to a subject for therapeutic purposes.

As used herein, the terms "pharmaceutically acceptable," "physiologically tolerable" and grammatical variations thereof, as they refer to compositions, carriers, diluents and reagents, are used interchangeably and represent that the materials are capable of administration to or upon a subject—e.g., a mammal—without the production of undesirable physiological effects such as nausea, dizziness, gastric upset and the like.

For example, the present invention comprises therapeutic compositions useful in the specific targeting of epithelial or non-epithelial cells as well as in delivering a therapeutic nucleotide sequence to those cells. Therapeutic compositions designed to preferentially target to epithelial cells may comprise a recombinant adenovirus-derived vector particle including a therapeutic nucleotide sequence. As described herein, a number of adenovirus-derived moieties are described, including particles lacking fiber, particles that contain wild type adenovirus fiber, and particles that contain modified or chimeric fiber, each type providing a different tissue tropism to the particle.

The preparation of a pharmacological composition that contains active ingredients dissolved or dispersed therein is well understood in the art. Typically such compositions are prepared as injectables—either as liquid solutions or suspensions—however, solid forms suitable for solution or suspension in liquid prior to use can also be prepared. A preparation can also be emulsified, or formulated into suppositories, ointments, creams, dermal patches, or the like, depending on the desired route of administration.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions can also contain liquid phases in addition to and to the exclusion of water. Exemplary of such additional liquid phases are glycerin, vegetable oils such as cottonseed oil, and water-oil emulsions.

A therapeutic composition typically contains an amount of a therapeutic material, i.e., a nucleotide sequence or adenovirus vector particle of the present invention, sufficient to deliver a therapeutically effective amount to the target tissue, typically an amount of at least 0.1 weight percent to about 90 weight percent of therapeutic material per weight of total therapeutic composition. A weight percent is a ratio by weight of therapeutic material, e.g., a nucleotide sequence, to total composition. Thus, for example, 0.1 weight percent is 0.1 grams of DNA segment per 100 grams of total composition.

VII. Other Applications

The cell lines, viral vectors and methods of the present invention may also be used for purposes other than the direct administration of therapeutic nucleotide sequences. In one such application, the production of large quantities of biologically active proteins or polypeptides in cells transfected with the within-disclosed viral vectors is contemplated herein. For example, human lymphoblastoid cells maybe transfected with a viral vector of the present invention carrying a human hematopoietic growth factor such as the gene for erythropoietin (EPO); cells so transfected are thus able to produce biologically active EPO. (See, e.g., Lopez et al., *Gene* 148: 285–91, 1994).

Various other applications and uses of the within-described methods, cell lines, plasmids, vectors, and compositions of the present invention shall become apparent upon closer examination of the Examples that follow.

EXAMPLES

The following examples are intended to illustrate, but not limit, the present invention. As such, the following description provides details of the manner in which particular embodiments of the present invention may be made and used. This description, while exemplary of the present invention, is not to be construed as specifically limiting the invention. Variations and equivalents, now known or later developed, which would be within the understanding and technical competence of one skilled in this art are to be considered as falling within the scope of this invention.

Example 1

Preparation of Adenovirus Packaging Cell Lines

Cell lines that are commonly used for growing adenovirus are useful as host cells for the preparation of adenovirus packaging cell lines. Preferred cells include 293 cells, an adenovirus-transformed human embryonic kidney cell line obtained from the ATCC, having Accession Number CRL 1573; HeLa, a human epithelial carcinoma cell line (ATCC Accession Number CCL-2); A549, a human lung carcinoma cell line (ATCC Accession Number CCL 1889); and the like epithelial-derived cell lines. As a result of the adenovirus transformation, the 293 cells contain the E1 early region regulatory gene. All cells were maintained in complete DMEM+10% fetal calf serum unless otherwise noted.

The cell lines of this invention allow for the production and propagation of novel adenovirus-based gene delivery vectors having deletions in preselected gene regions, that are obtained by cellular complementation of adenoviral genes. To provide the desired complementation of such deleted adenoviral genomes in order to generate a novel viral vector of the present invention, plasmid vectors that contain preselected functional units were designed as described herein. Such units include but are not limited to E1 early region, E4 and the viral fiber gene. The preparation of plasmids providing such complementation, thereby being "complementary plasmids or constructs," that are stably inserted into host cell chromosomes are described below.

A. Preparation of an E4-Expressing Plasmid for Complementation of E4-Gene-Deleted Adenoviruses The viral E4 regulatory region contains a single transcription unit which is alternately spliced to produce several different mRNAs. The E4-expressing plasmid prepared as described herein and used to transfect the 293 cell line contains the entire E4 transcriptional unit as shown in FIG. 1. A DNA fragment extending from 175 nucleotides upstream of the E4 transcriptional start site including the natural E4 promoter to 153 nucleotides downstream of the E4 polyadenylation signal including the natural E4 terminator signal, corresponding to nucleotides 32667–35780 of the adenovirus type 5 (hereinafter referred to as Ad5) genome as described in Chroboczek et al. (*Virol.*, 186: 280–285 (1992), GenBank Accession Number M73260), was amplified from Ad5 genomic DNA, obtained from the ATCC, via the polymerase chain reaction (PCR). Sequences of the primers used were 5'CGGTACACA<u>GAATTC</u>AGGAGACACAACTCC3' (forward or 5' primer referred to as E4L) (SEQ ID NO: 1) and 5'GCCT<u>GGATCC</u>GGGAAGTTACGTAACGTGGGAAAAC3' (SEQ ID NO:2) (backward or 3' primer referred to as E4R). To facilitate cloning of the PCR fragment, these oligonucleotides were designed to create novel sites for the restriction enzymes EcoRI and BamHI, respectively, as indicated with underlined nucleotides. DNA was amplified via PCR using 30 cycles of 92 C for 1 minute, 50 C for 1 minute, and 72 C for 3 minutes resulting in amplified full-length E4 gene products.

The amplified DNA E4 products were then digested with EcoRI and BamHI for cloning into the compatible sites of pBluescript/SK+ by standard techniques to create the plasmid pBS/E4. A 2603 base pair (bp) cassette including the herpes simplex virus thymidine kinase promoter, the hygromycin resistance gene, and the thymidine kinase polyadenylation signal was excised from the plasmid pMEP4 (Invitrogen, San Diego, Calif.) by digestion with FspI followed by addition of BamHI linkers (5'CGCGGATCCGCG3') (SEQ ID NO: 3) for subsequent digestion with BamHI to isolate the hygromycin-containing fragment.

Figure 2:
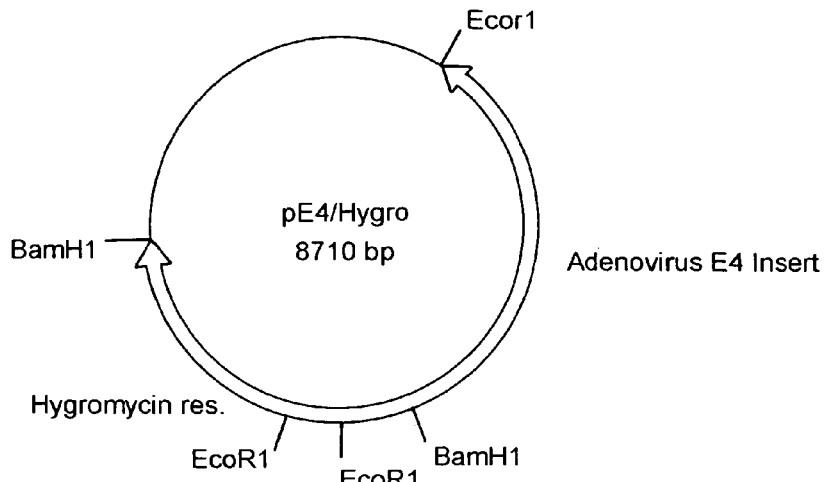
FIG. 2 is a schematic map of plasmid pE4/Hygro as further described in Example 1B.

The isolated BamHI-modified fragment was then cloned into the BamHI site of pBS/E4 containing the E4 region to create the plasmid pE4/Hygro containing 8710 bp (FIG. 2). The pE4/Hygro plasmid has been deposited with the ATCC as described in Example 3. The complete nucleotide sequence of pE4/Hygro is listed in SEQ ID NO: 4. Position number 1 of the linearized vector corresponds to approximately the middle portion of the pBS/SK+ backbone as shown in FIG. 2 as a thin line between the 3' BamHI site in the hygromycin insert and the 3' EcoRI site in the E4 insert. The 5' and 3' ends of the E4 gene are located at respective nucleotide positions 3820 and 707 of SEQ ID NO: 4 while the 5' and 3' ends of the hygromycin insert are located at respective nucleotide positions 3830 and 6470. In the clone that was selected for use, the E4 and hygromycin resistance genes were divergently transcribed.

B. Preparation of a Fiber-Expressing Plasmid for Complementation of Fiber-Gene-Deleted Adenoviruses To prepare a fiber-encoding construct, primers were designed to amplify the fiber coding region from Ad5 genomic DNA with the addition of unique BamHI and NotI sites at the 5' and 3' ends of the fragment, respectively. The Ad5 nucleotide sequence is available with the GenBank Accession Number M18369. The 5' and 3' primers had the respective nucleotide sequences of 5'ATG<u>GGATCC</u>AAGATGAAGCGCGCAAGACCG3' (SEQ ID NO: 5) and 5'CATAAC<u>GCGGCCGC</u>TTCTTTATTCTTGGGC3' (SEQ ID NO: 6), where the inserted BamHI and NotI sites are indicated by underlining. The 5' primer also contained a nucleotide substitution 3 nucleotides 5' of the second ATG codon (C to A) that is the initiation site. The nucleotide substitution was included so as to improve the consensus for initiation of fiber protein translation.

The amplified DNA fragment was inserted into the BamHI and NotI sites of pcDNA3 (Invitrogen) to create the plasmid designated pCDNA3/Fiber having 7148 bp, the plasmid map of which is shown in FIG. 3. The parent plasmid contained the CMV promoter, the bovine growth hormone (BHG) terminator and the gene for conferring neomycin resistance. The viral sequence included in this construct corresponds to nucleotides 31040–32791 of the Ad5 genome.

The complete nucleotide sequence of pCDNA3/Fiber is listed in SEQ ID NO: 7 where the nucleotide position 1 corresponds to approximately the middle of the pcDNA3 vector sequence. The 5' and 3' ends of the fiber gene are located at respective nucleotide positions 916 with ATG and 2661 with TAA.

Figure 4:
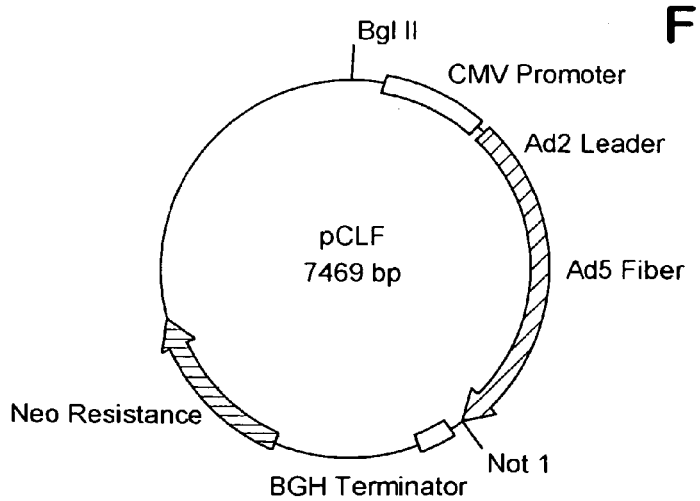
FIG. 4 is a schematic map of plasmid pCLF as further described in Example 1B.

To enhance expression of fiber protein by the constitutive CMV promoter provided by the pcDNA vector, a BglII fragment containing the tripartite leader (TPL) of adenovirus type 2 was excised from pRD112a (Sheay etal., BioTechniques, 15:856–862 (1993) and inserted into the BamHI site of pCDNA3/Fiber to create the plasmid pCLF having 7469 bp, the plasmid map of which is shown in FIG. 4. The adenovirus tripartite leader sequence, present at the 5' end of all major late adenoviral mRNAs as described by Logan et al., Proc. Natl. Acad. Sci., USA, 81:3655–3659 (1984) and Berkner, *Bio Techniques*, 6:616–629 (1988), also referred to as a "partial TPL" since it contains a partial exon 1, shows correspondence with the Ad5 leader sequence having three spatially separated exons corresponding to nucleotide positions 6081–6089 (the 3' end of the first leader segment), 7111–7182 (the entire second leader segment), and 9644–9845 (the third leader segment and sequence downstream of that segment). The corresponding cDNA sequence of the partial tripartite leader sequence present in pCLF is listed in SEQ ID NO: 8 bordered by BamHI/BGlII 5' and 3' sites at respective nucleotide positions 907–912 to 1228–1233. The nucleotide sequence of an isolated partial TPL of the present invention is also listed separately as SEQ ID NO: 26 with the noted 5' and 3' restriction sites and with the following nucleotide regions identified: 1–6 nt BglII site; 1–18 nt polylinker; 19–27 nt last 9 nt of the first leader segment (exon 1); 28–99 nt second leader segment (exon 2); 100–187 nt third leader segment (exon 3); 188–301 nt contains the nt sequence immediately following the third leader in the genome with an unknown function; and 322–327 nt BglII site.

The pCLF plasmid has been deposited with the ATCC as described in Example 3. The complete nucleotide sequence of pCLF is listed in SEQ ID NO: 8 where the nucleotide position 1 corresponds to approximately the middle of the pcDNA3 parent vector sequence. The 5' and 3 ends of the Ad5 fiber gene are located at respective nucleotide positions 1237–1239 with ATG and 2980–2982 with TAA. The rest of the vector construct has been previously described above.

C. Generation of an Adenovirus Packaging Cell Line Carrying Plasmids Encoding Functional E4 and Fiber Proteins The 293 cell line was selected for preparing the first adenovirus packaging line as it already contains the E1 gene as prepared by Graham et al., *J. Gen. Virol.*, 36:59–74 (1977) and as further characterized by Spector, *Virol.*, 130:533–538 (1983). Before electroporation, 293 cells were grown in RPMI medium+10% fetal calf serum. Four×10⁶ cells were electroporated with 20 µg each of pE4/Hygro DNA and pCLF DNA using a BioRad GenePulser and settings of 300 V, 25 µF. DNA for electroporation was prepared using the Qiagen system according to the manufacturer's instructions (Bio-Rad, Richmond, Calif.).

Following electroporation, cells were split into fresh complete DMEM+10% fetal calf serum containing 200 µg/ml Hygromycin B (Sigma, St. Louis, Mo.).

From expanded colonies, genomic DNA was isolated using the "MICROTURBOGEN" system (Invitrogen) according to manufacturer's instructions. The presence of integrated E4 DNA was assessed by PCR using the primer pair E4R and ORF6L (5'TGCTTAAGCGGCCGCGAAGGAGA AGTCC3') (SEQ ID NO: 9), the latter of which is a 5' forward primer near adenovirus 5 open reading frame 6. Refer to FIG. 1 for position of the primers relative to the E4 genes.

Figure 5:
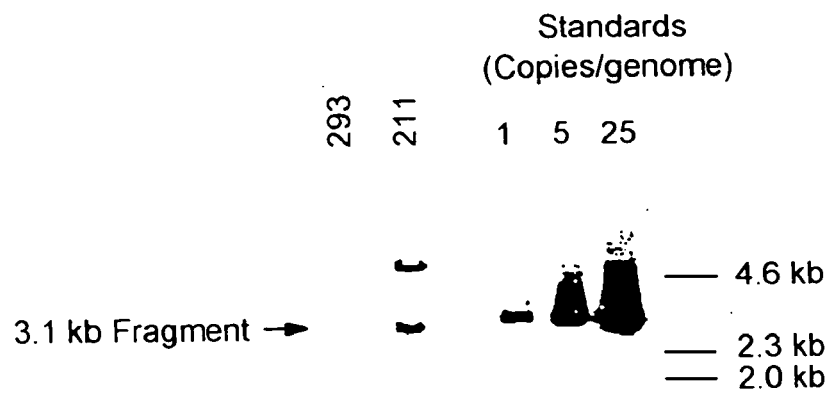
FIG. 5 is a photograph of a Southern blot showing the presence of intact adenovirus E4 3.1 kilobase (kb) insert in the 211 cell line as further described in Example 1C.

One clone, designated 211, was selected exhibiting altered growth properties relative to that seen in parent cell line 293. The 211 clone contained the expected product, indicating the presence of inserted DNA corresponding to most, if not all, of the E4 fragment contained in the pE4/Hygro plasmid. The 211 cell line has been deposited with the ATCC as described in Example 3. This line was further evaluated by amplification using the primer pair E4L/E4R described above, and a product corresponding to the full-length E4 insert was detected. Genomic Southern blotting was performed on DNA restricted with EcoRI and BamHI. The E4 fragment was then detected at approximately one copy/genome compared to standards with the EcoRI/BamHI E4 fragment as cloned into pBS/E4 for use as a labeled probe with the Genius system according to manufacturer's instructions (Boehringer Mannheim, Indianapolis, Ind.). In DNA from the 211 cell line, the expected labeled internal fragment pE4/Hygro hybridized with the isolated E4 sequences. In addition, the probe hybridized to a larger fragment which may be the result of a second insertion event (FIG. 5).

Although the 211 cell line was not selected by neomycin resistance, thus indicating the absence of fiber gene, to confirm the lack of fiber gene, the 211 cell line was analyzed for expression of fiber protein by indirect immunofluorescence with an anti-fiber polyclonal antibody and a FITC-labeled anti-rabbit IgG (KPL) as secondary. No immunoreactivity was detected. Therefore, to generate 211 clones containing recombinant fiber genes, the 211 clone was expanded by growing in RPMI medium and subjected to additional electroporation with the fiber-encoding pCLF plasmid as described above.

Following electroporation, cells were plated in DMEM+ 10% fetal calf serum and colonies were selected with 200 µg/ml G418 (Gibco, Gaithersburg, Md.). Positive cell lines remained hygromycin resistant. These candidate sublines of 211 were then screened for fiber protein expression by indirect immunofluorescence as described above. The three sublines screened, 211A, 211B and 211R, along with a number of other sublines, all exhibited nuclear staining qualitatively comparable to the positive control of 293 cells infected with AdRSVβgal (1 pfu/cell) and stained 24 hours post-infection.

Lines positive for nuclear staining in this assay were then subjected to Western blot analysis under denaturing conditions using the same antibody. Several lines in which the antibody detected a protein of the expected molecular weight (62 kd for the Ad5 fiber protein) were selected for further study including 211A, 211B and 211R. The 211A cell line has been deposited with ATCC as described in Example 3.

Figure 6:
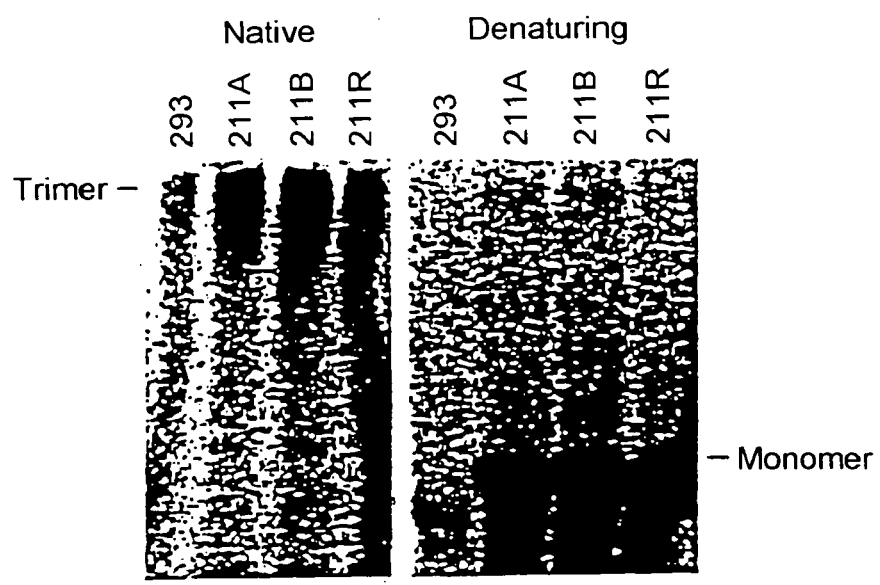
FIG. 6 is an autoradiograph showing labeled fiber protein immunoprecipitated from cells and electrophoresed under native and denaturing electrophoresis conditions as described in Example 1C. The 293 cells lack fiber while the sublines 211A, 211B and 211R contain fiber protein detectable in functional trimerized form and denatured monomeric form.

Immunoprecipitation analysis using soluble nuclear extracts from these three cell lines and a seminative electrophoresis system demonstrated that the fiber protein expressed is in the functional trimeric form characteristic of the native fiber protein as shown in FIG. 6. The predicted molecularweight of a trimerized fiber is 186 kd. The lane marked 293 lacks fiber while the sublines contain detectable fiber. Under denaturing conditions, the trimeric form was destroyed resulting in detectable fiber monomers as shown in FIG. 6. Those clones containing endogenous E1, newly expressed recombinant E4 and fiber proteins were selected for use in complementing adenovirus gene delivery vectors having the corresponding adenoviral genes deleted as described in Example 2.

D. Preparation of an E1-Expressing Plasmid for Complementation of E1-Gene-Deleted Adenoviruses In order to prepare adenoviral packaging cell lines other than those based on the E1-gene containing 293 cell line as described in Example 1C above, plasmid vectors containing E1 alone or in various combinations with E4 and fiber genes are constructed as described below.

Figure 7:
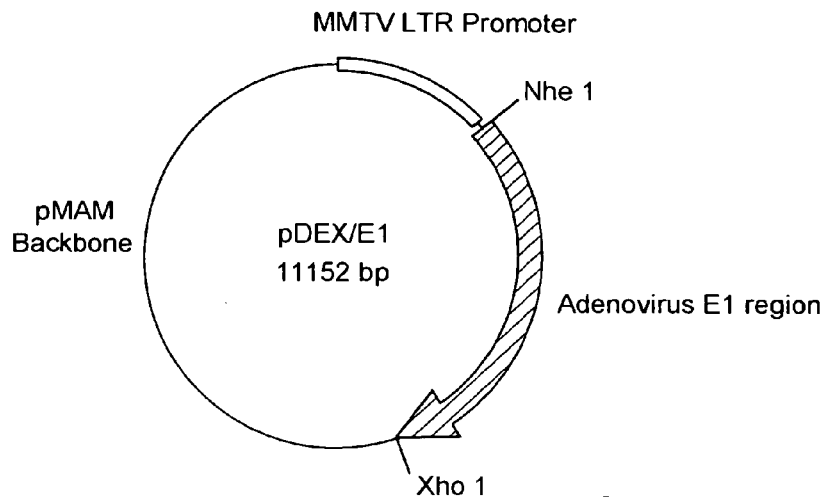
FIG. 7 is a schematic map of plasmid pDEX/E1 as further described in Example 1D.

The region of the adenovirus genome containing the E1a and E1b gene is amplified from viral genomic DNA by PCR as previously described. The primers used are E1L, the 5' or forward primer, and E1R, the 3' or backward primer, having the respective nucleotide sequences 5'CCG A GCTAGCGACTGAAAATGAG3' (SEQ ID NO: 10) and 5'CCTCTCGAG AGACAGC AAGACAC3' (SEQ ID NO: 11). The E1L and E1R primers include the respective restriction sites NheI and XhoI as indicated by the underlines. The sites are used to clone the amplified E1 gene fragment into the NheI/XhoI sites in pMAM commercially available from Clontech (Palo Alto, Calif.) to form the plasmid pDEX/E1 having 11152 bp, the plasmid map of which is shown in FIG. 7.

The complete nucleotide sequence of pDEX/E1 is listed in SEQ ID NO: 12 where the nucleotide position 1 corresponds to approximately 1454 nucleotides from the 3' end of the pMAM backbone vector sequence. The pDEX/E1 plasmid includes nucleotides 552 to 4090 of the adenovirus genome positioned downstream (beginning at nucleotide position 1460 and ending at 4998 in the pDEX/E1 plasmid) of the glucocorticoid-inducible mouse mammary tumor virus (MMTV) promoter of pMAM. The pMAM vector contains the *E. coli* gpt gene that allows stable transfectants to be isolated using hypoxanthine/aminopterin/thymidine (HAT) selection. The pMAM backbone occupies nucleotide positions 1–1454 and 5005–11152 of SEQ ID NO: 12.

E. Generation of an Adenovirus Packaging Cell Line Carrying Plasmids Encoding Functional E1, and Fiber Proteins To create separate adenovirus packaging cell lines equivalent to that of the 211 sublines, 211A, 211B and 211R, as described in Example 1C, alternative cell lines lacking adenoviral genomes are selected for transfection with the plasmid constructs as described below. Acceptable host cells include A549, Hela, Vero and the like cell lines as described in Example 1. The selected cell line is transfected with the separate plasmids, pDEX/E1 and pCLF, respectively for expressing E1, and fiber complementary proteins. Following transfection procedures as previously described, clones containing stable insertions of the two plasmids are isolated by selection with neomycin and HAT. Integration of full-length copy of the E1 gene is assessed by PCR amplification from genomic DNA using the primer set E1L/E1R, as described above. Functional insertion of the fiber gene is assayed by staining with the anti-fiber antibody as previously described.

The resultant stably integrated cell line is then used as a packaging cell system to complement adenoviral gene delivery vectors having the corresponding adenoviral gene deletions as described in Example 2.

F. Preparation of a Plasmid Containing Two or More Adenoviral Genes for Complementing Gene-Deleted Adenoviruses The methods described in the preceding Examples rely on the use of two plasmids, pE4/Hygro and pCLF, or, pCLF and pDEX/E1 for generating adenoviral cell packaging systems. In alternative embodiments contemplated for use with the methods of this invention, complementing plasmids containing two or more adenoviral genes for expressing of encoded proteins in various combinations are also prepared as described below. The resultant plasmids are then used in various cell systems with delivery plasmids having the corresponding adenoviral gene deletions. The selection of packaging cell, content of the delivery plasmids and content of the complementing plasmids for use in generating recombinant adenovirus viral vectors of this invention thus depends on whether other adenoviral genes are deleted along with the adenoviral fiber gene, and, if so, which ones.

1. Preparation of a Complementing Plasmid Containing Fiber and E1 Adenoviral Genes A DNA fragment containing sequences for the CMV promoter, adenovirus tripartite leader, fiber gene and bovine growth hormone terminator is amplified from pCLF prepared in Example 1B using the forward primer 5'GACGGATCGGGAGATCTCC3' (SEQ ID NO: 13), that anneals to the nucleotides 1–19 of the pCDNA3 vector backbone in pCLF, and the backward primer 5'CCGCCTCAGAAGCCATAGAGCC3' (SEQ ID NO: 14) that anneals to nucleotides 1278–1257 of the pCDNA3 vector backbone. The fragment is amplified as previously described and then cloned into the pDEX/E1 plasmid, prepared in Example 1D. For cloning in the DNA fragment, the pDEX/E1 vector is first digested with NdeI, that cuts at a unique site in the pMAM vector backbone in pDEX/E1, then the ends are repaired by treatment with bacteriophage T4 polymerase and dNTPs.

Figure 8:
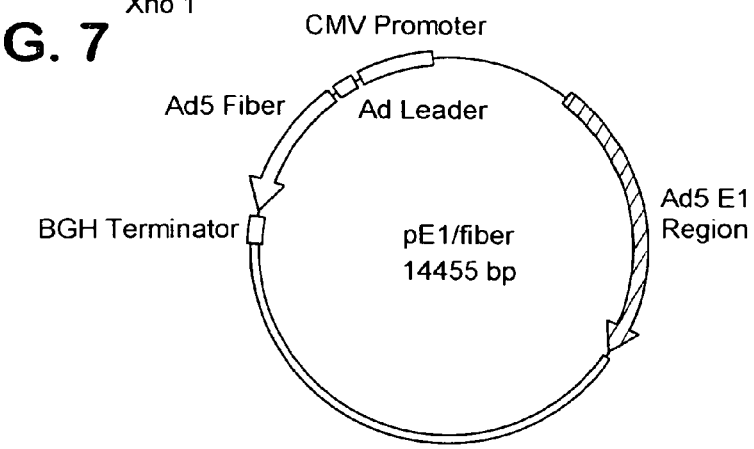
FIG. 8 is a schematic map of plasmid pE1/Fiber as further described in Example 1F1.

The resulting plasmid containing E1 and fiber genes, designated pE1/Fiber, provides both dexamethasone-inducible E1 function as described for DEX/E1 and expression of Ad5 fiber protein as described above. A schematic plasmid map of pE1/Fiber, having 14455 bp, is shown in FIG. 8.

The complete nucleotide sequence of pE1/Fiber is listed in SEQ ID NO: 15 where the nucleotide position 1 corresponds to approximately to 1459 nucleotides from the 3' end of the parent vector pMAM sequence. The 5' and 3 ends of the Ad5 E1 gene are located at respective nucleotide positions 1460 and 4998 followed by pMAM backbone and then separated from the Ad5 fiber from pCLF by the filled-in blunt ended NdeI site. The 5' and 3' ends of the pCLF fiber gene fragment are located at respective nucleotide positions 10922–14223 containing elements as previously described for pCLF.

The resultant pE1/Fiber plasmid is then used to complement one or more delivery plasmids expressing E1 and fiber.

The pE1/Fiber construct is then used to transfect a selected host cell as described in Example 1E to generate stable chromosomal insertions preformed as previously described followed by selection on HAT medium. The stable cells are then used as packaging cells as described in Example 2.

2. Preparation of a Complementing Plasmid Containing E4 and Fiber Adenoviral Genes pCLF prepared as described in Example 1B is partially digested with BglII to cut only at the site in the pCDNA3 backbone. The pE4/Hygro plasmid prepared in Example 1A is digested with BamHI to produce a fragment containing E4. The E4 fragment is then inserted into the BamHI site of pCLF to form plasmid pE4/Fiber. The resultant plasmid provides expression of the fiber gene as described for pCLF and E4 function as described for pE4/Hygro.

Figure 9:
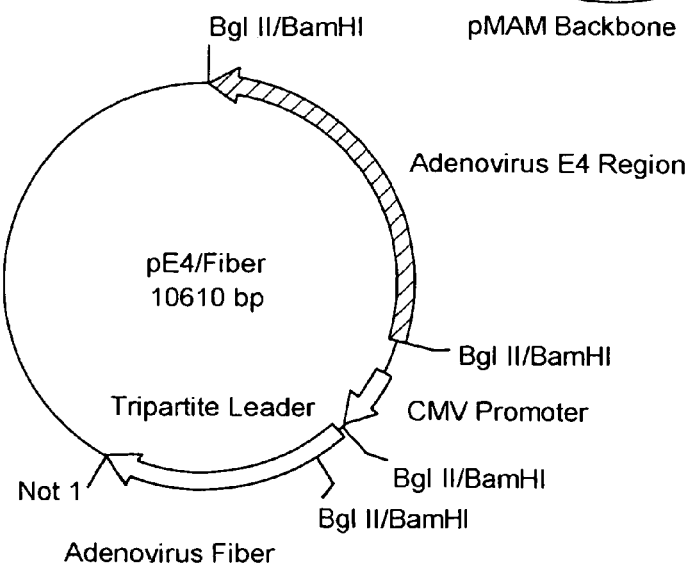
FIG. 9 is a schematic map of plasmid pE4/Fiber as further described in Example 1F2).
Figure 10:
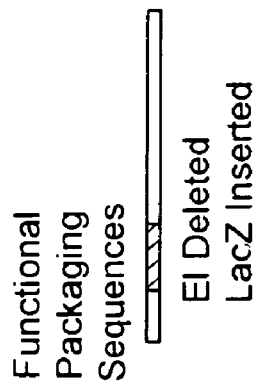
FIG. 10 is a schematic illustration of linearized pD E1Bb gal delivery plasmids for use in cotransfection and recombination to form a recombinant adenoviral vector having multiple adenoviral gene deletions. The plasmids and recombination event are more fully described in Example 2A.
Figure 11:
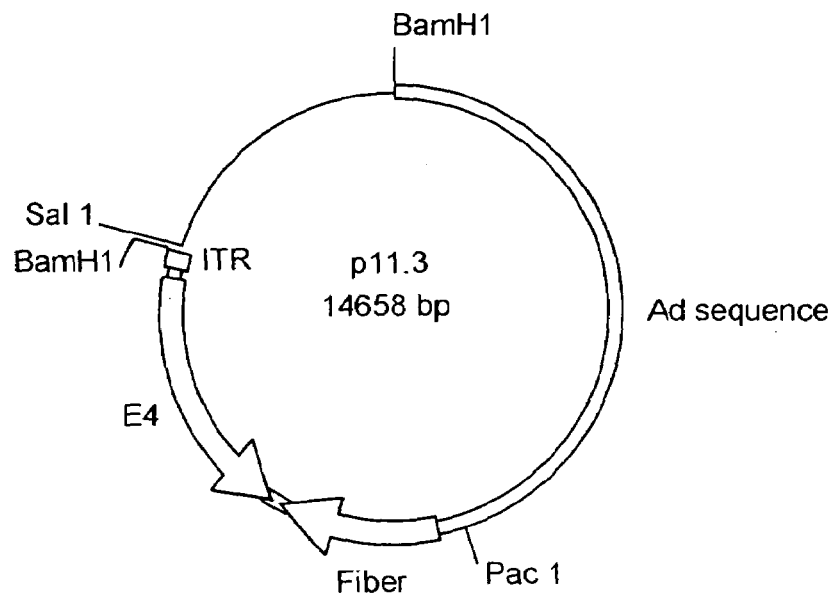
FIG. 11 is a schematic of plasmid p11.3 as further described in Example 2A used in the construction of pDV44 delivery plasmid.
Figure 12:
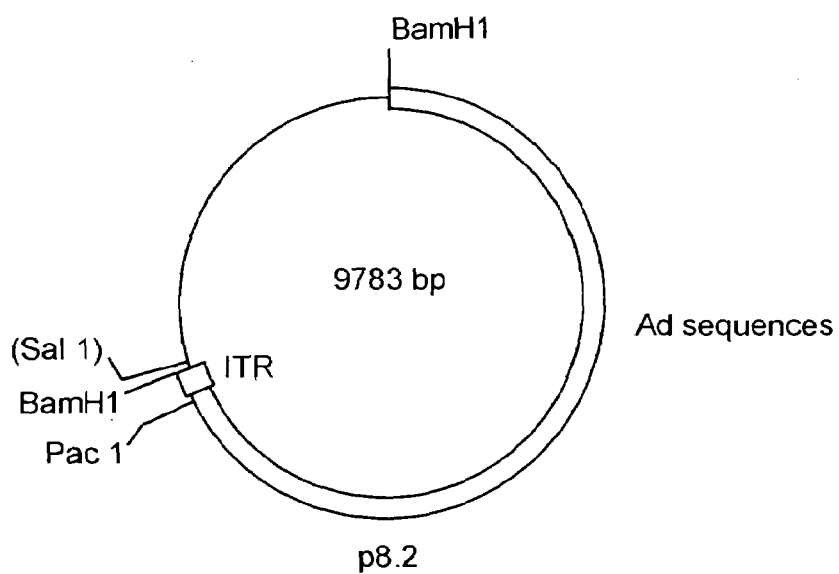
FIG. 12 is a schematic of plasmid 8.2.

A schematic plasmid map of pE4/Fiber, having 10610 bp, is shown in FIG. 9. The complete nucleotide sequence of pE4/Fiber is listed in SEQ ID NO: 16 where the nucleotide position 1 corresponds to approximately 14 bp from the 3' end of the parent vector pCDNA3 backbone sequence. The 5' and 3 ends of the Ad5 E4 gene are located at respective nucleotide positions 21 and 3149 followed by fused BglII/BamHI sites and pCDNA3 backbone including the CMV promoter again followed by BglII/BamHI sites. The adenovirus leader sequence begins at nucleotide position 4051 and extends to 4366 followed by fused BamHI/BglII sites and the 5' and 3' ends of the fiber gene located at respective nucleotide positions 4372 and 6124.

Stable chromosonal insertions of pE4/Fiber in host cells are obtained as described above.

Example 2

Preparation of Adenoviral Gene Delivery Vectors Using Adenoviral Packaging Cell Lines Adenoviral delivery vectors of this invention are prepared to separately lack the combinations of E1/fiber and E4/fiber. Such vectors are more replication-defective than those previously in use due to the absence of multiple viral genes. A preferred adenoviral delivery vector of this invention that is replication competent but only via a non-fiber means is one that only lacks the fiber gene but contains the remaining functional adenoviral regulatory and structural genes. Furthermore, the adenovirus delivery vectors of this invention have a higher capacity for insertion of foreign DNA.

A. Preparation of Adenoviral Gene Delivery Vectors Having Specific Gene Deletions and Methods of Use To construct the E1/fiber deleted viral vector containing the LacZ reporter gene construct, two new plasmids were constructed. The plasmid pΔ E1Bβgal was constructed as follows. A DNA fragment containing the SV40 regulatory sequences and *E. coli* β-galactosidase gene was isolated from pSVβgal (Promega) by digesting with VspI, filling the overhanging ends by treatment with Klenow fragment of DNA polymerase I in the presence of dNTP's and digesting with Bam H1. The resulting fragment was cloned into the EcoRV and BamHI sites in the polylinker of pΔ E1sp1B (Microbix Bio systems, Hamilton, Ontario) to form pΔ E1B βgal that therefore contained the left end of the adenovirus genome with the E1a region replaced by the LacZ cassette (nucleotides 6690 to 4151) of pSVβ gal. Plasmid DNA may be prepared by the alkaline lysis method as described by Birnboim and Doly, *Nuc. Acids Res.*, 7:1513–1523 (1978) or by the Quiagen method according to the manufacturer's instruction, from transformed cells used to expand the plasmid DNA was then purified by CsCl-ethidium bromide density gradient centrifugation. Alternatively, plasmid DNAs may be purified from *E. coli* by standard methods known in the art (e.g. see Sambrook et al.)

Figure 13:
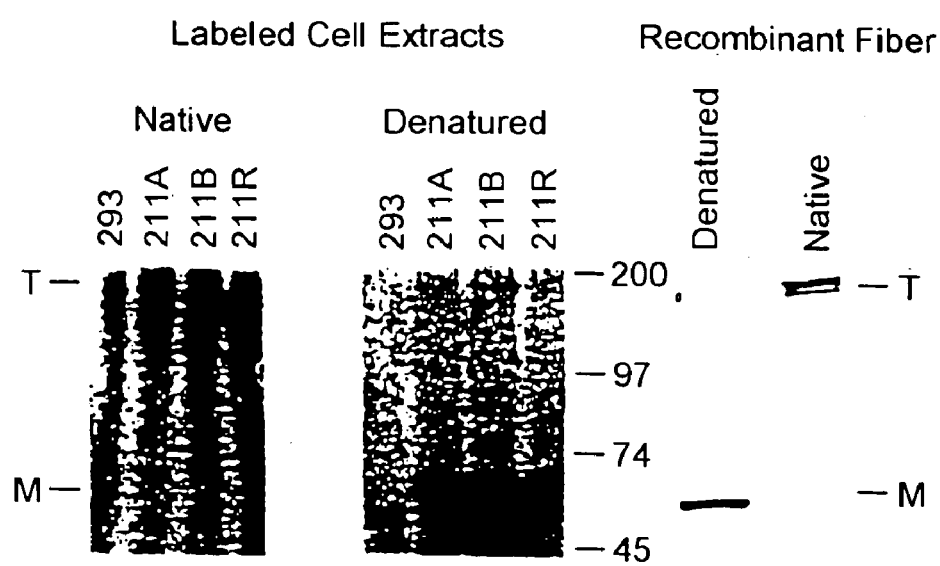
FIG. 13 shows the trimeric structure of the recombinant fiber. 293, 211A, 211B, or 211R cells as indicated were metabolically labeled with [$^{35}$S]methionine, soluble protein extracts prepared, and fiber was immunoprecipitated. A portion of the precipitated protein was electrophoresed on an 8% SDS-PAGE gel under either semi-native or denaturing conditions. The positions of trimeric (T) and monomeric (M) fiber are indicated. As a control for electrophoretic conditions, recombinant Ad2 fiber produced in baculovirus-infected cells was run under identical conditions and stained with Coomassie blue.

The second plasmid (pDV44), prepared as described herein, is derived from pBHG10, a vector prepared as described by Bett et al., *Proc. Natl. Acad. Sci., USA*, 91:8802–8806 (1994), now described in International Application Publication Number WO 9500655, with methodology well known to one of ordinary skill in the art and also is commercially available from Microbix, which contains an Ad5 genome with the packaging signals at the left end deleted and the E3 region (nucleotides 28133:30818) replaced by a linker with a unique site for the restriction enzyme PacI. An 11.9 kb BamHI fragment, which contains the right end of the adenovirus genome, is isolated from pBHG10 and cloned into the BamHI site of pBS/SK(+) to create plasmid p11.3 having approximately 14,658 bp. A schematic of the plasmid map is shown in FIG. 13. The p11.3 plasmid was then digested with PacI and SalI to remove the fiber, E4, and inverted terminal repeat (ITR) sequences.

This fragment was replaced with a 3,4 kb fragment containing the ITR segments and the E4 gene which was generated by PCR amplification from pBHG10 using the following oligonucleotide sequences (5' TGTACACCG GATCCGGCGCACACC3' SEQ ID NO: 17) and (5'CA-CAACGAGCTC AATTAATTAATTGCCACATCCTC3' SEQ ID NO: 18). These primers incorporated sites for PacI and BamHI. Cloning this fragment into the PacI and blunt ended SalI sites of the p11.3 backbone resulted in a substitution of the fused ITRs, E4 region and fiber gene present in pBHG10, by the ITRs and E4 region alone. The resultant p11.3 plasmid containing the ITR and E4 regions, now called plasmid pDV43a, was then digested with BamHI. This BamHI fragment was then used to replace a BamHI fragment in pBHG10 thereby creating pDV44 in a pBHG10 backbone.

In an alternative approach to preparing pDV44 with an additional subcloning step to facilitate the incorporation of restriction cloning sites, the following cloning procedure was performed. pDV44 as above was constructed by removing the fiber gene and some of the residual E3 sequences from pBHG10 (Microbix Biosystems). As above, to simplify manipulations, the 11.9 kb BamHI fragment including the rightmost part of the Ad5 genome was removed from pBHG10 and inserted into pBS/SK. The resulting plasmid was termed p11.3. The 3.4 kb DNA fragment corresponding to the E4 region and both ITRs of adenovirus type 5 was amplified as described above from pBHG10 using the oligonucleotides listed above and subcloned into the vector pCR2.1 (Invitrogen) to create pDV42. This step is the additional cloning step to facilitate the incorporation of a SalI restriction site. pDV42 was then digested with PacI, which cuts at a unique site (bold type) in one of the PCR primers, and with SalI, which cuts at a unique site in the pCR2.1 polylinker. This fragment was used to replace the corresponding PacI/XhoI fragment of p11.3 (the pBS polylinker adjacent to the Ad DNA fragment contains a unique XhoI site), creating pDV43. Finally, pDV44 was constructed by replacing the 11.9 kb BamHI fragment of pBHG10 by the analogous BamHI fragment of pDV43. As generated in the first procedure, pDV44 therefore differs from pBHG10 by the deletion of Ad5 nucleotides 30819: 32743 (residual E3 sequences and all but the 3'-most 41 nucleotides of the fiber open reading frame).

Figure 16A:
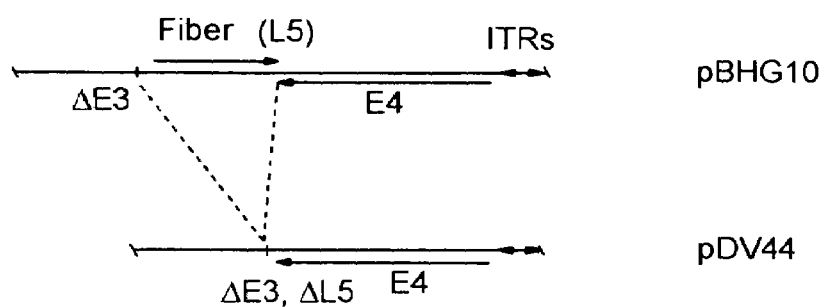
FIG. 16A shows pDV44 that was constructed by removing the fiber gene and residual E3 sequences (nt 30819:32743 of AD5) from pBHG10.

Thus, to summarize, the cloning procedures described above result in the production of a fiber-deleted Ad5 genomic plasmid (pDV44) that was constructed by removing the fiber gene and some of the residual E3 sequences from pBHG10 (FIG. 16A). pDV44 contains a wild-type E4 region, but only the last 41 nucleotides of the fiber ORF (this sequence was retained to avoid affecting expression of the adjacent E4 transcription unit). Both pBHG10 and pDV44 contain unpackageable Ad5 genomes, and must be rescued by cotransfection and subsequent homologous recombination with DNA carrying functional packaging signals. In order to generate vectors marked with a reporter gene, either pDV44 or pBHG10 was cotransfected with pΔE1Bβgal, which contains the left end of the Ad5 genome with an SV40-driven β-galactosidase reporter gene inserted in place of the E1 region.

In general, and as described below, the method for virus production by recombination of plasmids followed by complementation in cell culture involves the isolation of recombinant viruses by cotransfection of any one of the adenovirus packaging cell systems prepared in Example 1, namely 211A, 211B, 211R, A549, Vero cells, and the like, with plasmids carrying sequences corresponding to viral gene delivery vectors.

A selected cell line is plated in dishes and cotransfected with pDV44 and pΔE1Bβ gal using the calcium phosphate method as described by Bett et al., *Proc. Natl. Acad. Sci., USA*, 91:8802–8806 (1994). Recombination between the overlapping adenovirus sequences in the two plasmids leads to the creation of a full-length viral chromosome where pDV44 and pΔE1Bβ gal recombine to form a recombinant adenovirus vector having multiple deletions. The deletion of E1 and of the fiber gene from the viral chromosome is compensated for by the sequences integrated into the packaging cell genome, and infectious virus particles are produced. The plaques thus generated are isolated and stocks of the recombinant virus are produced by standard methods.

A pDV44-derived virus is expected to be replication-defective due to the fiber deletion, so that the cells in which it is grown must complement this defect. The 211B cell line (a derivative of 293 cells which expresses the wild-type (wt) AD5 fiber and is equivalent to 211A on deposit with ATCC as described in Example 3) was used for rescue and propagation of the virus described here. pDV44 and pΔE1βgal were cotransfected into 211B cells, and the monolayers were observed for evidence of cytopathic effect (CPE). Briefly, for virus construction, cells were transfected with the indicated plasmids using the Gibco Calcium Phosphate Transfection system according to the manufacturer's instructions and observed daily for evidence of CPE.

One of a total of 58 transfected dishes showed evidence of spreading cell death at day 15. A crude freeze-thaw lysate was prepared from these cells and the resulting virus (termed Ad5.βgal.ΔF) was plaque purified twice and then expanded. To prepare purified viral preparations, cells were infected with the indicated Ad and observed for completion of CPE. Briefly, at day zero, 211B cells were plated in DMEM plus 10% fetal calf serum at approximately $1 \times 10^7$ cells/150 cm$^2$ flask or equivalent density. At day one, the medium was replaced with one half the original volume of fresh DMEM containing the indicated Ad, in this case Ad5.βgal.ΔF, at approximately 100 particles/cell. At day two, an equal volume of medium was added to each flask and the cells were observed for CPE. Two to five days after infection, cells were collected and virus isolated by lysis via four rapid freeze-thaw cycles. Virus was then purified by centrifugation on preformed 15–40% CsCl gradients (111,000×g for three hours at 4° C.). The bands were harvested, dialyzed into storage buffer (10 mM Tris-pH 8.1, 0.9% NaCl, and 10% glycerol), aliquoted and stored at −70° C. Purified Ad5.βgal.ΔF virus particles containing human adenovirus Ad5.βgal.ΔF genome (described further below) have been deposited with the ATCC on Jan. 15, 1999 as further described in Example 3.

For viral titering, as necessary in the below Examples, Ad preparations were titered by plaque assay on 211B cells. Cells were plated on polylysine-coated 6 well plates at $1.5 \times 10^6$ cells/well. Duplicate dilutions of virus stock were added to the plates in 1 ml/well of complete DMEM. After a five hour incubation at 37° C., virus was removed and the wells overlaid with 2 ml of 0.6% low-melting agarose in Medium 199 (Gibco). An additional 1 ml of overlay was added at five day intervals.

Figure 16B:
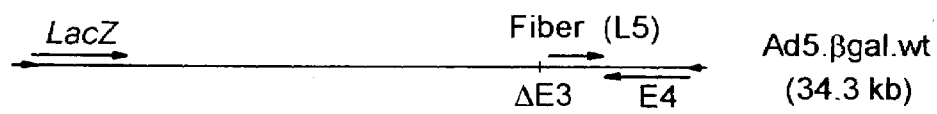
FIG. 16B shows viruses constructed by cotransfection of either pBHG10 or pDV44 with pΔE1Bβgal. Both are E1/E3 deleted Ad5 vectors, and Ad5.βgal.ΔF has the additional fiber (L5) deletion as in pDV44.
Figure 16B:
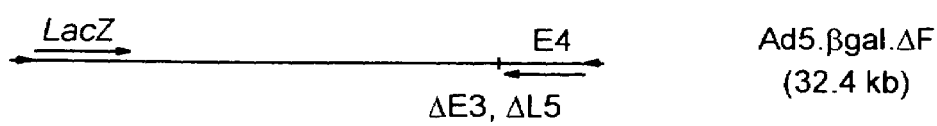

As a control, the first-generation virus Ad5.βgal.wt, which is identical to Ad5.βgal.ΔF except for the fiber deletion, was constructed by cotransfection of pBHG10 and pΔE1Bβgal (FIG. 16B). In contrast to the low efficiency of recovery of the fiberless genome (1/58 dishes), all of 9 dishes cotransfected with pΔE1Bβgal and pBHG10 produced virus.

In a preferred embodiment of this invention as more fully described herein and below, a delivery plasmid is prepared that does not require the above-described recombination events to prepare a viral vector having a fiber gene deletion. In one embodiment, a single delivery plasmid containing all the adenoviral genome necessary for packaging but lacking the fiber gene is prepared from plasmid pFG140 containing full-length Ad5 that is commercially available from Microbix. The resultant delivery plasmid referred to as pFG140-f is then used with pCLF stably integrated cells as described above to prepare a viral vector lacking fiber. In a preferred aspect of this invention, the fiber gene is replaced with a therapeutic gene of interest for preparing a therapeutic delivery adenoviral vector. Other embodiments including production of fiberless vector with a complete TPL are described in Example 5.

Vectors for the delivery of any desired gene and preferably a therapeutic gene are prepared by cloning the gene of interest into the multiple cloning sites in the polylinker of commercially available pΔE1sp1B (Microbix Biosystems), in an analogous manner as performed for preparing p E1Bβ gal as described above. The same cotransfection and recombination procedure is then followed as described herein to obtain viral gene delivery vectors as further discussed in later Examples.

1. Characterization of the Ad5.βgal.ΔF Genome

Figure 17A:
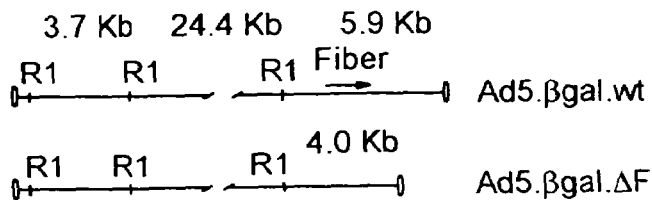
FIG. 17A shows the predicted EcoRI restriction maps of Ad5.βgal.wt and Ad5.βgal.ΔF. The 5.9 kb fragment at the right end of the Ad5.βgal.wt genome is reduced to 4.0 kb by the deletion of fiber sequences in Ad5.gal.ΔF.
Figure 17B:
FIG. 17B shows an ethidium bromide-stained gel of EcoRI-digested viral DNA.
Figure 17C:
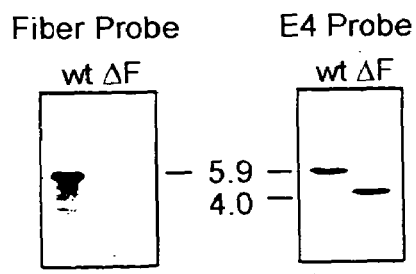
FIG. 17C shows a Southern blot of the gel as described in Example 2 probed either with labeled fiber or E4 sequences.

To confirm that the vector genomes had the expected structures and that the fiber gene was absent from the Ad5.βgal.ΔF chromosome, the DNA isolated from viral particles was analyzed. Briefly, purified viral DNA was obtained by adding 10 μl of 10 mg/ml proteinase K, 40 μl of 0.5 M EDTA and 50 μl of 10% SDS to 800 μl of adenovirus-containing culture supernatant. The suspension was then incubated at 55° C. for 60 minutes. The solution was then extracted once with 40 μl of a 24:1 mixture of chloroform:isoamyl alchohol. The aqueous phase was then removed and precipitated with sodium acetate/ethanol. The pellet was washed once with 70% ethanol and lightly dried. The pellet was then suspended in 40 μl of 10 mM Tris-HCl, pH 8.0, 1 mM EDTA. Genomic DNA from both Ad5.βgal.wt and Ad5.βgal.ΔF produced the expected restriction patterns (FIG. 17A) following digestion with either EcoRI (FIG. 17B) or with NdeI (data not shown). Southern blotting, performed with standard methods, with labeled fiber DNA as a probe demonstrated the presence of fiber sequence in Ad5.βgal.wt but not in Ad5.βgal.ΔF DNA (FIG. 17C). As a positive control, the blot was stripped and reprobed with labeled E4 sequence. Fiber and E4 sequences were detected by using labeled inserts from pCLF and pE4/Hygro, respectively. As expected, E4 signal was readily detectable in both genomes at equal intensities (FIG. 17C).

The complete nucleotide sequence of Ad5.βgal.ΔF is presented in SEQ ID NO: 27 and is contained in the virus particle on deposit with ATCC.

2. Characterization of the Fiberless Adenovirus Ad5.βgal.ΔF

To verify that Ad5.βgal.ΔF was fiber-defective, 293 cells (which are permissive for growth of E1-deleted Ad vectors but do not express fiber) were infected with Ad5.βgal.ΔF or with Ad5.βgal.wt. Twenty-four hours post infection, the cells were stained with polyclonal antibodies directed either against fiber or against the penton base protein. Cells infected with either virus were stained by the anti-penton base antibody, while only cells infected with the Ad5.βgal.wt control virus reacted with the anti-fiber antibody. This confirms that the fiber-deleted Ad mutant does not direct the synthesis of fiber protein.

3. Growth of the Fiber-Deleted Ad5.βgal.ΔF Vector in Complementing Cells

Ad5.βgal.ΔF was found to readily be propagated in 211B cells. As assayed by protein concentration, CsCl-purified stocks of either Ad5.βgal.ΔF or Ad5.βgal.wt contained similar numbers of viral particles (Table 1), and the particles appeared to band normally on CsCl gradients. However, infectivity of the Ad5.βgal.ΔF particles was lower than the Ad5.βgal.wt control, as indicated by an increased particle/PFU ratio (Table 1). This is likely due to a reduced amount of fiber protein incorporated into mutant particles during growth in the

TABLE 3

| Virus | CsCl-purified prepn | Cell line | Particles/ml[a] | PFU/ml[b] | Particle/PFU ratio | Fiber source |
|---|---|---|---|---|---|---|
| Ad5.βgal wt | 1 | 211B | $7.4 \times 10^{11}$ | $7.5 \times 10^{10}$ | 10 | Ad chromosome |
|  | 2 | 211B | $3.0 \times 10^{11}$ | $5.0 \times 10^{9}$ | 60 | Ad chromosome |
| Ad5.βgal.ΔF | 3 | 211B | $7.7 \times 10^{11}$ | $3.5 \times 10^{8}$ | 2,200 | Packaging cells |
|  | 4 | 211B | $1.9 \times 10^{12}$ | $2.3 \times 10^{9}$ | 808 | Packaging cells |
|  | 5 | 293 | $4.5 \times 10^{11}$ | $9.5 \times 10^{6}$ | 47,400 | None |
|  | 6 | 293 | $3.4 \times 10^{11}$ | $3.5 \times 10^{7}$ | 9,700 | None |

[a]Calculated from viral protein concentration (1 ug of protein = $4 \times 10^{9}$ particles).
[b]Assayed by plaquing on 211B cells.

*Particle numbers and infectious titers of representative adenovirus preps. Each line represents a single CsCl-purified preparation of the indicated virus. Particle numbers were calculated from viral protein concentration (1 μg protein=$4 \times 10^{9}$ particles). Pfu was assayed by plaquing on 211B cells (see above). 211B cells (see below). Ad5.βgal.ΔF was also found to plaque more slowly than the control virus. When plated on 211B cells, Ad5.βgal.wt plaques appeared within 5–7 days, while plaques of Ad5.βgal.ΔF continued to appear until as much as 15–18 days post infection. Despite their slower formation, the morphology of Ad5.βgal.ΔF plaques was essentially normal.

4. Production of Fiberless Ad5.βgal.ΔF Particles

As Ad5.βgal.ΔF represents a true fiber null mutation and its stocks are free of helper virus, the fiber mutant phenotype was readily investigated. A single round of growth in cells (such as 293) which do not produce fiber generating a homogeneous preparation of fiberless Ad allowed for the determination of whether such particles would be stable and/or infectious. Either Ad5.βgal.wt or Ad5.βgal.ΔF was grown in 293 or 211B cells, and the resulting particles purified on CsCl gradients as previously described. Ad5.βgal.ΔF particles were readily produced in 293 cells at approximately the same level as the control virus and behaved similarly on the gradients, indicating that there was not a gross defect in morphogenesis of fiberless capsids (Table 1).

Figure 18:
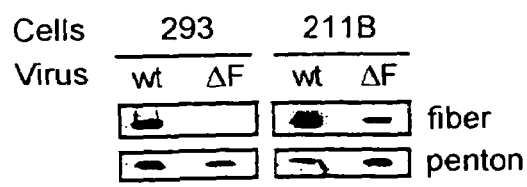
FIG. 18 shows the analysis of vertex proteins in the viral particles. 293 (non-fiber expressing) or 211B (fiber-expressing) cells were infected with Ad5.gal.wt ('wt') or with Ad5.βgal.ΔF ('ΔF') and the resulting viral particles were purified on CsCl gradients. 10 µg of purified virions was then electrophoresed on 5–16% gradient gels and Western blotted. Proteins were detected with polyclonal anti-fiber or anti-penton base antibodies.

As shown in FIG. 18, particles of either virus contained similar amounts of penton base regardless of the cell type in which they were grown. This demonstrated that fiber is not required for assembly of the penton base complex into virions. However, as predicted, the Ad5.βgal.ΔF particles produced in 293 cells did not contain fiber protein. 211B-grown Ad5.βgal.ΔF also contained less fiber than the Ad5.βgal.wt control virus (FIG. 18). Importantly, the infectivities of the different viral preparations on epithelial cells (Table 1) correlated with the amount of fiber protein present. The fiberless Ad particles were several thousand-fold less infectious than the first-generation vector control on a per-particle basis, while infectivity of 211B-grown Ad5.βgal.ΔF was only 50–100 fold less than that of Ad5.βgal.wt. These studies confirmed fiber's crucial role in infection of epithelial cells via CAR binding.

5. Composition and Structure of the Fiberless Ad5.βgal.ΔF Particles

The proteins contained in particles of 293-grown Ad5.βgal.ΔF were compared to those in Ad5.βgal.wt, to determine whether proteolysis or particle assembly was defective in this fiber null mutant (data not shown). The overall pattern of proteins in the fiberless particles was observed to be quite similar to that of a first-generation vector, with the exception of reduced intensity of the composite band resulting from both proteins IIIa and IV (fiber) (data not shown). The fiberless particles also had a reduced level of protein VII. Although substantial amounts of uncleaved precursors to proteins VI, VII, and VIII were not seen, it is possible that the low-molecular weight bands migrating ahead of protein VII represent either aberrantly cleaved viral proteins or their breakdown products.

Cryo-electron microscopy was used to more closely examine the structure of the 293 grown Ad5.βgal.ΔF and of Ad5.βgal.wt. The fiber, which consists of an extended stalk with a knob at the end, was faintly visible in favorable orientations of wild-type Ad5 particles, but not in images of the fiberless particles (data not shown). Filamentous material likely corresponding to free viral DNA was seen in micrographs of fiberless particles. This material was also present in micrographs of the first-generation control virus, albeit at much lower levels.

Three-dimensional image reconstructions of fiberless and wild-type particles at ~20 Å resolution showed similar sizes and overall features, with the exception that fiberless particles lacked density corresponding to the fiber protein. The densities corresponding to other capsid proteins, including penton base and proteins IIIa, VI, and IX, were comparable in the two structures. This confirms that absence of fiber does not prevent assembly of these components into virions. The fiber was truncated in the wild-type structure as only the lower portion of its flexible shaft follows icosahedral symmetry. The RGD protrusions on the fiberless penton base were angled slightly inward relative to those of the wild-type structure. Another difference between the two penton base proteins was that there is a ~30 Å diameter depression in the fiberless penton base around the five-fold axis where the fiber would normally sit. The Ad5 reconstructions confirm that capsid assembly, including addition of penton base to the vertices, is able to proceed in the complete absence of fiber.

6. Integrin-Dependent Infectivity of Fiberless Ad5.βgal.ΔF Particles

While attachment via the viral fiber protein is a critical step in the infection of epithelial cells, an alternative pathway for infection of certain hematopoietic cells has been described. In this case, penton base mediates both binding to the cells (via β2 integrins) and internalization (through interaction with αv integrins). Particles lacking fiber might therefore be expected to be competent for infection of these cells, even though on a per-particle basis they are several thousand-fold less infectious than normal Ad vectors on epithelial cells.

To investigate this, THP-1 monocytic cells were infected with Ad5.βgal.wt or with Ad5.βgal.ΔF grown in the absence of fiber. Infection of THP-1 cells was assayed by infecting $2 \times 10^{5}$ cells at the indicated m.o.i. in 0.5 ml of complete RPMI. Forty-eight hours post-infection, the cells were fixed with glutaraldehyde and stained with X-gal, and the percentage of stained cells was determined by light microscopy.

Figure 19A:
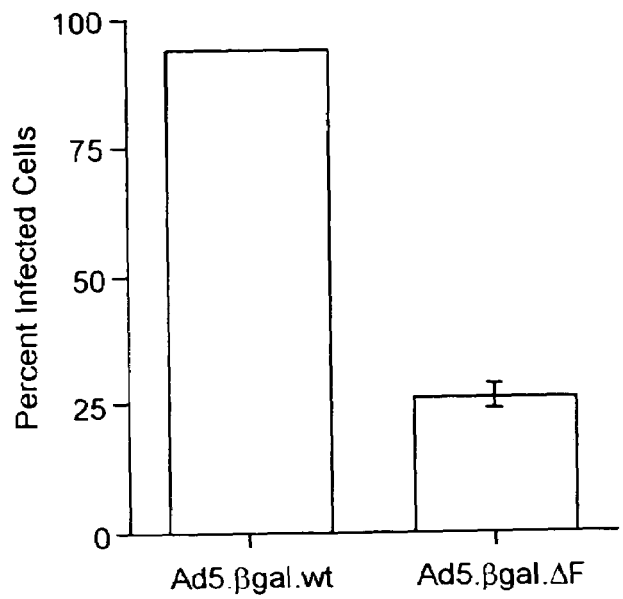
FIG. 19A shows THP-1 cells that were infected with Ad5.βgal.wt or with fiberless Ad5.βgal.ΔF at 100,000 particles/cell. Forty-eight hours after infection, cells were fixed and stained with X-gal and the fraction of infected cells was determined by light microscopy.
Figure 19B:
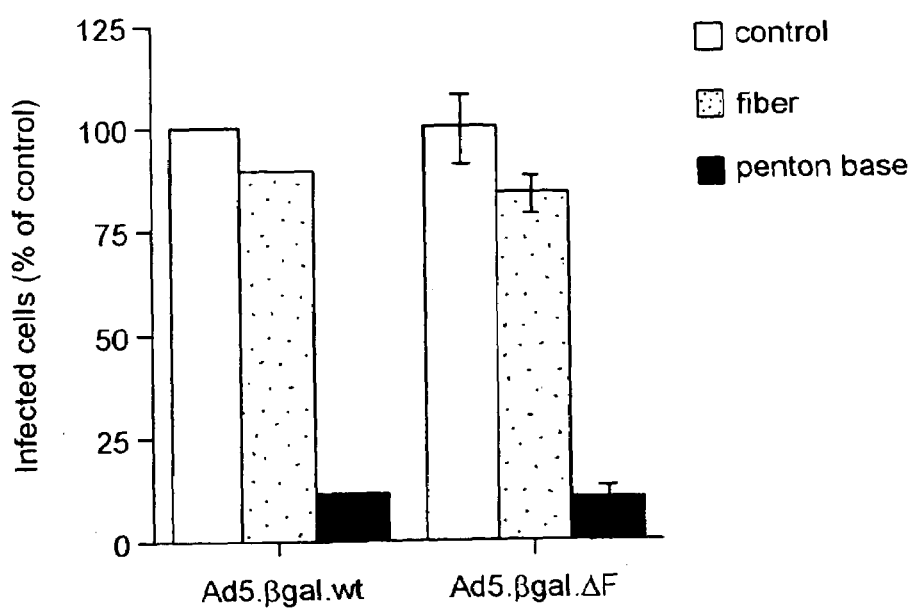
FIG. 19B shows cells that were infected with 1000 particles per cell of Ad5.βgal.wt or with 100,000 particles/cell of Ad5.gal.ΔF. As indicated, cells were pretreated with 100 µg/ml of recombinant penton base or with 20 µg/ml of recombinant Ad2 fiber.

The results of the infection assay showed that the fiberless particles were only a few-fold less infectious than first-generation Ad on TBP-1 cells (FIG. 19A). In contrast to this, very large differences were seen in plaquing efficiency on epithelial (211B) cells (Table 1). Infection of TEP-1 cells by either Ad5.βgal.ΔF or Ad5.βgal.wt was not blocked by an excess of soluble recombinant fiber protein, but could be inhibited by the addition of recombinant penton base (FIG. 19B). These results indicate that the fiberless Ad particles use a fiber-independent pathway to infect these cells. Furthermore, the lack of fiber protein did not prevent Ad5.βgalΔF from internalizing into the cells and delivering its genome to the nucleus, demonstrating that fiberless particles are properly assembled and are capable of uncoating.

The foregoing results with the recombinant viruses thus produced indicates that they can be used as gene delivery tools both in cultured cells and in vivo as described more fully in the Examples. For example, for studies of the effectiveness and relative immunogenicity of multiply-deleted vectors, virus particles are produced by growth in the packaging lines described in Example 1 and are purified by CsCl gradient centrifugation. Following titering, virus particles are administered to mice via systemic or local injection or by aerosol delivery to lung. The LacZ reporter gene allows the number and type of cells which are successfully transduced to be evaluated. The duration of transgene expression is evaluated in order to determine the long-term effectiveness of treatment with multiply-deleted recombinant adenoviruses relative to the standard technologies which have been used in clinical trials to date. The immune response to the improved vectors described here is determined by assessing parameters such as inflammation, production of cytotoxic T lymphocytes directed against the vector, and the nature and magnitude of the antibody response directed against viral proteins.

Versions of the vectors which contain therapeutic genes such as CFTR for treatment of cystic fibrosis or tumor suppressor genes for cancer treatment are evaluated in the animal system for safety and efficiency of gene transfer and expression. Following this evaluation, they are used as experimental therapeutic agents in human clinical trials.

B. Retargeting of Adenoviral Gene Delivery Vectors by Producing Viral Particles Containing Different or Altered Fiber Proteins As the specificity of adenovirus binding to target cells is largely determined by the fiber protein, viral particles that incorporate modified fiber proteins or fiber proteins from different adenoviral serotypes (pseudotyped vectors) have different specificities. Thus, the methods of expression of the native Ad5 fiber protein in adenovirus packaging cells as described above is also applicable to production of different fiber proteins.

In one aspect of invention, chimeric fiber proteins are produced according to the methods of Stevenson et al., *J. Virol.*, 69:2850–2857 (1995). The authors showed that the determinants for fiber receptor binding activity are located in the head domain of the fiber and that isolated head domain is capable of trimerization and binding to cellular receptors. The head domains of adenovirus type 3 (Ad3) and Ad5 were exchanged in order to produce chimeric fiber proteins. Similar constructs for encoding chimeric fiber proteins for use in the methods of this invention are contemplated. Thus, instead of the using the intact Ad5 fiber-encoding construct prepared in Example 1 as a complementing viral vector in adenoviral packaging cells, the constructs described herein are used to transfect cells along with E4 and/or E1-encoding constructs.

Briefly, full-length Ad5 and Ad3 fiber genes were amplified from purified adenovirus genomic DNA as a template. The Ad5 and Ad3 nucleotides sequences are available with the respective GenBank Accession Numbers M18369 and M12411. Oligonucleotide primers are designed to amplify the entire coding sequence of the full-length fiber genes, starting from the start codon, ATG, and ending with the termination codon TAA. For cloning purposes, the 5' and 3' primers contain the respective restriction sites BamHI and NotI for cloning into pcDNA plasmid as described in Example 1A. PCR is performed as described above.

The resultant products are then used to construct chimeric fiber constructs by PCR gene overlap extension, as described by Horton et al., *BioTechniques*, 8:525–535 (1990). The Ad5 fiber tail and shaft regions (5TS; the nucleotide region encoding amino acid residue positions 1 to 403) are connected to the Ad3 fiber head region (3H; the nucleotide region encoding amino acid residue positions 136 to 319) to form the 5TS3H fiber chimera. Conversely, the Ad3 fiber tail and shaft regions (3TS; the nucleotide region encoding amino acid residues positions 1 to 135) are connected to the Ad5 fiber head region (5H; the nucleotide region encoding the amino acid residue positions 404 to 581) to form the 3TS5H fiber chimera. The fusions are made at the conserved TLWT (SEQ ID NO: 19) sequence at the fiber shaft-head junction.

The resultant chimeric fiber PCR products are then digested with BamHI and NotI for separate directional ligation into a similarly digested pcDNA 3.1. The TPL sequence is then subcloned into the BamHI as described in Example 1A for preparing an expression vector for subsequent transfection into 211 cells as described above or into the alternative packaging cell systems as previously described. The resultant chimeric fiber construct-containing adenoviral packaging cell lines are then used to complement adenoviral delivery vectors as previously described. Other fiber chimeric constructs are obtained using a similar approach with the various adenovirus serotypes known.

In an alternative embodiment, the methods of this invention contemplate the use of the modified proteins including novel epitopes as described by Michael et al., *Gene Therapy*, 2:660–668 (1995) and in International Publication WO 95/26412, the disclosures of which are incorporated by reference herein. Both publications describe the construction of a cell-type specific therapeutic viral vector having a new binding specificity incorporated into the virus concurrent with the destruction of the endogenous viral binding specificity. In particular, the authors described the production of an adenoviral vector encoding a gastrin releasing peptide (GRP) at the 3' end of the coding sequence of the Ad5 fiber gene. The resulting fiber-GRP fusion protein was expressed and shown to assemble functional fiber trimers that were correctly transported to the nucleus of HeLa cells following synthesis.

Based on the teachings in the paper and International Publication, similar constructs are contemplated for use in the complementing adenoviral packaging cell systems of this invention for generating new adenoviral gene delivery vectors that are targetable, replication-deficient and less immunogenic. Heterologous ligands contemplated for use herein to redirect fiber specificity range from as few as 10 amino acids in size to large globular structures, some of which necessitate the addition of a spacer region so as to reduce or preclude steric hindrance of the heterologous ligand with the fiber or prevent trimerization of the fiber protein. The ligands are inserted at the end or within the linker region. Preferred ligands include those that target specific cell receptors or those that are used for coupling to other moieties such as biotin and avidin.

A preferred spacer includes a short 12 amino acid peptide linker composed of a series of serines and alanine flanked by a proline residue at each end. One of ordinary skill in the art is familiar with the preparation of linkers to accomplish sufficient protein presentation and for altering the binding specificity of the fiber protein without compromising the cellular events that follow viral internalization. Moreover, within the context of this invention, preparation of modified fibers having ligands positioned internally within the fiber protein and at the carboxy terminus as described below are contemplated for use with the methods described herein.

The preparation of a fiber having a heterologous binding ligand is prepared essentially as described in the above-cited paper. Briefly, for the ligand of choice, site-directed mutagenesis is used to insert the coding sequence for a linker into the 3' end of the Ad5 fiber construct in pCLF as prepared in Example 1.

The 3' or antisense or mutagenic oligonucleotide encodes a preferred linker sequence of ProSerAlaSerAlaSerAlaSer-AlaProGlySer (SEQ ID NO: 20) followed by a unique restriction site and two stop codons, respectively, to allow the insertion of a coding sequence for a selected heterologous ligand and to ensure proper translation termination. Flanking this linker sequence, the mutagenic oligonucloetide contains sequences that overlap with the vector sequence and allo its incorporation into the construct. Following mutagenesis of the pCLF sequence adding the linker and stop codon sequences, a nucleotide sequence encoding a preselected ligand is obtained, linkers corresponding to the unique restriction site in the modified construct are attached and then the sequence is cloned into linearized corresponding restriction site.

The resultant fiber-ligand construct is then used to transfect 211 or the alternative cell packaging systems previously described to produce complementing viral vector packaging systems for use with the methods of this invention.

In a further embodiment, intact fiber genes from different Ad serotypes are expressed by 211 cells or an alternative packaging system as previously described. A gene encoding the fiber protein of interest is first cloned to create a plasmid analogous to pCLF, and stable cell lines producing the fiber protein are generated as described above for Ad5 fiber. The adenovirus vector described which lacks the fiber gene is then propagated in the cell line producing the fiber protein relevant for the purpose at hand. As the only fiber gene present is the one in the packaging cells, the adenoviruses produced contain only the fiber protein of interest and therefore have the binding specificity conferred by the complementing protein. Such viral particles are used in studies such as those described above to determine their properties in experimental animal systems.

Example 3

Deposit of Materials

The following cell lines and plasmids have been deposited on Sep. 25, 1996, with the American Type Culture Collection, 10801 University Blvd, Manassas, Va., USA (ATCC) under the provisions of the Budapest Treaty on the International Recognition of the Deposit of Microorganisms for the Purpose of Patent Procedure and the Regulations thereunder (Budapest Treaty):Plasmid pE4/Hygro (accession number 97739), Plasmid pCLF (accession number 97737), 211 Cell Line (accession number CRL-12193) and 211A Cell Line (accession number CRL-12194)

The following virus, Ad5.βgal.ΔF, was deposited on Jan. 15, 1999, with the ATCC as listed above and provided with accession number VR2636.

Additionally, plasmids pDV60, pDV67, pDV69, pDV80 and pDV90 were deposited at the ATCC on Jan. 5, 2000 and provided with accession numbers PTA-1144, PTA-1145, PTA-1146, PTA-1147 and PTA-1148 respectively.

Example 4

Complementation of Fiber-Defective and Fiber-Modified Virus

The native fiber protein is a homotrimer (Henry L. J. et al., J. Virol. 68:5239–5246 (1994)), and trimerization is essential for assembly of the penton/fiber complex (Novelli A et al., J. Biol. Chem. 266:9299–9303 (1991)). To assess the multimeric structure of the recombinant fiber protein produced by the cell lines, cells were labeled with 50 μCi/ml [$^{35}$S] Translabel (ICN) for two hours at 37° C., lysed in RIPA buffer, and fiber protein was immunoprecipitated as described (Harlow E et a., Antibodies. Cold Spring Harbour Laboratory, Cold Spring Harbor (1988). Immune complexes were collected on Protein A-Sepharose beads (Pierce), extensively washed with RIPA buffer, and incubated at room temperature in 0.1 M triethylamine, pH 11.5 to release bound fiber protein. A portion of the precipitated fiber was electrophoresed on a 8% SDS-PAGE gel under denaturing (1% SDS in loading buffer, samples boiled for 5 minutes) or semi-native (0.1% SDS in loading buffer, samples not heated) conditions.

As seen in FIG. 13, lines 211A, 211B, and 211R, but not the control 293 cells, expressed an immunologically reactive protein which migrated at the predicted molecular weight for trimer (186 kD) under seminative conditions and for monomer (62 kD) under denaturing conditions. The behavior of the precipitated fiber was indistinguishable from that of purified baculovirus-produced recombinant Ad2 fiber (Wickham T et al., Cell 73:309–319 (1993)) (the 58 kD Ad2 and 62 kD Ad5 fibers have very similar mobilities under these conditions).

To determine whether the fiber-expressing lines could support the growth of a fiber-defective adenovirus, we performed one-step growth experiments using the temperature-sensitive fiber mutant Ad H5ts142 (the gift of Harold Ginsberg). At the restrictive temperature (39.5° C.), this mutant produces an underglycoslyated fiber protein which is not incorporated into mature virions (Chee-Sheung C. C et al., J. Virol 42: 932–950 (1982)). This results in the accumulation of non-infectious viral particles. We asked whether the recombinant fiber protein expressed by our cell lines could complement the H5ts142 defect and rescue viral growth.

Figure 14:
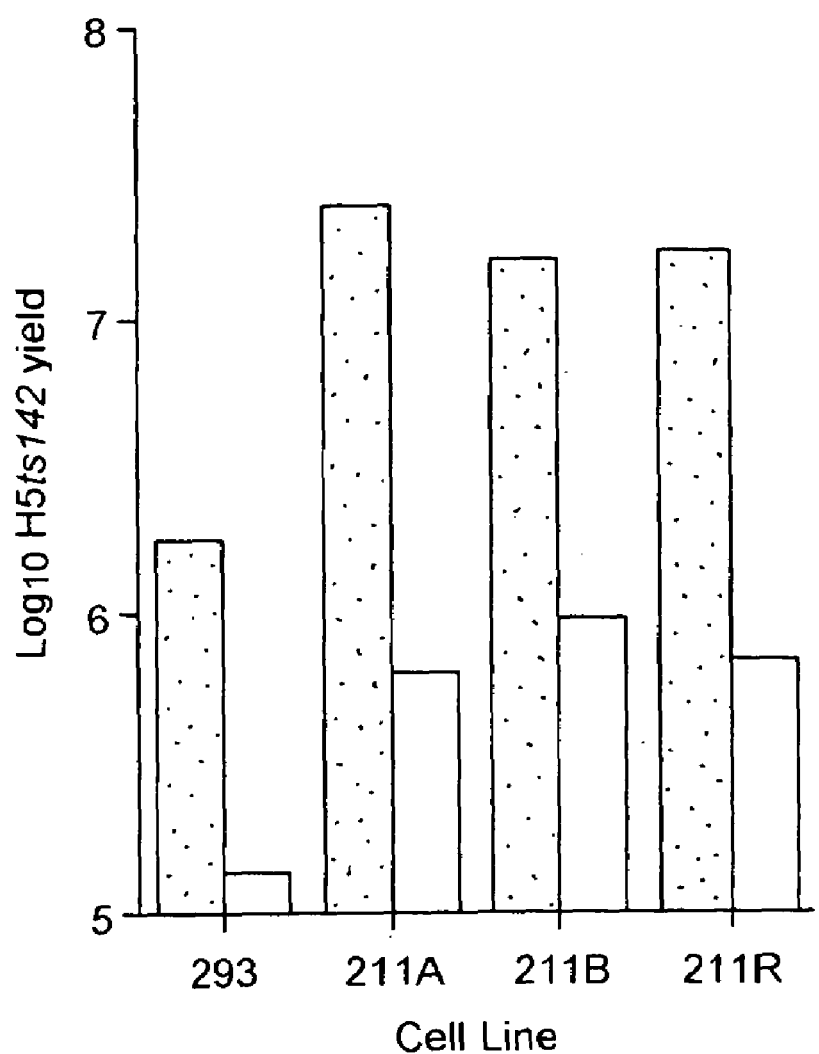
FIG. 14 shows the complementation of a fiber mutant adenovirus by fiber-producing cells. The cell lines indicated ($2 \times 10^6$ cells per sample) were infected with the temperature-sensitive fiber mutant adenovirus H5ts142 at 10 PFU/cell and incubated at either the permissive (32.5° C., stippled bars) or the restrictive (39.5° C., solid bars) temperature. 48 hours post-infection, virus was isolated by freeze-thaw lysis and yields determined by fluorescent focus assay on SW480 cells. Each value represents the mean of duplicate samples, and the data shown is representative of multiple experiments.

Cell lines 293, 211A, 211B and 211R (2×10$^6$ cells/sample) were infected with H5ts142 at 10 pfu/cell. 48 hours later, cells were detached with 25 mM EDTA and virus was harvested by four rapid freeze-thaw cycles. Debris was removed by a 10 minute spin at 1500×g, and viral titers determined by fluorescent focus assay (Thiel J. F et al., Proc. Soc. Exp. Biol. Med. 125:892–895 (1967)) on SW480 cells with a polyclonal anti-penton base Ab (Wickham T et al., Cell 73:309–319 (1993)). As shown in FIG. 14, the fiber mutant virus replicated to high titers in 293 cells at 32.5° C. (the permissive temperature), but to a much lower extent at the restrictive temperature of 39.5° C. The fiber-producing packaging lines 211A, 211B, or 211R supported virus production at 39° C. to levels within two- to three-fold of those seen at the permissive temperature in 293 cells, indicating that these cells provided partial complementation of the fiber defect.

Interestingly, virus yields from the fiber-producing cell lines were also somewhat higher than those from 293 cells at 32.5° C. (the 'permissive' temperature). This suggests that fiber produced by the ts142 virus may be partially defective even at the permissive temperature. Alternatively, a non-specific increase in adenoviral titer could result when viruses are grown in the packaging cells, by a mechanism not involving fiber complementation. However, it was found that viruses with wild type fiber genes (such as Ad.RSVβgal) replicate to identical levels either in our packaging lines or in 293 cells (data not shown). Taken together, these results demonstrate that the observed increase in H5ts142 growth is due to specific complementation of the fiber mutation.

Even in the fiber-expressing cell lines, the fiber mutant grows to higher titers at 32° C. than at 39.5° C. This incomplete complementation may be due to the packaging lines' expression of fiber at a level somewhat below that seen in a wild-type infection (data not shown). A recent study reported an E4-deleted vector which coincidentally reduced fiber protein expression, resulting in a large reduction in the titer of virus produced (Brough et al., *J. Virol.* 70:6497–6501 (1996)). Another possibility is that the defective ts142 fiber protein produced at the restrictive temperature might form complexes with some of the wild type protein produced by the cells and prevent its assembly into particles.

Figures 15A, 15B:
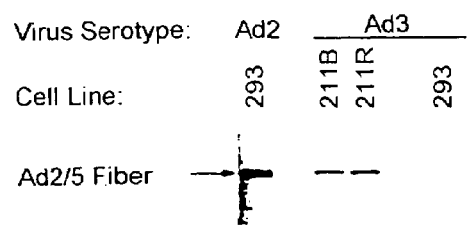
In FIG. 15A, the alignment of the N-terminal (penton base-binding) domains of fiber proteins from several different adenovirus serotypes is shown. From top to bottom, the five different serotypes are listed as SEQ ID NOs 21–25.
In FIG. 15B, type 3 adenovirus was propagated in 293, 211B, or 211R cells as indicated and purified by two sequential CsCl centrifugations. 10 µg of the purified viral particles was then electrophoresed under denaturing conditions and transferred to a PVDF membrane. Ad5 fiber was detected with a polyclonal rabbit antibody raised against recombinant Ad2 fiber. As a positive control for detection, 400 ng of wild-type Ad2 was run in the lane marked "Ad2". Under these conditions, the mobilities of the Ad2 and Ad5 fibers are indistinguishable and the antibody reacts with both proteins.

Although the fiber proteins of different Ad serotypes differ in the length of their shaft domains and in their receptor-binding knob domains, the N-terminal regions responsible for interaction with the viral penton base are highly conserved Arnberg N et al., *Virology* 227:239–244 (1997)) (FIG. 15A). This suggests that fibers from many viral serotypes, with their different cell-binding specificities, may be amenable for use in producing gene delivery vectors.

In order to determine whether the recombinant Ad5 fiber produced by the packaging cells could be incorporated into particles of another adenovirus serotype, adenovirus type 3 was grown either in fiber-producing cell lines or in 293 cells. Viral particles were purified by two sequential centrifugations (3 h at 111,000×g) on preformed 15–40% CsCl gradients to remove soluble cellular proteins and then dialyzed extensively against 10 mM Tris-HCl, pH 8.1, 150 mM NaCl, 10% glycerol. Ad5 fiber protein was detected by immunoblotting using the polyclonal anti-fiber serum, followed by detection with a horseradish peroxidase-conjugated goat anti-rabbit antibody (Kirkegaard and Perry Laboratories) and the ECL chemiluminescence substrate (Amersham). The purified Ad3 particles contained Ad5 fiber protein after a single passage through a fiber-expressing cell line but not after passage through 293 cells (FIG. 15B). Previous work has demonstrated that Ad2 fiber is capable of interacting in vitro with Ad3 penton base (Fender et al., *Nature Biotech.* 15:52–56 (1997)), and our result demonstrates that the type 5 fiber protein produced by the cells is capable of assembling into complete Ad3 particles.

A vector based on Ad5 but containing the gene for the Ad7 fiber protein has been described (Gall J. et al., *J. Virol.* 70:2116–2123 (1996)), as well as Ads containing chimeric fiber genes (Krasnykh et al., *J. Virol.* 70:6839–6846 (1996) and Stevenson et al., *J. Virol.* 69:2850–2857 (1995)). Chimeric Ad5/Ad3 vectors have also been reported (Stevenson, S. el al., *J. Virol.* 71:4782–4790, (1997). Addition of a short peptide linker to the fiber in order to confer binding to a different cellular protein has also been reported (Michael et al., *Gene Therapy* 2:660–668 (1995). By using packaging technology such as that presented here, Ad vectors equipped with different fiber proteins may be produced simply by growth in cells expressing the fiber of interest, without the time-consuming step of generating a new vector genome for each application.

Replacing or modifying the fiber gene in the vector chromosome would also require that the new fiber protein bind a receptor on the surface of the cells it which it is to be grown. The packaging cell approach will allow the generation of Ad particles containing a fiber which can no longer bind to its host cells, by a single round of growth in cells expressing the desired fiber gene. This will greatly expand the repertoire of fiber proteins which can be incorporated into particles, as well as simplifying the process of retargeting gene delivery vectors.

Finally, a novel fiber-independent pathway of infection has recently been described in hematopoietic cells, in which penton base provides the initial virus-cell interaction by binding to integrin $a_m b_2$ (Huang S. et al, *J. Virol* 70: 4502–4508 (1996)). This suggests that viral particles lacking fiber protein may be useful in targeting gene delivery to specific cell types via this pathway.

Example 5

Preparation of Alternative TPLs

The present invention contemplates the use of tripartite leader sequences (TPLs) that are useful in enhancing the expression of complementing adenoviral proteins, particularly fiber protein, for use in preparing an adenoviral gene delivery vector. One preferred TPL is the complete Ad5 tripartite leader contained in complementing vectors such as pDV67 and pDV69, both of which are prepared as described below. The complete Ad5 TPL was constructed by assembling PCR fragments. First, the third TPL exon (exon 3) (nt 9644–9731 of the Ad5 genome) was amplified from Ad5 genomic DNA using the synthetic oligonucleotide primers 5'CTCAACAATTGTGGATCCGTACTCC3'(SEQ ID NO: 28) and 5'GTGCTCAGCAGATCTTGCGACTGTG3' (SEQ ID NO: 29). The resulting product was cloned to the BamHI and BglII sites of pΔE1Sp1a (Microbix Biosystems) using novel sites in the primers (shown in bold) to create plasmid pDV52. A fragment corresponding to the first TPL exon (exon 1), the natural first intron (intron 1), and the second TPL exon (exon 2) (Ad5 nt 6049–7182) was then amplified using primers 5'GGCGCGTTCGGATCCACTCTCTTCC3' (SEQ ID NO:30) and 5'CTA CATGCTAGGCA-GATCTCGTTCGGAG3' (SEQ ID NO: 31), and cloned into the BamHI site of pDV52 (again using novel sites in the primers) to create pDV55. This plasmid contains a 1.2 kb BamHI/BglII fragment consisting of the first TPL exon, the natural first intron, and the fused second and third TPL exons. The nucleotide sequence of the complete TPL containing the noted 5' and 3' restriction sites is shown in SEQ ID NO: 32 with the following nucleotide regions identified: 1–6 nt BamHI site; 7–47 nt first leader segment (exon 1); 48–1068 nt natural first intron (intron 1); 1069–1140 nt second leader segment (exon 2); 1141–1146 nt fused BamHI and BglII sites; 1147–1234 nt third leader segment (exon 3); and 1235–1240 nt BglII site.

TPLs fragments containing two of the three exons, exons in non-native order, or containing either the first or second TPL intron are also constructed for use in preparing complementing plasmids for use in the methods of the present invention. Briefly, DNA fragments containing any combination of 2 TPL exons can be constructed as follows: Exon 1 is amplified from genomic DNA as prepared above by using the oligonucleotides 5'GGCGCGTTCGGATC-CACTCTCTTCC3'(SEQ ID NO: 33) and 5'GGGAGTA-GATCTCCCAACAG3' (SEQ ID NO: 34). Exon 2 is similarly amplified from the same genomic DNA using oligonucleotides 5'CCCTTTTTTTTGGATCCCTCGCGG3' (SEQ ID NO: 35) and 5'CTACATGCTAGGCA-GATCTCGTTCGGAG3' (SEQ ID NO: 36). Exon 3 is amplified using the oligonucleotides 5'CTCAACAATTGT-TGGATCCGTACTCC3' (SEQ ID NO: 37) and 5'GTGCT-CAGCAGATCTTGCGACTGTG3' (SEQ ID NO: 38).

The amplified exons are ligated together in any desired number and/or order by virtue of the unique BamHI and BglII restriction sites (bold) in the primers for subsequent ligation into a construct analogous to pDV67, prepared as described below, for expression of viral structural genes.

Similarly, a fragment consisting of the first TPL exon (exon 1), the native first intron (intron 1), and the second TPL exon (exon 2) is produced by amplification from Ad5 genomic DNA with the oligonucleotide pair 5'GGCGCGT-TCGGATCC ACTCTCTTCC3' (SEQ ID NO: 39) and 5'CTACATGCTAGGCAGATCT CGTTCGGAG3' (SEQ ID NO: 40). Finally, a fragment consisting of the second TPL exon (exon 2), the native second intron (intron 2), and the third TPL exon (exon 3) is produced by amplification using the oligonucleotides 5'CCCTTTTTTTTGGATCC CTCGCGG3' (SEQ ID NO: 41) and 5'GTGCTCAGCA-GATCTTGCGACTGTG3' (SEQ ID NO: 42). Either of the intron-containing fragments are used either alone or in combination with another TPL fragment(s) in constructs analogous to pDV67. Introns in addition to adenoviral intron 1 used herein that have been shown to increase the expression of recombinant proteins when included in expression constructs include SV40 VP1 intron, rabbit β-globin intron among others. The use of these alternative intron sequences are contemplated for use in preparing a TPL in the present invention.

Example 6

Preparation and Use of Adenoviral Packaging Cell Lines Containing Plasmids Containing Alternative TPLs Plasmids were first constructed as described below that contained TPLs are described above. The resultant plasmids containing different selectable markers such as neomycin or zeocin were then used to prepare stable cell lines for use as complementing vectors for preparing adenoviral vectors for use in the present invention. In a preferred embodiment, the resulting cell lines represent improvements over preexisting fiber-complementing cell lines in that fiber expression is enhanced with the use of alternative TPLs.

A. pDV60 pDV60 was constructed by inserting this TPL cassette of SEQ ID NO: 32 into the BamHI site upstream of the Ad5 fiber gene in pcDNA3/Fiber, a neomycin selectable plasmid, prepared as described in Example 1 and also as described by Von Seggern et al., *J. Gen Virol.*, 79: 1461 (1998). The nucleotide sequence of pDV60 is listed in SEQ ID NO: 43.

B. pDV61

To construct pDV61, an Asp718/NotI fragment containing the CMV promoter, partial Ad5 TPL, wildtype Ad5Ad2 fiber gene, and bovine growth hormone terminator was transferred from pCLE, prepared as described in Example 1 and also as described by Von Seggern et al., *J Gen Virol.*, 79: 1461 (1998), to a zeocin selectable cloning vector referred to as pCDNA3.1/Zeo (+) (commercially available from Invitrogen and the sequence is also available).

C. pDV67

In an analogous process, pDV67 containing complete TPL was constructed by transferring an Asp 718/XbaI fragment from pDV60 to the pcDNA3.1/Zeo(+) backbone. The nucleotide sequence of pDV67 is listed in SEQ ID NO: 44.

D. pDV69

To prepare pDV69 containing a modified fiber protein, the chimeric Ad3/Ad5 fiber gene was amplified from pGEM5TS3H (Stevenson et al., *J. Virol.*, 69: 2850–2857, 1995)) using the primers 5'ATGGGAT CAAGAT-GAAGCGCGCAAGACCG3' (SEQ ID NO: 45) and 5'CAC-TATAGCGGCCGCATTCTCAGTCATCTT3' (SEQ ID NO: 46), and cloned to the BamHI and NotI sites of pcDNA3.1/Zeo(+) via novel BamHI and NotI sites engineered into the primers to create pDV68. Finally, the complete TPL fragment described above was then added to the unique BamH1 site of pDV68 to create pDV69. The nucleotide sequence of pDV69 is listed in SEQ ID NO: 47.

E. Preparation of Stable Adenovirus Packaging Cell Lines

E1–2a S8 cells are derivatives of the A549 lung carcinoma line (ATCC #CCL 185) with chromosomal insertions of the plasmids pGRE5–2.E1 (also referred to as GRE5-E1-SV40-Hygro construct and listed in SEQ ID NO: 48) and pMNeoE2a-3.1 (also referred to as MMTV-E2a-SV40-Neo construct and listed in SEQ ID NO: 49), which provide complementation of the adenoviral E1 and E2a functions, respectively. This line and its derivatives were grown in Richter's modified medium (BioWhitaker)+10% FCS. E1–2a S8 cells were electroporated as previously described (Von Seggern et al., *J. Gen Virol.*, 79:1461(1998)) with pDV61, pDV67, or with pDV69, and stable lines were selected with zeocin (600 μg/ml). The cell line generated with pDV61 is designated 601. The cell line generated with pDV67 is designated 633 while that generated with pDV69 is designated 644. Candidate clones were evaluated by immunofluorescent staining with a polyclonal antibody raised against the Ad2 fiber. Lines expressing the highest level of fiber protein were further characterized.

For the S8 cell complementing cell lines, to induce E1 expression, 0.3 μM of dexamethasone was added to cell cultures 16–24 hours prior to challenge with virus for optimal growth kinetics. For preparing viral plaques, 5×10$^5$ cells/well in 6 well plates are prepared and pre-induced with the same concentration of dexamethasone the day prior to infection with 0.5 μM included at a final concentration in the agar overlay after infection.

F. Development of Cell Lines for Complementation of E1$^-$/E2a$^-$ Vectors

This example shows the construction of S.8 cells

Figure 23:
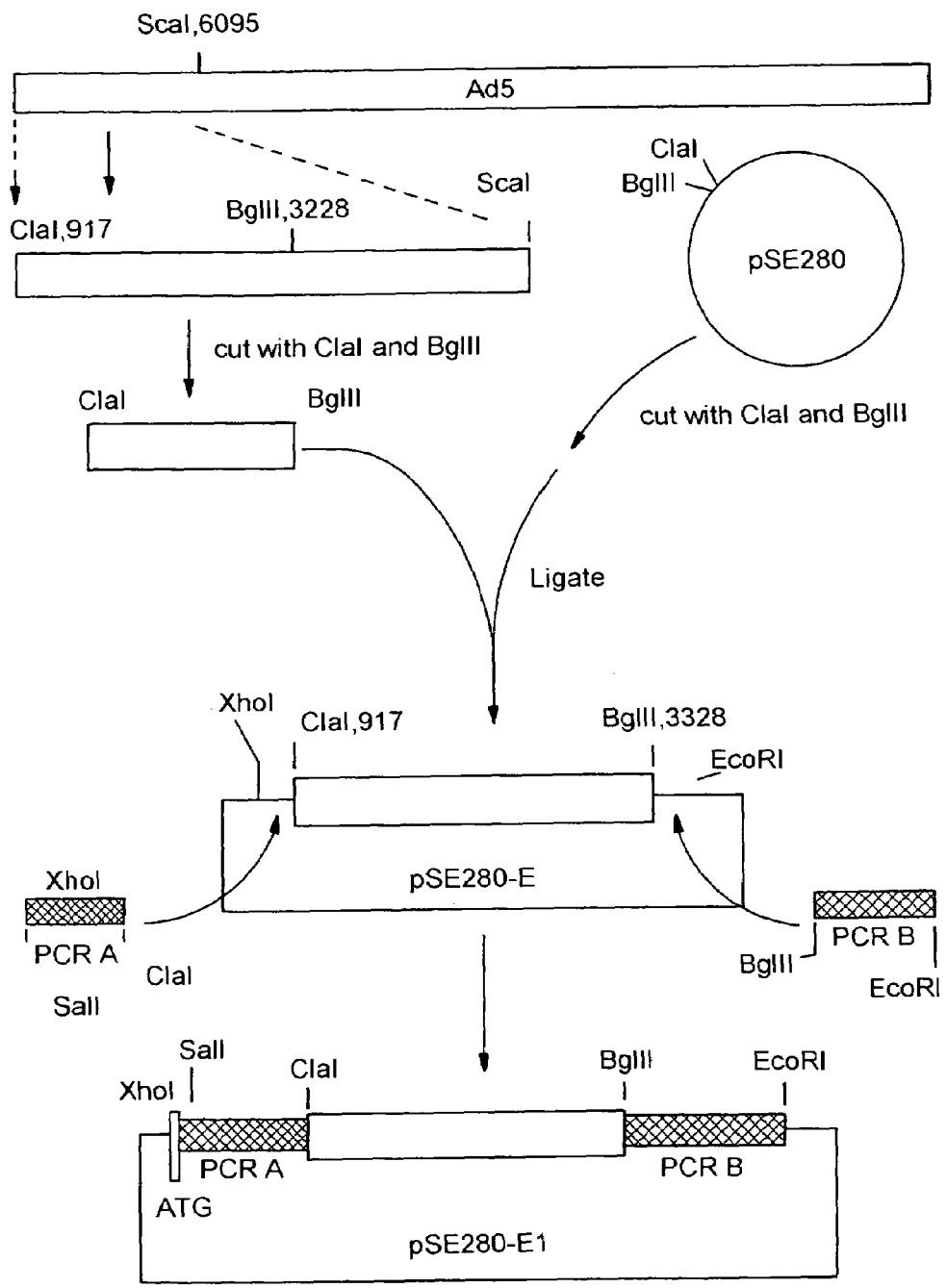
FIG. 23 shows the ClaI to BglII fragment of Ad5.

The Adenovirus 5 genome was digested with ScaI enzyme, separated on an agarose gel, and the 6,095 bp fragment comprising the left end of the virus genome was isolated. The complete Adenovirus 5 genome is registered as Genbank accession #M73260, incorporated herein by reference, and the virus is available from the American Type Culture Collection, Manassas, Va., U.S.A., under accession number VR-5. The ScaI 6,095 bp fragment was digested further with ClaI at bp 917 and BglII at bp 3,328. The resulting 2,411 bp ClaI to BglII fragment was purified from an agarose gel and ligated into the superlinker shuttle plasmid pSE280 (Invitrogen, San Diego, Calif.), which was digested with ClaI and BglII, to form pSE280-E. (FIG. 23).

Polymerase chain reaction (PCR) was performed to synthesize DNA encoding an XhoI and SalI restriction site contiguous with Adenovirus 5 DNA bp 552 through 924. The primers which were employed were as follows:

```
5' end, Ad5 bp 552–585:
5'-GTCACTCGAGGACTCGGTC-GACTGAAAATGAGACATATTATCTGCCA    (SEQ ID NO: 66)
CGGACC-3'

3' end, Ad5 bp 922–891:
5'-CGAGATCGATCACCTCCGGTACAAGGTTTGGCATAG-3'            (SEQ ID NO: 67)
```

This amplified DNA fragment (sometimes hereinafter referred to as Fragment A) then was digested with XhoI and ClaI, which cleaves at the native ClaI site (bp 917), and ligated to the XhoI and ClaI sites of pSE280-E, thus reconstituting the 5(end of the E1 region beginning 8 bp upstream of the ATG codon.

PCR then was performed to amplify Adenovirus 5 DNA from bp 3,323 through 4,090 contiguous with an EcoRI restriction site. The primers which were employed were as follows:

```
5' end, Ad5 bp 3323–3360:
5'-CATGAAGATCTGGAAGGTGCTGAGGTACGATGAGACC-3'           (SEQ ID NO: 68)

3' end, Ad5 bp 4090–4060:
5-GCGACTTAAGCAGTCAGCTG-AGACAGCAAGACACTTGCTTGATC-     (SEQ ID NO: 69)
CAAATCC-3'
```

This amplified DNA fragment (sometimes hereinafter referred to as Fragment B) was digested with BglII, thereby cutting at the Adenovirus 5BglII site (bp 3,382) and EcoRI, and ligated to the BglII and EcoRI sites of pSE280-AE to reconstruct the complete E1a and E1b region from Adenovirus 5 bp 552 through 4,090. The resulting plasmid is referred to as pSE280-E1 (FIG. 23).

Figure 24:
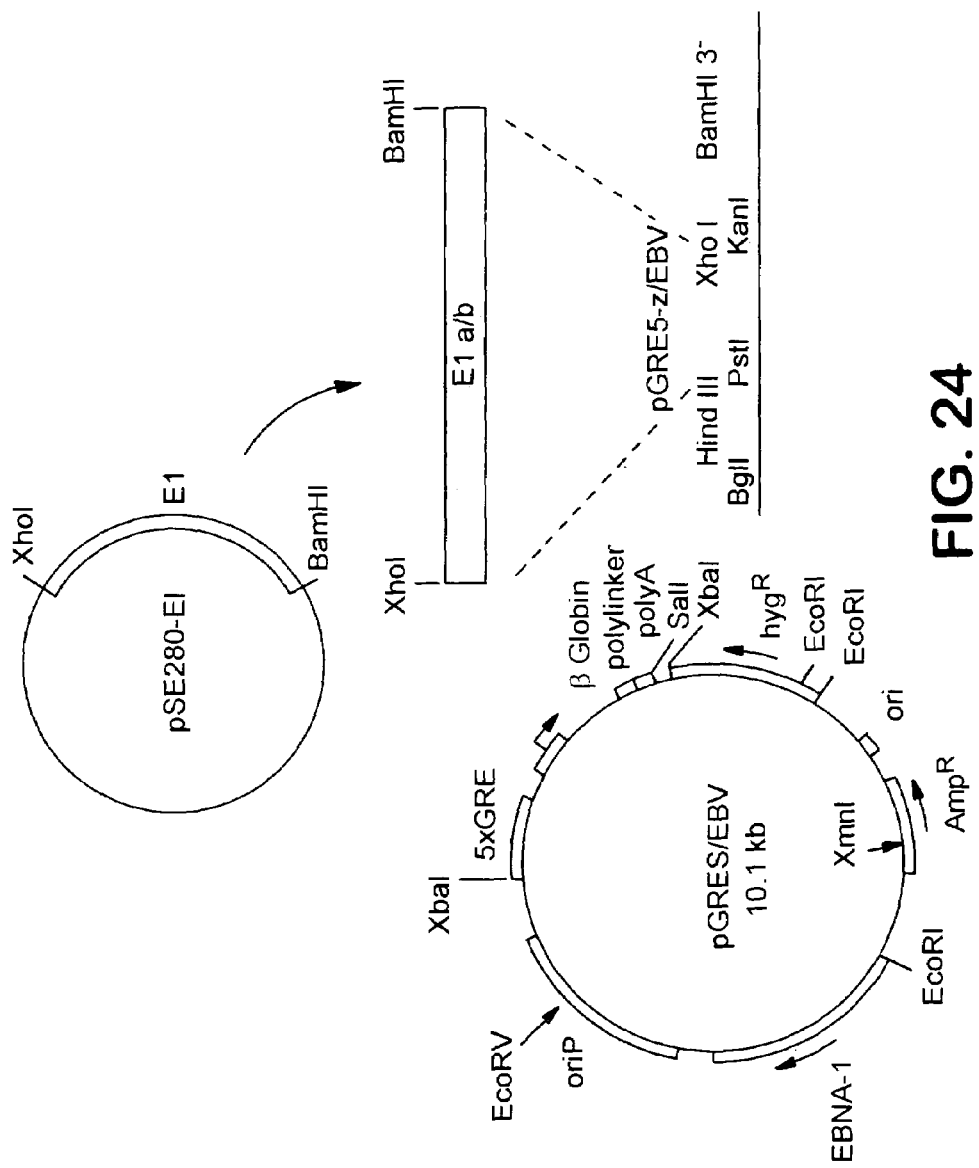
FIG. 24 shows the plasmid pGRE5-2/EBV
Figure 25:
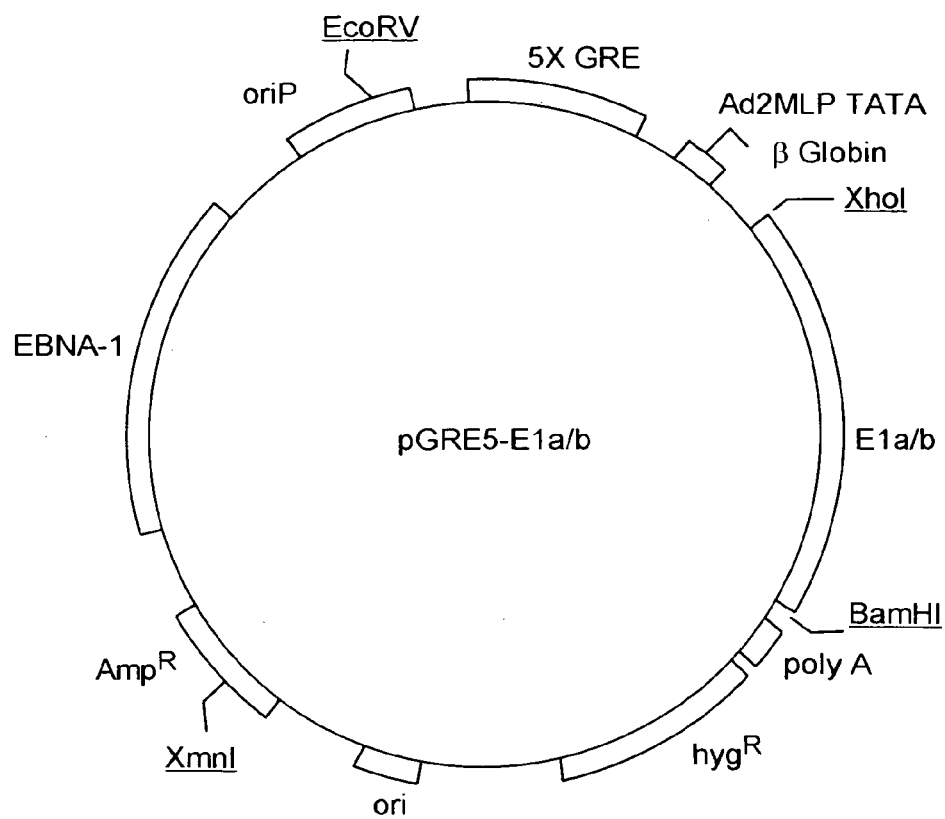
FIG. 25 shows the plasmid pGRE5-E1.

A construct containing the intact E1a/b region under the control of the synthetic promoter GRE5 was prepared as follows. The intact E1a/b region was excised from pSE280-E1, which was modified previously to contain a BamHI site 3' to the E1 gene, by digesting with XhoI and BamHI. The XhoI to BamHI fragment containing the E1a/b fragment was cloned into the unique XhoI and BamHI sites of pGRE5–2/EBV (FIG. 4, U.S. Biochemicals, Cleveland, Ohio) to form pGRE5-E1 (FIG. 24).

Bacterial transformants containing the final construct were identified. Plasmid DNA was prepared and purified by banding in CsTFA prior to use for transfection of cells.

Construction of Plasmid Including Adenovirus 5 E2A Sequence.

Figure 26:
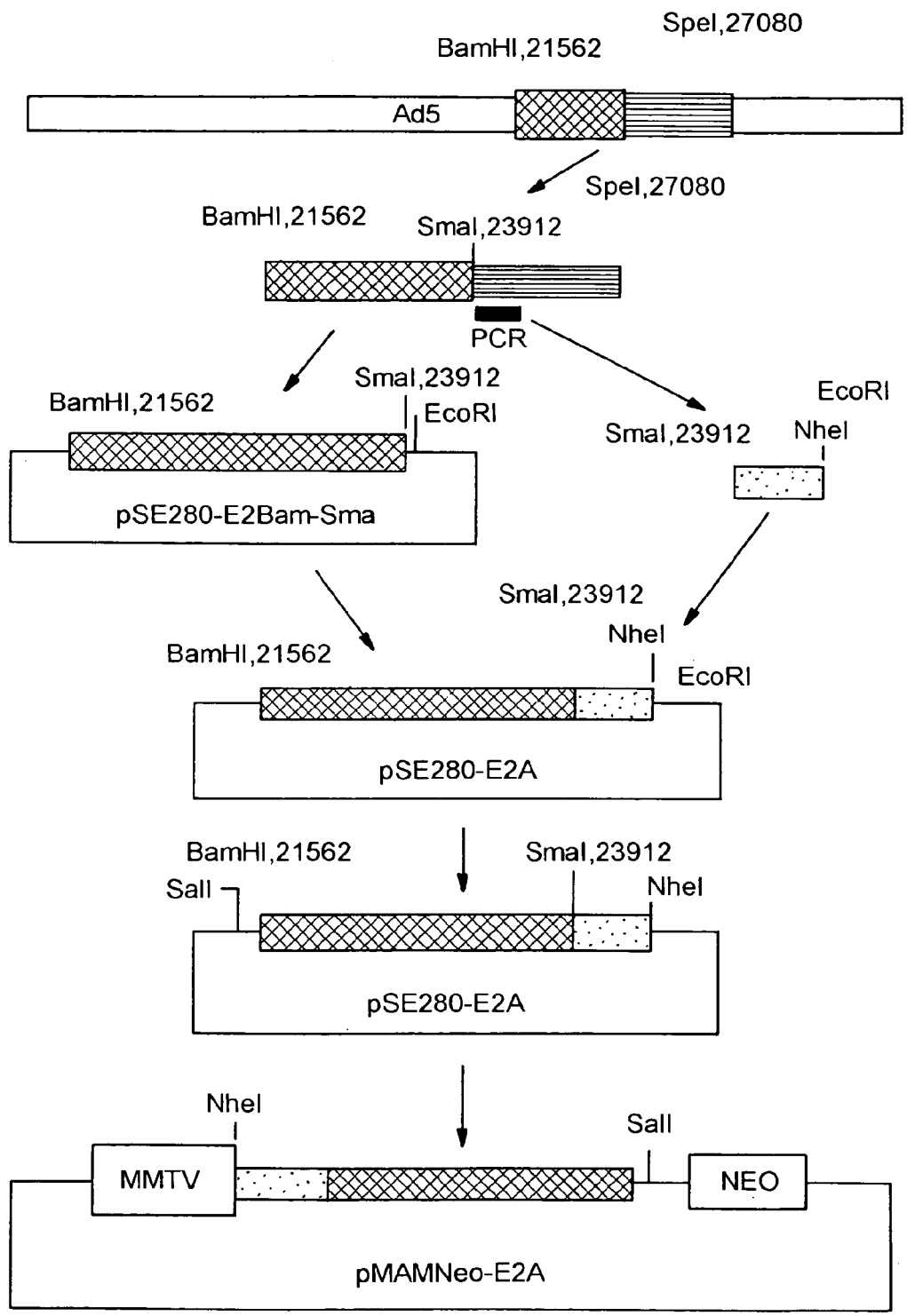
FIG. 26 shows the plasmid pSE280-E2 BamHI-SmaI.

The Adenovirus 5 genome was digested with BamHI and SpeI, which cut at bp 21,562 and 27,080, respectively. Fragments were separated on an agarose gel and the 5,518 bp BamHI to SpeI fragment was isolated. The 5,518 bp BamHI to SpeI fragment was digested further with SmaI, which cuts at bp 23,912. The resulting 2,350 bp BamHI to SmaI fragment was purified from an agarose gel, and ligated into the superlinker shuttle plasmid pSE280, and digested with BamHI and SmaI to form pSE280-E2BamHI-SmaI (FIG. 26).

PCR then was performed to amplify Adenovirus 5 DNA from the SmaI site at bp 23,912 through 24,730 contiguous with NheI and EcoRI restriction sites. The primers which were employed were as follows:

```
5' end, Ad5 bp                                        (SEQ ID NO: 70)
24,732–24,708:
5'-CACGAATTCGTCAGCGCTTCTCGTCGCGTCCAAGACCC-3'

3' end, Ad5 bp                                        (SEQ ID NO: 71)
23,912–23,934:
5'-CACCCCGGGGAGGCGGCGGCGACGGGGACGGG-3'
```

Figure 27:
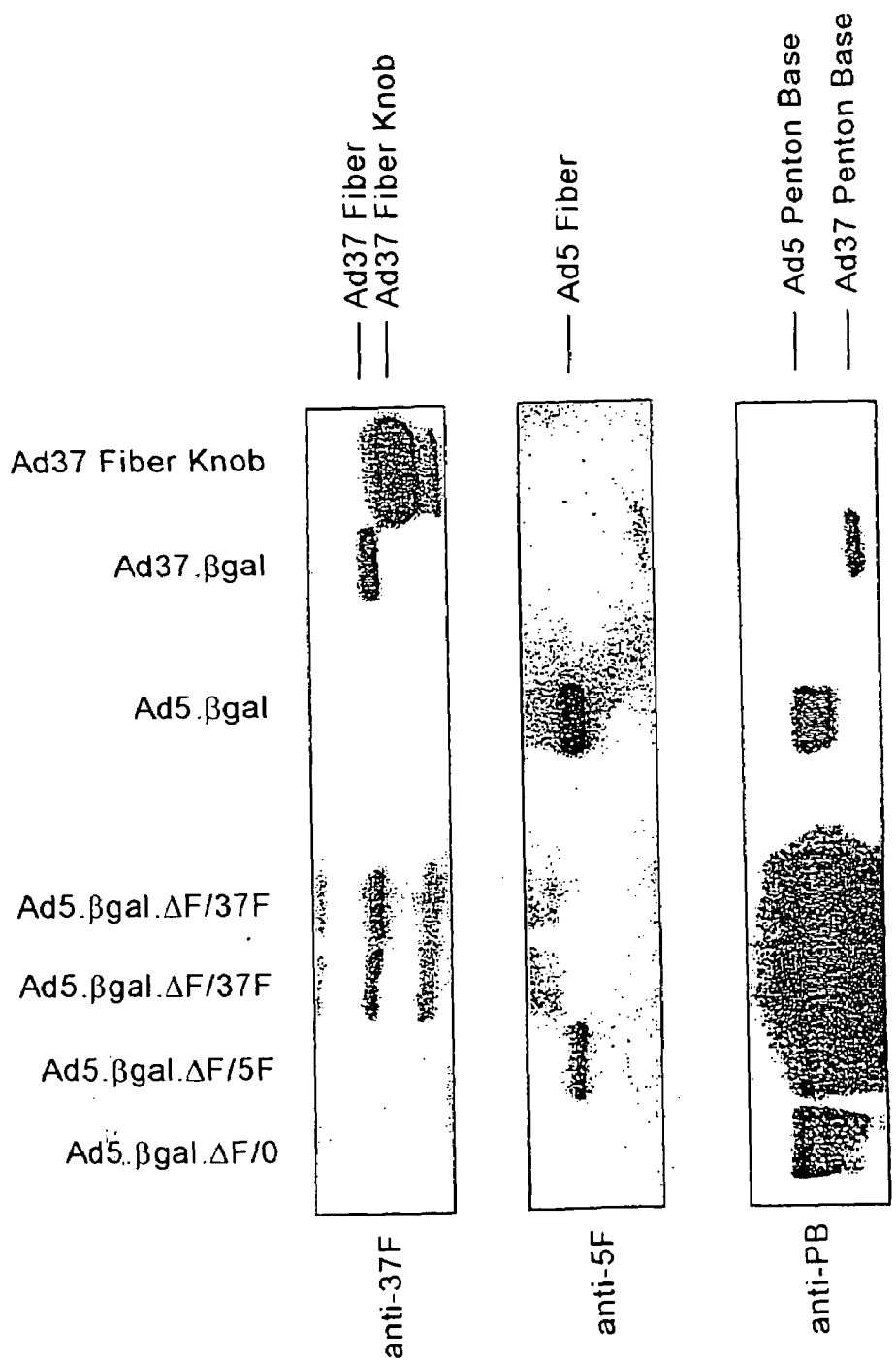
FIG. 27. The fiber-deleted adenovirus vector Ad5.βgal.ΔF was grown in cells expressing either no fiber (293; 'Ad5.βgal.ΔF/0'), the Ad5 fiber (633; 'Ad5.βgal.ΔF/5F'), or the Ad37 fiber with modifications as described in the text (705; 'Ad5.βgal.ΔF/37F') and CsCl-purified. 10 µg of the purified particles were electrophoresed and transferred to a nylon membrane. As controls, 10 µg of wild-type Ad37 or the fiber gene-containing vector Ad5.βgal.wt or a sample of purified recombinant Ad37 fiber knob were also run. The blot was probed with polyclonal antisera against recombinant Ad37 fiber or Ad2 fiber proteins. As a loading control, the same filter was reprobed with an antibody against the Ad2 penton base (the anti-Ad2 sera cross-recognized the very similar Ad5 fiber and Ad5 penton base proteins).

This amplified DNA fragment was digested with SmaI and EcoRI, and ligated to the SmaI and EcoRI sites of pSE280-E2Bam-Sma to reconstruct the complete E2a region from Ad5 bp 24,730 through 21,562. The resulting construct is pSE280-E2a. (FIG. 27.)

In order to convert the BamHI site at the 3' end of E2a to a SalI site, the E2a region was excised from pSE280-E2a by cutting with BamHI and NheI, and recloned into the unique BamHI and NheI sites of pSE280. (FIG. 27.) Subsequently, the E2a region was excised from this construction with NheI and SalI in order to clone into the NheI and SalI sites of the pMAMneo (Clonetech, Palo Alto, Calif.) multiple cloning site in a 5' to 3' orientation, respectively. The resulting construct is pMAMneo E2a. (FIG. 27).

Bacterial transformants containing the final pMAMneo-E2a were identified. Plasmid DNA was prepared and purified by banding in CsTFA. Circular plasmid DNA was linearized at the XmnI site within the ampicillin resistance gene of pMAMneo-E2a, and further purified by the phenol/chloroform extraction and ethanol precipitation prior to use for transfection of cells. Transfection and selection of cells.

In general, this process involved the sequential introduction, by calcium phosphate precipitation, or other means of DNA delivery, of two plasmid constructions each with a different viral gene, into a single tissue culture cell. The cells were transfected with a first construct and selected for expression of the associated drug resistance gene to establish stable integrants. Individual cell clones were established and assayed for function of the introduced viral gene. Appropriate candidate clones then were transfected with a second construct including a second viral gene and a second selectable marker. Transfected cells then were selected to establish stable integrants of the second construct, and cell clones were established. Cell clones were assayed for functional expression of both viral genes.

In order to determine the most suitable cell lines for the above-mentioned transfections, sequential transfections and selections were carried out with the following parental cell types:

A549 (ATCC Accession No. CCL-185);

Hep-2 (ATCC Accession No. CCL-23); or

KB (ATCC Accession No. CCL-17).

Appropriate selection conditions were established for both G418 and hygromycin B for all three cell lines by standard kill curve determination. Transfection of cell lines with plasmids including E1 and E2a regions.

pMAMNeo-E2a was linearized with XmnI with the $Amp^R$ gene, introduced into cells by transfection, and cells were selected for stable integration of this plasmid by G418 selection until drug resistant colonies arose. The clones were isolated and screened for E2a expression by staining for E2a protein with a polyclonal antiserum, and visualizing by immunofluorescence. E2a function was screened by complementation of the temperature-sensitive mutant Ad5ts125 virus which contains a temperature-sensitive mutation in the E2a gene. (Van Der Vliet, et al., J. Virology, Vol. 15, pgs. 348–354 (1975)). Positive clones expressing the E2a gene were identified and used for transfection with the 7 kb EcoRV to XmnI fragment from pGRE5-E1 (FIG. 5), which contains the GRE5 promoted E1a/b region plus the hygromycin$^R$ gene. Cells were selected for hygromycin resistance and assayed for E1a/b expression by staining with a monoclonal antibody for the E1 protein (Oncogene Sciences, Uniondale, N.Y.). E1 function was assayed by ability to complement an E1-deleted vector. At this point, expression and function of E2a was verified as described above, thus establishing the expression of both E1a/b and E2a in the positive cell clones.

One of the transfected A549 cell lines showed good E1/b and E2a expression and was selected for further characterization. It was designated the S8 cell line.

G. Preparation of Adenoviral Vectors Containing Ad5.βgal.ΔF Genome in S8 Improved Fiber-Complementing Cell Lines To prepare adenoviral vectors containing Ad5.βgal.ΔF in S8 cells containing alternative forms of TPL for enhancing the expression of fiber proteins, the protocol as described in Example 2 for preparing Ad5.βgal.ΔF in 211B cells was followed with the exception of pretreatment with 0.3 μM dexamethasone for 24 hours as described above. Thus, viral particles with the wildtype Ad5 fiber protein on their surface and containing the fiberless Ad5.βgal.ΔF genome were produced in 633 cells. Particles produced in 644 cells also contained the fiberless Ad5.βgal.ΔF genome, but had the chimeric 5T3H fiber protein, with the Ad3 fiber knowb, on their surface.

Figure 20:
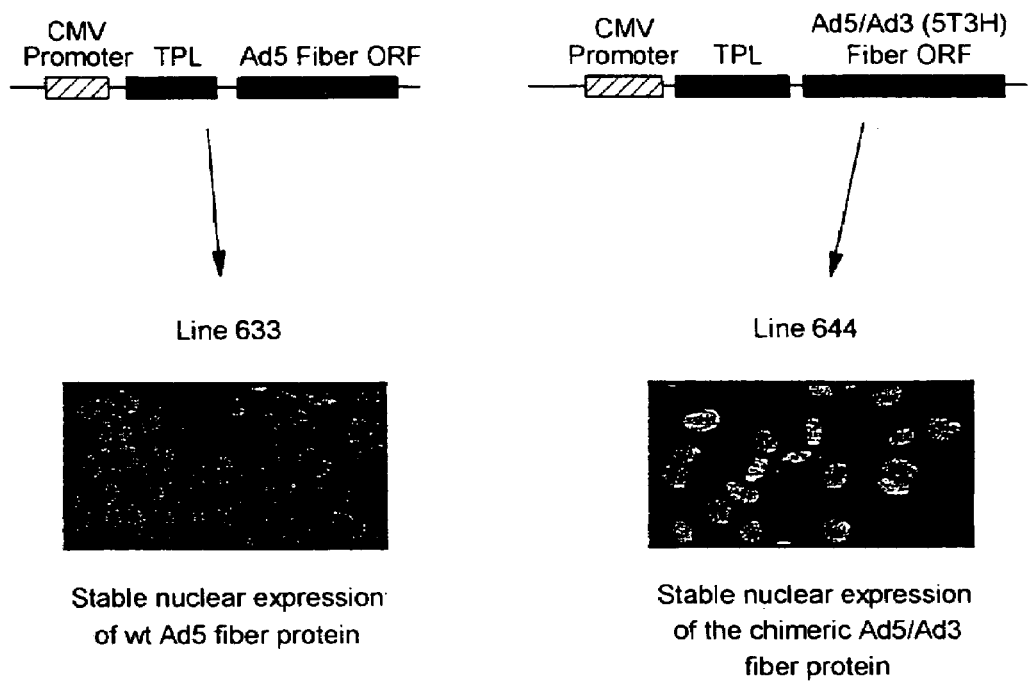
FIG. 20 shows a schematic of improved fiber-complementing cell lines, 633 and 644 as further described in the Examples.

The preparation of the cell lines and demonstration of stable nuclear expression of either wild-type Ad5 fiber protein or chimeric Ad5/Ad3 protein is shown in FIG. 20. In the figure, schematic diagrams are presented of the constructs used to generate the cell lines as well as immunofluorescence results indicating the presence of expressed fiber protein in the nucleus of the cells.

Thus, these viral preparations, prepared as described herein and in Example 2, are useful for targeting delivery of Ad5.βgal.ΔF fiberless genome with either wild-type or modified fibers, embodiments of which uses have been previously discussed and as further exemplified with the pseudotyping and infectivity results described in Example 7.

Example 7

Figure 21:
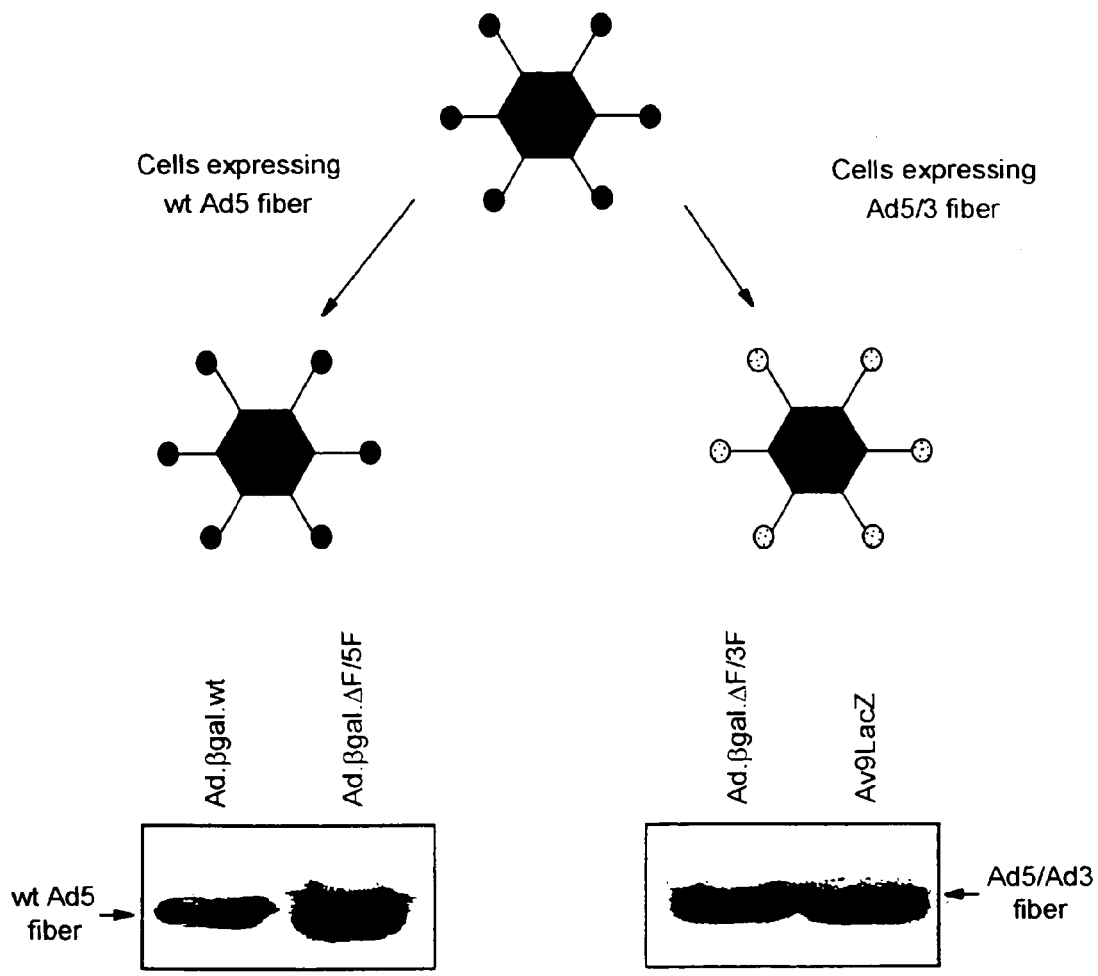
FIGS. 21 and 22 illustrates pseudotyping of fiberless particles with fiber proteins and infectivity data as further described in the Examples.

Pseudotyping and Infectivity of Recombinant Adenoviral Vectors Produced with Improved Fiber-Complementing Cell Lines A. Pseudotyping of Ad5.βgal.ΔF To verify that adenoviral vectors were produced had altered tropisms, viral particles were purified from either 633 or 644 cells and were then Western blotted and probed with a polyclonal rabbit antibody against the Ad2 fiber (which detects both the Ad5 and chimeric 5T3H fiber proteins.). The results are shown in FIG. 21 where both fiber proteins were detectable confirming pseudotyping.

B. Infectivity of Cells with 633 or 644 Generated Virus Particles

Figure 22:
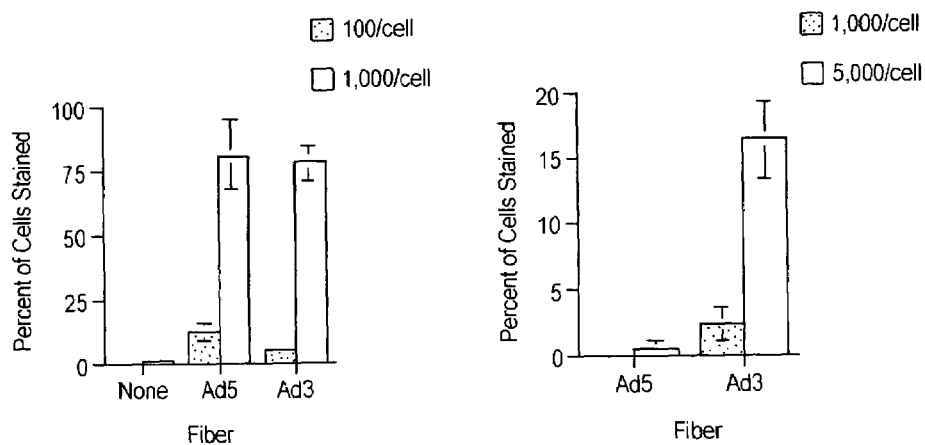
Figure 22:
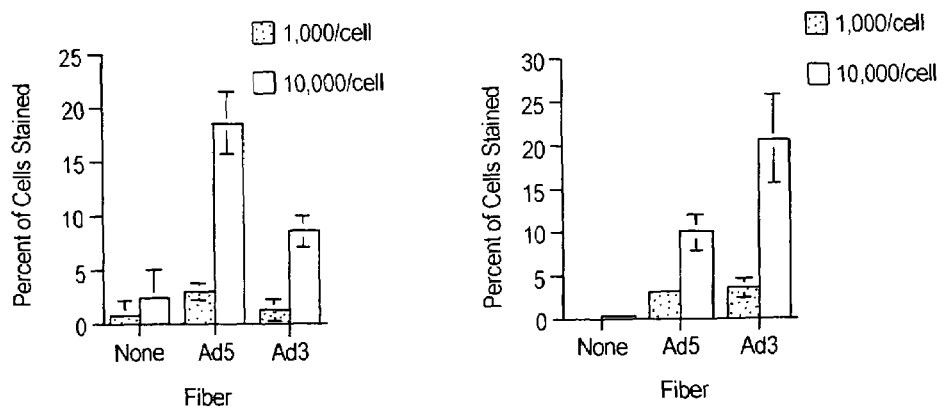

The cell lines, 633 or 644, prepared as described above, were infected with the indicated number of particles/cell of Ad5.βgal.ΔF and virus particles produced. Virus was then used to infect, as previously described, selected cell lines as shown in FIG. 22, including 211B, MRC-5 human fibroblasts, A-10 rat aortic endothelial cells, and THP-1 human monocytic cells. Unbound virus was removed by washing the cells and the cells were further incubated at 37° C. for 48 hours. Cells were then fixed with glutaraldehyde and stained with X-gal. The percentage of stained cells was then determined by light microscopy where all experiments were done in triplicate.

The results shown in FIG. 22 indicate that adenoviral vectors could be retargeted by pseudotyping using packaging cell lines expressing different fiber proteins. The data marked with "none" indicates virus grown in 293 cells and lacking fiber, while "Ad5" indicates virus prepared in 633 cells (containing the wild type fiber) and Ad3 indicates virus prepared in 644 cells (containing the chimeric 5T3H fiber.) Particles containing either fiber were equally infectious on 211B cells, while MRC-5 fibroblasts and THP-1 cells were more readily infected by virus containing the chimeric fiber. The A-10 rat endothelial cells were more readily infected by particles containing the wildtype Ad5 fiber protein.

Example 8

Targeted Gene Delivery Using Viral Vector Particles Lacking Fiber Protein

An alternative mode of entry for adenoviral infection of hematopoietic cells has been described by Huang, et al., J. Virol., 69:2257–2263 (1995) which does not involve the fiber protein-host cell receptor interaction. As infection of most other cell types does require the presence of fiber protein, vector particles which lack fiber may preferentially infect hematopoietic cells, such as monocytes or macrophages.

To produce a fiber-free adenovirus vector particle, a vector lacking the fiber gene as described above in Example 2A but containing a gene of interest for delivery is amplified by growth in cells which do not produce a fiber protein, such as the 211 cells prepared in Example 1 or 293 or S8 cells as described herein, thereby producing large numbers of particles lacking fiber protein. The recovered fiber-free viral particles are then used to deliver the inserted gene of interest following the methods of this invention via targeting mechanisms provided by other regions of the adenoviral vector, i.e., via the native penton base.

A. Construction of an Adenovirus Vector Deleted for E1, E3, and Fiber, and Carrying a Therapeutic Gene of Interest A general method of constructing a fiber-deleted Ad vector containing a therapeutic gene of interest (in this example, the Herpes Simplex Virus Thymidine Kinase (TK) gene) is described here. Linear viral DNA is isolated from a preparation of Ad5.βgal.ΔF particles. This DNA is digested with the restriction enzyme ClaI, which removes the leftmost viral sequences including the left ITR, the packaging signals, and part of the SV40-driven β-galactosidase gene. The large ClaI fragment with the remainder of the fiber-deleted viral genome is then isolated by centrifugation on a sodium chloride or sucrose gradient. The plasmid pAdShuttleTK, which contains the left part of the Ad chromosome with an RSV-driven TK gene inserted in place of the E1 region, is linearized by digestion with NotI. The nucleotide sequence of the pAdShuttleTK is shown in SEQ ID NO: 50. The large ClaI fragment of Ad5.βgal.ΔF and the linearized pAdShuttleTK are cotransfected into 211B cells, and an infectious adenovirus genome is generated by homologous recombination. A virus deleted for E1, E3, and fiber that contains the TK cassette in the place of the E1 deletion is thus recovered. A virus containing any desired therapeutic gene of interest can be created in this manner by replacing the TK gene of the example with the gene of interest.

An alternative method of constructing a fiber-deleted genome containing a therapeutic gene (in this example the retinal degeneration-slow (S) gene driven by the CMV immediate early promoter) is described here. RDS is a protein expressed in photoreceptors, and essential for their proper development and functioning. RDS mutations have been implicated in retinal degenerative disorders, and transfer of the wildtype RDS gene by means of an Ad vector provides an avenue towards treating such disorders.

A plasmid (pDV50) analogous to pΔE1Bβgal but containing a CMV-driven RDS gene was constructed as follows. First, a fragment containing the CMV promoter and enhancer was excised from pCHaMIEP by digestion withh HindIII, filling the overhanging ends with the large fragment of E. coli DNA polymerase 1, ligation of BamHI linkers (5'CGCGGATCCCG3' SEQ ID NO: 51) to the blunt ends, and digesting with BamHI. The resulting fragment was then ligated into the BamHI site of pΔE1sp1a (Mikrobix) to create pDV45. A fragment containing the SV40 polyadenylation signal was amplified from pSVβgal (Promega) using the oligonucleotides 5'CTGACAAACTCAGATCTTGTT-TATTG3' (SEQ ID NO: 51) and 5'GTCGACTCTAGAG-GATCCAGA3' (SEQ ID NO: 52). This fragment was ligated into the BglII site of pDV45 to create pDV46, using the unique BamHI and BglII sites (bold type) in the primers. Finally, the human RDS open reading frame was amplified from the plasmid pRDS-T7 using the oligonucleotides 5'CCGGACTCT AGATGGCAACCATGGCGCTAC3' (SEQ ID NO: 53) and 5'GGA GGGGAAGCTTGGCCCT-CAGCCAGCCTCT3' (SEQ ID NO: 54). This fragment was inserted into the HindIII and XbaI sites of pDV46, again using unique restriction sites in the primers, to create pDV50. pDV50 therefore contains a cassette consisting of the CMV promoter, the RDS open reading frame, and the SV40 terminator sequences inserted in place of the Ad5 E1 region.

In a manner analogous to the construction of Ad5.βgal.ΔF, pDV50 and pDV44 are then co-transfected into 211B cells, and an infectious Ad genome (Ad5.RDS.ΔF) is recovered. A fiber-deleted Ad vector containing any desired gene to be expressed can be constructed by replacing the RDS gene of this example with the gene of interest.

Example 9

Transient Transcomplementation

Human adenovirus type 5 (Ad5) is being developed as a vector for gene therapy. Its ability to deliver therapeutic genes to cells is mediated by the interaction of the adenoviral fiber protein with the coxsackievirus-adenoviral receptor (CAR). Because a wide-range of cells express CAR, it can be difficult to use adenoviruses to deliver genes to specific cell types. One way to address this is to target the virus to a particular cell type by genetically altering the fiber. However, the genetic manipulations involved in cloning and production of the viruses with altered fibers can be time-consuming. Thus it would be a significant advancement in the field of adenoviral gene therapy to have a more streamlined system for testing modified fiber genes. An in vitro system has thus been developed that involves infection of tissue culture cells with a fiber-deleted Ad and transient co-transfection with a plasmid directing fiber expression. This system allows one to produce and evaluate such modified fibers in the context of a viral particle easily and quickly. In addition this system can be envisioned to actually produce therapeutic quantities of adenoviral vectors with modified fiber proteins, with such fibers having a new tropism added by insertion of a desired ligand into the fiber gene. These fibers may also have the natural tropism (i.e. binding to CAR) ablated.

Plasmids used were pDV60 and pDV55, prepared as described herein. pDV60 is an pcDNA3.1-based expression plasmid that contains the CMV promoter, Ad5 tripartite leader, an intron, and the Ad5 fiber gene sequence. pDV55 contains no fiber gene and serves as the negative control. Ad5.βgal.ΔF and 211B are described above. 293T cells are identical to 293 cells except they express an integrated SV40 large T antigen gene. HDF cells are human diploid fibroblasts. 293T cells express CAR and $\alpha_v$ integrins; HDF cells express $\alpha_v$ integrins but no CAR. Transfections with fiber expression plasmids were performed with Lipofectamine (GIBCO-BRL) using 20 mg DNA and 50 ml Lipofectamine per 15 cm dish. Cells were maintained in DMEM supplemented with 10% fetal bovine serum.

The fiber deletion mutation of Ad5.βgal.ΔF is complemented in trans by passaging virions through 211B, a cell line that stably expresses functional Ad5 fiber. The present system was designed to complement Ad5.βgal.ΔF by modified fibers expressed from transfected episomal plasmids in 293T cells. The result is a simplified and rapid method to incorporate modified fibers on a viral particle containing the Ad5.βgal.ΔF genome that does not require propagation of the virus.

The feasibility of transcomplementation of Ad5.βgal.ΔF with episomal fiber-expressing plasmids was demonstrated in the following experiment. 293T cells were transfected with one of two plasmids: pDV55, which expresses no fiber or pDV60, which expresses wildtype Ad5 fiber. Fiber expression persists for at least six days, suggesting that the plasmid is stable as an episome for this amount of time Twenty-four hours after transfection, these cells were infected at 2000 particles/cell with Ad5.βgal.ΔF passaged through 211B cells. Seventy-two hours later, a crude viral lysate (CVL) was generated by exposing the cells to five freeze-thaw cycles. Viral particles were purified by cesium chloride gradient centrifugation. The resulting virions incorporated the fiber expressed from the episomal plasmid, as confirmed by Western blots performed with an antibody specific to the Ad5 fiber.

To demonstrate the functionality of these virions, the transduction efficiency was tested. The virions containing no fiber (pDV55) or wildtype fiber (pDV60) were applied to monolayers of 293T and HDF cells at different multiplicity of infection (MOI's). 293T cells express CAR and $\alpha_v$ integrinss; HDF cells express $\alpha_v$ integrins but no CAR. After 2 days, the cells were fixed and stained with X-gal to detect the β-galactosidase reporter gene activity. The results showed low transduction efficiency for the pDV55-complemented virions in both cell lines. As expected, the pDV60-complemented virions transduced 293T cells to a high degree but did not transduce HDF cells, indicating that functional fiber proteins had been expressed from the episomal plasmids and incorporated into the virions. This transduction efficiency was comparable to or better than that of Ad5.βgal.ΔF virions passaged through the 211B cells.

Episomal plasmid transcomplementation system is suitable for quickly expressing and evaluating the properties of modified fibers in the context of a viral particle. Episomal plasmid transcomplementation will also be of great utility for quickly evaluating a bank of modified fibers for other binding properties, including novel tropism and the ablation of the native tropism. In addition to the rapid generation and testing of large numbers of modified fibers, there are other advantages to the Ad5.βgal.ΔF transcomplementation system in terms of production and safety. Episomal plasmid transcomplementation has the inherent advantage over transcomplementation in that it is not necessary to make a stable cell line for every modified fiber with which you want to complement Ad5.βgal.ΔF. Because the Ad5.βgal.ΔF is deleted in E1, E3 and fiber, there is an additional gene deletion compared to other first generation vectors. This makes t Ad5.βgal.ΔF more replication defective and presumably safer. In addition, the presence of the fiber gene deletion decreases the opportunity to generate replication-competent virus via recombination in the packaging cells. In terms of production a single Ad vector prep could be retargeted to any number of different cell types simply by transfecting the cells with the appropriate fiber-expression construct.

Example 10

Adenoviral Gene Delivery Vectors Containing the Ad37 Fiber Protein

Adenovirus type 37 (subgroup D) has been associated with infections of the eye and genital tract, and may be useful for targeting these tissues or other mucous membranes, as well as other cell types. The tropism of Ad37 is due to the binding preference of its fiber protein, which binds to an as yet-unidentified receptor located on the surface of cells including Chang C, conjunctival epithelial cell line (Huang et al., *J. Virology* 73(4):2798–2802 (1999)). As this fiber directs viral infection to cell types different than those infected by Ad5, it is likely to provide a method for targeting gene delivery. This example describes construction of packaging cell lines expressing the Ad37 fiber protein, and their use in generating particles of a fiber-deleted Ad vector (such as Ad5.βgal.ΔF) containing this fiber protein. The fiber protein is attached to the viral capsid by binding to the penton base protein through its N-terminus, and the Ad37 fiber was modified in order to make its N-terminal sequence more closely match that of the Ad5 protein to ensure that it would efficiently bind the Ad5 penton base in these vectors.

1. Construction of an Expression Plasmid for the Ad37 Fiber Protein (pDV80)

This plasmid uses the same regulatory elements as contained in pDV60, pDV67, and pDV69 to express the Ad37 fiber in packaging lines, and was constructed in two steps. First, the Ad37 fiber open reading frame was amplified from Ad37 genomic DNA (obtained from the ATCC—accession number VR-929)using the synthetic oligonucleotides primers L37 (5' TGT CTT GGA TCC AAG ATG <u>AAGCGCGCC CGC CCCAGC</u> GAA GAT GAC TTC 3') (SEQ ID NO: 56) and 37FR (5' AAA CAC GGC GGC CGC TCT TTC ATT CTT G 3') (SEQ ID NO: 57). L37 contains nucleotides that differ from the Ad37 genomic sequence in order to add an unique Bam H1 site (bold in the above sequence) and create point mutations to make the N-terminal sequence of the fiber more closely match that of the Ad6 protein (underlined in the above sequence; the start codon is italicized). 37FR incorporates changes to create a unique Not 1 site (bold). The PCR product was inserted into the Bam H1 and Not 1 sites of pCDNA3.1zeo(+) (Invitrogen) to create pDV78. The correct sequence of the Ad37 fiber gene, including the predicted changes, was confirmed by sequencing.

Second, a 1.2 kb Bam H1/BglII fragment containing an adenovirus type 5 tripartite leader was excised from pDV55 (DVS 1999) and inserted into the Bam H1site of pDV78 to create pDV80 (SEQ ID NO:64).

2. Isolation of Cell Lines Expressing the Ad37 Fiber Protein pDV80 DNA was purified using the Qiagen method and electroporated into the adenovirus-complementing cell line E1–2a S8 (Gorziglia et al., *J. Virology* 70(5):4173–4178 (1996)) as previously described (Von Seggern, et al., *J. Gen. Virol.* 79:1461–1418), and stable clones were selected with 600 µg/ml zeocin (Invitrogen). Clones were expanded and screened for fiber expression by indirect immunofluorescence using a rabbit polyclonal antibody directed against the Ad37 fiber. Two clones (lines 705 and 731) that expressed the protein at a uniformly high level were selected for further study.

3. Production of Pseudotyped Ad Vector Particles

To generate vector particles equipped ('pseudotyped') with the Ad37 fiber protein, the Ad37 fiber-expressing 705 cells were infected (approximately 1000 particles/cell) with Ad5.βgal.ΔF or with Ad5.GFP.ΔF.

Ad5.βgal.ΔF is prepared as previously described. Ad5.GFP.ΔF was constructed by recombination in bacteria using a modification of the method of (He, et al., *PNAS* 95:2509–2514 (1998)). First, a fiber-deleted genomic plasmid was constructed by removing the fiber gene from pAdEasy1 (He, et al., *PNAS* 95:2509–2514 (1998)). pDV43 (Von Seggern, et al., *J. Virol.* 73:1601–1608 (1999)) was digested with Pac 1, the ends blunted by treatment with the large fragment of *E. coli* DNA polymerase and dNTPs, and the product re-ligated. The resulting plasmid, pDV76, is identical to pDV43 except for loss of the Pac 1 site and contains the right end of the Ad5 genome with E3 and fiber deletions. A 4.2 kb fragment was amplified from pDV76 using the oligonucleotides primers 5' CGC GCT GAC TCT TA GGA CTA GTT TC 3' (SEQ ID NO: 58) (including the unique Spe 1 site in the Ad5 genome, bold) and 5' GCG CTT AAT TAA CAT CAT CAA TAA TAT ACC TTA TTT T 3' (SEQ ID NO: 59) (including a novel Pac 1 site (bold) adjacent to the right Ad5 ITR). This PCR fragment therefore contains nucleotides 27,082 to 35,935 of the Ad5 genome with a deletion of nucleotides 28133 to 32743 (the E3 and fiber genes), and was used to replace the corresponding Spe 1/Pac 1 fragment of PAdEasy1 to create pDV77.

E. coli strain BJ5183 was electroporated with a mixture of pDV77 and Pme 1-linearized pAdTrack as described (He et al., 1998), and DNA was isolated from kanamycin-resistant colonies. The resulting plasmid, pDV83, contains a complete E1-, E3-, and fiber-deleted Ad5 genome with a CMV-driven GFP reporter gene inserted at the site of the E1 deletion. The full-length Ad chromosome was isolated by Pac 1 digestion, and transfected to the E1- and fiber-complementing 633 cells (Von Seggern et al., *J. Virol* January 2000). The recovered virus was then plaque purified by plating on 633 cells and stocks were prepared.

Ad5-pseudotyped particles were generated by virus growth in 633 cells, which express the wild type Ad5 fiber protein. Viral particles were isolated and purified over CsCl gradients as previously described (Von Seggern et al., *J. Virol.* 73:1601–1608, 1999). For analysis of viral proteins, ten µg of the purified particles were electrophoresed on 8–16% gradient gels and the protein transferred to nylon membranes. The blot was then probed with rabbit polyclonal antibodies raised against recombinant Ad37 fiber or Ad5 fiber or penton base proteins expressed in baculovirus-infected cells (FIG. 27).

Example 11

Construction of a Fiber Expression Construct Containing a Post-Transcriptional Regulatory Element Previous studies have shown that mRNA transcribed from the woodchuck hepatitis virus (WHV) genome contains an element (the WHV post-transcriptional regulatory element, or WPRE) which can increase expression of a protein encoded by the mRNA via a post-transcriptional mechanism (Loeb et al., *Human Gene Therapy* 10:2295–2305 (1999)). The WPRE has also been shown to enhance expression of transgenes delivered by retroviral vectors. (Zufferey, R. et al., *J. Virol.* 73:2886–2892 (1999)). This example describes the construction of a fiber expression construct (pDV90) (SEQ ID NO:65) containing a WPRE as well as the promoter and TPL sequences as contained in pDV67.

A plasmid (pBS/WPRE) which contains the WPRE was obtained from Dr. Thomas Hope, Salk Institute. Digestion of pBS/WPRE with Cla1 releases a 600 bp fragment containing the WPRE (nt 193–1684 of the WHV genome.) Following Cla1 digestion, the ends of this fragment were filled by treatment with the large fragment of *E. coli* DNA polymerase 1 in the presence of dNTPs to render them blunt. pDV67 DNA was digested with Xba1 (which cuts at a unique site in the transcribed region downstream of the Ad5 fiber open reading frame) and the ends filled by the same treatment. The filled WPRE fragment was then ligated into the filled Xba 1 site of pDV67 to create pDV90. The sequence is found at GenBank accession no. J04514 (entire genome) in Zufferey, R. et al., *J. Virol.* 73:2886–2892 (1999).

pDV90 (SEQ ID NO:65) was electroporated into E1–2a S8 cells and stable clones expressing fiber isolated as described previously for pDV80.

Example 12

Construction of an Ad5 Fiber Protein with Heterologous Peptide Sequences Inserted in the HI Loop The receptor-binding knob domain of the Ad5 fiber protein contains several surface loops which are attractive candidates for the insertion of heterologous peptide sequence, as an additional ligand for vector targeting. This example describes the construction of a fiber gene which encodes a fiber protein containing a 6 amino acid peptide linker in the HI loop, and retains the ability to trimerize. The modified gene also contains a unique novel restriction site at the position of the linker insertion to facilitate addition of the targeting ligand into the HI loop.

The Ad5 fiber gene was amplified from Ad5 genomic DNA (ATCC accession number VR-5) using the primers Fiber ATG (5' TGA AGC GCG CAA GAC CGT CTG AAG 3') (SEQ ID NO: 60) and Fiber TAA (5' CAT AAC ACT GCA GAT TCT TTA TTC TTG G 3') (SEQ ID NO: 61), and cloned to the NdeI (filled with the large fragment of *E. coli* DNA polymerase 1 in the presence of dNTPs) and Pst 1 sites of pT7–7 using a unique Pst 1 site (bold) in the 'Fiber TAA' oligo. The resulting plasmid, pT7/fiber, was digested with Xba 1 and Pst 1 to excise the fiber gene, which was then cloned into the Pst 1 and Xba 1 sites of pUC119 to create pUC/fiber. This pUC-derived plasmid contains an origin for single-stranded DNA replication and can therefore be used to create template DNA for site-directed mutagenesis.

Site-directed mutagenesis was carried out according to the method of Kunkel (T. A. Kunkel, *PNAS* 82:488–492 (1985)) using the oligonucleotide primer T542 (5' GGT ACA CAG GAA ACA <u>GGAGGTTCCGGAGGTGGA</u> GGA GAC ACA ACT CC 3') (SEQ ID NO: 62). This results in the addition of 18 new bases (underlined) encoding the sequence Gly Gly Ser Gly Gly Gly (SEQ ID NO: 63), with a novel BspE1 site (bold) for the addition of further sequences. The inserted sequence is between Thr542 and Gly543 of the Ad5 fiber protein, in the HI loop. The modified plasmid is termed pDV14.

Finally, the modified fiber gene was excised from pDV14 by digestion with Pst 1 and Xba 1 and cloned into the Pst 1 and Xba 1 sites of pGEM3Z (Promega) to create pDV18. In vitro transcription/translation experiments with pDV18 (using the TNT™ kit, Promega) demonstrated that the modified fiber gene encoded a protein which was capable of trimerizing.

Alternatively an Ad5 fiber open reading frame (ORF) is amplified from Ad5 genomic DNA (wildtype Ad5 was purchased from the ATCC) using the oligonucleotides 5' ATG GGA TCC <u>A</u>AG ATG AAG CGC GCA AGA CCG 3' (SEQ ID NO: 72) and 5'CAT AAC CTG CAG GAT TCT TTA TTC TTG GGC 3' (SEQ ID NO: 73), and inserted into the BamHI and Pst 1 sites of pGEM-3Zf(+) (Promega Inc., Madison, Wis.) via novel restriction sites (bold type) designed into the primers. The 5' oligonucleotide also contains a G to A change 3 nucleotides 5' of the initial ATG codon (underlined), designed to improve the consensus for translation initiation.

Site-directed mutagenesis is performed by the method of Kunkel (Proc. Nat. Acad. Sci. 82:488–492 (1985)), using the synthetic oligonucleotide 5' GGT ACA CAG GAA ACA GGA GGT <u>TCCGGA</u> GGT GGA GGA GAC ACA ACT CC 3' (SEQ ID NO: 74). This operation introduced sequence (bold type) encoding 6 novel amino acids (Gly Gly Ser Gly Gly Gly) immediately following Threonine 542 of the Ad5 fiber, and including a unique restriction site for the insertion of further heterologous sequences (underlined). The resulting plasmid (pDV18A) contains the modified fiber gene under the control of the T7 promoter in the parental pGEM-3Zf(+) and can be used for in vitro transcription/translation reactions to produce labeled fiber protein.

Example 13

Use of the Fiber Expression System to Retarget ('Pseudotype') Hybrid Ad/AAV Vectors Adenoviral vectors which lack essentially all Ad genes ('helper-dependent' or 'gutless' vectors) have recently been developed. In a modification of this idea, vectors ('hybrid' vectors) which contain an adeno-associated virus (AAV) or retroviral genome have been generated. As AAV and retroviral genomes integrate into the chromosome of the target cells, the hybrid Ad/AAV or Ad/retroviral vectors have the potential to provide very long-term gene expression.

Lieber et al., (J. Virol. 73(11):9314–9324) describe an Ad vector (Ad.AAV1) which contains an AAV vector genome (a transgene insert flanked by the AAV inverted terminal repeats) inserted into the E1 region. When 293 cells are infected by Ad.AAV1, recombination between the AAV sequences generates a minimal Ad chromosome which carries the Ad inverted terminal repeats and packaging signal flanking the AAV vector genome. This chromosome cannot direct the synthesis of Ad proteins, but can be packaged into Ad vector particles. The remaining unrecombined Ad chromosomes provide the Ad structural proteins in trans, and both the full-length and minimal genomes are packaged into particles. The particles carrying the minimal Ad/AAV hybrid vector are then isolated by CsCl centrifugation.

These particles have the capsid structure of adenovirus, and infect cells using the efficient fiber- and penton base-mediated pathway used by Ad. Following infection, the hybrid genome is able to integrate into the cell's chromosomes by virtue of its AAV sequences. In this example, the AAV vector genome is inserted into the E1 region of a fiber-deleted vector, and the resulting vector is grown in packaging lines expressing either the Ad5 or Ad37 fiber proteins. The particles recovered therefore have the tropisms expected from the respective fiber proteins combined with the ability to integrate their AAV genome into target cells. Such pseudotyping should be possible with any of a number of modified fiber proteins, as for the fiber-deleted vectors already described by us.

The Ad vector is constructed in a manner analogous to that described for Ad5.βgal.ΔF, by recombination between pAd.AAV1 (Lieber et al. J. Virol. 73:9314–9324, 1999) and pDV44 (as described earlier in the specification.) pAd.AAV1 carries an MLV promoter-driven secreted alkaline phosphatase gene (SEAP) as areporter, and an SV40-driven neomycin phosphotransferase (neo) gene to allow the selection of cells stable transduced by the AAV cassette. The resulting vector (Ad.AAV1.ΔF) has the AAV vector cassette of Ad.AAV1 inserted into the E1 region of a genome with the fiber deletion of Ad5.βgal.ΔF. Growth of Ad.AAV1.ΔF in 633 cells resultsinparticles carrying the AAV genome and the Ad5 fiber, and which have the tropism associated with Ad5. Growth of Ad.AAV1.ΔF in 705 cells produces particles bearing the Ad37 fiber and therefore having its associated different tropism.

Tropism is evaluated by infecting Chang C cells (which express the Ad37 receptor) and A549 cells which do not express this protein but do express the Ad5 receptor(CAR). The extent of infection is monitored by assaying alkaline phosphatase expression, and the fraction of cells stable transduced is assayed by selection with neomycin. By using purified recombinant Ad5 or Ad37 fiber proteins as competitors during infection, the usage of the expected receptors by the pseudotyped particles is evaluated.

Example 14

Use of the Fiber Expression System to Retarget ('Pseudotype') Helper-Dependent Ad Vectors Gutted Ad vectors are those from which most or all viral genes have been deleted. They are grown by co-infection of the producing cells with a "helper" virus (using an E1-deleted Ad vector). The helper virus trans-complements the missing Ad functions, including production of the viral structural proteins needed for particle assembly. In one embodiment of this invention, the helper virus is a fiber-deleted Ad (such as that described in Von Seggern et al., J. Virol. 73:1601–1608 (1999)). The vector is prepared in a fiber expressing cell line such as has been previously described by Von Seggern et al., J. Gen. Virol. 79:1461–1468 (1998), Von Seggern et al., J. Virol. 74:354–362 (2000). All the necessary Ad proteins except fiber are provided by the fiber-deleted helper virus, and the particles are equipped with the particular fiber expressed by the host cells. A concern with gutted vectors has been contamination of a vector preparation with residual helper virus. As the helper virus in one aspect of this invention is deleted for both E1 and for fiber, it is more replication defective and therefore safer than those currently used.

A helper adenovirus vector genome and a gutless adenoviral vector genome are delivered to the packaging cells of the invention. The cells are maintained under standard cell maintenance or growth conditions, whereby the helper vector genome and the packaging cell together provide the complementing proteins for the packaging of the adenoviral vector particle. Such gutless adenoviral vector particles are recovered by standard techniques. The helper vector genome may be delivered in the form of a plasmid or similar construct by standard transfection techniques, or it may be delivered through infection by a viral particle containing the genome. Such viral particle is commonly called a helper virus. Similarly, the gutless adenoviral vector genome may be delivered to the cell by transfection or viral infection.

The helper virus genome is preferably the fiberless adenovirus vector genome as disclosed herein. Preferably, such genome also lacks the genes encoding the adenovirus E1A and E1B proteins. More preferably, the genome further lacks the adenovirus genes encoding the adenovirus E3 proteins. Alternatively, the genes encoding such proteins may be present but mutated so that they do not encode functional E1A, E1B and E3 proteins. Furthermore, such vector genome may not encode other functional early proteins, such as E2A, E2B, and E4 proteins. Alternatively, the genes encoding such other early proteins may be present but mutated so that they do not encode functional proteins.

The helper virus genome is used in conjunction with the packaging cell of the invention. As disclosed elsewhere herein, the packaging cell also provides proteins necessary for the complementation of the gutless vector so that an adenovirus particle containing the gutless vector genome may be produced. Thus, the packaging cell can provide wild-type or modified fiber protein as described herein.

Alternatively, the cell could package a fiberless particle which could be used by itself or to which exogenously provided fiber could be added as described elsewhere herein.

In producing the gutless vectors, the helper virus genome is also packaged, thereby producing helper virus. In order the minimize the amount of helper virus produced and maximize the amount of gutless vector particles produced, it is preferable to delete or otherwise modify the packaging sequence in the helper virus genome, so that packaging of the genome is prevented or limited. Since the gutless vector genome will have a packaging sequence, it will be preferentially packaged.

One way to do this is to mutate the packaging sequence by deleting one or more of the nucleotides comprising the sequence or otherwise mutating the sequence to inactivate or hamper the packaging function. An alternative approach is to engineer the helper genome so that recombinase target sites flank the packaging sequence and to provide a recombinase in the packaging cell. The action of recombinase on such sites results in the removal of the packaging sequence from the helper virus genome. Preferably, the recombinase is provided by a nucleotide sequence in the packaging cell that encodes the recombinase. Most preferably, such sequence is stably integrated into the genome of the packaging cell. Various kinds of recombinase are known by those skilled in the art. The preferred recombinase is Cre recombinase, which operates on so-called lox sites, which are engineered on either side of the packaging sequence as discussed above. Further information about the use of Cre-loxP recombination is found in U.S. Pat. No. 5,919,676 and Morsy and Caskey, *Molecular Medicine Today*, January 1999, pgs. 18–24, both incorporated herein by reference.

This example demonstrates how the fiber-expressing packaging lines can be used to generate pseudotyped particles of helper-dependent or 'gutless' vectors with altered tropisms. As the gutless vectors lack many or all Ad genes, they must be grown as mixed cultures in the presence of a helper virus which can provide the missing functions. To date, such helper viruses have provided all Ad functions except E1, and E 1 is complemented by growth in 293 cells or the equivalent. The resulting virus particles are harvested, and the helper virus is typically removed by CsCl gradient centrifugation (the vector chromosome is generally shorter than the helper chromosome, resulting in a difference in buoyant density between the two particles).

An example of a gutless vector is pAdΔRSVDys (Haecker et al., *Human Gene Therapy* 7:1907–1914 (1996)). This plasmid contains a full-length human dystrophin cDNA driven by the RSV promoter and flanked by Ad inverted terminal repeats and packaging signals. 293 cells are infected with a first-generation Ad which serves as a helper virus, and then transfected with purified pAdΔRSVDys DNA. Both the helper Ad genome and the pAdΔRSVDys DNA are replicated as Ad chromosomes, and packaged into particles using the viral proteins produced by the helper virus. Particles are isolated and the pAdΔRSVDys-containing particles separated from the helper by virtue of their smaller genome size and therefore different density on CsCl gradients.

To generate pseudotyped particles containing the pAdΔRSVDys genome, the vector is grown in either 633 or 705 cells and Ad5.βgal.ΔF is used as a helper virus. As in the published method, both the Ad5.βgal.ΔF and AdΔRSVDys genomes replicate and are packaged into particles. The Ad5.βgal.ΔF helper provides all the essential Ad proteins except fiber, and the fiber protein is that produced by the cells (Ad5 fiber in 633 cells and Ad37 fiber in the case of 705 cells). The particles containing AdΔRVDys genomes are then isolated by centrifugation.

Tropism is evaluated by infecting Chang C cells (which express the Ad37 receptor) and A549 cells which do not express this protein but do express the natural Ad5 receptor (CAR). The extent of infection is assessed by immunofluorescence staining of the infected cells with an anti-dystrophin antibody. By using purified recombinant Ad5 and Ad37 fiber proteins as competitors during infection, the usage of the expected receptors by the pseudotyped particles is evaluated.

Example 15

Targeting EBV-Infected B Cells

There are a number of cell types, such as EBV-transformed B-lymphocytes, that are involved in human disease which are not transducible using standard Ad vectors. To address this problem 'pseudotyped' Ad5 βgal.ΔF particles containing either the wildtype Ad5 fiber protein or a chimeric fiber with the receptor-binding knob domain of the adenovirus type 3 (Ad3) fiber were generated. (Von Seggem et al., *J. Virol*. January, 2000). The strategy used for targeting the B-cells should be broadly applicable for targeting gene delivery to other specific cell types.

Cells and Viruses. THp-1, MRC-5, FaDu, and A-10 cells were purchased from the ATCC. 211B is a 293-derived cell line that expresses the wild-type Ad5 fiber protein (Von Seggern et al., *J. Gen. Virol*. 79:1461–1468 (1998)). E1–2a (Gorziglia et al., *J. Virol*. 70:4173–4178 (1996)) is an A549-derived cell line which complements adenoviral E1 and E2a functions. The JR, TO, and TL LCL lines were established as described (Huang et al., *Proc. Natl. Acad. Sci*. 94:8156–8161 (1997) by EBV infection of lymphocytes from three normal donors. THP-1 and all LCL lines were maintained in RPMI 1640 medium (Gibco)+10% fetal calf serum (FCS) (Hyclone). 211B, MRC-5, and A-10 cells were grown in DMEM+10% FCS. E1–2a and its derivatives were grown in Richter's modified medium (BioWhitaker)+10% FCS. Peripheral blood mononuclear cells were isolated from normal human blood (General Clinical Research Center, Scripps Clinic) by sedimentation on Ficoll-Paque (Pharmacia) per the manufacturer's instructions. Wild type Ad2 and Ad3 were purchased from the ATCC. Construction of Ad5.βgal.wt and Ad5.βgal.ΔF (Von Seggern et al., *J. Virol*. 73:1601–1608 (1999)) has been previously described. Av1LacZ4 (Mittereder et al., *J. Virol*. 70:7498–7509 (1996)) is a first-generation Ad5 vector containing an RSV-driven β-galactosidase reporter gene. Av9LacZ4 (Stevenson et al., *J. Virol*. 71:4782–4790 (1997)) is identical to Av1LacZ4 except that the fiber gene in the vector chromosome was replaced by a recombinant gene encoding a chimeric fiber protein with the receptor-binding domain of the Ad3 fiber (Stevenson et al., *J. virol*. 69:2850–2857 (1995)). Accession numbers for the above are as follows. THP-1: TIB-202, MRC-5: CCL-171, FaDu: HTB-43, A-10: CRL-1476, Ad2: VR-846, Ad3: VR-3.

DNA constructs. The complete Ad5 tripartite leader contained in pDV67 and pDV69 was constructed by assembly of PCR fragments. pDV55 was constructed similar to Example 5. This plasmid contains a 1.2 kb Bam HI/BglII fragment consisting of the first TPL exon, the natural first intron, and the fused second and third TPL exons. Finally, pDV60 was constructed by inserting this TPL cassette into the Bam HI site upstream of the Ad5 fiber gene in pcDNA3/

Fiber (Von Seggern et al., *J. Gen. Virol.* 79:1461–1468 (1998)). pDV61 and pDV67 were then constructed similar to example 6.

The chimeric Ad3/Ad5 fiber gene was amplified from pGEM5T3H (Stevenson et al., *J. Virol.* 69:2850–2857 (1995) using the primers 5' ATG GGA TCC AAG ATG AAG CGC GCA AGA CCG 3' (SEQ ID NO: 75) and 5'CAC TAT AGC GGC CGC ATT CTC AGT CAT CTT 3' (SEQ ID NO: 76), and cloned to the Bam HI and Not I sites of pcDNA3.1/Zeo(+) via novel Bam HI and Not I sites (bold) engineered into the primers to create pDV68. Finally, the complete TPL fragment described above was then added to the unique Bam HI site of this plasmid to create pDV69.

Construction of Stable Cell Lines. E1-2a cells were electroporated as previously described (Von Seggern et al., *J. Gen. Virol.* 79:1461–1468 (1998)) with pDV61, pDV67, or pDV69, and stable lines were selected with 600 µg/ml Zeocin (Invitrogen). Candidate clones were evaluated by immunofluorescence (Von Seggern et al., *J. Gen. Virol.* 79:1461–1468 (1998)) using a polyclonal antibody generated against the Ad2 fiber (Wickham et al., *Cell* 73:309–319 (1993). Those lines expressing the highest level of nuclear fiber expression were further characterized. Line 601 and 633 were produced by transfection of pDV61 and pDV67, respectively, and therefore express the wildtype Ad5 fiber. Line 644 contains pDV69 and expresses the chimeric 5T3H fiber.

Virus Growth and Analysis. Adenovirus stocks were prepared in the indicated cell lines, and plaque-titered on 633 cells essentially as described (Von Seggern et al., *J. Virol.* 73:1601–1608 (1999)). E1-2a cells (Gorziglia et al., *J. Virol.* 70:4173–4178 (1996). and their derivatives contain a dexamethasone-inducible construct for complementation of E1a. 601, 633, or 644 cells were therefore treated with 0.3 µM dexamethasone for 24 hours prior to infection, and 0.5 µM dexamethasone was included in the overlay for plaque assays. Protein concentration of viral preparations was determined using the BioRad Protein Assay (BioRad) with purified bovine serum albumin as a standard. Particle number was calculated using the formula 1 µg protein=$4 \times 10^9$ viral particles. Western blotting was performed as described (Von Seggern et al., *J. Gen. Virol.* 79:1461–1468 (1998)) using polyclonal rabbit antibodies raised against either the Ad2 (Wickham et al., *Cell* 73:309–319 (1993) or Ad3 fibers (Stevenson et al., *J. Virol.* 71:4782–4790 (1997).

Determination of infection and binding to receptor was performed using methods known to those of skill in the art. $2 \times 10^5$ cells in a total volume of 200 µl were incubated with the indicated Ad preparation for three hours at 37° C. Cells were then washed twice with fresh medium, and returned to 37° C. Two days later, cells were fixed and stained with X-gal and counted by light microscopy as described (Von Seggern et al., *J. Virol.* 73:1601–1608 (1999)). For competition assays, cells were pre-incubated on ice for one hour with either recombinant Ad3 fiber (10 µg/ml) purified from baculovirus or with a crude baculovirus lysate (100 µg/ml) containing the recombinant Ad2 fiber protein (Wickham et al., *Cell* 73:309–319 (1997)). Expression of $\alpha_v$ integrins on cell surfaces was assayed by FACS assay using monoclonal antibodies (the gift of David Cheresh, TSRI) against either $\alpha_v\beta_3$ (LM609) or $\alpha_v\beta_3$ (P1F6) as previously described (Huang et al., *Proc. Natl. Acad. Sci. USA* 94:8156–8161 (1997)). For virus binding assays, CsCl-purified Ad2 or Ad3 was labeled with $^{125}$I using Iodogen tubes (Pierce). Free iodine was removed by filtration with a PD-10 Sephadex column (Pharmacia). Cells ($1 \times 10^6$ cells in a volume of 200 µl either with or without a 100-fold excess of unlabeled virus) were rocked at 4° C. for two hours with $1 \times 10^6$ cpm of the labeled virus, washed three times with PBS and counted.

Altered in vitro tropism and infection of B lymphoid cell lines. Experiments with genetically modified viruses showed that a number of different cell types are more readily infected through interaction with the Ad3 receptor than by the CAR-dependent pathway used by Ad5 (Stevenson et al., *J. Virol.* 71:4782–4790 (1997)). In order to further evaluate the pseudotyping system, the ability of Ad5.βgal.ΔF carrying either the Ad5 or chimeric 5T3H fibers to infect several cell lines was assayed: FaDu (ahead and neck tumor line), THP-1 monocytic cells, and MRC-5 fibroblasts were assayed. Consistent with the previous studies (Stevenson et al., *J. Virol.* 71:4782–4790 (1997)), use of the chimeric Ad5/Ad3 fiber protein increased infection of all of these lines at equal particle/cell ratios. In contrast, the rat smooth muscle cell line A-10 was infected somewhat more readily by Ad5- than by Ad3-pseudotyped particles.

Gene delivery to EBV-infected B cells could allow the development of therapies for a variety of lymphoproliferative disorders. For example, ex vivo purging of donor marrow to eliminate infected cells could reduce the risk of EBV-associated lymphoproliferative disease, and EBV-induced malignancies such as AIDS-associated lymphoma are also potential targets. However, neither B cells nor EBV-transformed lymphoblastoid cell lines (LCLs) are efficiently infected by Ad5-based vectors. As the tropism of Ad3-pseudotyped particles appeared to be somewhat broader, it was asked whether EBV-infected LCLs could be infected using this system. The ability of Ad3-pseudotyped particles to infect LCLs generated by EBV infection of lymphocytes from three different normal human donors was tested. In agreement with previous reports, there was little or no infection of the se by particles carrying the Ad5 fiber. In contrast, virus particles equipped with the chimeric fiber protein were able to efficiently infect all of these lines. At equal particle/cell ratios, all LCLs examined were at least 10-fold more infectible using the Ad3 receptor.

Further studies were performed to correlate the efficiency of infection with the level of attachment and internalization receptors expressed by the cells. The three LCL lines tested all bound very low levels of radiolabeled Ad2 particles, indicating that they expressed little or no CAR. In contrast, all three were able to specifically bind labeled Ad3 particles. This result suggested that fiber receptor distribution was largely responsible for the increased infection of these cells by Ad3-pseudotyped particles.

Selective gene delivery to EBV-infected cells. The results above suggested that the minority of EBV-infected B cells present in donor marrow or peripheral blood would be preferentially infected by vectors using the Ad3 receptor. To test this hypothesis, a mixing experiment with normal uninfected peripheral blood mononuclear cells (PBMCs) and EBV-infected cells was performed. JR-LCL cells were mixed at varying ratios with PBMCs isolated from a normal human donor, and the mixture was then infected with Ad5.βgal.ΔF particles containing the 5T3H fiber protein. No infection of normal PBMCs alone was detected. Moreover, the percent of total cells infected increased with the fraction of JR cells added. These experiments indicate that EBV-infected cells can be selectively infected in vitro by relatively short (3 hours) exposure to a retargeted Ad vector.

Example 16

Production of Adenovirus Vectors by Addition of Exogenous Fiber

The production of fiberless viruses by growth in a complementing cell line may result in a preparation that also contains contaminating fiber genome resulting from recombination in the complementing cell lines. This disadvantage is eliminated by addition of exogenous fiber to a fiberless adenovirus vector.

Production of fiberless virus by standard methods may include a two-step preparation protocol. This has been described in the earlier examples and is briefly described here again as follows:

Step I—amplification of fiber containing fiberless virus (Ad5/F$^-$/F$^+$ or Ad5.βgalΔF—fiberless, but there is fiber on the surface, not encoded in genome) on 211B cell line (which stably expresses fiber), followed by CsCl-purification and characterization.

Step II—preparation of virus particles lacking fiber (Ad5F$^-$) by infection of S.8 cell line with Ad5/F$^-$/F$^+$, followed by CsCl purification and characterization. This produces a large stock of particles which do not contain fiber.

Step 1 is necessary because the infection efficiency of fiberless virus is extremely low, e.g. the dose of 20,000 particles/cell of Ad5/βgalF$^-$ gives only 10% infected cells.

Contrary to the above, the production of fiberless virus by addition of exogenous fiber involves only a one-step protocol. The fiberless virus is amplified using the S.8 cell line with addition of exogenous fiber into infection media. The amount of exogenous fiber necessary for production is very low, no more than 75 ng of purified fiber required per roller bottle. If desired the process may be followed by CsCl purification. As mentioned above, one advantage to this protocol is that it should provide no chance for recombination of adenovector during preparation.

A 10 roller bottle (RB) preparation of fiberless virus was made using the above two-step procedure. The yield of adenovector was $6.6 \times 10^{12}$ particles—total Ad/βgalF$^-$ (two step procedure.) A 1 RB preparation of fiberless adenovector was also made from the same initial material using a one-step procedure with exogenous fiber. The total yield was $2.5 \times 10^{11}$ particles—Ad5βgalF$^-$ (one step procedure).

Figure 28:
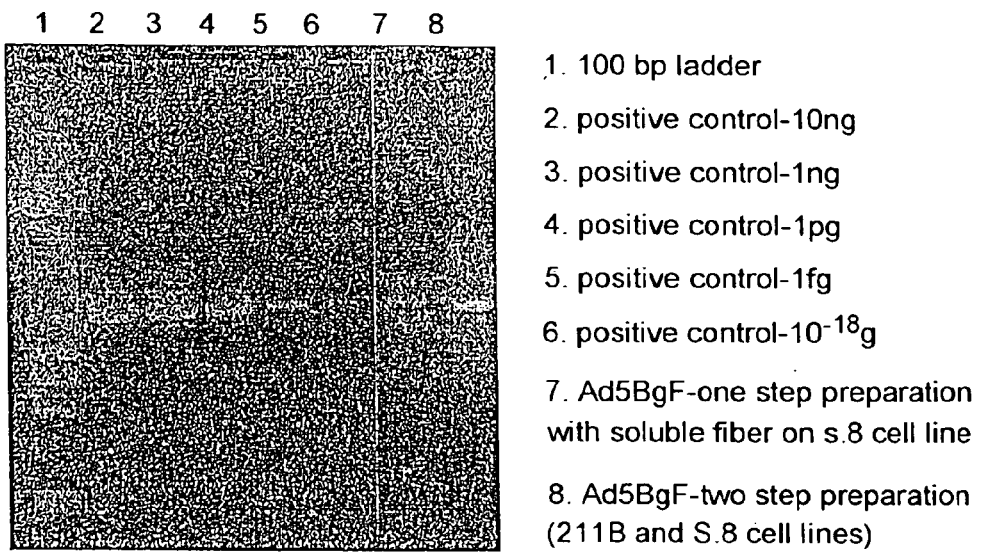
FIG. 28 shows PCR analysis for fiber presence.

DNA was isolated from both preparations and a PCR assay for fiber contamination was performed. (FIG. 28). The PCR assay was developed for detection of very low amounts of fiber contamination, as low as $10^{-18}$ g. PCR assay showed much lower contamination for the preparation which was done by adding exogenous fiber ($10^{-15}$ g one-step procedure) vs. $10^{-8}$ two-step procedure). Therefore, less contamination was obtained by simpler one-step approach.

Experiments were done using soluble purified fiber which does not have His-taq on the end (Ad5Fiber=5F) and with His-taq on the end (Ad5Fiber His=5FHis). These experiments showed that addition of Ad5Fiber can dramatically increase transduction efficiency of fiberless adenovector by simply adding it exogenously to a fiberless vector. The presence of the His tag on the Ad5FiberHis doesn't have any effect.

Figure 29:
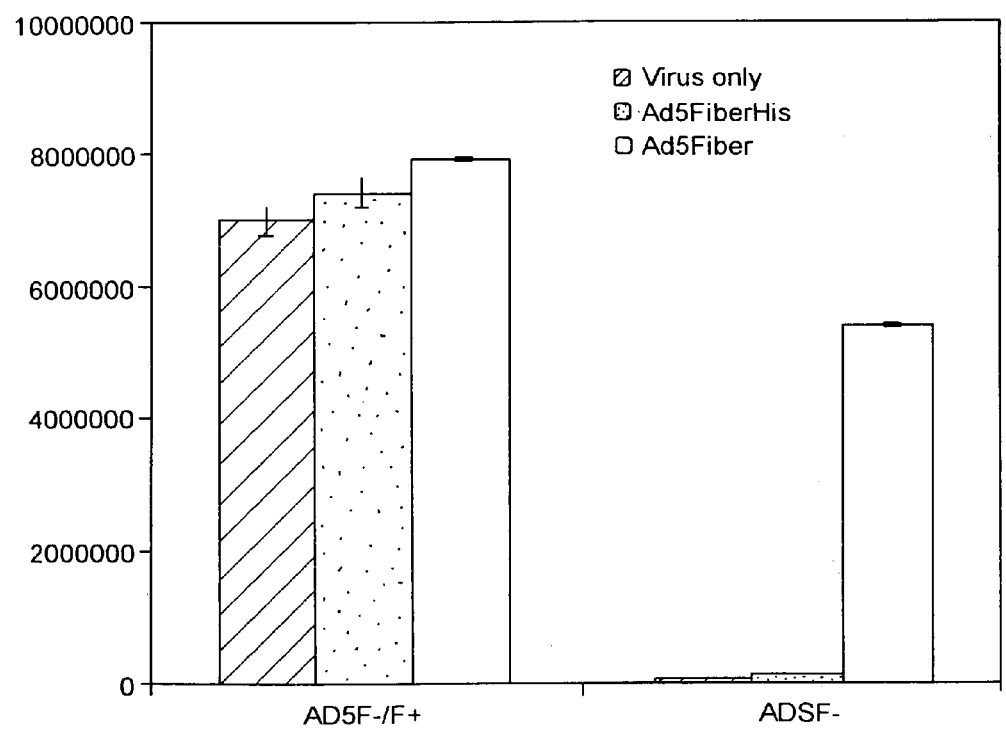
FIG. 29 shows the transduction efficiency for fiberless virus with and without soluble fiber.
Figure 30:
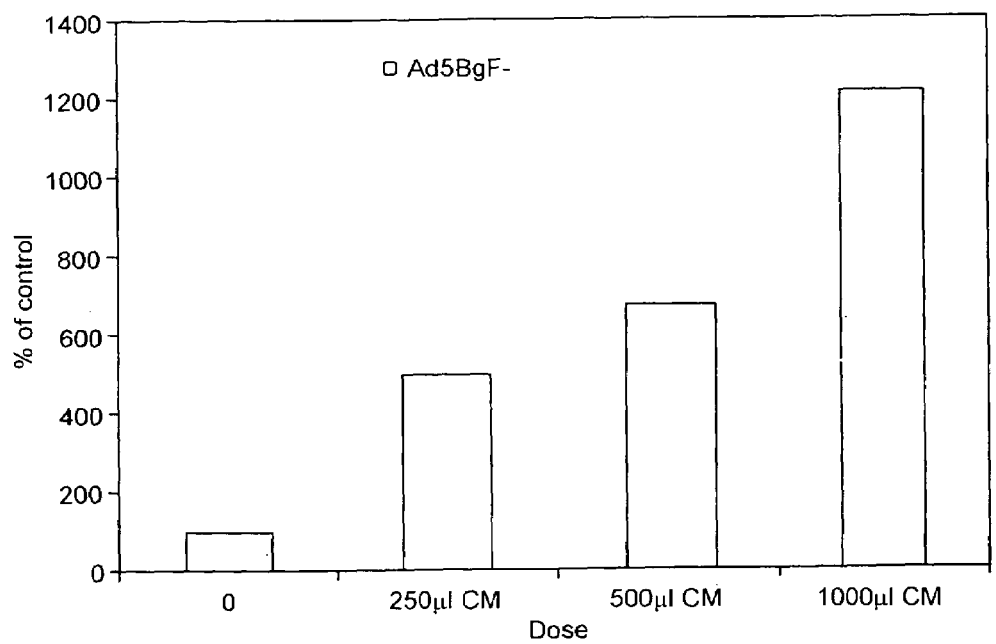
FIG. 30 shows the transduction efficiency of AD5BgF⁻ on HDF cell line with the presence of different amounts of 633 conditioned media.

The results of these experiments suggest that the fiber is self-assembling with the fiberless vector. This self-assembled virus can then infect cell through the normal entry pathway. (FIG. 29) Also, an experiment was done using conditioned media from 633 cell line, which can stably express fiber. A Western blot analysis for 633 condition media, showed that soluble fiber was present in the media during the period of cultivation of this cell line. Presence of soluble fiber in the media gives the possibility to increase transduction efficiency of fiberless adenovector on the HDF cell line. (FIG. 30) Because the HDF cell line doesn't have a CAR-receptor, it is especially difficult to transduce this particular cell line, not only with fiberless vector, but also with regular fiber containing adenovector. Different amounts of 633 conditioned media (250 μl, 500 μl or 1000 μl) were added to infectious media during the incubation period with fiberless adenovector.

This experiment also showed a role of soluble fiber in the process of cell entry. The conclusion is that by adding any fiber (wild-type, mutated, with ligand fusions) as long as on has the wild-type shaft (or region necessary to bind penton) one can retarget fiberless vector with any genome inside (gutless, oncolytic, expressing any transgene, etc.) to any cell type that your fiber is specific to. The advantage of this approach is that one does not have to make vectors with each new ligand. Just one fiberless vector need be made that can then be used to make different backbones by adding an exogenous "targetable" fiber off the shelf.

The foregoing specification, including the specific embodiments and examples, is intended to be illustrative of the present invention and is not to be taken as limiting. Numerous other variations and modifications can be effected without departing from the true spirit and scope of the present invention. All publications, patents and patent applications cited herein are incorporated by reference in their entirety into the present disclosure.

What is claimed is:

1. An isolated nucleic acid molecule comprising: a sequence of nucleotides encoding an adenovirus tripartite leader (TPL), wherein said TPL nucleotide sequence comprises the sequence set forth in SEQ ID NO: 32.

2. An isolated nucleic acid molecule of claim 1, further comprising a promoter and a sequence of nucleotides that encodes an adenoviral structural protein, operatively linked to said promoter an&said TPL-encoding sequence of nucleotides.

3. The isolated nucleic acid molecule of claim 2, wherein said adenoviral structural protein is a fiber protein or a chimeric protein which includes an adenovirus fiber protein tail domain.

4. The isolated nucleic acid molecule of claim 3, wherein said chimeric protein comprises an Ad3 head domain and an Ad5 tail domain or an Ad5 head domain and an Ad3 tail domain.

5. An isolated nucleic acid molecule comprising a nucleotide sequence selected from the group consisting of pDV60 (SEQ ID NO: 43), pDV67 (SEQ ID NO: 44), pDV69 (SEQ ID NO: 47), pDV80 (SEQ ID NO: 64) and pDV90 (SEQ ID NO: 65).

6. An adenovirus vector complementing plasmid comprising an isolated nucleic acid molecule according to claim 1.

7. An adenovirus vector packaging cell line for packaging an adenovirus 5 vector, comprising:
   i) a stably integrated nucleic acid molecule, comprising an adenovirus tripartite leader (TPL) nucleotide sequence, said TPL sequence comprising complete TPL exon 1 having the nucleotide sequence of SEQ ID NO: 32 or partial TPL exon I having the nucleotide of SEQ ID NO:26; and
   ii) an operatively-linked promoter and a nucleic acid sequence that encodes an adenovirus structural protein selected from the group consisting of penton base, hexon, fiber, polypeptide IIIa, polypeptide V, polypeptide VI, polypeptide VII, polypeptide VIII, a chimeric protein and biologically active fragments thereof.

8. The cell line of claim 7, wherein said promoter is an inducible promoter.

9. The cell line of claim 7, wherein said adenovirus structural protein is adenovirus fiber protein or a chimeric protein which includes an adenovirus fiber protein tail domain.

10. The cell line of claim 9, wherein said chimeric protein comprises an Ad3 head domain and an Ad5 tail domain or an Ad5 head domain and an Ad3 tail domain.

11. An adenovirus vector packaging cell line, comprising:
   i) a stably integrated nucleic acid molecule, comprising an adenovirus tripartite leader (TPL) nucleotide sequence, said TPL sequence comprising complete TPL exon 1 having the nucleotide sequence of SEQ ID NO: 32 or partial TPL exon 1 having the nucleotide of SEQ ID NO: 26; and
   ii) an operatively-linked promoter and a nucleic acid sequence that encodes an adenovirus structural protein, wherein the sequence of nucleotides that encodes the TPL comprises a first TPL exon operatively linked to a complete second TPL exon operatively linked to a complete third TPL exon, wherein said nucleic acid molecule is selected from the group consisting of pDV60 (SEQ ID NO: 43), pDV67 (SEQ ID NO: 44), pDV69 (SEQ ID NO: 47), pDV80 (SEQ ID NO: 64) and pDV90 (SEQ ID NO: 65).

12. The cell line of claim 7, wherein said cell line is an epithelial cell line.

13. The cell line of claim 7, wherein said cell line supports the production of a recombinant adenovirus vector genome by complementation of a deficient viral gene in said vector genome.

14. The cell line of claim 13, wherein said cell line expresses an adenovirus early protein gene and a fiber gene.

15. The cell line of claim 13, wherein deletion of a deficient viral gene is complemented by the expression of a gene under the control of an inducible promoter.

16. An adenovirus packaging cell line wherein said cell line comprises a stably integrated nucleic acid molecules comprising an adenovirus tripartite leader (TPL) nucleotide sequence, said TPL sequence comprising complete TPL exon I having the nucleotide sequence of SEQ ID NO: 32 or partial TPL exon I having the nucleotide of SEQ: 26; and is selected from the group consisting of 293, A549, W163, HeLa, Vero, 211, 211A and an epithelial cell line.

17. A method for producing an adenovirus particle comprising:
   1) providing a packaging cell line according to claim 7,
   2) introducing into said packaging cell line a recombinant adenovirus vector genome, and
   3) producing said adenovirus particle.

18. A method for producing an adenovirus particle comprising:
   1) providing a packaging cell line according to claim 7, wherein said nucleic acid sequence that encodes an adenovirus structural protein encodes an adenovirus fiber protein; and
   2) introducing into said packaging cell line a recombinant adenovirus vector genome comprising exogenous genes, and
   3) producing an adenovirus particle.

19. The method of claim 17, wherein said adenovirus particle comprises a genome encoding an exogenous protein.

20. The method of claim 17, wherein said exogenous protein is selected from a group consisting of a tumor-suppressor protein, a biologically active fragment thereof that has tumor-suppressor activity, a suicide protein and a biologically active fragment thereof that has activity as a suicide protein.

21. The method of claim 17, wherein said nucleotide sequence that encodes an adenovirus structural protein is operatively' linked to an inducible promoter.

22. The method of claim 17, wherein the adenovirus structural protein is adenovirus fiber protein.

* * * * *

SEQUENCE LISTING

```
<160> NUMBER OF SEQ ID NOS: 76

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 1
cggtacacag aattcaggag acacaactcc                                        30

<210> SEQ ID NO 2
```

-continued

```
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 2
gcctggatcc gggaagttac gtaacgtggg aaaac                          35

<210> SEQ ID NO 3
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 3
cgcggatccg cg                                                   12

<210> SEQ ID NO 4
<211> LENGTH: 8710
<212> TYPE: DNA
<213> ORGANISM: Artificial Sequence
<220> FEATURE:
<223> OTHER INFORMATION: Description of Artificial Sequence: plasmid

<400> SEQUENCE: 4
cacctaaatt gtaagcgtta atattttgtt aaaattcgcg ttaaattttt gttaaatcag    60 ctcattttt  aaccaatagg ccgaaatcgg caaaatccct tataaatcaa agaatagac   120 cgagatagggg ttgagtgttg ttccagtttg gaacaagagt ccactattaa agaacgtgga  180
ctccaacgtc aaagggcgaa aaaccgtcta tcagggcgat ggcccactac gtgaaccatc   240
accctaatca agttttttgg ggtcgaggtg ccgtaaagca ctaaatcgga acccctaaagg  300 gagcccccga tttagagctt gacggggaaa gccggcgaac gtggcgagaa aggaagggaa   360
gaaagcgaaa ggagcgggcg ctagggcgct ggcaagtgta gcggtcacgc tgcgcgtaac   420
caccacaccc gccgcgctta atgcgccgct acagggcgcg tcccattcgc cattcaggct   480
gcgcaactgt tgggaagggc gatcggtgcg ggcctcttcg ctattacgcc agctggcgaa   540
agggggatgt gctgcaaggc gattaagttg ggtaacgcca gggttttccc agtcacgacg   600
ttgtaaaacg acggccagtg aattgtaata cgactcacta tagggcgaat tgggtaccgg   660
gccccccctc gaggtcgacg gtatcgataa gcttgatatc gaattcagga gacacaactc   720
caagtgcata ctctatgtca ttttcatggg actggtctgg ccacaactac attaatgaaa   780
tatttgccac atcctcttac acttttttcat acattgccca agaataaaga atcgtttgtg   840
ttatgtttca acgtgtttat ttttcaattg cagaaaattt caagtcattt ttcattcagt   900
agtatagccc caccaccaca tagcttatac agatcaccgt accttaatca aactcacaga   960
accctagtat tcaacctgcc acctccctcc aacacacagt gtacacagt cctttctccc    1020 cggctggcct taaaaagcat catatcatgg gtaacagaca tattcttagg tgttatattc   1080
cacacggttt cctgtcgagc caaacgctca tcagtgatat taataaactc cccgggcagc   1140
tcacttaagt tcatgtcgct gtccagctgc tgagccacag gctgctgtcc aacttgcggt   1200
tgcttaacgg gcggcgaagg agaagtccac gcctacatgg gggtagagtc ataatcgtgc   1260
atcaggatag ggcggtggtg ctgcagcagc gcgcgaataa actgctgccg ccgccgctcc   1320
gtcctgcagg aatacaacat ggcagtggtc tcctcagcga tgattcgcac cgcccgcagc   1380
ataaggcgcc ttgtcctccg ggcacagcag cgcaccctga tctcacttaa atcagcacag   1440
```

-continued

```
taactgcagc acagcaccac aatattgttc aaaatcccac agtgcaaggc gctgtatcca      1500
aagctcatgg cggggaccac agaacccacg tggccatcat accacaagcg caggtagatt      1560
aagtggcgac ccctcataaa cacgctggac ataaacatta cctcttttgg catgttgtaa      1620
ttcaccacct cccggtacca tataaacctc tgattaaaca tggcgccatc caccaccatc      1680
ctaaaccagc tggccaaaac ctgcccgccg gctatacact gcagggaacc gggactggaa      1740
caatgacagt ggagagccca ggactcgtaa ccatggatca tcatgctcgt catgatatca      1800
atgttggcac aacacaggca cacgtgcata cacttcctca ggattacaag ctcctcccgc      1860
gttagaacca tatcccaggg aacaacccat tcctgaatca gcgtaaatcc cacactgcag      1920
ggaagacctc gcacgtaact cacgttgtgc attgtcaaag tgttacattc gggcagcagc      1980
ggatgatcct ccagtatggt agcgcgggtt tctgtctcaa aaggaggtag acgatcccta      2040
ctgtacggag tgcgccgaga caaccgagat cgtgttggtc gtagtgtcat gccaaatgga      2100
acgccggacg tagtcatatt tcctgaagca aaaccaggtg cgggcgtgac aaacagatct      2160
gcgtctccgg tctcgccgct tagatcgctc tgtgtagtag ttgtagtata tccactctct      2220
caaagcatcc aggcgccccc tggcttcggg ttctatgtaa actccttcat gcgccgctgc      2280
cctgataaca tccaccaccg cagaataagc cacacccagc caacctacac attcgttctg      2340
cgagtcacac acgggaggag cgggaagagc tggaagaacc atgttttttt ttttattcca      2400
aaagattatc caaaacctca aaatgaagat ctattaagtg aacgcgctcc cctccggtgg      2460
cgtggtcaaa ctctacagcc aaagaacaga taatggcatt tgtaagatgt tgcacaatgg      2520
cttccaaaag gcaaacggcc ctcacgtcca agtggacgta aaggctaaac ccttcagggt      2580
gaatctcctc tataaacatt ccagcacctt caaccatgcc caaataattc tcatctcgcc      2640
accttctcaa tatatctcta agcaaatccc gaatattaag tccggccatt gtaaaaatct      2700
gctccagagc gccctccacc ttcagcctca agcagcgaat catgattgca aaaattcagg      2760
ttcctcacag acctgtataa gattcaaaag cggaacatta acaaaatac cgcgatcccg       2820 taggtcccctt cgcagggcca gctgaacata atcgtgcagg tctgcacgga ccagcgcggc     2880
cacttccccg ccaggaacct tgacaaaaga acccacactg attatgacac gcatactcgg     2940
agctatgcta accagcgtag ccccgatgta agctttgttg catgggcggc gatataaaat     3000
gcaaggtgct gctcaaaaaa tcaggcaaag cctcgcgcaa aaagaaagc acatcgtagt     3060 catgctcatg cagataaagg caggtaagct ccggaaccac cacagaaaaa gacaccattt     3120
ttctctcaaa catgtctgcg ggtttctgca taaacacaaa ataaaataac aaaaaaacat     3180
ttaaacatta gaagcctgtc ttacaacagg aaaacaacc cttataagca taagacggac     3240
tacggccatg ccggcgtgac cgtaaaaaaa ctggtcaccg tgattaaaaa gcaccaccga     3300
cagctcctcg gtcatgtccg gagtcataat gtaagactcg gtaaacacat caggttgatt     3360
catcggtcag tgctaaaaag cgaccgaaat agcccggggg aatacatacc cgcaggcgta     3420
gagacaacat tacagccccc ataggaggta taacaaaatt aataggagag aaaaacacat     3480
aaacacctga aaaccctcc tgcctaggca aaatagcacc ctcccgctcc agaacaacat      3540
acagcgcttc acagcggcag cctaacagtc agccttacca gtaaaaaaga aaacctatta     3600
aaaaaacacc actcgacacg gcaccagctc aatcagtcac agtgtaaaaa agggccaagt     3660
gcagagcgag tatatatagg actaaaaaat gacgtaacgg ttaaagtcca caaaaaacac     3720
ccagaaaacc gcacgcgaac ctacgcccag aaacgaaagc caaaaaaccc acaacttcct     3780
```

```
caaatcgtca cttccgtttt cccacgttac gtaacttccc ggatccgcgg cattcacagt   3840
tctccgcaag aattgattgg ctccaattct tggagtggtg aatccgttag cgaggtgccg   3900
ccggcttcca ttcaggtcga ggtggcccgg ctccatgcac cgcgacgcaa cgcggggagg   3960
cagacaaggt atagggcggc gcctacaatc catgccaacc cgttccatgt gctcgccgag   4020
gcggcataaa tcgccgtgac gatcagcggt ccagtgatcg aagttaggct ggtaagagcc   4080
gcgagcgatc cttgaagctg tccctgatgg tcgtcatcta cctgcctgga cagcatggcc   4140
tgcaacgcgg gcatcccgat gccgccggaa gcgagaagaa tcataatggg gaaggccatc   4200
cagcctcgcg tcgcgaacgc cagcaagacg tagcccagcg cgtcggccgc catgccctgc   4260 ttcatcccg tggcccgttg ctcgcgtttg ctggcggtgt ccccggaaga aatatatttg    4320
catgtcttta gttctatgat gacacaaacc ccgcccagcg tcttgtcatt ggcgaattcg   4380
aacacgcaga tgcagtcggg gcggcgcggt cccaggtcca cttcgcatat taaggtgacg   4440
cgtgtggcct cgaacaccga gcgaccctgc agcgacccgc ttaacagcgt caacagcgtg   4500
ccgcagatcc cgggcaatga gatatgaaaa agcctgaact caccgcgacg tctgtcgaga   4560
agtttctgat cgaaaagttc gacagcgtct ccgacctgat gcagctctcg gagggcgaag   4620
aatctcgtgc tttcagcttc gatgtaggag ggcgtggata tgtcctgcgg gtaaatagct   4680
gcgccgatgt tttctacaaa gatcgttatg tttatcggca ctttgcatcg gccgcgctcc   4740
cgattccgga agtgcttgac attggggaat tcagcgagag cctgacctat tgcatctccc   4800
gccgtgcaca gggtgtcacg ttgcaagacc tgcctgaaac cgaactgccc gctgttctgc   4860
agccggtcgc ggaggccatg gatgcgatcg ctgcggccga tcttagccag acgagcgggt   4920
tcggcccatt cggaccgcaa ggaatcggtc aatacactac atggcgtgat ttcatatgcg   4980
cgattgctga tccccatgtg tatcactggc aaactgtgat ggacgacacc gtcagtgcgt   5040
ccgtcgcgca ggctctcgat gagctgatgc tttgggccga ggactgcccc gaagtccggc   5100
acctcgtgca cgcggatttc ggctccaaca atgtcctgac ggacaatggc cgcataacag   5160
cggtcattga ctggagcgag gcgatgttcg gggattccca atacgaggtc gccaacatct   5220
tcttctggag gccgtggttg gcttgtatgg agcagcagac gcgctacttc gagcggaggc   5280
atccggagct tgcaggatcg ccgcggctcc gggcgtatat gctccgcatt ggtcttgacc   5340
aactctatca gagcttggtt gacggcaatt tcgatgatgc agcttgggcg cagggtcgat   5400
gcgacgcaat cgtccgatcc ggagccggga ctgtcgggcg tacacaaatc gcccgcagaa   5460
gcgcggccgt ctggaccgat ggctgtgtag aagtactcgc cgatagtgga aaccgacgcc   5520
ccagcactcg tccgagggca aaggaatagg ggagatgggg gaggctaact gaaacacgga   5580
aggagacaat accggaagga acccgcgcta tgacggcaat aaaaagacag aataaaacgc   5640
acgggtgttg ggtcgtttgt tcataaacgc ggggttcggt cccagggctg cactctgtc   5700 gatacccac cgagacccca ttggggccaa tacgcccgcg tttcttcctt tccccaccc    5760 caccccccaa gttcgggtga aggcccaggg ctcgcagcca acgtcggggc ggcaggccct   5820
gccatagcca ctgccccgt gggttaggga cggggtcccc catggggaat ggtttatggt    5880 tcgtggggt tattattttg ggcgttgcgt ggggtctggt ccacgactgg actgagcaga    5940
cagacccatg gtttttggat ggcctgggca tggaccgcat gtactggcgc gacacgaaca   6000
ccgggcgtct gtggctgcca aacacccccg acccccaaaa accaccgcgc ggatttctgg   6060
cgcccagtgc cgtcgaccgg tcatggctgc gccccgacac ccgccaacac ccgctgacgg   6120
gccctgacgg gcttgtctgc tcccggcatc cgcttacaga caagctgtga ccgtctccgg   6180
```

-continued

```
gagctgcatg tgtcagaggt tttcaccgtc atcaccgaaa cgcgcgaggc agccggatca    6240
taatcagcca taccacattt gtagaggttt tacttgcttt aaaaaacctc cccacctccc    6300
cctgaacctg aaacataaaa tgaatgcaat tgttgttgtt aacttgttta ttgcagctta    6360
taatggttac aaataaagca atagcatcac aaatttcaca aataaagcat ttttttcact    6420
gcattctagt tgtggtttgt ccaaactcat caatgtatct tatcatgtct ggatccacta    6480
gttctagagc ggccgccacc gcggtggagc tccagctttt gttcccttta gtgagggtta    6540
atttcgagct ggcgtaatc atggtcatag ctgtttcctg tgtgaaattg ttatccgctc    6600
acaattccac acaacatacg agccggaagc ataaagtgta aagcctgggg tgcctaatga    6660
gtgagctaac tcacattaat tgcgttgcgc tcactgcccg ctttccagtc gggaaacctg    6720
tcgtgccagc tgcattaatg aatcggccaa cgcgcgggga gaggcggttt gcgtattggg    6780
cgctcttccg cttcctcgct cactgactcg ctgcgctcgg tcgttcggct gcggcgagcg    6840
gtatcagctc actcaaaggc ggtaatacgg ttatccacag aatcagggga taacgcagga    6900
aagaacatgt gagcaaaagg ccagcaaaag gccaggaacc gtaaaaaggc cgcgttgctg    6960
gcgtttttcc ataggctccg ccccctgac gagcatcaca aaaatcgacg ctcaagtcag    7020
aggtggcgaa acccgacagg actataaaga taccaggcgt ttccccctgg aagctccctc    7080
gtgcgctctc ctgttccgac cctgccgctt accggatacc tgtccgcctt tctcccttcg    7140
ggaagcgtgg cgctttctca tagctcacgc tgtaggtatc tcagttcggt gtaggtcgtt    7200
cgctccaagc tgggctgtgt gcacgaaccc cccgttcagc ccgaccgctg cgccttatcc    7260
ggtaactatc gtcttgagtc aacccggta agacacgact tatcgccact ggcagcagcc    7320
actggtaaca ggattagcag agcgaggtat gtaggcggtg ctacagagtt cttgaagtgg    7380
tggcctaact acggctacac tagaaggaca gtatttggta tctgcgctct gctgaagcca    7440
gttaccttcg gaaaaagagt tggtagctct tgatccggca acaaaccac cgctggtagc    7500
ggtggttttt tgtttgcaa gcagcagatt acgcgcagaa aaaaggatc tcaagaagat    7560
cctttgatct tttctacggg gtctgacgct cagtggaacg aaaactcacg ttaagggatt    7620
ttggtcatga gattatcaaa aaggatcttc acctagatcc ttttaaatta aaaatgaagt    7680
tttaaatcaa tctaaagtat atatgagtaa acttggtctg acagttacca atgcttaatc    7740
agtgaggcac ctatctcagc gatctgtcta tttcgttcat ccatagttgc ctgactcccc    7800
gtcgtgtaga taactacgat acgggagggc ttaccatctg gccccagtgc tgcaatgata    7860
ccgcgagacc cacgctcacc ggctccagat ttatcagcaa taaaccagcc agccggaagg    7920
gccgagcgca gaagtggtcc tgcaacttta tccgcctcca tccagtctat taattgttgc    7980
cgggaagcta gagtaagtag ttcgccagtt aatagtttgc gcaacgttgt tgccattgct    8040
acaggcatcg tggtgtcacg ctcgtcgttt ggtatggctt cattcagctc cggttcccaa    8100
cgatcaaggc gagttacatg atcccccatg ttgtgcaaaa aagcggttag ctccttcggt    8160
cctccgatcg ttgtcagaag taagttggcc gcagtgttat cactcatggt tatggcagca    8220
ctgcataatt ctcttactgt catgccatcc gtaagatgct tttctgtgac tggtgagtac    8280
tcaaccaagt cattctgaga atagtgtatg cggcgaccga gttgctcttg cccggcgtca    8340
atacgggata ataccgcgcc acatagcaga actttaaaag tgctcatcat tggaaaacgt    8400
tcttcgggc gaaaactctc aaggatctta ccgctgttga tccagttc gatgtaaccc    8460
actcgtgcac ccaactgatc ttcagcatct tttactttca ccagcgtttc tgggtgagca    8520
```

-continued

```
aaaacaggaa ggcaaaatgc cgcaaaaaag ggaataaggg cgacacgaa atgttgaata      8580 ctcatactct tccttttca atattattga agcatttatc agggttattg tctcatgagc      8640
ggatacatat ttgaatgtat ttagaaaaat aaacaaatag gggttccgcg cacatttccc      8700
cgaaaagtgc                                                            8710
```

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 5

```
atgggatcca agatgaagcg cgcaagaccg                                        30
```

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 6

```
cataacgcgg ccgcttcttt attcttgggc                                        30
```

<210> SEQ ID NO 7
<211> LENGTH: 7148
<212> TYPE: DNA
<213> ORGANISM: Artificial Sequence
<220> FEATURE:
<223> OTHER INFORMATION: Description of Artificial Sequence: plasmid

<400> SEQUENCE: 7

```
gacggatcgg gagatctccc gatccctat ggtcgactct cagtacaatc tgctctgatg       60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gcttggtacc    900
gagctcggat ccaagatgaa gcgcgcaaga ccgtctgaag ataccttcaa ccccgtgtat    960
ccatatgaca cggaaaccgg tcctccaact gtgccttttc ttactcctcc ctttgtatcc   1020
cccaatgggt tcaagagag tcccctgggg gtactctctt tgcgcctatc cgaacctcta   1080
gttacctcca atggcatgct tgcgctcaaa atgggcaacg gcctctctct ggacgaggcc   1140
```

-continued

```
ggcaacctta cctcccaaaa tgtaaccact gtgagcccac ctctcaaaaa aaccaagtca    1200
aacataaacc tggaaatatc tgcacccctc acagttacct cagaagccct aactgtggct    1260
gccgccgcac ctctaatggt cgcgggcaac acactcacca tgcaatcaca ggccccgcta    1320
accgtgcacg actccaaact tagcattgcc acccaaggac ccctcacagt gtcagaagga    1380
aagctagccc tgcaaacatc aggcccctc accaccaccg atagcagtac ccttactatc    1440
actgcctcac cccctctaac tactgccact ggtagcttgg gcattgactt gaaagagccc    1500
atttatacac aaaatggaaa actaggacta aagtacgggg ctcctttgca tgtaacagac    1560
gacctaaaca ctttgaccgt agcaactggt ccaggtgtga ctattaataa tacttccttg    1620
caaactaaag ttactggagc cttgggtttt gattcacaag caatatgca acttaatgta    1680 gcaggaggac taaggattga ttctcaaaac agacgcctta tacttgatgt tagttatccg    1740
tttgatgctc aaaaccaact aaatctaaga ctaggacagg gccctctttt tataaactca    1800
gcccacaact tggatattaa ctacaacaaa ggcctttact tgtttacagc ttcaaacaat    1860
tccaaaaagc ttgaggttaa cctaagcact gccaaggggt tgatgtttga cgctacagcc    1920
atagccatta atgcaggaga tgggcttgaa tttggttcac ctaatgcacc aaacacaaat    1980
cccctcaaaa caaaaattgg ccatggccta gaatttgatt caaacaaggc tatggttcct    2040
aaactaggaa ctggccttag ttttgacagc acaggtgcca ttacagtagg aaacaaaaat    2100
aatgataagc taactttgtg gaccacacca gctccatctc ctaactgtag actaaatgca    2160
gagaaagatg ctaaactcac tttggtctta acaaaatgtg gcagtcaaat acttgctaca    2220
gtttcagttt tggctgttaa aggcagtttg gctccaatat ctggaacagt tcaaagtgct    2280
catcttatta taagatttga cgaaaatgga gtgctactaa acaattcctt cctgacccca    2340
gaatattgga actttagaaa tggagatctt actgaaggca cagcctatac aaacgctgtt    2400
ggatttatgc ctaacctatc agcttatcca aaatctcacg gtaaaactgc caaaagtaac    2460
attgtcagtc aagtttactt aaacggagac aaaactaaac ctgtaacact aaccattaca    2520
ctaaacggta cacaggaaac aggagacaca actccaagtg catactctat gtcattttca    2580
tgggactggt ctggccacaa ctacattaat gaaatatttg ccacatcctc ttacactttt    2640
tcatacattg cccaagaata agaagcggc cgctcgagca tgcatctaga gggcccctat    2700
ctatagtgtc acctaaatgc tagagctcgc tgatcagcct cgactgtgcc ttctagttgc    2760
cagccatctg ttgtttgccc ctcccccgtg ccttccttga ccctggaagg tgccactccc    2820
actgtccttt cctaataaaa tgaggaaatt gcatcgcatt gtctgagtag gtgtcattct    2880
attctggggg gtggggtggg gcaggacagc aaggggagg attgggaaga caatagcagg    2940
catgctgggg atgcggtggg ctctatggct tctgaggcgg aaagaaccag ctgggctct    3000 aggggtatc cccacgcgcc ctgtagcggc gcattaagcg cggcgggtgt ggtggttacg    3060
cgcagcgtga ccgctacact tgccagcgcc ctagcgcccg ctcctttcgc tttcttccct    3120
tcctttctcg ccacgttcgc cggctttccc cgtcaagctc taaatcgggg catccctta    3180 gggttccgat ttagtgcttt acggcacctc gaccccaaaa aacttgatta gggtgatggt    3240
tcacgtagtg ggccatcgcc ctgatagacg ttttcgcc ctttgacgtt ggagtccacg    3300
ttctttaata gtggactctt gttccaaact ggaacaacac tcaaccctat ctcggtctat    3360
tcttttgatt tataagggat tttgggatt tcggcctatt ggttaaaaaa tgagctgatt    3420
taacaaaaat ttaacgcgaa ttaattctgt ggaatgtgtg tcagttaggg tgtggaaagt    3480
```

| | |
|---|---|
| ccccaggctc cccaggcagg cagaagtatg caaagcatgc atctcaatta gtcagcaacc | 3540 |
| aggtgtggaa agtccccagg ctccccagca ggcagaagta tgcaaagcat gcatctcaat | 3600 |
| tagtcagcaa ccatagtccc gccccctaact ccgcccatcc cgcccctaac tccgcccagt | 3660 |
| tccgcccatt ctccgcccca tggctgacta atttttttta tttatgcaga ggccgaggcc | 3720 |
| gcctctgcct ctgagctatt ccagaagtag tgaggaggct tttttggagg cctaggcttt | 3780 |
| tgcaaaaagc tcccgggagc ttgtatatcc attttcggat ctgatcaaga acaggatga | 3840 |
| ggatcgtttc gcatgattga acaagatgga ttgcacgcag gttctccggc cgcttgggtg | 3900 |
| gagaggctat tcggctatga ctgggcacaa cagacaatcg gctgctctga tgccgccgtg | 3960 |
| ttccggctgt cagcgcaggg gcgcccggtt ctttttgtca agaccgacct gtccggtgcc | 4020 |
| ctgaatgaac tgcaggacga ggcagcgcgg ctatcgtggc tggccacgac gggcgttcct | 4080 |
| tgcgcagctg tgctcgacgt tgtcactgaa gcgggaaggg actggctgct attgggcgaa | 4140 |
| gtgccggggc aggatctcct gtcatctcac cttgctcctg ccgagaaagt atccatcatg | 4200 |
| gctgatgcaa tgcggcggct gcatacgctt gatccggcta cctgcccatt cgaccaccaa | 4260 |
| gcgaaacatc gcatcgagcg agcacgtact cggatggaag ccggtcttgt cgatcaggat | 4320 |
| gatctggacg aagagcatca ggggctcgcg ccagccgaac tgttcgccag gctcaaggcg | 4380 |
| cgcatgcccg acggcgagga tctcgtcgtg acccatggcg atgcctgctt gccgaatatc | 4440 |
| atggtggaaa atggccgctt ttctggattc atcgactgtg gccggctggg tgtggcggac | 4500 |
| cgctatcagg acatagcgtt ggctacccgt gatattgctg aagagcttgg cggcgaatgg | 4560 |
| gctgaccgct tcctcgtgct ttacggtatc gccgctcccg attcgcagcg catcgccttc | 4620 |
| tatcgccttc ttgacgagtt cttctgagcg ggactctggg gttcgaaatg accgaccaag | 4680 |
| cgacgcccaa cctgccatca cgagatttcg attccaccgc cgccttctat gaaaggttgg | 4740 |
| gcttcggaat cgttttccgg gacgccggct ggatgatcct ccagcgcggg gatctcatgc | 4800 |
| tggagttctt cgcccacccc aacttgttta ttgcagctta taatggttac aaataaagca | 4860 |
| atagcatcac aaatttcaca aataaagcat ttttttcact gcattctagt tgtggtttgt | 4920 |
| ccaaactcat caatgtatct tatcatgtct gtataccgtc gacctctagc tagagcttgg | 4980 |
| cgtaatcatg gtcatagctg tttcctgtgt gaaattgtta tccgctcaca attccacaca | 5040 |
| acatacgagc cggaagcata aagtgtaaag cctggggtgc ctaatgagtg agctaactca | 5100 |
| cattaattgc gttgcgctca ctgcccgctt tccagtcggg aaacctgtcg tgccagctgc | 5160 |
| attaatgaat cggccaacgc gcggggagag gcggtttgcg tattgggcgc tcttccgctt | 5220 |
| cctcgctcac tgactcgctg cgctcggtcg ttcggctgcg gcgagcggta tcagctcact | 5280 |
| caaaggcggt aatacggtta tccacagaat caggggataa cgcaggaaag aacatgtgag | 5340 |
| caaaaggcca gcaaaaggcc aggaaccgta aaaaggccgc gttgctggcg ttttccata | 5400 |
| ggctccgccc cctgacgag catcacaaaa atcgacgctc aagtcagagg tggcgaaacc | 5460 |
| cgacaggact ataaagatac caggcgtttc ccctggaag ctccctcgtg cgctctcctg | 5520 |
| ttccgaccct gccgcttacc ggatacctgt ccgcctttct cccttcggga agcgtggcgc | 5580 |
| tttctcaatg ctcacgctgt aggtatctca gttcggtgta ggtcgttcgc tccaagctgg | 5640 |
| gctgtgtgca cgaacccccc gttcagcccg accgctgcgc cttatccggt aactatcgtc | 5700 |
| ttgagtccaa cccggtaaga cacgacttat cgccactggc agcagccact ggtaacagga | 5760 |
| ttagcagagc gaggtatgta ggcggtgcta cagagttctt gaagtggtgg cctaactacg | 5820 |
| gctacactag aaggacagta tttggtatct gcgctctgct gaagccagtt accttcggaa | 5880 |

-continued

```
aaagagttgg tagctcttga tccggcaaac aaaccaccgc tggtagcggt ggttttttg     5940 tttgcaagca gcagattacg cgcagaaaaa aaggatctca agaagatcct ttgatctttt     6000
ctacggggtc tgacgctcag tggaacgaaa actcacgtta agggattttg gtcatgagat     6060
tatcaaaaag gatcttcacc tagatccttt taaattaaaa atgaagtttt aaatcaatct     6120
aaagtatata tgagtaaact tggtctgaca gttaccaatg cttaatcagt gaggcaccta     6180
tctcagcgat ctgtctattt cgttcatcca tagttgcctg actccccgtc gtgtagataa     6240
ctacgatacg ggagggctta ccatctggcc ccagtgctgc aatgataccg cgagacccac     6300
gctcaccggc tccagattta tcagcaataa accagccagc cggaagggcc gagcgcagaa     6360
gtggtcctgc aactttatcc gcctccatcc agtctattaa ttgttgccgg gaagctagag     6420
taagtagttc gccagttaat agtttgcgca acgttgttgc cattgctaca ggcatcgtgg     6480
tgtcacgctc gtcgtttggt atggcttcat tcagctccgg ttcccaacga tcaaggcgag     6540
ttacatgatc ccccatgttg tgcaaaaaag cggttagctc cttcggtcct ccgatcgttg     6600
tcagaagtaa gttggccgca gtgttatcac tcatggttat ggcagcactg cataattctc     6660
ttactgtcat gccatccgta agatgctttt ctgtgactgg tgagtactca accaagtcat     6720
tctgagaata gtgtatgcgg cgaccgagtt gctcttgccc ggcgtcaata cgggataata     6780
ccgcgccaca tagcagaact ttaaaagtgc tcatcattgg aaaacgttct tcggggcgaa     6840
aactctcaag gatcttaccg ctgttgagat ccagttcgat gtaacccact cgtgcaccca     6900
actgatcttc agcatctttt actttcacca gcgtttctgg gtgagcaaaa acaggaaggc     6960
aaaatgccgc aaaaaaggga ataagggcga cacggaaatg ttgaatactc atactcttcc     7020
tttttcaata ttattgaagc atttatcagg gttattgtct catgagcgga tacatatttg     7080
aatgtattta gaaaaataaa caaataggggg ttccgcgcac atttccccga aaagtgccac     7140
ctgacgtc                                                              7148
```

<210> SEQ ID NO 8
<211> LENGTH: 7469
<212> TYPE: DNA
<213> ORGANISM: Artificial Sequence
<220> FEATURE:
<223> OTHER INFORMATION: Description of Artificial Sequence: plasmid

<400> SEQUENCE: 8

```
gacggatcgg gagatctccc gatccctat ggtcgactct cagtacaatc tgctctgatg       60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggac tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
```

-continued

```
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gcttggtacc    900
gagctcggat ctgaattcga gctcgctgtt gggctcgcgg ttgaggacaa actcttcgcg    960
gtctttccag tactcttgga tcggaaaccc gtcggcctcc gaacggtact ccgccaccga   1020
gggacctgag cgagtccgca tcgaccggat cggaaaacct ctcgagaaag gcgtctaacc   1080
agtcacagtc gcaaggtagg ctgagcaccg tggcgggcgg cagcgggtgg cggtcggggt   1140
tgtttctggc ggaggtgctg ctgatgatgt aattaaagta ggcggtcttg agacggcgga   1200
tggtcgaggt gaggtgtggc aggcttgaga tccaagatga agcgcgcaag accgtctgaa   1260
gataccttca accccgtgta tccatatgac acggaaaccg gtcctccaac tgtgcctttt   1320
cttactcctc cctttgtatc ccccaatggg tttcaagaga gtcccctgg ggtactctct    1380 ttgcgcctat ccgaacctct agttacctcc aatggcatgc ttgcgctcaa aatgggcaac   1440
ggcctctctc tggacgaggc cggcaacctt acctcccaaa atgtaaccac tgtgagccca   1500
cctctcaaaa aaaccaagtc aaacataaac ctggaaatat ctgcacccct acagttacc    1560 tcagaagccc taactgtggc tgccgccgca cctctaatgg tcgcgggcaa cacactcacc   1620
atgcaatcac aggccccgct aaccgtgcac gactccaaac ttagcattgc cacccaagga   1680
cccctcacag tgtcagaagg aaagctagcc ctgcaaacat caggccccct caccaccacc   1740
gatagcagta cccttactat cactgcctca ccccctctaa ctactgccac tggtagcttg   1800
ggcattgact tgaaagagcc catttataca caaaatggaa aactaggact aaagtacggg   1860
gctcctttgc atgtaacaga cgacctaaac actttgaccg tagcaactgg tccaggtgtg   1920
actattaata atacttcctt gcaaactaaa gttactggag ccttgggttt tgattcacaa   1980
ggcaatatgc aacttaatgt agcaggagga ctaaggattg attctcaaaa cagacgcctt   2040
atacttgatg ttagttatcc gtttgatgct caaaaccaac taaatctaag actaggacag   2100
ggccctcttt ttataaactc agcccacaac ttggatatta actacaacaa aggcctttac   2160
ttgtttacag cttcaaacaa ttccaaaaag cttgaggtta acctaagcac tgccaagggg   2220
ttgatgtttg acgctacagc catagccatt aatgcaggag atgggcttga atttggttca   2280
cctaatgcac caaacacaaa tcccctcaaa acaaaaattg ccatggccct agaatttgat   2340
tcaaacaagg ctatggttcc taaactagga actggcctta gttttgacag cacaggtgcc   2400
attacagtag gaaacaaaaa taatgataag ctaactttgt ggaccacacc agctccatct   2460
cctaactgta gactaaatgc agagaaagat gctaaactca ctttggtctt aacaaaatgt   2520
ggcagtcaaa tacttgctac agtttcagtt ttggctgtta aaggcagttt ggctccaata   2580
tctggaacag ttcaaagtgc tcatcttatt ataagatttg acgaaaatgg agtgctacta   2640
aacaattcct tcctggaccc agaatattgg aactttagaa atggagatct tactgaaggc   2700
acagcctata caaacgctgt tggatttatg cctaacctat cagcttatcc aaaatctcac   2760
ggtaaaactg ccaaaagtaa cattgtcagt caagtttact aaacggaga caaaactaaa    2820 cctgtaacac taaccattac actaaacggt acacaggaaa caggagacac aactccaagt   2880
gcatactcta tgtcattttc atgggactgg tctggccaca actacattaa tgaaatattt   2940
gccacatcct cttacacttt ttcatacatt gcccaagaat aaagaagcgg ccgctcgagc   3000
atgcatctag agggccctat tctatagtgt cacctaaatg ctagagctcg ctgatcagcc   3060
tcgactgtgc cttctagttg ccagccatct gttgtttgcc cctcccccgt gccttccttg   3120
```

```
accctggaag gtgccactcc cactgtcctt tcctaataaa atgaggaaat tgcatcgcat    3180
tgtctgagta ggtgtcattc tattctgggg ggtggggtgg ggcaggacag caaggggag    3240
gattgggaag acaatagcag gcatgctggg gatgcggtgg gctctatggc ttctgaggcg    3300
gaaagaacca gctgggctc  tagggggtat ccccacgcgc cctgtagcgg cgcattaagc    3360
gcggcgggtg tggtggttac gcgcagcgtg accgctacac ttgccagcgc cctagcgccc    3420
gctcctttcg ctttcttccc ttcctttctc gccacgttcg ccggctttcc ccgtcaagct    3480
ctaaatcggg gcatcccttt agggttccga tttagtgctt tacggcacct cgaccccaaa    3540
aaacttgatt agggtgatgg ttcacgtagt gggccatcgc cctgatagac ggtttttcgc    3600
cctttgacgt tggagtccac gttctttaat agtggactct tgttccaaac tggaacaaca    3660
ctcaaccta  tctcggtcta ttcttttgat ttataaggga ttttggggat tcggcctat     3720
tggttaaaaa atgagctgat ttaacaaaaa tttaacgcga attaattctg tggaatgtgt    3780
gtcagttagg gtgtggaaag tccccaggct ccccaggcag gcagaagtat gcaaagcatg    3840
catctcaatt agtcagcaac caggtgtgga agtccccag  gctccccagc aggcagaagt    3900
atgcaaagca tgcatctcaa ttagtcagca accatagtcc cgcccctaac tccgcccatc    3960
ccgcccctaa ctccgcccag ttccgcccat tctccgcccc atggctgact aattttttt     4020
atttatgcag aggccgaggc cgcctctgcc tctgagctat ccagaagta  gtgaggaggc    4080
ttttttggag gcctaggctt ttgcaaaaag ctcccgggag cttgtatatc cattttcgga    4140
tctgatcaag agacaggatg aggatcgttt cgcatgattg aacaagatgg attgcacgca    4200
ggttctccgg ccgcttgggt ggagaggcta ttcggctatg actgggcaca acagacaatc    4260
ggctgctctg atgccgccgt gttccggctg tcagcgcagg ggcgcccggt tctttttgtc    4320
aagaccgacc tgtccggtgc cctgaatgaa ctgcaggacg aggcagcgcg gctatcgtgg    4380
ctggccacga cgggcgttcc ttgcgcagct gtgctcgacg ttgtcactga agcgggaagg    4440
gactggctgc tattgggcga agtgccgggg caggatctcc tgtcatctca ccttgctcct    4500
gccgagaaag tatccatcat ggctgatgca atgcggcggc tgcatacgct tgatccggct    4560
acctgcccat tcgaccacca agcgaaacat cgcatcgagc gagcacgtac tcggatggaa    4620
gccggtcttg tcgatcagga tgatctggac gaagagcatc aggggctcgc gccagccgaa    4680
ctgttcgcca ggctcaaggc gcgcatgccc gacggcgagg atctcgtcgt gacccatggc    4740
gatgcctgct tgccgaatat catggtggaa aatggccgct tttctggatt catcgactgt    4800
ggccggctgg gtgtggcgga ccgctatcag gacatagcgt tggctacccg tgatattgct    4860
gaagagcttg gcggcgaatg ggctgaccgc ttcctcgtgc tttacggtat cgccgctccc    4920
gattcgcagc gcatcgcctt ctatcgcctt cttgacgagt tcttctgagc gggactctgg    4980
ggttcgaaat gaccgaccaa gcgacgccca acctgccatc acgagatttc gattccaccg    5040
ccgccttcta tgaaaggttg ggcttcggaa tcgttttccg ggacgccggc tggatgatcc    5100
tccagcgcgg ggatctcatg ctggagttct tcgcccaccc caacttgttt attgcagctt    5160
ataatggtta caaataaagc aatagcatca caaatttcac aaataaagca tttttttcac    5220
tgcattctag ttgtggtttg tccaaactca tcaatgtatc ttatcatgtc tgtataccgt    5280
cgacctctag ctagagcttg gcgtaatcat ggtcatagct gtttcctgtg tgaaattgtt    5340
atccgctcac aattccacac aacatacgag ccggaagcat aaagtgtaaa gcctggggtg    5400
cctaatgagt gagctaactc acattaattg cgttgcgctc actgcccgct ttccagtcgg    5460
```

```
gaaacctgtc gtgccagctg cattaatgaa tcggccaacg cgcggggaga ggcggtttgc    5520
gtattgggcg ctcttccgct tcctcgctca ctgactcgct gcgctcggtc gttcggctgc    5580
ggcgagcggt atcagctcac tcaaaggcgg taatacggtt atccacagaa tcagggggata   5640 acgcaggaaa gaacatgtga gcaaaaggcc agcaaaaggc caggaaccgt aaaaaggccg    5700
cgttgctggc gtttttccat aggctccgcc cccctgacga gcatcacaaa aatcgacgct    5760
caagtcagag gtggcgaaac ccgacaggac tataaagata ccaggcgttt ccccctggaa    5820
gctccctcgt gcgctctcct gttccgaccc tgccgcttac cggatacctg tccgcctttc    5880
tcccttcggg aagcgtggcg ctttctcaat gctcacgctg taggtatctc agttcggtgt    5940
aggtcgttcg ctccaagctg ggctgtgtgc acgaaccccc cgttcagccc gaccgctgcg    6000
ccttatccgg taactatcgt cttgagtcca acccggtaag acacgactta tcgccactgg    6060
cagcagccac tggtaacagg attagcagag cgaggtatgt aggcggtgct acagagttct    6120
tgaagtggtg gcctaactac ggctacacta gaaggacagt atttggtatc tgcgctctgc    6180
tgaagccagt taccttcgga aaaagagttg gtagctcttg atccggcaaa caaaccaccg    6240
ctggtagcgg tggtttttttt gtttgcaagc agcagattac gcgcagaaaa aaaggatctc    6300
aagaagatcc tttgatcttt tctacggggt ctgacgctca gtggaacgaa aactcacgtt    6360
aagggatttt ggtcatgaga ttatcaaaaa ggatcttcac ctagatcctt ttaaattaaa    6420
aatgaagttt taaatcaatc taaagtatat atgagtaaac ttggtctgac agttaccaat    6480
gcttaatcag tgaggcacct atctcagcga tctgtctatt tcgttcatcc atagttgcct    6540
gactccccgt cgtgtagata actacgatac gggagggctt accatctggc cccagtgctg    6600
caatgatacc gcgagaccca cgctcaccgg ctccagattt atcagcaata aaccagccag    6660
ccggaagggc cgagcgcaga agtggtcctg caactttatc cgcctccatc cagtctatta    6720
attgttgccg ggaagctaga gtaagtagtt cgccagttaa tagtttgcgc aacgttgttg    6780
ccattgctac aggcatcgtg gtgtcacgct cgtcgtttgg tatggcttca ttcagctccg    6840
gttcccaacg atcaaggcga gttacatgat cccccatgtt gtgcaaaaaa gcggttagct    6900
ccttcggtcc tccgatcgtt gtcagaagta agttggccgc agtgttatca ctcatggtta    6960
tggcagcact gcataattct cttactgtca tgccatccgt aagatgcttt tctgtgactg    7020
gtgagtactc aaccaagtca ttctgagaat agtgtatgcg gcgaccgagt tgctcttgcc    7080
cggcgtcaat acgggataat accgcgccac atagcagaac tttaaaagtg ctcatcattg    7140
gaaaacgttc ttcggggcga aaactctcaa ggatcttacc gctgttgaga tccagttcga    7200
tgtaacccac tcgtgcaccc aactgatctt cagcatcttt tactttcacc agcgtttctg    7260
ggtgagcaaa aacaggaagg caaaatgccg caaaaaaggg aataagggcg acacggaaat    7320
gttgaatact catactcttc cttttttcaat attattgaag catttatcag ggttattgtc    7380
tcatgagcga atacatattt gaatgtattt agaaaaataa acaaataggg gttccgcgca    7440
catttccccg aaaagtgcca cctgacgtc                                      7469
```

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 9
tgcttaagcg gccgcgaagg agaagtcc                                        28

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 10
ccgagctagc gactgaaaat gag                                              23

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 11
cctctcgaga gacagcaaga cac                                              23

<210> SEQ ID NO 12
<211> LENGTH: 11152
<212> TYPE: DNA
<213> ORGANISM: Artificial Sequence
<220> FEATURE:
<223> OTHER INFORMATION: Description of Artificial Sequence: plasmid

<400> SEQUENCE: 12
aagcttgggc agaaatggtt gaactcccga gagtgtccta cacctagggg agaagcagcc      60
aaggggttgt ttcccaccaa ggacgacccg tctgcgcaca aacggatgag cccatcagac     120
aaagacatat tcattctctg ctgcaaactt ggcatagctc tgctttgcct ggggctattg     180
ggggaagttg cggttcgtgc tcgcagggct ctcacccttg actcttttaa tagctcttct     240
gtgcaagatt acaatctaaa caattcggag aactcgacct tcctcctgag gcaaggacca     300
cagccaactt cctcttacaa gccgcatcga ttttgtcctt cagaaataga aataagaatg     360
cttgctaaaa attatatttt taccaataag accaatccaa taggtagatt attagttact     420
atgttaagaa atgaatcatt atcttttagt actatttta ctcaaattca gaagttagaa     480
atgggaatag aaaatagaaa gagacgctca acctcaattg aagaacaggt gcaaggacta     540
ttgaccacag gcctagaagt aaaaaaggga aaaagagtg ttttttgtcaa aataggagac     600 aggtggtggc aaccagggac ttataggga ccttacatct acagaccaac agatgccccc     660
ttaccatata caggaagata tgacttaaat tgggataggt gggttacagt caatggctat     720
aaagtgttat atagatccct ccttttcgt gaaagactcg ccagagctag acctccttgg     780
tgtatgttgt ctcaagaaga aaaagacgac atgaaacaac aggtacatga ttatatttat     840
ctaggaacag gaatgcactt tgggggaaag attttccata ccaaggaggg gacagtggct     900
ggactaatag aacattattc tgcaaaaact catggcatga gttattatga atagcccttta     960 ttggcccaac cttgcggttc ccagggctta agtaagtttt tggttacaaa ctgttcttaa    1020
aacgaggatg tgagacaagt ggtttcctga cttggtttgg tatcaaaggt tctgatctga    1080
gctctgagtg ttctattttc ctatgttctt ttggaattta tccaaatctt atgtaaatgc    1140
ttatgtaaac caagatataa aagagtgctg atttttgag taaacttgca acagtcctaa    1200
cattcacctc ttgtgtgttt gtgtctgttc gccatcccgt ctccgctcgt cacttatcct    1260
tcactttcca gagggtcccc ccgcagaccc cggcgaccct caggtcggcc gactgcggca    1320

```
gctggcgccc gaacagggac cctcggataa gtgacccttg tctctatttc tactatttgg    1380
tgtttgtctt gtattgtctc tttcttgtct ggctatcatc acaagagcgg aacggactca    1440
ccatagggac caagctagcg actgaaaatg agacatatta tctgccacgg aggtgttatt    1500
accgaagaaa tggccgccag tcttttggac cagctgatcg aagaggtact ggctgataat    1560
cttccacctc ctagccattt tgaaccacct acccttcacg aactgtatga tttagacgtg    1620 acggccccg aagatcccaa cgaggaggcg gtttcgcaga ttttcccga ctctgtaatg    1680 ttggcggtgc aggaagggat tgacttactc acttttccgc cggcgcccgg ttctccggag    1740
ccgcctcacc tttcccggca gcccgagcag ccggagcaga gagccttggg tccggtttct    1800
atgccaaacc ttgtaccgga ggtgatcgat cttacctgcc acgaggctgg ctttccaccc    1860
agtgacgacg aggatgaaga gggtgaggag tttgtgttag attatgtgga gcaccccggg    1920
cacggttgca ggtcttgtca ttatcaccgg aggaatacgg gggacccaga tattatgtgt    1980
tcgctttgct atatgaggac ctgtggcatg tttgtctaca gtaagtgaaa attatgggca    2040
gtgggtgata gagtggtggg tttggtgtgg taatttttt tttaattttt acagttttgt    2100
ggtttaaaga attttgtatt gtgatttttt taaaaggtcc tgtgtctgaa cctgagcctg    2160
agcccgagcc agaaccggag cctgcaagac ctacccgccg tcctaaaatg gcgcctgcta    2220
tcctgagacg cccgacatca cctgtgtcta gagaatgcaa tagtagtacg gatagctgtg    2280
actccggtcc ttctaacaca cctcctgaga tacacccggt ggtcccgctg tgccccatta    2340
aaccagttgc cgtgagagtt ggtgggcgtc gccaggctgt ggaatgtatc gaggacttgc    2400
ttaacgagcc tgggcaacct ttggacttga gctgtaaacg ccccaggcca taaggtgtaa    2460
acctgtgatt gcgtgtgtgg ttaacgcctt tgtttgctga atgagttgat gtaagtttaa    2520
taaagggtga gataatgttt aacttgcatg gcgtgttaaa tggggcgggg cttaaagggt    2580
atataatgcg ccgtgggcta atcttggtta catctgacct catggaggct tgggagtgtt    2640
tggaagattt ttctgctgtg cgtaacttgc tggaacagag ctctaacagt acctcttggt    2700
tttggaggtt tctgtggggc tcatcccagg caaagttagt ctgcagaatt aaggaggatt    2760
acaagtggga atttgaagag cttttgaaat cctgtggtga gctgtttgat tctttgaatc    2820
tgggtcacca ggcgcttttc caagagaagg tcatcaagac tttggatttt tccacaccgg    2880
ggcgcgctgc ggctgctgtt gcttttttga gttttataaa ggataaatgg agcgaagaaa    2940
cccatctgag cggggggtac ctgctggatt ttctggccat gcatctgtgg agagcggttg    3000
tgagacacaa gaatcgcctg ctactgttgt cttccgtccg cccggcgata ataccgacgg    3060
aggagcagca gcagcagcag gaggaagcca ggcggcggcg gcaggagcag agcccatgga    3120
acccgagagc cggcctggac cctcgggaat gaatgttgta caggtggctg aactgtatcc    3180
agaactgaga cgcatttga caattacaga ggatgggcag gggctaaagg gggtaaagag    3240
ggagcggggg gcttgtgagg ctacagagga ggctaggaat ctagctttta gcttaatgac    3300
cagacaccgt cctgagtgta ttacttttca acagatcaag gataattgcg ctaatgagct    3360
tgatctgctg gcgcagaagt attccataga gcagctgacc acttactggc tgcagccagg    3420
ggatgatttt gaggaggcta ttagggtata tgcaaaggtg gcacttaggc cagattgcaa    3480
gtacaagatc agcaaacttg taaatatcag gaattgttgc tacatttctg ggaacgggc    3540 cgaggtggag atagatacgg aggataggt ggcctttaga tgtagcatga taaatatgtg    3600
gccgggggtg cttggcatgg acgggtggt tattatgaat gtaaggttta ctggccccaa    3660
ttttagcggt acggttttcc tggccaatac caaccttatc ctacacggtg taagcttcta    3720
```

```
tgggtttaac aatacctgtg tggaagcctg gaccgatgta agggttcggg gctgtgcctt   3780
ttactgctgc tggaagggggg tggtgtgtcg ccccaaaagc agggcttcaa ttaagaaatg   3840 cctcttttgaa aggtgtacct tgggtatcct gtctgagggt aactccaggg tgcgccacaa   3900
tgtggcctcc gactgtggtt gcttcatgct agtgaaaagc gtggctgtga ttaagcataa   3960
catggtatgt ggcaactgcg aggacagggc ctctcagatg ctgacctgct cggacggcaa   4020
ctgtcacctg ctgaagacca ttcacgtagc cagccactct cgcaaggcct ggccagtgtt   4080
tgagcataac atactgaccc gctgttcctt gcatttgggt aacaggaggg gggtgttcct   4140
accttaccaa tgcaatttga gtcacactaa gatattgctt gagcccgaga gcatgtccaa   4200
ggtgaacctg aacggggtgt ttgacatgac catgaagatc tggaaggtgc tgaggtacga   4260
tgagacccgc accaggtgca gaccctgcga gtgtggcggt aaacatatta ggaaccagcc   4320
tgtgatgctg gatgtgaccg aggagctgag gcccgatcac ttggtgctgg cctgcacccg   4380
cgctgagttt ggctctagcg atgaagatac agattgaggt actgaaatgt gtgggcgtgg   4440 cttaaggggtg ggaaagaata tataaggtgg gggtcttatg tagttttgta tctgttttgc   4500
agcagccgcc gccgccatga gcaccaactc gtttgatgga agcattgtga gctcatattt   4560
gacaacgcgc atgcccccat gggccggggt gcgtcagaat gtgatgggct ccagcattga   4620
tggtcgcccc gtcctgcccg caaactctac taccttgacc tacgagaccg tgtctggaac   4680
gccgttggag actgcagcct ccgccgccgc ttcagccgct gcagccaccg cccgcgggat   4740
tgtgactgac tttgctttcc tgagcccgct tgcaagcagt gcagcttccc gttcatccgc   4800
ccgcgatgac aagttgacgg ctctttttggc acaattggat tctttgaccc gggaacttaa   4860
tgtcgtttct cagcagctgt tggatctgcg ccagcaggtt tctgccctga aggcttcctc   4920
ccctcccaat gcggtttaaa acataaaataa aaaaccagac tctgtttgga tttggatcaa   4980
gcaagtgtct tgctgtctct cgagggatct ttgtgaagga accttacttc tgtggtgtga   5040
cataattgga caaactacct acagagattt aaagctctaa ggtaaatata aaatttttaa   5100
gtgtataatg tgttaaacta ctgattctaa ttgtttgtgt attttagatt ccaacctatg   5160
gaactgatga atgggagcag tggtggaatg cctttaatga ggaaaacctg ttttgctcag   5220
aagaaatgcc atctagtgat gatgaggcta ctgctgactc tcaacattct actcctccaa   5280
aaaagaagag aaaggtagaa gaccccaagg actttccttc agaattgcta agttttttga   5340
gtcatgctgt gtttagtaat agaactcttg cttgctttgc tatttacacc acaaaggaaa   5400
aagctgcact gctatacaag aaaattatgg aaaaatattc tgtaaccttt ataagtaggc   5460
ataacagtta taatcataac atactgtttt ttcttactcc acacaggcat agagtgtctg   5520
ctattaataa ctatgctcaa aaattgtgta cctttagctt tttaatttgt aaaggggtta   5580
ataaggaata tttgatgtat agtgccttga ctagagatca taatcagcca taccacattt   5640
gtagaggttt tacttgcttt aaaaaacctc ccacacctcc cctgaacct gaaacataaa   5700 atgaatgcaa ttgttgttgt taacttgttt attgcagctt ataatggtta caaataaagc   5760
aatagcatca caaatttcac aaataaagca ttttttttcac tgcattctag ttgtggtttg   5820
tccaaactca tcaatgtatc ttatcatgtc tggatccggc tgtggaatgt gtgtcagtta   5880
gggtgtggaa agtcccccagg ctcccccagca ggcagaagta tgcaaagcat gcatctcaat   5940
tagtcagcaa ccaggtgtgg aaagtcccca ggctccccag caggcagaag tatgcaaagc   6000
atgcatctca attagtcagc aaccatagtc ccgcccctaa ctccgcccat cccgccccta   6060
```

```
actccgccca gttccgccca ttctccgccc catggctgac taattttttt tatttatgca    6120
gaggccgagg ccgcctcggc ctctgagcta ttccagaagt agtgaggagg cttttttgga    6180
ggcctaggct tttgcaaaaa gcttggacac aagacaggct tgcgagatat gtttgagaat    6240
accactttat cccgcgtcag ggagaggcag tgcgtaaaaa gacgcggact catgtgaaat    6300
actggttttt agtgcgccag atctctataa tctcgcgcaa cctatttcc cctcgaacac     6360 ttttaagcc gtagataaac aggctgggac acttcacatg agcgaaaaat acatcgtcac     6420
ctgggacatg ttgcagatcc atgcacgtaa actcgcaagc cgactgatgc cttctgaaca    6480
atggaaaggc attattgccg taagccgtgg cggtctggta ccgggtgcgt tactggcgcg    6540
tgaactgggt attcgtcatg tcgataccgt ttgtatttcc agctacgatc acgacaacca    6600
gcgcgagctt aaagtgctga aacgcgcaga aggcgatggc gaaggcttca tcgttattga    6660
tgacctggtg gataccggtg gtactgcggt tgcgattcgt gaaatgtatc aaaagcgca     6720 cttttgtcacc atcttcgcaa aaccggctgg tcgtccgctg gttgatgact atgttgttga   6780
tatcccgcaa gatacctgga ttgaacagcc gtgggatatg ggcgtcgtat tcgtcccgcc    6840
aatctccggt cgctaatctt ttcaacgcct ggcactgccg ggcgttgttc tttttaactt    6900
caggcgggtt acaatagttt ccagtaagta ttctggaggc tgcatccatg acacaggcaa    6960
acctgagcga aaccctgttc aaaccccgct ttaaacatcc tgaaacctcg acgctagtcc    7020
gccgctttaa tcacggcgca aaccgcctg tgcagtcggc ccttgatggt aaaaccatcc     7080
ctcactggta tcgcatgatt aaccgtctga tgtggatctg gcgcggcatt gacccacgcg    7140
aaatcctcga cgtccaggca cgtattgtga tgagcgatgc cgaacgtacc gacgatgatt    7200
tatacgatac ggtgattggc taccgtggcg gcaactggat ttatgagtgg gccccggatc    7260
tttgtgaagg aaccttactt ctgtggtgtg acataattgg acaaactacc tacagagatt    7320
taaagctcta aggtaaatat aaaatttta agtgtataat gtgttaaact actgattcta     7380
attgtttgtg tattttagat tccaacctat ggaactgatg aatgggagca gtggtggaat    7440
gcctttaatg aggaaaacct gttttgctca gaagaaatgc catctagtga tgatgaggct    7500
actgctgact ctcaacattc tactcctcca aaaagaaga gaaaggtaga agaccccaag     7560
gactttcctt cagaattgct aagtttttg agtcatgctg tgtttagtaa tagaactctt     7620
gcttgctttg ctatttacac cacaaaggaa aaagctgcac tgctatacaa gaaaattatg    7680
gaaaaatatt ctgtaaccct tataagtagg cataacagtt ataatcataa catactgttt    7740
tttcttactc cacacaggca tagagtgtct gctattaata actatgctca aaaattgtgt    7800
acctttagct ttttaatttg taaggggtt aataaggaat atttgatgta tagtgccttg     7860
actagagatc ataatcagcc ataccacatt tgtagaggtt tacttgctt taaaaaacct    7920 cccacacctc cccctgaacc tgaaacataa aatgaatgca attgttgttg ttaacttgtt    7980
tattgcagct tataatggtt acaaataaag caatagcatc acaaatttca caataaagc     8040 attttttca ctgcattcta gttgtggttt gtccaaactc atcaatgtat cttatcatgt      8100
ctggatcccc aggaagctcc tctgtgtcct cataaaccct aacctcctct acttgagagg    8160
acattccaat cataggctgc ccatccaccc tctgtgtcct cctgttaatt aggtcactta    8220
acaaaaagga aattgggtag gggttttca cagaccgctt tctaagggta atttttaaaat    8280 atctgggaag tcccttccac tgctgtgttc cagaagtgtt ggtaaacagc ccacaaatgt    8340
caacagcaga acatacaag ctgtcagctt tgcacaaggg cccaacaccc tgctcatcaa     8400
gaagcactgt ggttgctgtg ttagtaatgt gcaaaacagg aggcacattt tccccacctg    8460
```

```
tgtaggttcc aaaatatcta gtgttttcat ttttacttgg atcaggaacc cagcactcca    8520
ctggataagc attatcctta tccaaaacag ccttgtggtc agtgttcatc tgctgactgt    8580
caactgtagc attttttggg gttacagttt gagcaggata tttggtcctg tagtttgcta    8640
acacaccctg cagctccaaa ggttccccac caacagcaaa aaaatgaaaa tttgacccta    8700
gaatgggttt tccagcacca ttttcatgag ttttttgtgt ccctgaatgc aagtttaaca    8760
tagcagttac cccaataacc tcagttttaa cagtaacagc ttcccacatc aaaatatttc    8820
cacaggttaa gtcctcattt aaattaggca aaggaattct tgaagacgaa agggcctcgt    8880
gatacgccta tttttatagg ttaatgtcat gataataatg gtttcttaga cgtcaggtgg    8940
cactttttcgg ggaaatgtgc gcggaacccc tatttgttta tttttctaaa tacattcaaa    9000
tatgtatccg ctcatgagac aataaccctg ataaatgctt caataatatt gaaaaggaa    9060
gagtatgagt attcaacatt tccgtgtcgc ccttattccc ttttttgcgg catttttgcct    9120
tcctgttttt gctcacccag aaacgctggt gaaagtaaaa gatgctgaag atcagttggg    9180
tgcacgagtg ggttacatcg aactggatct caacagcggt aagatccttg agagttttcg    9240
ccccgaagaa cgttttccaa tgatgagcac ttttaaagtt ctgctatgtg gcgcggtatt    9300
atcccgtgtt gacgccgggc aagagcaact cggtcgccgc atacactatt ctcagaatga    9360
cttggttgag tactcaccag tcacagaaaa gcatcttacg gatggcatga cagtaagaga    9420
attatgcagt gctgccataa ccatgagtga taacactgcg gccaacttac ttctgacaac    9480
gatcggagga ccgaaggagc taaccgcttt tttgcacaac atgggggatc atgtaactcg    9540
ccttgatcgt tgggaaccgg agctgaatga agccatacca aacgacgagc gtgacaccac    9600
gatgcctgca gcaatggcaa caacgttgcg caaactatta actggcgaac tacttactct    9660
agcttcccgg caacaattaa tagactggat ggaggcggat aaagttgcag gaccacttct    9720
gcgctcggcc cttccggctg gctggtttat tgctgataaa tctggagccg gtgagcgtgg    9780
gtctcgcggt atcattgcag cactggggcc agatggtaag ccctcccgta tcgtagttat    9840
ctacacgacg gggagtcagg caactatgga tgaacgaaat agacagatcg ctgagatagg    9900
tgcctcactg attaagcatt ggtaactgtc agaccaagtt tactcatata cttttagat    9960
tgatttaaaa cttcattttt aatttaaaag gatctaggtg aagatccttt ttgataatct    10020
catgaccaaa atcccttaac gtgagttttc gttccactga gcgtcagacc ccgtagaaaa    10080
gatcaaagga tcttcttgag atcctttttt tctgcgcgta atctgctgct tgcaaacaaa    10140
aaaaccaccg ctaccagcgg tggtttgttt gccggatcaa gagctaccaa ctcttttttcc    10200
gaaggtaact ggcttcagca gagcgcagat accaaatact gtccttctag tgtagccgta    10260
gttaggccac cacttcaaga actctgtagc accgcctaca tacctcgctc tgctaatcct    10320
gttaccagtg ctgctgcca gtggcgataa gtcgtgtctt accgggttgg actcaagacg    10380
atagttaccg gataaggcgc agcggtcggg ctgaacgggg ggttcgtgca cacagcccag    10440
cttggagcga acgacctaca ccgaactgag atacctacag cgtgagctat gagaaagcgc    10500
cacgcttccc gaagggagaa aggcggacag gtatccggta agcggcaggg tcggaacagg    10560
agagcgcacg agggagcttc caggggggaaa cgcctggtat ctttatagtc ctgtcgggtt    10620
tcgccacctc tgacttgagc gtcgattttt gtgatgctcg tcagggggcc ggagcctatg    10680
gaaaaacgcc agcaacgcgg ccttttttacg gttcctggcc ttttgctggc cttttgctca    10740
catgttcttt cctgcgttat cccctgattc tgtggataac cgtattaccg cctttgagtg    10800
```

```
agctgatacc gctcgccgca gccgaacgac cgagcgcagc gagtcagtga gcgaggaagc      10860
ggaagagcgc ctgatgcggt attttctcct tacgcatctg tgcggtattt cacaccgcat      10920
atggtgcact ctcagtacaa tctgctctga tgccgcatag ttaagccagt atacactccg      10980
ctatcgctac gtgactgggt catggctgcg ccccgacacc cgccaacacc cgctgacgcg      11040
ccctgacggg cttgtctgct cccggcatcc gcttacagac aagctgtgac cgtctccggg      11100
agctgcatgt gtcagaggtt ttcaccgtca tcaccgaaac gcgcgaggca gc              11152

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 13
gacggatcgg gagatctcc                                                    19

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 14
ccgcctcaga agccatagag cc                                                22

<210> SEQ ID NO 15
<211> LENGTH: 14455
<212> TYPE: DNA
<213> ORGANISM: Artificial Sequence
<220> FEATURE:
<223> OTHER INFORMATION: Description of Artificial Sequence: plasmid

<400> SEQUENCE: 15
aagcttgggc agaaatggtt gaactcccga gagtgtccta cacctagggg agaagcagcc       60
aaggggttgt ttcccaccaa ggacgacccg tctgcgcaca aacggatgag cccatcagac      120
aaagacatat tcattctctg ctgcaaactt ggcatagctc tgctttgcct ggggctattg      180
ggggaagttg cggttcgtgc tcgcagggct ctcacccttg actcttttaa tagctcttct      240
gtgcaagatt acaatctaaa caattcggag aactcgacct tcctcctgag gcaaggacca      300
cagccaactt cctcttacaa gccgcatcga ttttgtcctt cagaaataga aataagaatg      360
cttgctaaaa attatatttt taccaataag accaatccaa taggtagatt attagttact      420
atgttaagaa atgaatcatt atcttttagt actattttta ctcaaattca gaagttagaa      480
atgggaatag aaaatagaaa gagacgctca acctcaattg aagaacaggt gcaaggacta      540
ttgaccacag gcctagaagt aaaaaaggga aaaagagtg tttttgtcaa ataggagac        600 aggtggtggc aaccagggac ttataggga ccttacatct acagaccaac agatgccccc       660
ttaccatata caggaagata tgacttaaat tgggataggt gggttacagt caatggctat      720
aaagtgttat atagatccct ccctttttcgt gaaagactcg ccagagctag acctccttgg      780
tgtatgttgt ctcaagaaga aaaagacgac atgaaacaac aggtacatga ttatatttat      840
ctaggaacag gaatgcactt tgggaaag attttccata ccaaggaggg gacagtggct        900
ggactaatag aacattattc tgcaaaaact catggcatga gttattatga atagccttta     960
ttggcccaac cttgcggttc ccagggctta agtaagtttt tggttacaaa ctgttcttaa    1020
```

```
aacgaggatg tgagacaagt ggtttcctga cttggtttgg tatcaaaggt tctgatctga   1080
gctctgagtg ttctatttc ctatgttctt ttggaattta tccaaatctt atgtaaatgc    1140
ttatgtaaac caagatataa aagagtgctg atttttgag taaacttgca acagtcctaa    1200
cattcacctc ttgtgtgttt gtgtctgttc gccatcccgt ctccgctcgt cacttatcct   1260
tcactttcca gagggtcccc ccgcagaccc cggcgaccct caggtcggcc gactgcggca    1320
gctggcgccc gaacagggac cctcggataa gtgacccttg tctctatttc tactatttgg    1380
tgtttgtctt gtattgtctc tttcttgtct ggctatcatc acaagagcgg aacggactca    1440
ccatagggac caagctagcg actgaaaatg agacatatta tctgccacgg aggtgttatt    1500
accgaagaaa tggccgccag tcttttggac cagctgatcg aagaggtact ggctgataat    1560
cttccacctc ctagccattt tgaaccacct acccttcacg aactgtatga tttagacgtg    1620
acggcccccg aagatcccaa cgaggaggcg gtttcgcaga ttttcccga ctctgtaatg     1680 ttggcggtgc aggaagggat tgacttactc acttttccgc cggcgcccgg ttctccggag    1740
ccgcctcacc tttcccggca gcccgagcag ccggagcaga gagccttggg tccggtttct    1800
atgccaaacc ttgtaccgga ggtgatcgat cttacctgcc acgaggctgg ctttccaccc    1860
agtgacgacg aggatgaaga gggtgaggag tttgtgttag attatgtgga gcaccccggg    1920
cacggttgca ggtcttgtca ttatcaccgg aggaatacgg gggacccaga tattatgtgt    1980
tcgctttgct atatgaggac ctgtggcatg tttgtctaca gtaagtgaaa attatgggca    2040
gtgggtgata gagtggtggg tttggtgtgg taattttttt tttaattttt acagttttgt    2100
ggtttaaaga atttttgtatt gtgattttt taaaaggtcc tgtgtctgaa cctgagcctg    2160
agcccgagcc agaaccggag cctgcaagac ctacccgccg tcctaaaatg gcgcctgcta    2220
tcctgagacg cccgacatca cctgtgtcta gagaatgcaa tagtagtacg gatagctgtg    2280
actccggtcc ttctaacaca cctcctgaga tacacccggt ggtcccgctg tgccccatta    2340
aaccagttgc cgtgagagtt ggtgggcgtc gccaggctgt ggaatgtatc gaggacttgc    2400
ttaacgagcc tgggcaacct ttggacttga gctgtaaacg ccccaggcca taaggtgtaa    2460
acctgtgatt gcgtgtgtgg ttaacgcctt tgtttgctga atgagttgat gtaagtttaa    2520
taaagggtga gataatgttt aacttgcatg gcgtgttaaa tggggcgggg cttaaagggt    2580
atataatgcg ccgtgggcta atcttggtta catctgacct catggaggct gggagtgtt    2640 tggaagattt ttctgctgtg cgtaacttgc tggaacagag ctctaacagt acctcttggt    2700
tttggaggtt tctgtggggc tcatcccagg caaagttagt ctgcagaatt aaggaggatt    2760
acaagtggga atttgaagag cttttgaaat cctgtggtga gctgtttgat tctttgaatc    2820
tgggtcacca ggcgcttttc caagagaagg tcatcaagac tttggatttt tccacaccgg    2880
ggcgcgctgc ggctgctgtt gcttttttga gtttttataaa ggataaatgg agcgaagaaa    2940
cccatctgag cgggggtac ctgctggatt ttctggccat gcatctgtgg agagcggttg     3000
tgagacacaa gaatcgcctg ctactgttgt cttccgtccg cccggcgata taccgacgg     3060 aggagcagca gcagcagcag gaggaagcca ggcggcggcg gcaggagcag agcccatgga    3120
acccgagagc cggcctggac cctcgggaat gaatgttgta caggtggctg aactgtatcc    3180
agaactgaga cgcattttga caattacaga ggatgggcag gggctaaagg gggtaaagag    3240
ggagcggggg gcttgtgagg ctacagagga ggctaggaat ctagctttta gcttaatgac    3300
cagacaccgt cctgagtgta ttacttttca acagatcaag gataattgcg ctaatgagct    3360
```

-continued

```
tgatctgctg gcgcagaagt attccataga gcagctgacc acttactggc tgcagccagg    3420
ggatgatttt gaggaggcta ttagggtata tgcaaaggtg gcacttaggc cagattgcaa    3480
gtacaagatc agcaaacttg taaatatcag gaattgttgc tacatttctg gaacgggggc    3540
cgaggtggag atagatacgg aggatagggt ggcctttaga tgtagcatga taaatatgtg    3600
gccgggggtg cttggcatgg acggggtggt tattatgaat gtaaggttta ctggccccaa    3660
ttttagcggt acgttttcc tggccaatac caaccttatc ctacacggtg taagcttcta    3720
tgggtttaac aatacctgtg tggaagcctg gaccgatgta agggttcggg gctgtgcctt    3780
ttactgctgc tggaaggggg tggtgtgtcg ccccaaaagc agggcttcaa ttaagaaatg    3840
cctctttgaa aggtgtacct tgggtatcct gtctgagggt aactccaggg tgcgccacaa    3900
tgtggcctcc gactgtggtt gcttcatgct agtgaaaagc gtggctgtga ttaagcataa    3960
catggtatgt ggcaactgcg aggacagggc ctctcagatg ctgacctgct cggacggcaa    4020
ctgtcacctg ctgaagacca ttcacgtagc cagccactct cgcaaggcct ggccagtgtt    4080
tgagcataac atactgaccc gctgttcctt gcatttgggt aacaggaggg gggtgttcct    4140
accttaccaa tgcaatttga gtcacactaa gatattgctt gagcccgaga gcatgtccaa    4200
ggtgaacctg aacgggtgt ttgacatgac catgaagatc tggaaggtgc tgaggtacga    4260
tgagacccgc accaggtgca gaccctgcga gtgtggcggt aaacatatta ggaaccagcc    4320
tgtgatgctg gatgtgaccg aggagctgag gcccgatcac ttggtgctgg cctgcacccg    4380
cgctgagttt ggctctagcg atgaagatac agattgaggg actgaaatgt gtgggcgtgg    4440
cttaagggtg ggaaagaata tataaggtgg gggtcttatg tagttttgta tctgttttgc    4500
agcagccgcc gccgccatga gcaccaactc gtttgatgga agcattgtga gctcatattt    4560
gacaacgcgc atgcccccat gggccgggt gcgtcagaat gtgatgggct ccagcattga    4620
tggtcgcccc gtcctgcccg caaactctac taccttgacc tacgagaccg tgtctggaac    4680
gccgttggag actgcagcct ccgccgccgc ttcagccgct gcagccaccg cccgcgggat    4740
tgtgactgac tttgctttcc tgagcccgct tgcaagcagt gcagcttccc gttcatccgc    4800
ccgcgatgac aagttgacgg ctctttttggc acaattggat tctttgaccc gggaacttaa    4860
tgtcgtttct cagcagctgt tggatctgcg ccagcaggtt tctgccctga aggcttcctc    4920
ccctcccaat gcggtttaaa acataaataa aaaaccagac tctgtttgga tttggatcaa    4980
gcaagtgtct tgctgtctct cgagggatct ttgtgaagga accttacttc tgtggtgtga    5040
cataattgga caaactacct acagagattt aaagctctaa ggtaaatata aattttttaa    5100
gtgtataatg tgttaaacta ctgattctaa ttgtttgtgt atttttagatt ccaacctatg    5160 gaactgatga atgggagcag tggtggaatg cctttaatga ggaaaacctg ttttgctcag    5220
aagaaatgcc atctagtgat gatgaggcta ctgctgactc tcaacattct actcctccaa    5280
aaaagaagag aaaggtagaa gaccccaagg actttccttc agaattgcta agttttttga    5340
gtcatgctgt gtttagtaat agaactcttg cttgctttgc tatttacacc acaaaggaaa    5400
aagctgcact gctatacaag aaaattatgg aaaatattc tgtaacctt ataagtaggc    5460 ataacagtta taatcataac atactgtttt tcttactcc acacaggcat agagtgtctg    5520
ctattaataa ctatgctcaa aaattgtgta ccttagctt tttaatttgt aaggggttta    5580
ataaggaata tttgatgtat agtgccttga ctagagatca taatcagcca taccacattt    5640
gtagaggttt tacttgcttt aaaaaacctc ccacacctcc cctgaacct gaaacataaa    5700 atgaatgcaa ttgttgttgt taacttgttt attgcagctt ataatggtta caaataaagc    5760
```

```
aatagcatca caaatttcac aaataaagca ttttttttcac tgcattctag ttgtggtttg    5820
tccaaactca tcaatgtatc ttatcatgtc tggatccggc tgtggaatgt gtgtcagtta    5880
gggtgtggaa agtccccagg ctccccagca ggcagaagta tgcaaagcat gcatctcaat    5940
tagtcagcaa ccaggtgtgg aaagtcccca ggctcccag caggcagaag tatgcaaagc    6000
atgcatctca attagtcagc aaccatagtc ccgcccctaa ctccgcccat cccgcccta    6060 actccgccca gttccgccca ttctccgccc catggctgac taattttttt tatttatgca    6120
gaggccgagg ccgcctcggc ctctgagcta ttccagaagt agtgaggagg cttttttgga    6180
ggcctaggct tttgcaaaaa gcttggacac aagacaggct tgcgagatat gtttgagaat    6240
accactttat cccgcgtcag ggagaggcag tgcgtaaaaa gacgcggact catgtgaaat    6300
actggttttt agtgcgccag atctctataa tctcgcgcaa cctatttttcc cctcgaacac    6360 ttttttaagcc gtagataaac aggctgggac acttcacatg agcgaaaaat acatcgtcac    6420
ctgggacatg ttgcagatcc atgcacgtaa actcgcaagc cgactgatgc cttctgaaca    6480
atggaaaggc attattgccg taagccgtgg cggtctggta ccgggtgcgt tactggcgcg    6540
tgaactgggt attcgtcatg tcgataccgt ttgtatttcc agctacgatc acgacaacca    6600
gcgcgagctt aaagtgctga aacgcgcaga aggcgatggc gaaggcttca tcgttattga    6660
tgacctggtg gataccggtg gtactgcggt tgcgattcgt gaaatgtatc caaaagcgca    6720
ctttgtcacc atcttcgcaa aaccggctgg tcgtccgctg gttgatgact atgttgttga    6780
tatcccgcaa gatacctgga ttgaacagcc gtgggatatg ggcgtcgtat tcgtcccgcc    6840
aatctccggt cgctaatctt ttcaacgcct ggcactgccg ggcgttgttc tttttaactt    6900
caggcgggtt acaatagttt ccagtaagta ttctggaggc tgcatccatg acacaggcaa    6960
acctgagcga aaccctgttc aaaccccgct ttaaacatcc tgaaacctcg acgctagtcc    7020
gccgctttaa tcacggcgca caaccgcctg tgcagtcggc ccttgatggt aaaaccatcc    7080
ctcactggta tcgcatgatt aaccgtctga tgtggatctg gcgcggcatt gacccacgcg    7140
aaatcctcga cgtccaggca cgtattgtga tgagcgatgc cgaacgtacc gacgatgatt    7200
tatacgatac ggtgattggc taccgtggcg gcaactggat ttatgagtgg gccccggatc    7260
tttgtgaagg aaccttactt ctgtggtgtg acataattgg acaaactacc tacagagatt    7320
taaagctcta aggtaaatat aaaattttta agtgtataat gtgttaaact actgattcta    7380
attgtttgtg tattttagat tccaacctat ggaactgatg aatgggagca gtggtggaat    7440
gcctttaatg aggaaaacct gttttgctca gaagaaatgc catctagtga tgatgaggct    7500
actgctgact ctcaacattc tactcctcca aaaaagaaga gaaaggtaga agaccccaag    7560
gactttcctt cagaattgct aagttttttg agtcatgctg tgtttagtaa tagaactctt    7620
gcttgctttg ctatttacac cacaaaggaa aaagctgcac tgctatacaa gaaaattatg    7680
gaaaaatatt ctgtaacctt tataagtagg cataacagtt ataatcataa catactgttt    7740
tttcttactc cacacaggca tagagtgtct gctattaata actatgctca aaaattgtgt    7800
acctttagct ttttaatttg taagggggtt aataaggaat atttgatgta tagtgccttg    7860
actagagatc ataatcagcc ataccacatt tgtagaggtt ttacttgctt taaaaaacct    7920
cccacacctc ccctgaacc tgaaacataa atgaatgca attgttgttg ttaacttgtt    7980
tattgcagct tataatggtt acaaataaag caatagcatc acaaatttca caataaagc    8040 attttttttca ctgcattcta gttgtggttt gtccaaactc atcaatgtat cttatcatgt    8100
```

```
ctggatcccc aggaagctcc tctgtgtcct cataaaccct aacctcctct acttgagagg    8160
acattccaat cataggctgc ccatccaccc tctgtgtcct cctgttaatt aggtcactta    8220
acaaaaagga aattgggtag gggttttca cagaccgctt tctaagggta attttaaaat    8280
atctgggaag tcccttccac tgctgtgttc cagaagtgtt ggtaaacagc ccacaaatgt    8340
caacagcaga aacatacaag ctgtcagctt tgcacaaggg cccaacaccc tgctcatcaa    8400
gaagcactgt ggttgctgtg ttagtaatgt gcaaaacagg aggcacattt tccccacctg    8460
tgtaggttcc aaaatatcta gtgttttcat ttttacttgg atcaggaacc cagcactcca    8520
ctggataagc attatcctta tccaaaacag ccttgtggtc agtgttcatc tgctgactgt    8580
caactgtagc attttttggg gttacagttt gagcaggata tttggtcctg tagtttgcta    8640
acacaccctg cagctccaaa ggttccccac caacagcaaa aaaatgaaaa tttgacccttt   8700 gaatgggttt tccagcacca ttttcatgag ttttttgtgt ccctgaatgc aagtttaaca    8760
tagcagttac cccaataacc tcagttttaa cagtaacagc ttcccacatc aaaatatttc    8820
cacaggttaa gtcctcattt aaattaggca aaggaattct tgaagacgaa agggcctcgt    8880
gatacgccta ttttataggt ttaatgtcat gataataatg gtttcttaga cgtcaggtgg    8940 cactttcgg ggaaatgtgc gcggaacccc tatttgttta tttttctaaa tacattcaaa      9000
tatgtatccg ctcatgagac aataaccctg ataaatgctt caataatatt gaaaaggaa     9060 gagtatgagt attcaacatt tccgtgtcgc ccttattccc tttttttgcgg cattttgcct    9120 tcctgttttt gctcacccag aaacgctggt gaaagtaaaa gatgctgaag atcagttggg    9180
tgcacgagtg ggttacatcg aactggatct caacagcggt aagatccttg agagttttcg    9240
ccccgaagaa cgttttccaa tgatgagcac ttttaaagtt ctgctatgtg gcgcggtatt    9300
atcccgtgtt gacgccgggc aagagcaact cggtcgccgc atacactatt ctcagaatga    9360
cttggttgag tactcaccag tcacagaaaa gcatcttacg gatggcatga cagtaagaga    9420
attatgcagt gctgccataa ccatgagtga taacactgcg gccaacttac ttctgacaac    9480
gatcggagga ccgaaggagc taaccgcttt tttgcacaac atgggggatc atgtaactcg    9540
ccttgatcgt tgggaaccgg agctgaatga agccatacca aacgacgagc gtgacaccac    9600
gatgcctgca gcaatggcaa caacgttgcg caaactatta actggcgaac tacttactct    9660
agcttcccgg caacaattaa tagactggat ggaggcggat aaagttgcag gaccacttct    9720
gcgctcggcc cttccggctg gctggtttat tgctgataaa tctggagccg gtgagcgtgg    9780
gtctcgcggt atcattgcag cactggggcc agatggtaag ccctcccgta tcgtagttat    9840
ctacacgacg gggagtcagg caactatgga tgaacgaaat agacagatcg ctgagatagg    9900
tgcctcactg attaagcatt ggtaactgtc agaccaagtt tactcatata ctttagat      9960 tgatttaaaa cttcattttt aatttaaaag gatctaggtg aagatccttt ttgataatct   10020
catgaccaaa atcccttaac gtgagttttc gttccactga gcgtcagacc ccgtagaaaa   10080
gatcaaagga tcttcttgag atcctttttt tctgcgcgta atctgctgct tgcaaacaaa   10140 aaaccaccg ctaccagcgg tggtttgttt gccggatcaa gagctaccaa ctctttttcc    10200
gaaggtaact ggcttcagca gagcgcagat accaaatact gtccttctag tgtagccgta   10260
gttaggccac cacttcaaga actctgtagc accgcctaca tacctcgctc tgctaatcct   10320
gttaccagtg gctgctgcca gtggcgataa gtcgtgtctt accgggttgg actcaagacg   10380
atagttaccg gataaggcgc agcggtcggg ctgaacgggg ggttcgtgca cacagcccag   10440
cttggagcga acgacctaca ccgaactgag atacctacag cgtgagctat gagaaagcgc   10500
```

```
cacgcttccc gaagggagaa aggcggacag gtatccggta agcggcaggg tcggaacagg   10560
agagcgcacg agggagcttc caggggggaaa cgcctggtat ctttatagtc ctgtcgggtt   10620
tcgccacctc tgacttgagc gtcgattttt gtgatgctcg tcaggggggc ggagcctatg   10680
gaaaaacgcc agcaacgcgg ccttttacg gttcctggcc ttttgctggc cttttgctca   10740
catgttcttt cctgcgttat ccctgattc tgtggataac cgtattaccg cctttgagtg   10800
agctgatacc gctcgccgca gccgaacgac cgagcgcagc gagtcagtga gcgaggaagc   10860
ggaagagcgc ctgatgcggt attttctcct tacgcatctg tgcggtattt cacaccgcat   10920
accgcctcag aagccataga gcccaccgca tccccagcat gcctgctatt gtcttcccaa   10980
tcctccccct tgctgtcctg ccccacccca cccccagaa tagaatgaca cctactcaga   11040
caatgcgatg caatttcctc attttattag gaaaggacag tgggagtggc accttccagg   11100
gtcaaggaag gcacggggga ggggcaaaca acagatggct ggcaactaga aggcacagtc   11160
gaggctgatc agcgagctct agcatttagg tgacactata aatagggcc ctctagatgc   11220 atgctcgagc ggccgcttct ttattcttgg gcaatgtatg aaaagtgta agaggatgtg   11280 gcaaatattt cattaatgta gttgtggcca gaccagtccc atgaaaatga catagagtat   11340
gcacttggag ttgtgtctcc tgtttcctgt gtaccgttta gtgtaatggt tagtgttaca   11400
ggtttagttt tgtctccgtt taagtaaact tgactgacaa tgttactttt ggcagtttta   11460
ccgtgagatt ttggataagc tgataggtta ggcataaatc caacagcgtt tgtataggct   11520
gtgccttcag taagatctcc atttctaaag ttccaatatt ctgggtccag gaaggaattg   11580
tttagtagca ctccatttttc gtcaaatctt ataataagat gagcactttg aactgttcca   11640
gatattggag ccaaactgcc tttaacagcc aaaactgaaa ctgtagcaag tatttgactg   11700
ccacattttg ttaagaccaa agtgagttta gcatctttct ctgcatttag tctacagtta   11760
ggagatggag ctggtgtggt ccacaaagtt agcttatcat tattttttgtt tcctactgta   11820 atggcacctg tgctgtcaaa actaaggcca gttcctagtt taggaaccat agccttgttt   11880
gaatcaaatt ctaggccatg gccaattttt gttttgaggg gatttgtgtt tggtgcatta   11940
ggtgaaccaa attcaagccc atctcctgca ttaatggcta tggctgtagc gtcaaacatc   12000
aaccccttgg cagtgcttag gttaacctca agcttttttgg aattgtttga agctgtaaac   12060
aagtaaaggc ctttgttgta gttaatatcc aagttgtggg ctgagtttat aaaaagaggg   12120
ccctgtccta gtcttagatt tagttggttt tgagcatcaa acggataact aacatcaagt   12180
ataaggcgtc tgttttgaga atcaatcctt agtcctcctg ctacattaag ttgcatattg   12240
ccttgtgaat caaacccaa ggctccagta actttagttt gcaaggaagt attattaata   12300
gtcacacctg gaccagttgc tacggtcaaa gtgtttaggt cgtctgttac atgcaaagga   12360
gccccgtact ttagtcctag ttttccattt tgtgtataaa tgggctcttt caagtcaatg   12420
cccaagctac cagtggcagt agttagaggg ggtgaggcag tgatagtaag ggtactgcta   12480
tcggtggtgg tgagggggcc tgatgtttgc agggctagct ttccttctga cactgtgagg   12540
ggtccttggg tggcaatgct aagtttggag tcgtgcacgg ttagcggggc ctgtgattgc   12600
atggtgagtg tgttgcccgc gaccattaga ggtgcggcgg cagccacagt tagggcttct   12660
gaggtaactg tgaggggtgc agatatttcc aggtttatgt ttgacttggt ttttttgaga   12720
ggtgggctca cagtggttac attttgggag gtaaggttgc cggcctcgtc cagagagagg   12780
ccgttgccca ttttgagcgc aagcatgcca ttggaggtaa ctagaggttc ggataggcgc   12840
```

```
aaagagagta ccccaggggg actctcttga aacccattgg gggatacaaa gggaggagta      12900
agaaaaggca cagttggagg accggtttcc gtgtcatatg gatacacggg gttgaaggta      12960
tcttcagacg gtcttgcgcg cttcatcttg gatctcaagc ctgccacacc tcacctcgac      13020
catccgccgt ctcaagaccg cctactttaa ttacatcatc agcagcacct ccgcagaaa       13080 caaccccgac cgccacccgc tgccgcccgc cacggtgctc agcctacctt gcgactgtga      13140
ctggttagac gcctttctcg agaggttttc cgatccggtc gatgcggact cgctcaggtc      13200
cctcggtggc ggagtaccgt tcggaggccg acgggtttcc gatccaagag tactggaaag      13260
accgcgaaga gtttgtcctc aaccgcgagc ccaacagcga gctcgaattc agatccgagc      13320
tcggtaccaa gcttgggtct ccctatagtg agtcgtatta atttcgataa gccagtaagc      13380
agtgggttct ctagttagcc agagagctct gcttatatag acctcccacc gtacacgcct      13440
accgcccatt tgcgtcaatg gggcggagtt gttacgacat tttggaaagt cccgttgatt      13500
ttggtgccaa aacaaactcc cattgacgtc aatggggtgg agacttggaa atccccgtga      13560
gtcaaaccgc tatccacgcc cattgatgta ctgccaaaac cgcatcacca tggtaatagc      13620
gatgactaat acgtagatgt actgccaagt aggaaagtcc cataaggtca tgtactgggc      13680
ataatgccag gcgggccatt taccgtcatt gacgtcaata ggggcgtac ttggcatatg       13740 atacacttga tgtactgcca agtgggcagt ttaccgtaaa tagtccaccc attgacgtca      13800
atggaaagtc cctattggcg ttactatggg aacatacgtc attattgacg tcaatgggcg      13860
ggggtcgttg gcggtcagc caggcgggcc atttaccgta agttatgtaa cgcggaactc       13920
catatatggg ctatgaacta atgaccccgt aattgattac tattaataac tagtcaataa      13980
tcaatgtcaa cgcgtatatc tggcccgtac atcgcgaagc agcgcaaaac gcctaaccct      14040
aagcagattc ttcatgcaat tgtcggtcaa gccttgcctt gttgtagctt aaattttgct      14100
cgcgcactac tcagcgacct ccaacacaca agcagggagc agatactggc ttaactatgc      14160
ggcatcagag cagattgtac tgagagtcga ccataggga tcgggagatc tcccgatccg       14220
tctatggtgc actctcagta caatctgctc tgatgccgca tagttaagcc agtatacact      14280
ccgctatcgc tacgtgactg ggtcatggct gcgccccgac acccgccaac acccgctgac      14340
gcgccctgac gggcttgtct gctcccggca tccgcttaca caagctgt gaccgtctcc        14400 gggagctgca tgtgtcagag gttttcaccg tcatcaccga aacgcgcgag gcagc           14455
```

<210> SEQ ID NO 16
<211> LENGTH: 10610
<212> TYPE: DNA
<213> ORGANISM: Artificial Sequence
<220> FEATURE:
<223> OTHER INFORMATION: Description of Artificial Sequence: plasmid

<400> SEQUENCE: 16

```
gacggatcgg gagatccgcg cggtacacag aattcaggag acacaactcc aagtgcatac        60
tctatgtcat tttcatggga ctggtctggc cacaactaca ttaatgaaat atttgccaca       120
tcctcttaca cttttttcata cattgcccaa gaataaagaa tcgtttgtgt tatgtttcaa      180
cgtgtttatt tttcaattgc agaaaatttc aagtcatttt tcattcagta gtatagcccc      240
accaccacat agcttataca gatcaccgta ccttaatcaa actcacagaa ccctagtatt      300
caacctgcca cctccctccc aacacacaga gtacacagtc ctttctcccc ggctggcctt      360
aaaaagcatc atatcatggg taacagacat attcttaggt gttatattcc acacggtttc      420
ctgtcgagcc aaacgctcat cagtgatatt aataaactcc ccgggcagct cacttaagtt      480
```

-continued

```
catgtcgctg tccagctgct gagccacagg ctgctgtcca acttgcggtt gcttaacggg    540
cggcgaagga gaagtccacg cctacatggg ggtagagtca taatcgtgca tcaggatagg    600
gcggtggtgc tgcagcagcg cgcgaataaa ctgctgccgc cgccgctccg tcctgcagga    660
atacaacatg gcagtggtct cctcagcgat gattcgcacc gcccgcagca taaggcgcct    720
tgtcctccgg gcacagcagc gcaccctgat ctcacttaaa tcagcacagt aactgcagca    780
cagcaccaca atattgttca aaatcccaca gtgcaaggcg ctgtatccaa agctcatggc    840
ggggaccaca gaacccacgt ggccatcata ccacaagcgc aggtagatta gtggcgacc    900
cctcataaac acgctggaca taaacattac ctcttttggc atgttgtaat tcaccacctc    960
ccggtaccat ataaacctct gattaaacat ggcgccatcc accaccatcc taaaccagct   1020
ggccaaaacc tgcccgccgg ctatacactg cagggaaccg ggactggaac aatgacagtg   1080
gagagcccag gactcgtaac catggatcat catgctcgtc atgatatcaa tgttggcaca   1140
acacaggcac acgtgcatac acttcctcag gattacaagc tcctcccgcg ttagaaccat   1200
atcccaggga caacccatt cctgaatcag cgtaaatccc acactgcagg gaagacctcg    1260
cacgtaactc acgttgtgca ttgtcaaagt gttacattcg ggcagcagcg gatgatcctc   1320
cagtatggta gcgcggggtt ctgtctcaaa aggaggtaga cgatccctac tgtacggagt   1380
gcgccgagac aaccgagatc gtgttggtcg tagtgtcatg ccaaatggaa cgccggacgt   1440
agtcatattt cctgaagcaa aaccaggtgc gggcgtgaca aacagatctg cgtctccggt   1500
ctcgccgctt agatcgctct gtgtagtagt tgtagtatat ccactctctc aaagcatcca   1560
ggcgccccct ggcttcgggt tctatgtaaa ctccttcatg cgccgctgcc ctgataacat   1620
ccaccaccgc agaataagcc acacccagcc aacctacaca ttcgttctgc gagtcacaca   1680
cgggaggagc gggaagagct ggaagaacca tgtttttttt tttattccaa aagattatcc   1740
aaaacctcaa aatgaagatc tattaagtga acgcgctccc ctccggtggc gtggtcaaac   1800
tctacagcca aagaacagat aatggcattt gtaagatgtt gcacaatggc ttccaaaagg   1860
caaacggccc tcacgtccaa gtggacgtaa aggctaaacc cttcagggtg aatctcctct   1920
ataaacattc cagcaccttc aaccatgccc aaataattct catctcgcca ccttctcaat   1980
atatctctaa gcaaatcccg aatattaagt ccggccattg taaaaatctg ctccagagcg   2040
ccctccacct tcagcctcaa gcagcgaatc atgattgcaa aaattcaggt tcctcacaga   2100
cctgtataag attcaaaagc ggaacattaa caaaaatacc gcgatcccgt aggtcccttc   2160
gcagggccag ctgaacataa tcgtgcaggt ctgcacggac cagcgcggcc acttccccgc   2220
caggaacctt gacaaaagaa cccacactga ttatgacacg catactcgga gctatgctaa   2280
ccagcgtagc cccgatgtaa gctttgttgc atgggcggcg atataaaatg caaggtgctg   2340
ctcaaaaaat caggcaaagc ctcgcgcaaa aagaaagca catcgtagtc atgctcatgc   2400
agataaaggc aggtaagctc cggaaccacc acagaaaaag acaccatttt tctctcaaac   2460
atgtctgcgg gtttctgcat aaacacaaaa taaaataaca aaaaaacatt taaacattag   2520
aagcctgtct tacaacagga aaaacaaccc ttataagcat aagacggact acggccatgc   2580
cggcgtgacc gtaaaaaaac tggtcaccgt gattaaaaag caccaccgac agctcctcgg   2640
tcatgtccgg agtcataatg taagactcgg taaacacatc aggttgattc atcggtcagt   2700
gctaaaaagc gaccgaaata gcccggggga atacataccc gcaggcgtag agacaacatt   2760
acagccccca taggaggtat aacaaaatta ataggagaga aaaacacata aacacctgaa   2820
```

-continued

```
aaaccctcct gcctaggcaa aatagcaccc tcccgctcca gaacaacata cagcgcttca    2880
cagcggcagc ctaacagtca gccttaccag taaaaaagaa aacctattaa aaaaacacca    2940
ctcgacacgg caccagctca atcagtcaca gtgtaaaaaa gggccaagtg cagagcgagt    3000
atatatagga ctaaaaaatg acgtaacggt taaagtccac aaaaaacacc cagaaaaccg    3060
cacgcgaacc tacgcccaga aacgaaagcc aaaaaaccca caacttcctc aaatcgtcac    3120
ttccgttttc ccacgttacg taacttcccg gatcctctcc cgatcccta tggtcgactc    3180 tcagtacaat ctgctctgat gccgcatagt taagccagta tctgctccct gcttgtgtgt    3240
tggaggtcgc tgagtagtgc gcgagcaaaa tttaagctac aacaaggcaa ggcttgaccg    3300
acaattgcat gaagaatctg cttagggtta ggcgttttgc gctgcttcgc gatgtacggg    3360
ccagatatac gcgttgacat tgattattga ctagttatta atagtaatca attacgggt    3420 cattagttca tagcccatat atggagttcc gcgttacata acttacggta aatggcccgc    3480
ctggctgacc gcccaacgac ccccgcccat tgacgtcaat aatgacgtat gttcccatag    3540
taacgccaat agggactttc cattgacgtc aatgggtgga ctatttacgg taaactgccc    3600
acttggcagt acatcaagtg tatcatatgc caagtacgcc ccctattgac gtcaatgacg    3660
gtaaatggcc cgcctggcat tatgcccagt acatgacctt atgggacttt cctacttggc    3720
agtacatcta cgtattagtc atcgctatta ccatggtgat gcggttttgg cagtacatca    3780
atgggcgtgg atagcggttt gactcacggg gatttccaag tctccacccc attgacgtca    3840
atgggagttt gttttggcac caaaatcaac gggactttcc aaaatgtcgt aacaactccg    3900
ccccattgac gcaaatgggc ggtaggcgtg tacggtggga ggtctatata agcagagctc    3960
tctggctaac tagagaaccc actgcttact ggcttatcga aattaatacg actcactata    4020
gggagaccca agcttggtac cgagctcgga tctgaattcg agctcgctgt tgggctcgcg    4080
gttgaggaca aactcttcgc ggtctttcca gtactcttgg atcggaaacc cgtcggcctc    4140
cgaacggtac tccgccaccg agggacctga gcgagtccgc atcgaccgga tcggaaaacc    4200
tctcgagaaa ggcgtctaac cagtcacagt cgcaaggtag gctgagcacc gtggcgggcg    4260
gcagcgggtg gcggtcgggg ttgtttctgg cggaggtgct gctgatgatg taattaaagt    4320
aggcggtctt gagacggcgg atggtcgagg tgaggtgtgg caggcttgag atccaagatg    4380
aagcgcgcaa gaccgtctga agataccttc aaccccgtgt atccatatga cacggaaacc    4440
ggtcctccaa ctgtgccttt tcttactcct ccctttgtat cccccaatgg gtttcaagag    4500
agtccccctg gggtactctc tttgcgccta tccgaacctc tagttacctc caatggcatg    4560
cttgcgctca aaatgggcaa cggcctctct ctggacgagg ccggcaacct tacctcccaa    4620
aatgtaacca ctgtgagccc acctctcaaa aaaccaagt caaacataaa cctggaaata    4680
tctgcacccc tcacagttac ctcagaagcc ctaactgtgg ctgccgccgc acctctaatg    4740
gtcgcgggca acacactcac catgcaatca caggccccgc taaccgtgca cgactccaaa    4800
cttagcattg ccacccaagg acccctcaca gtgtcagaag gaaagctagc cctgcaaaca    4860
tcaggccccc tcaccaccac cgatagcagt acccttacta tcactgcctc accccctcta    4920
actactgcca ctggtagctt gggcattgac ttgaaagagc ccatttatac acaaaatgga    4980
aaactaggac taaagtacgg ggctcctttg catgtaacag acgacctaaa cactttgacc    5040
gtagcaactg gtccaggtgt gactattaat aatacttcct tgcaaactaa agttactgga    5100
gccttgggtt ttgattcaca aggcaatatg caacttaatg tagcaggagg actaaggatt    5160
gattctcaaa acagacgcct tatacttgat gttagttatc cgtttgatgc tcaaaaccaa    5220
```

```
ctaaatctaa gactaggaca gggccctctt tttataaact cagcccacaa cttggatatt    5280
aactacaaca aaggccttta cttgtttaca gcttcaaaca attccaaaaa gcttgaggtt    5340
aacctaagca ctgccaaggg gttgatgttt gacgctacag ccatagccat taatgcagga    5400
gatgggcttg aatttggttc acctaatgca ccaaacacaa atcccctcaa aacaaaaatt    5460
ggccatggcc tagaatttga ttcaaacaag gctatggttc ctaaactagg aactggcctt    5520
agttttgaca gcacaggtgc cattacagta ggaaacaaaa ataatgataa gctaactttg    5580
tggaccacac cagctccatc tcctaactgt agactaaatg cagagaaaga tgctaaactc    5640
actttggtct taacaaaatg tggcagtcaa atacttgcta cagtttcagt tttggctgtt    5700
aaaggcagtt tggctccaat atctggaaca gttcaaagtg ctcatcttat tataagattt    5760
gacgaaaatg gagtgctact aaacaattcc ttcctggacc cagaatattg gaactttaga    5820
aatggagatc ttactgaagg cacagcctat acaaacgctg ttggatttat gcctaaccta    5880
tcagcttatc caaaatctca cggtaaaact gccaaaagta acattgtcag tcaagtttac    5940
ttaaacggag acaaaactaa acctgtaaca ctaaccatta cactaaacgg tacacaggaa    6000
acaggagaca caactccaag tgcatactct atgtcatttt catgggactg gtctggccac    6060
aactacatta atgaaatatt tgccacatcc tcttacactt tttcatacat tgcccaagaa    6120
taaagaagcg gccgctcgag catgcatcta gagggccccta ttctatagtg tcacctaaat    6180
gctagagctc gctgatcagc ctcgactgtg ccttctagtt gccagccatc tgttgtttgc    6240
ccctcccccg tgccttcctt gaccctggaa ggtgccactc ccactgtcct ttcctaataa    6300
aatgaggaaa ttgcatcgca ttgtctgagt aggtgtcatt ctattctggg ggtggggtg    6360 gggcaggaca gcaagggga ggattgggaa gacaatagca ggcatgctgg ggatgcggtg    6420
ggctctatgg cttctgaggc ggaaagaacc agctggggct ctaggggta tccccacgcg    6480 ccctgtagcg gcgcattaag cgcggcgggt gtggtggtta cgcgcagcgt gaccgctaca    6540
cttgccagcg ccctagcgcc cgctcctttc gctttcttcc cttcctttct cgccacgttc    6600
gccggctttc cccgtcaagc tctaaatcgg ggcatccctt tagggttccg atttagtgct    6660
ttacggcacc tcgaccccaa aaaacttgat tagggtgatg gttcacgtag tgggccatcg    6720
ccctgataga cggtttttcg ccctttgacg ttggagtcca cgttctttaa tagtggactc    6780
ttgttccaaa ctggaacaac actcaaccct atctcggtct attcttttga tttataaggg    6840
attttgggga tttcggccta ttggttaaaa aatgagctga tttaacaaaa atttaacgcg    6900
aattaattct gtggaatgtg tgtcagttag ggtgtggaaa gtccccaggc tccccaggca    6960
ggcagaagta tgcaaagcat gcatctcaat tagtcagcaa ccaggtgtgg aaagtcccca    7020
ggctccccag caggcagaag tatgcaaagc atgcatctca attagtcagc aaccatagtc    7080
ccgcccctaa ctccgcccat cccgcccta actccgccca gttccgccca ttctccgccc    7140
catggctgac taatttttt tatttatgca gaggccgagg ccgcctctgc ctctgagcta    7200
ttccagaagt agtgaggagg cttttttgga ggcctaggct tttgcaaaaa gctcccggga    7260
gcttgtatat ccatttcgg atctgatcaa gagacaggat gaggatcgtt tcgcatgatt    7320
gaacaagatg gattgcacgc aggttctccg gccgcttggg tggagaggct attcggctat    7380
gactgggcac aacagacaat cggctgctct gatgccgccg tgttccggct gtcagcgcag    7440
gggcgcccgg ttcttttgt caagaccgac ctgtccggtg ccctgaatga actgcaggac    7500
gaggcagcgc ggctatcgtg gctggccacg acgggcgttc cttgcgcagc tgtgctcgac    7560
```

```
gttgtcactg aagcgggaag ggactggctg ctattgggcg aagtgccggg gcaggatctc    7620
ctgtcatctc accttgctcc tgccgagaaa gtatccatca tggctgatgc aatgcggcgg    7680
ctgcatacgc ttgatccggc tacctgccca ttcgaccacc aagcgaaaca tcgcatcgag    7740
cgagcacgta ctcggatgga agccggtctt gtcgatcagg atgatctgga cgaagagcat    7800
caggggctcg cgccagccga actgttcgcc aggctcaagg cgcgcatgcc cgacggcgag    7860
gatctcgtcg tgacccatgg cgatgcctgc ttgccgaata tcatggtgga aaatggccgc    7920
ttttctggat tcatcgactg tggccggctg ggtgtggcgg accgctatca ggacatagcg    7980
ttggctaccc gtgatattgc tgaagagctt ggcggcgaat gggctgaccg cttcctcgtg    8040
ctttacggta tcgccgctcc cgattcgcag cgcatcgcct tctatcgcct tcttgacgag    8100
ttcttctgag cgggactctg gggttcgaaa tgaccgacca agcgacgccc aacctgccat    8160
cacgagattt cgattccacc gccgccttct atgaaaggtt gggcttcgga atcgttttcc    8220
gggacgccgg ctggatgatc ctccagcgcg ggatctcat gctggagttc ttcgcccacc    8280
ccaacttgtt tattgcagct tataatggtt acaaataaag caatagcatc acaaatttca    8340
caaataaagc atttttttca ctgcattcta gttgtggttt gtccaaactc atcaatgtat    8400
cttatcatgt ctgtataccg tcgacctcta gctagagctt ggcgtaatca tggtcatagc    8460
tgtttcctgt gtgaaattgt tatccgctca caattccaca acatacga gccggaagca    8520 taaagtgtaa agcctggggt gcctaatgag tgagctaact cacattaatt gcgttgcgct    8580
cactgcccgc tttccagtcg ggaaacctgt cgtgccagct gcattaatga atcggccaac    8640
gcgcggggag aggcggtttg cgtattgggc gctcttccgc ttcctcgctc actgactcgc    8700
tgcgctcggt cgttcggctg cggcgagcgg tatcagctca ctcaaaggcg gtaatacggt    8760
tatccacaga atcaggggat aacgcaggaa agaacatgtg agcaaaaggc cagcaaaagg    8820
ccaggaaccg taaaaaggcc gcgttgctgg cgttttttcca taggctccgc cccctgacg    8880 agcatcacaa aaatcgacgc tcaagtcaga ggtggcgaaa cccgacagga ctataaagat    8940
accaggcgtt ccccctgga agctcccctcg tgcgctctcc tgttccgacc ctgccgctta    9000
ccggatacct gtccgccttt ctcccttcgg gaagcgtggc gctttctcaa tgctcacgct    9060
gtaggtatct cagttcggtg taggtcgttc gctccaagct gggctgtgtg cacgaacccc    9120
ccgttcagcc cgaccgctgc gccttatccg gtaactatcg tcttgagtcc aacccggtaa    9180
gacacgactt atcgccactg gcagcagcca ctggtaacag gattagcaga gcgaggtatg    9240
taggcggtgc tacagagttc ttgaagtggt ggcctaacta cggctacact agaaggacag    9300
tatttggtat ctgcgctctg ctgaagccag ttaccttcgg aaaaagagtt ggtagctctt    9360
gatccggcaa acaaaccacc gctggtagcg gtggtttttt tgtttgcaag cagcagatta    9420
cgcgcagaaa aaaaggatct caagaagatc ctttgatctt ttctacgggg tctgacgctc    9480
agtggaacga aaactcacgt taagggattt tggtcatgag attatcaaaa aggatcttca    9540
cctagatcct tttaaattaa aaatgaagtt ttaaatcaat ctaaagtata tatgagtaaa    9600
cttggtctga cagttaccaa tgcttaatca gtgaggcacc tatctcagcg atctgtctat    9660
ttcgttcatc catagttgcc tgactccccg tcgtgtagat aactacgata cgggagggct    9720
taccatctgg ccccagtgct gcaatgatac cgcgagaccc acgctcaccg gctccagatt    9780
tatcagcaat aaaccagcca gccggaaggg ccgagcgcag aagtggtcct gcaactttat    9840
ccgcctccat ccagtctatt aattgttgcc gggaagctag agtaagtagt tcgccagtta    9900
atagtttgcg caacgttgtt gccattgcta caggcatcgt ggtgtcacgc tcgtcgtttg    9960
```

```
gtatggcttc attcagctcc ggttcccaac gatcaaggcg agttacatga tcccccatgt    10020
tgtgcaaaaa agcggttagc tccttcggtc ctccgatcgt tgtcagaagt aagttggccg    10080
cagtgttatc actcatggtt atggcagcac tgcataattc tcttactgtc atgccatccg    10140
taagatgctt ttctgtgact ggtgagtact caaccaagtc attctgagaa tagtgtatgc    10200
ggcgaccgag ttgctcttgc ccggcgtcaa tacgggataa taccgcgcca catagcagaa    10260
ctttaaaagt gctcatcatt ggaaaacgtt cttcgggcg aaaactctca aggatcttac     10320
cgctgttgag atccagttcg atgtaaccca ctcgtgcacc caactgatct tcagcatctt    10380
ttactttcac cagcgtttct gggtgagcaa aaacaggaag gcaaaatgcc gcaaaaaagg    10440
gaataagggc gacacggaaa tgttgaatac tcatactctt cctttttcaa tattattgaa    10500
gcatttatca gggttattgt ctcatgagcg gatacatatt tgaatgtatt tagaaaaata    10560
aacaaatagg ggttccgcgc acatttcccc gaaaagtgcc acctgacgtc                10610
```

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 17
tgtacaccgg atccggcgca cacc                                            24

<210> SEQ ID NO 18
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 18
cacaacgagc tcaattaatt aattgccaca tcctc                                35

<210> SEQ ID NO 19
<211> LENGTH: 4
<212> TYPE: PRT
<213> ORGANISM: adenovirus

<400> SEQUENCE: 19

Thr Leu Trp Thr
  1

<210> SEQ ID NO 20
<211> LENGTH: 12
<212> TYPE: PRT
<213> ORGANISM: adenovirus

<400> SEQUENCE: 20

Pro Ser Ala Ser Ala Ser Ala Ser Ala Pro Gly Ser
  1               5                  10

<210> SEQ ID NO 21
<211> LENGTH: 44
<212> TYPE: PRT
<213> ORGANISM: adenovirus

<400> SEQUENCE: 21

Met Lys Arg Ala Arg Pro Ser Glu Asp Thr Phe Asn Pro Val Tyr Pro
  1               5                  10                  15

```
Tyr Asp Thr Glu Thr Gly Pro Pro Thr Val Pro Phe Leu Thr Pro Pro
            20                  25                  30

Phe Val Ser Pro Asn Gly Phe Gln Glu Ser Pro Pro
            35                  40
```

<210> SEQ ID NO 22
<211> LENGTH: 43
<212> TYPE: PRT
<213> ORGANISM: adenovirus

<400> SEQUENCE: 22

```
Met Ala Lys Arg Ala Arg Leu Ser Thr Ser Phe Asn Pro Val Tyr Pro
 1               5                  10                  15

Tyr Glu Asp Glu Ser Ser Ser Gln His Pro Phe Ile Asn Pro Gly Phe
            20                  25                  30

Ile Ser Pro Asp Gly Phe Thr Gln Ser Pro Asn
            35                  40
```

<210> SEQ ID NO 23
<211> LENGTH: 43
<212> TYPE: PRT
<213> ORGANISM: adenovirus

<400> SEQUENCE: 23

```
Met Ser Lys Arg Leu Arg Val Glu Asp Asp Phe Asn Pro Val Tyr Pro
 1               5                  10                  15

Tyr Gly Tyr Ala Arg Asn Gln Asn Ile Pro Phe Leu Thr Pro Pro Phe
            20                  25                  30

Val Ser Ser Asp Gly Phe Lys Asn Phe Pro Pro
            35                  40
```

<210> SEQ ID NO 24
<211> LENGTH: 42
<212> TYPE: PRT
<213> ORGANISM: adenovirus

<400> SEQUENCE: 24

```
Met Lys Arg Ala Arg Phe Glu Asp Asp Phe Asn Pro Val Tyr Pro Tyr
 1               5                  10                  15

Glu His Tyr Asn Pro Leu Asp Ile Pro Phe Ile Thr Pro Pro Phe Ala
            20                  25                  30

Ser Ser Asn Gly Leu Gln Glu Lys Pro Pro
            35                  40
```

<210> SEQ ID NO 25
<211> LENGTH: 42
<212> TYPE: PRT
<213> ORGANISM: adenovirus

<400> SEQUENCE: 25

```
Met Lys Arg Thr Arg Ile Glu Asp Phe Asn Pro Val Tyr Pro Tyr
 1               5                  10                  15

Asp Thr Ser Ser Thr Pro Ser Ile Pro Tyr Val Ala Pro Pro Phe Val
            20                  25                  30

Ser Ser Asp Gly Leu Gln Glu Asn Pro Pro
            35                  40
```

<210> SEQ ID NO 26
<211> LENGTH: 327
<212> TYPE: DNA

```
<213> ORGANISM: adenovirus

<400> SEQUENCE: 26
agatctgaat tcgagctcgc tgttgggctc gcggttgagg acaaactctt cgcggtcttt      60
ccagtactct tggatcggaa acccgtcggc ctccgaacgg tactccgcca ccgagggacc     120
tgagcgagtc cgcatcgacc ggatcggaaa acctctcgag aaaggcgtct aaccagtcac     180
agtcgcaagg taggctgagc accgtggcgg gcggcagcgg gtggcggtcg gggttgtttc     240
tggcggaggt gctgctgatg atgtaattaa agtaggcggt cttgagacgg cggatggtcg     300
aggtgaggtg tggcaggctt gagatct                                         327

<210> SEQ ID NO 27
<211> LENGTH: 32480
<212> TYPE: DNA
<213> ORGANISM: adenovirus

<400> SEQUENCE: 27
catcatcaat aatataccttt attttggatt gaagccaata tgataatgag ggggtggagt     60
ttgtgacgtg gcgcggggcg tgggaacggg gcgggtgacg tagtagtgtg gcggaagtgt    120
gatgttgcaa gtgtggcgga acacatgtaa gcgacggatg tggcaaaagt gacgttttttg   180 gtgtgcgccg gtgtacacag gaagtgacaa ttttcgcgcg gttttaggcg gatgttgtag    240
taaatttggg cgtaaccgag taagatttgg ccattttcgc gggaaaactg aataagagga    300
agtgaaatct gaataatttt gtgttactca tagcgcgtaa tctctagcat cgatgtcgac    360
aagcttgaat tcgattaatg tgagttagct cactcattag gcaccccagg ctttacactt    420
tatgcttccg gctcgtatgt tgtgtggaat tgtgagcgga taacaatttc acacaggaaa    480
cagctatgac catgattacg aattcggcgc agcaccatgg cctgaaataa cctctgaaag    540
aggaacttgg ttaggtacct tctgaggcgg aaagaaccag ctgtggaatg tgtgtcagtt    600
agggtgtgga agtccccag gctccccagc aggcagaagt atgcaaagca tgcatctcaa    660
ttagtcagca accaggtgtg gaaagtcccc aggctcccca gcaggcagaa gtatgcaaag    720
catgcatctc aattagtcag caaccatagt cccgccccta actccgccca tcccgcccct    780
aactccgccc agttccgccc attctccgcc ccatggctga ctaatttttt ttatttatgc    840
agaggccgag gccgcctcgg cctctgagct attccagaag tagtgaggag gcttttttgg    900
aggcctaggc ttttgcaaaa agcttgggat ctctataatc tcgcgcaacc tattttcccc    960
tcgaacactt tttaagccgt agataaacag gctgggacac ttcacatgag cgaaaaatac   1020
atcgtcacct gggacatgtt gcagatccat gcacgtaaac tcgcaagccg actgatgcct   1080
tctgaacaat ggaaaggcat tattgccgta agccgtggcg gtctggtacc ggtgggtgaa   1140
gaccagaaac agcacctcga actgagccgc gatattgccc agcgtttcaa cgcgctgtat   1200
ggcgagatcg atcccgtcgt tttacaacgt cgtgactggg aaaaccctgg cgttacccaa   1260
cttaatcgcc ttgcagcaca tccccctttc gccagctggc gtaatagcga agaggcccgc   1320
accgatcgcc cttcccaaca gttgcgcagc ctgaatggcg aatggcgctt tgcctggttt   1380
ccggcaccag aagcggtgcc ggaaagctgg ctggagtgcg atcttcctga ggccgatact   1440
gtcgtcgtcc cctcaaactg gcagatgcac ggttacgatg cgcccatcta caccaacgta   1500
acctatccca ttacggtcaa tccgccgttt gttcccacgg agaatccgac gggttgttac   1560
tcgctcacat ttaatgttga tgaaagctgg ctacaggaag gccagacgcg aattatttttt  1620 gatggcgtta actcggcgtt tcatctgtgg tgcaacgggc gctgggtcgg ttacggccag   1680
```

-continued

```
gacagtcgtt tgccgtctga atttgacctg agcgcatttt tacgcgccgg agaaaaccgc   1740
ctcgcggtga tggtgctgcg ttggagtgac ggcagttatc tggaagatca ggatatgtgg   1800
cggatgagcg gcattttccg tgacgtctcg ttgctgcata aaccgactac acaaatcagc   1860
gatttccatg ttgccactcg ctttaatgat gatttcagcc gcgctgtact ggaggctgaa   1920
gttcagatgt gcggcgagtt gcgtgactac ctacgggtaa cagtttcttt atggcagggt   1980
gaaacgcagg tcgccagcgg caccgcgcct tcggcggtg aaattatcga tgagcgtggt    2040
ggttatgccg atcgcgtcac actacgtctg aacgtcgaaa acccgaaact gtggagcgcc   2100
gaaatcccga atctctatcg tgcggtggtt gaactgcaca ccgccgacgg cacgctgatt   2160
gaagcagaag cctgcgatgt cggtttccgc gaggtgcgga ttgaaaatgg tctgctgctg   2220
ctgaacggca agccgttgct gattcgaggc gttaaccgtc acgagcatca tcctctgcat   2280
ggtcaggtca tggatgagca gacgatggtg caggatatcc tgctgatgaa gcagaacaac   2340
tttaacgccg tgcgctgttc gcattatccg aaccatccgc tgtggtacac gctgtgcgac   2400
cgctacggcc tgtatgtggt ggatgaagcc aatattgaaa cccacggcat ggtgccaatg   2460
aatcgtctga ccgatgatcc gcgctggcta ccggcgatga gcgaacgcgt aacgcgaatg   2520
gtgcagcgcg atcgtaatca cccgagtgtg atcatctggt cgctggggaa tgaatcaggc   2580
cacggcgcta atcacgacgc gctgtatcgc tggatcaaat ctgtcgatcc ttcccgcccg   2640
gtgcagtatg aaggcggcgg agccgacacc acggccaccg atattatttg cccgatgtac   2700
gcgcgcgtgg atgaagacca gcccttcccg gctgtgccga atggtccat caaaaaatgg    2760
ctttcgctac ctggagagac gcgcccgctg atcctttgcg aatacgccca cgcgatgggt   2820
aacagtcttg gcggtttcgc taaatactgg caggcgtttc gtcagtatcc ccgtttacag   2880
ggcggcttcg tctgggactg ggtggatcag tcgctgatta aatatgatga aaacggcaac   2940
ccgtggtcgc ttacggcgg tgattttggc gatacgccga acgatcgcca gttctgtatg    3000
aacggtctgg tctttgccga ccgcacgccg catccagcgc tgacggaagc aaaacaccag   3060
cagcagtttt tccagttccg tttatccggg caaaccatcg aagtgaccag cgaataccgt   3120
ttccgtcata gcgataacga gctcctgcac tggatggtgg cgctggatgg taagccgctg   3180
gcaagcggtg aagtgcctct ggatgtcgct ccacaaggta acagttgat gaactgcct    3240
gaactaccgc agccggagag cgccgggcaa ctctggctca cagtacgcgt agtgcaaccg   3300
aacgcgaccg catggtcaga agccgggcac atcagcgcct ggcagcagtg gcgtctggcg   3360
gaaaacctca gtgtgacgct ccccgccgcg tcccacgcca tcccgcatct gaccaccagc   3420
gaaatggatt tttgcatcga gctgggtaat aagcgttggc aatttaaccg ccagtcaggc   3480
tttctttcac agatgtggat tggcgataaa aaacaactgc tgacgccgct gcgcgatcag   3540
ttcacccgtg caccgctgga taacgacatt ggcgtaagtg aagcgacccg cattgaccct   3600
aacgcctggg tcgaacgctg gaaggcggcg ggccattacc aggccgaagc agcgttgttg   3660
cagtgcacgg cagatacact tgctgatgcg gtgctgatta cgaccgctca cgcgtggcag   3720
catcagggga aaccttatt tatcagccgg aaaacctacc ggattgatgg tagtggtcaa    3780
atggcgatta ccgttgatgt tgaagtggcg agcgatacac cgcatccggc gcggattggc   3840
ctgaactgcc agctggcgca ggtagcagag cgggtaaact ggctcggatt agggccgcaa   3900
gaaaactatc ccgaccgcct tactgccgcc tgttttgacc gctgggatct gccattgtca   3960
gacatgtata ccccgtacgt cttcccgagc gaaaacggtc tgcgctgcgg gacgcgcgaa   4020
```

```
ttgaattatg gcccacacca gtggcgcggc gacttccagt tcaacatcag ccgctacagt    4080
caacagcaac tgatggaaac cagccatcgc catctgctgc acgcggaaga aggcacatgg    4140
ctgaatatcg acggtttcca tatggggatt ggtggcgacg actcctggag cccgtcagta    4200
tcggcggaat tccagctgag cgccggtcgc taccattacc agttggtctg gtgtcaaaaa    4260
taataataac cgggcaggcc atgtctgccc gtatttcgcg taaggaaatc cattatgtac    4320
tatttaaaaa acacaaactt ttggatgttc ggttttattct ttttctttta ctttttttatc    4380 atgggagcct acttcccgtt tttcccgatt tggctacatg acatcaacca tatcagcaaa    4440
agtgatacgg gtattatttt tgccgctatt tctctgttct cgctattatt ccaaccgctg    4500
tttggtctgc tttctgacaa actcggaact tgtttattgc agcttataat ggttacaaat    4560
aaagcaatag catcacaaat ttcacaaata aagcatttt ttcactgcat tctagttgtg    4620
gtttgtccaa actcatcaat gtatcttatc atgtctggat ccagatctgg gcgtggctta    4680
agggtgggaa agaatatata aggtggggt cttatgtagt tttgtatctg ttttgcagca    4740
gccgccgccg ccatgagcac caactcgttt gatggaagca ttgtgagctc atatttgaca    4800
acgcgcatgc ccccatgggc cggggtgcgt cagaatgtga tgggctccag cattgatggt    4860
cgccccgtcc tgcccgcaaa ctctactacc ttgacctacg agaccgtgtc tggaacgccg    4920
ttggagactg cagcctccgc cgccgcttca gccgctgcag ccaccgcccg cgggattgtg    4980
actgactttg ctttcctgag cccgcttgca agcagtgcag cttcccgttc atccgcccgc    5040
gatgacaagt tgacggctct tttggcacaa ttggattctt tgacccggga acttaatgtc    5100
gtttctcagc agctgttgga tctgcgccag caggtttctg ccctgaaggc ttcctccct    5160 cccaatgcgg tttaaaacat aaataaaaaa ccagactctg tttggatttg gatcaagcaa    5220
gtgtcttgct gtcttatttt aggggttttg cgcgcgcggt aggcccggga ccagcggtct    5280
cggtcgttga gggtcctgtg tatttttttcc aggacgtggt aaaggtgact ctggatgttc    5340
agatacatgg gcataagccc gtctctgggg tggaggtagc accactgcag agcttcatgc    5400
tgcggggtgg tgttgtagat gatccagtcg tagcaggagc gctgggcgtg gtgcctaaaa    5460
atgtctttca gtagcaagct gattgccagg ggcaggccct tggtgtaagt gtttacaaag    5520
cggttaagct gggatgggtg catacgtggg gatatgagat gcatcttgga ctgtattttt    5580
aggttggcta tgttcccagc catatccctc cggggattca tgttgtgcag aaccaccagc    5640
acagtgtatc cggtgcactt gggaaatttg tcatgtagct tagaaggaaa tgcgtggaag    5700
aacttggaga cgcccttgtg acctccaaga ttttccatgc attcgtccat aatgatggca    5760
atgggcccac gggcggcggc ctgggcgaag atatttctgg gatcactaac gtcatagttg    5820
tgttccagga tgagatcgtc ataggccatt tttacaaagc gcggcggag ggtgccagac    5880 tgcggtataa tggttccatc cggcccaggg gcgtagttac cctcacagat ttgcatttcc    5940
cacgctttga gttcagatgg ggggatcatg tctacctgcg gggcgatgaa gaaaacggtt    6000
tccggggtag gggagatcag ctgggaagaa agcaggttcc tgagcagctg cgacttaccg    6060
cagccggtgg gcccgtaaat cacacctatt accgggtgca actggtagtt aagagagctg    6120
cagctgccgt catccctgag caggggggcc acttcgttaa gcatgtccct gactcgcatg    6180 ttttcccctga ccaaatccgc cagaaggcgc tcgccgccca gcgatagcag ttcttgcaag    6240
gaagcaaagt ttttcaacgg tttgagaccg tccgccgtag gcatgctttt gagcgtttga    6300
ccaagcagtt ccaggcggtc ccacagctcg gtcacctgct ctacggcatc tcgatccagc    6360
atatctcctc gtttcgcggg ttggggcggc tttcgctgta cggcagtagt cggtgctcgt    6420
```

```
ccagacgggc cagggtcatg tctttccacg ggcgcagggt cctcgtcagc gtagtctggg    6480
tcacggtgaa ggggtgcgct ccgggctgcg cgctggccag ggtgcgcttg aggctggtcc    6540
tgctggtgct gaagcgctgc cggtcttcgc cctgcgcgtc ggccaggtag catttgacca    6600
tggtgtcata gtccagcccc tccgcggcgt ggcccttggc gcgcagcttg cccttggagg    6660
aggcgccgca cgaggggcag tgcagacttt tgagggcgta gagcttgggc gcgagaaata    6720
ccgattccgg ggagtaggca tccgcgccgc aggccccgca gacggtctcg cattccacga    6780
gccaggtgag ctctggccgt tcggggtcaa aaaccaggtt tcccccatgc tttttgatgc    6840
gtttcttacc tctggtttcc atgagccggt gtccacgctc ggtgacgaaa aggctgtccg    6900
tgtccccgta tacagacttg agaggcctgt cctcgagcgg tgttccgcgg tcctcctcgt    6960
atagaaactc ggaccactct gagacaaagg ctcgcgtcca ggccagcacg aaggaggcta    7020
agtgggaggg gtagcggtcg ttgtccacta ggggtccac tcgctccagg gtgtgaagac     7080
acatgtcgcc ctcttcggca tcaaggaagg tgattggttt gtaggtgtag gccacgtgac    7140
cgggtgttcc tgaaggggg ctataaaagg ggtgggggc gcgttcgtcc tcactctctt      7200
ccgcatcgct gtctgcgagg gccagctgtt ggggtgagta ctccctctga aaagcgggca    7260
tgacttctgc gctaagattg tcagtttcca aaaacgagga ggatttgata ttcacctggc    7320
ccgcggtgat gcctttgagg gtggccgcat ccatctggtc agaaaagaca atcttttgt     7380 tgtcaagctt ggtggcaaac gacccgtaga gggcgttgga cagcaacttg gcgatggagc    7440
gcagggtttg gtttttgtcg cgatcggcgc gctccttggc cgcgatgttt agctgcacgt    7500
attcgcgcgc aacgcaccgc cattcgggaa agacggtggt gcgctcgtcg ggcaccaggt    7560
gcacgcgcca accgcggttg tgcagggtga caaggtcaac gctggtggct acctctccgc    7620
gtaggcgctc gttggtccag cagaggcggc cgcccttgcg cgagcagaat ggcggtaggg    7680
ggtctagctg cgtctcgtcc ggggggtctg cgtccacggt aaagaccccg ggcagcaggc    7740
gcgcgtcgaa gtagtctatc ttgcatcctt gcaagtctag cgcctgctgc catgcgcggg    7800
cggcaagcgc gcgctcgtat gggttgagtg ggggaccccca tggcatgggg tgggtgagcg    7860
cggaggcgta catgccgcaa atgtcgtaaa cgtagagggg ctctctgagt attccaagat    7920
atgtagggta gcatcttcca ccgcggatgc tggcgcgcac gtaatcgtat agttcgtgcg    7980
agggagcgag gaggtcggga ccgaggttgc tacgggcggg ctgctctgct cggaagacta    8040
tctgcctgaa gatggcatgt gagttggatg atatggttgg acgctggaag acgttgaagc    8100
tggcgtctgt gagacctacc gcgtcacgca cgaaggaggc gtaggagtcg cgcagcttgt    8160
tgaccagctc ggcggtgacc tgcacgtcta ggcgcagta gtccagggtt tccttgatga     8220
tgtcatactt atcctgtccc ttttttttcc acagctcgcg gttgaggaca aactcttcgc    8280
ggtctttcca gtactcttgg atcggaaacc cgtcggcctc cgaacggtaa gagcctagca    8340
tgtagaactg gttgacggcc tggtaggcgc agcatcccttt tctacgggt agcgcgtatg    8400 cctgcgcggc cttccggagc gaggtgtggg tgagcgcaaa ggtgtccctg accatgactt    8460
tgaggtactg gtatttgaag tcagtgtcgt cgcatccgcc ctgctcccag agcaaaaagt    8520
ccgtgcgctt tttggaacgc ggatttggca gggcgaaggt gacatcgttg aagagtatct    8580
ttcccgcgcg aggcataaag ttgcgtgtga tgcggaaggg tccggcacc tcggaacggt     8640 tgttaattac ctgggcggcg agcacgatct cgtcaaagcc gttgatgttg tgcccacaa     8700 tgtaaagttc caagaagcgc gggatgccct tgatggaagg caattttttta agttcctcgt   8760
```

```
aggtgagctc ttcaggggag ctgagcccgt gctctgaaag ggcccagtct gcaagatgag    8820
ggttggaagc gacgaatgag ctccacaggt cacgggccat tagcatttgc aggtggtcgc    8880
gaaaggtcct aaactggcga cctatggcca ttttttctgg ggtgatgcag tagaaggtaa    8940
gcgggtcttg ttcccagcgg tcccatccaa ggttcgcggc taggtctcgc gcggcagtca    9000
ctagaggctc atctccgccg aacttcatga ccagcatgaa gggcacgagc tgcttcccaa    9060
aggcccccat ccaagtatag gtctctacat cgtaggtgac aaagagacgc tcggtgcgag    9120
gatgcgagcc gatcgggaag aactggatct cccgccacca attggaggag tggctattga    9180
tgtggtgaaa gtagaagtcc ctgcgacggg ccgaacactc gtgctggctt ttgtaaaaac    9240
gtgcgcagta ctggcagcgg tgcacgggct gtacatcctg cacgaggttg acctgacgac    9300
cgcgcacaag gaagcagagt gggaatttga gcccctcgcc tggcgggttt ggctggtggt    9360
cttctacttc ggctgcttgt ccttgaccgt ctggctgctc gagggagtt acggtggatc    9420 ggaccaccac gccgcgcgag cccaaagtcc agatgtccgc gcgcggcggt cggagcttga    9480
tgacaacatc gcgcagatgg gagctgtcca tggtctggag ctcccgcggc gtcaggtcag    9540
gcgggagctc ctgcaggttt acctcgcata cgggtcag ggcgcgggct agatccaggt    9600 gataccctaat ttccaggggc tggttggtgg cggcgtcgat ggcttgcaag aggccgcatc    9660
cccgcggcgc gactacggta ccgcgcgcg gcggtgggc cgcggggtg tccttggatg    9720 atgcatctaa aagcggtgac gcgggcgagc ccccggaggt agggggggct ccggacccgc    9780
cgggagaggg ggcaggggca cgtcggcgcc gcgcgcgggc aggagctggt gctgcgcgcg    9840
taggttgctg gcgaacgcga cgacgcggcg gttgatctcc tgaatctggc gcctctgcgt    9900
gaagacgacg ggcccggtga gcttgagcct gaaagagagt tcgacagaat caatttcggt    9960
gtcgttgacg gcggcctggc gcaaaatctc ctgcacgtct cctgagttgt cttgataggc    10020
gatctcggcc atgaactgct cgatctcttc ctcctggaga tctccgcgtc cggctcgctc    10080
cacggtggcg gcgaggtcgt tggaaatgcg ggccatgagc tgcgagaagg cgttgaggcc    10140
tccctcgttc cagacgcggc tgtagaccac gcccccttcg gcatcgcggg cgcgcatgac    10200
cacctgcgcg agattgagct ccacgtgccg ggcgaagacg gcgtagtttc gcaggcgctg    10260
aaagaggtag ttgaggggtgg tggcggtgtg ttctgccacg aagaagtaca taacccagcg    10320
tcgcaacgtg gattcgttga tatcccccaa ggcctcaagg cgctccatgg cctcgtagaa    10380
gtccacggcg aagttgaaaa actgggagtt gcgcgccgac acggttaact cctcctccag    10440
aagacggatg agctcggcga cagtgtcgcg cacctcgcgc tcaaaggcta caggggcctc    10500
ttcttcttct tcaatctcct cttccataag ggcctcccct tcttcttctt ctggcggcgg    10560 tggggggaggg gggacacggc ggcgacgacg gcgcaccggg aggcggtcga caaagcgctc    10620
gatcatctcc ccgcggcgac ggcgcatggt ctcggtgacg gcgcggccgt tctcgcgggg    10680
gcgcagttgg aagacgccgc ccgtcatgtc ccggttatgg gttggcgggg gctgccatg    10740 cggcagggat acggcgctaa cgatgcatct caacaattgt tgtgtaggta ctccgccgcc    10800
gagggacctg agcgagtccg catcgaccgg atcggaaaac ctctcgagaa aggcgtctaa    10860
ccagtcacag tcgcaaggta ggctgagcac cgtggcgggc ggcagcgggc ggcggtcggg    10920
gttgtttctg gcgcgaggtgc tgctgatgat gtaattaaag taggcggtct tgagacggcg    10980
gatggtcgac agaagcacca tgtccttggg tccggcctgc tgaatgcgca ggcggtcggc    11040
catgccccag gcttcgtttt gacatcggcg caggtctttg tagtagtctt gcatgagcct    11100
ttctaccggc acttcttctt ctccttcctc ttgtcctgca tctcttgcat ctatcgctgc    11160
```

```
ggcggcggcg gagtttggcc gtaggtggcg ccctcttcct cccatgcgtg tgaccccgaa    11220 gccccctcatc ggctgaagca gggctaggtc ggcgacaacg cgctcggcta atatggcctg   11280
ctgcacctgc gtgagggtag actggaagtc atccatgtcc acaaagcggt ggtatgcgcc    11340
cgtgttgatg gtgtaagtgc agttggccat aacggaccag ttaacggtct ggtgacccgg    11400
ctgcgagagc tcggtgtacc tgagacgcga gtaagccctc gagtcaaata cgtagtcgtt    11460
gcaagtccgc accaggtact ggtatcccac caaaaagtgc ggcggcggct ggcggtagag    11520 gggcagcgt agggtggccg gggctccggg gcgagatct tccaacataa ggcgatgata     11580
tccgtagatg tacctggaca tccaggtgat gccggcggcg gtggtggagg cgcgcggaaa    11640 gtcgcgacg cggttccaga tgttgcgcag cggcaaaaag tgctccatgg tcgggacgct     11700
ctggccggtc aggcgcgcgc aatcgttgac gctctagacc gtgcaaaagg agagcctgta    11760
agcgggcact cttccgtggt ctggtggata aattcgcaag ggtatcatgg cggacgaccg    11820
gggttcgagc cccgtatccg gccgtccgcc gtgatccatg cggttaccgc ccgcgtgtcg    11880
aacccaggtg tgcgacgtca gacaacgggg gagtgctcct tttggcttcc ttccaggcgc    11940
ggcggctgct gcgctagctt ttttggccac tggccgcgcg cagcgtaagc ggttaggctg    12000
gaaagcgaaa gcattaagtg gctcgctccc tgtagccgga gggttatttt ccaagggttg    12060
agtcgcggga ccccggttc gagtctcgga ccggccggac tgcggcgaac ggggtttgc      12120 ctccccgtca tgcaagaccc cgcttgcaaa ttcctccgga aacaggacg agccccttt      12180 ttgcttttcc cagatgcatc cggtgctgcg gcagatgcgc ccccctcctc agcagcggca    12240
agagcaagag cagcggcaga catgcagggc accctcccct cctcctaccg cgtcaggagg    12300
ggcgacatcc gcggttgacg cggcagcaga tggtgattac gaaccccgc ggcgccgggc     12360 ccggcactac ctggacttgg aggagggcga gggcctggcg cggctaggag cgccctctcc    12420
tgagcggtac ccaagggtgc agctgaagcg tgatacgcgt gaggcgtacg tgccgcggca    12480
gaacctgttt cgcgaccgcg agggagagga gcccgaggag atgcgggatc gaaagttcca    12540
cgcagggcgc gagctgcggc atggcctgaa tcgcgagcgg ttgctgcgcg aggaggactt    12600
tgagcccgac gcgcgaaccg ggattagtcc cgcgcgcgca cacgtggcgg ccgccgacct    12660
ggtaaccgca tacgagcaga cggtgaacca ggagattaac tttcaaaaaa gctttaacaa    12720
ccacgtgcgt acgcttgtgg cgcgcgagga ggtggctata ggactgatgc atctgtggga    12780
ctttgtaagc gcgctggagc aaaacccaaa tagcaagccg ctcatggcgc agctgttcct    12840
tatagtgcag cacagcaggg acaacgaggc attcagggat gcgctgctaa acatagtaga    12900
gcccgagggc cgctggctgc tcgatttgat aaacatcctg cagagcatag tggtgcagga    12960
gcgcagcttg agcctggctg acaaggtggc cgccatcaac tattccatgc ttagcctggg    13020
caagttttac gcccgcaaga tataccatac cccttacgtt cccatagaca aggaggtaaa    13080
gatcgagggg ttctacatgc gcatggcgct gaaggtgctt accttgagcg acgacctggg    13140
cgtttatcgc aacgagcgca tccacaaggc cgtgagcgtg agccggcggc gcgagctcag    13200
cgaccgcgag ctgatgcaca gcctgcaaag ggccctggct ggcacgggca gcggcgatag    13260
agaggccgag tcctactttg acgcgggcgc tgacctgcgc tgggccccaa gccgacgcgc    13320
cctggaggca gctgggggcg gacctggct ggcggtggca cccgcgcgcg ctggcaacgt      13380
cggcggcgtg gaggaatatg acgaggacga tgagtacgag ccagaggacg gcagagtacta   13440 agcggtgatg tttctgatca gatgatgcaa gacgcaacgg acccggcggt gcgggcggcg    13500
```

```
ctgcagagcc agccgtccgg ccttaactcc acggacgact ggcgccaggt catggaccgc   13560
atcatgtcgc tgactgcgcg caatcctgac gcgttccggc agcagccgca ggccaaccgg   13620
ctctccgcaa ttctggaagc ggtggtcccg cgcgcgcaa accccacgca cgagaaggtg   13680
ctggcgatcg taaacgcgct ggccgaaaac agggccatcc ggcccgacga ggccggcctg   13740
gtctacgacg cgctgcttca gcgcgtggct cgttacaaca gcggcaacgt gcagaccaac   13800
ctggaccggc tggtggggga tgtgcgcgag gccgtgcgc agcgtgagcg cgcgcagcag   13860
cagggcaacc tgggctccat ggttgcacta acgccttcc tgagtacaca gcccgccaac   13920
gtgccgcggg gacaggagga ctacaccaac tttgtgagcg cactgcggct aatggtgact   13980
gagacaccgc aaagtgaggt gtaccagtct gggccagact attttttcca gaccagtaga   14040
caaggcctgc agaccgtaaa cctgagccag gcttcaaaa acttgcaggg gctgtggggg   14100
gtgcgggctc ccacaggcga ccgcgcgacc gtgtctagct tgctgacgcc caactcgcgc   14160
ctgttgctgc tgctaatagc gcccttcacg gacagtggca gcgtgtcccg ggacacatac   14220
ctaggtcact tgctgacact gtaccgcgag gccataggtc aggcgcatgt ggacgagcat   14280
actttccagg agattacaag tgtcagccgc gcgctgggc aggaggacac gggcagcctg   14340
gaggcaaccc taaactacct gctgaccaac cggcggcaga agatcccctc gttgcacagt   14400
ttaaacagcg aggaggagcg cattttgcgc tacgtgcagc agagcgtgag ccttaacctg   14460
atgcgcgacg gggtaacgcc cagcgtggcg ctggacatga ccgcgcgcaa catggaaccg   14520
ggcatgtatg cctcaaaccg gccgtttatc aaccgcctaa tggactactt gcatcgcgcg   14580
gccgccgtga ccccgagta tttcaccaat gccatcttga acccgcactg gctaccgccc   14640
cctggtttct acaccggggg attcgaggtg cccgagggta acgatggatt cctctgggac   14700
gacatagacg acagcgtgtt ttccccgcaa ccgcagaccc tgctagagtt gcaacagcgc   14760
gagcaggcag aggcggcgct gcgaaaggaa agcttccgca ggccaagcag cttgtccgat   14820
ctaggcgctg cggccccgcg gtcagatgct agtagcccat ttccaagctt gataggggtct   14880 cttaccagca ctcgcaccac ccgcccgcgc ctgctgggcg aggaggagta cctaaacaac   14940
tcgctgctgc agccgcagcg cgaaaaaaac ctgcctccgg catttcccaa caacgggata   15000
gagagcctag tggacaagat gagtagatgg aagacgtacg cgcaggagca cagggacgtg   15060
ccaggcccgc gcccgcccac ccgtcgtcaa aggcacgacc gtcagcgggg tctggtgtgg   15120
gaggacgatg actcggcaga cgacagcagc gtcctggatt tgggagggag tgcaacccg   15180 tttgcgcacc ttcgccccag gctggggaga atgttttaaa aaaaaaaag catgatgcaa   15240 aataaaaaac tcaccaaggc catggcaccg agcgttggtt ttcttgtatt ccccttagta   15300
tgcggcgcgc ggcgatgtat gaggaaggtc ctcctccctc ctacgagagt gtggtgagcg   15360
cggcgccagt ggcggcggcg ctgggttctc ccttcgatgc tcccctggac ccgccgtttg   15420
tgcctccgcg gtacctgcgg cctaccgggg ggagaaacag catccgttac tctgagttgg   15480 caccctatt cgacaccacc cgtgtgtacc tggtggacaa caagtcaacg gatgtggcat   15540
ccctgaacta ccagaacgac cacagcaact ttctgaccac ggtcattcaa acaatgact   15600 acagcccggg ggaggcaagc acacagacca tcaatcttga cgaccggtcg cactggggcg   15660
gcgacctgaa aaccatcctg cataccaaca tgccaaatgt gaacgagttc atgtttacca   15720
ataagtttaa ggcgcgggtg atggtgtcgc gcttgcctac taaggacaat caggtggagc   15780
tgaaatacga gtgggtggag ttcacgctgc ccgaggcaa ctactccgag accatgacca   15840 tagacccttat gaacaacgcg atcgtggagc actacttgaa agtgggcaga cagaacgggg   15900
```

```
ttctggaaag cgacatcggg gtaaagtttg acacccgcaa cttcagactg gggtttgacc   15960
ccgtcactgg tcttgtcatg cctggggtat atacaaacga agccttccat ccagacatca   16020
ttttgctgcc aggatgcggg gtggacttca cccacagccg cctgagcaac ttgttgggca   16080
tccgcaagcg gcaacccttc caggagggct ttaggatcac ctacgatgat ctggagggtg   16140
gtaacattcc cgcactgttg gatgtggacg cctaccaggc gagcttgaaa gatgacaccg   16200
aacagggcgg gggtggcgca ggcggcagca acagcagtgg cagcggcgcg aagagaact    16260
ccaacgcggc agccgcggca atgcagccgg tggaggacat gaacgatcat gccattcgcg   16320
gcgacacctt tgccacacgg gctgaggaga agcgcgctga ggccgaagca gcggccgaag   16380
ctgccgcccc cgctgcgcaa cccgaggtcg agaagcctca aagaaaccg gtgatcaaac     16440
ccctgacaga ggacagcaag aaacgcagtt acaacctaat aagcaatgac agcaccttca   16500
cccagtaccg cagctggtac cttgcataca actacggcga ccctcagacc ggaatccgct   16560
catggaccct gctttgcact cctgacgtaa cctgcggctc ggagcaggtc tactggtcgt   16620
tgccagacat gatgcaagac cccgtgacct tccgctccac gcgccagatc agcaactttc   16680
cggtggtggg cgccgagctg ttgcccgtgc actccaagag cttctacaac gaccaggccg   16740
tctactccca actcatccgc cagtttacct ctctgaccca cgtgttcaat cgctttcccg   16800
agaaccagat tttggcgcgc ccgccagccc ccaccatcac caccgtcagt gaaaacgttc   16860
ctgctctcac agatcacggg acgctaccgc tgcgcaacag catcggagga gtccagcgag   16920
tgaccattac tgacgccaga cgccgcacct gcccctacgt ttacaaggcc ctgggcatag   16980
tctcgccgcg cgtcctatcg agccgcactt tttgagcaag catgtccatc cttatatcgc   17040
ccagcaataa cacaggctgg ggcctgcgct tcccaagcaa gatgtttggc ggggccaaga   17100
agcgctccga ccaacaccca gtgcgcgtgc gcgggcacta ccgcgcgccc tggggcgcgc   17160
acaaacgcgg ccgcactggg cgcaccaccg tcgatgacgc catcgacgcg gtggtggagg   17220
aggcgcgcaa ctacacgccc acgccgccac cagtgtccac agtggacgcg gccattcaga   17280
ccgtggtgcg cggagcccgg cgctatgcta aaatgaagag acggcggagg cgcgtagcac   17340
gtcgccaccg ccgccgaccc ggcactgccg cccaacgcgc ggcggcggcc ctgcttaacc   17400
gcgcacgtcg caccggccga cgggcggcca tgcgggccgc tcgaaggctg gccgcgggta   17460
ttgtcactgt gccccccagg tccaggcgac gagcggccgc cgcagcagcc gcggccatta   17520
gtgctatgac tcagggtcgc agggcaacg tgtattgggt gcgcgactcg gttagcggcc     17580
tgcgcgtgcc cgtgcgcacc cgccccccgc gcaactagat tgcaagaaaa aactacttag   17640
actcgtactg ttgtatgtat ccagcggcgg cggcgcgcaa cgaagctatg tccaagcgca   17700
aaatcaaaga agagatgctc caggtcatcg cgccggagat ctatggcccc ccgaagaagg   17760
aagagcagga ttacaagccc cgaaagctaa agcgggtcaa aaagaaaaag aaagatgatg   17820
atgatgaact tgacgacgag gtggaactgc tgcacgctac cgcgcccagg cgacgggtac   17880
agtggaaagg tcgacgcgta aaacgtgttt tgcgacccgg caccaccgta gtctttacgc   17940
ccggtgagcg ctccacccgc acctacaagc gcgtgtatga tgaggtgtac ggcgacgagg   18000
acctgcttga gcaggccaac gagcgcctcg gggagtttgc ctacgaaag cggcataagg    18060
acatgctggc gttgccgctg gacgagggca acccaacacc tagcctaaag cccgtaacac   18120
tgcagcaggt gctgccgcgc cttgcaccgt ccgaagaaaa gcgcggccta aagcgcgagt   18180
ctggtgactt ggcaccccacc gtgcagctga tggtacccaa gcgccagcga ctggaagatg   18240
```

```
tcttggaaaa aatgaccgtg aacctgggc tggagcccga ggtccgcgtg cggccaatca    18300
agcaggtggc gccgggactg ggcgtgcaga ccgtggacgt tcagataccc actaccagta    18360
gcaccagtat tgccaccgcc acagagggca tggagacaca aacgtccccg gttgcctcag    18420
cggtggcgga tgccgcggtg caggcggtcg ctgcggccgc gtccaagacc tctacggagg    18480
tgcaaacgga cccgtggatg tttcgcgttt cagcccccg gcgcccgcgc ggttcgagga    18540
agtacggcgc cgccagcgcg ctactgcccg aatatgccct acatccttcc attgcgccta    18600
cccccggcta tcgtggctac acctaccgcc ccagaagacg agcaactacc cgacgccgaa    18660
ccaccactgg aacccgccgc cgccgtcgcc gtcgccagcc cgtgctggcc ccgatttccg    18720
tgcgcagggt ggctcgcgaa ggaggcagga ccctggtgct gccaacagcg cgctaccacc    18780
ccagcatcgt ttaaaagccg gtctttgtgg ttcttgcaga tatggccctc acctgccgcc    18840
tccgtttccc ggtgccggga ttccgaggaa gaatgcaccg taggaggggc atggccggcc    18900
acggcctgac gggcggcatg cgtcgtgcgc accaccggcg gcggcgcgcg tcgcaccgtc    18960
gcatgcgcgg cggtatcctg cccctcctta ttccactgat cgccgcggcg attggcgccg    19020
tgcccggaat tgcatccgtg gccttgcagg cgcagagaca ctgattaaaa acaagttgca    19080
tgtggaaaaa tcaaaataaa aagtctggac tctcacgctc gcttggtcct gtaactattt    19140
tgtagaatgg aagacatcaa cttttgcgtct ctggccccgc gacacggctc gcgcccgttc    19200
atgggaaact ggcaagatat cggcaccagc aatatgagcg gtggcgcctt cagctggggc    19260
tcgctgtgga gcggcattaa aaatttcggt tccaccgtta agaactatgg cagcaaggcc    19320
tggaacagca gcacaggcca gatgctgagg gataagttga agagcaaaa tttccaacaa    19380 aaggtggtag atggcctggc ctctggcatt agcggggtgg tggacctggc caaccaggca    19440
gtgcaaaata agattaacag taagcttgat ccccgccctc ccgtagagga gcctccaccg    19500
gccgtggaga cagtgtctcc agagggggcgt ggcgaaaagc gtccgcgccc cgacagggaa    19560
gaaactctgg tgacgcaaat agacgagcct ccctcgtacg aggaggcact aaagcaaggc    19620
ctgcccacca cccgtcccat cgcgcccatg gctaccggag tgctgggcca gcacacaccc    19680
gtaacgctgg acctgcctcc ccccgccgac acccagcaga aacctgtgct gccaggcccg    19740
accgccgttg ttgtaacccg tcctagccgc gcgtccctgc gccgcgccgc cagcggtccg    19800
cgatcgttgc ggcccgtagc cagtggcaac tggcaaagca cactgaacag catcgtgggt    19860 ctggggtgc aatccctgaa gcgccgacga tgcttctgaa tagctaacgt gtcgtatgtg    19920
tgtcatgtat gcgtccatgt cgccgccaga ggagctgctg agccgccgcg cgcccgcttt    19980
ccaagatggc tacccctcg atgatgccgc agtggtctta catgcacatc tcgggccagg    20040
acgcctcgga gtacctgagc cccgggctgg tgcagtttgc ccgcgccacc gagacgtact    20100
tcagcctgaa taacaagttt agaaacccca cggtggcgcc tacgcacgac gtgaccacag    20160
accgtcccca gcgtttgacg ctgcggttca tccctgtgga ccgtgaggat actgcgtact    20220
cgtacaaggc gcggttcacc ctagctgtgg gtgataaccg tgtgctggac atggcttcca    20280
cgtactttga catccgcggc gtgctggaca ggggccctac ttttaagccc tactctgcca    20340
ctgcctacaa cgccctggct cccaaggggtg ccccaaatcc ttgcgaatgg gatgaagctg    20400
ctactgctct tgaaataaac ctagaagaag aggacgatga caacgaagac gaagtagacg    20460
agcaagctga gcagcaaaaa actcacgtat ttgggcaggc gccttattct ggtataaata    20520
ttacaaagga gggtattcaa ataggtgtcg aaggtcaaac acctaaatat gccgataaaa    20580
catttcaacc tgaacctcaa ataggagaat ctcagtggta cgaaactgaa attaatcatg    20640
```

```
cagctgggag agtccttaaa aagactaccc caatgaaacc atgttacggt tcatatgcaa    20700
aacccacaaa tgaaaatgga gggcaaggca ttcttgtaaa gcaacaaaat ggaaagctag    20760
aaagtcaagt ggaaatgcaa tttttctcaa ctactgaggc gaccgcaggc aatggtgata    20820
acttgactcc taaagtggta ttgtacagtg aagatgtaga tatagaaacc ccagacactc    20880
atatttctta catgcccact attaaggaag gtaactcacg agaactaatg ggccaacaat    20940
ctatgcccaa caggcctaat tacattgctt ttagggacaa ttttattggt ctaatgtatt    21000
acaacagcac gggtaatatg ggtgttctgg cgggccaagc atcgcagttg aatgctgttg    21060
tagatttgca agacagaaac acagagcttt cataccagct tttgcttgat tccattggtg    21120
atagaaccag gtactttcct atgtggaatc aggctgttga cagctatgat ccagatgtta    21180
gaattattga aaatcatgga actgaagatg aacttccaaa ttactgcttt ccactgggag    21240
gtgtgattaa tacagagact cttaccaagg taaaacctaa aacaggtcag gaaaatggat    21300
gggaaaaaga tgctacagaa ttttcagata aaaatgaaat aagagttgga ataaattttg    21360
ccatggaaat caatctaaat gccaacctgt ggagaaattt cctgtactcc aacatagcgc    21420
tgtatttgcc cgacaagcta agtacagtc cttccaacgt aaaaatttct gataacccaa    21480
acacctacga ctacatgaac aagcgagtgg tggctcccgg gttagtggac tgctacatta    21540
accttggagc acgctggtcc cttgactata tggacaacgt caacccattt aaccaccacc    21600
gcaatgctgg cctgcgctac cgctcaatgt tgctgggcaa tggtcgctat gtgcccttcc    21660
acatccaggt gcctcagaag ttcttttgcca ttaaaaaacct ccttctcctg ccgggctcat    21720
acacctacga gtggaacttc aggaaggatg ttaacatggt tctgcagagc tccctaggaa    21780
atgacctaag ggttgacgga gccagcatta agtttgatag catttgcctt tacgccacct    21840
tcttccccat ggcccacaac accgcctcca cgcttgaggc catgcttaga aacgacacca    21900
acgaccagtc ctttaacgac tatctctccg ccgccaacat gctctaccct atacccgcca    21960
acgctaccaa cgtgcccata tccatcccct cccgcaactg ggcggctttc gcggctggg    22020 ccttcacgcg ccttaagact aaggaaaccc catcactggg ctcgggctac gacccttatt    22080
acacctactc tggctctata ccctacctag atggaacctt ttacctcaac cacaccttta    22140
agaaggtggc cattaccttt gactcttctg tcagctggcc tggcaatgac cgcctgctta    22200 ccccccaacga gtttgaaatt aagcgctcag ttgacgggga gggttacaac gttgcccagt    22260
gtaacatgac caaagactgg ttcctggtac aaatgctagc taactacaac attggctacc    22320
agggcttcta tatcccagag agctacaagg accgcatgta ctccttcttt agaaacttcc    22380
agcccatgag ccgtcaggtg gtggatgata ctaaatacaa ggactaccaa caggtgggca    22440
tcctacacca acacaacaac tctggatttg ttggctacct tgcccccacc atgcgcgaag    22500
gacaggccta ccctgctaac ttcccctatc cgcttatagg caagaccgca gttgacagca    22560
ttacccagaa aaagtttctt tgcgatcgca ccctttggcg catcccattc tccagtaact    22620
ttatgtccat gggcgcactc acagacctgg gccaaaacct tctctacgcc aactccgccc    22680
acgcgctaga catgactttt gaggtggatc ccatggacga gcccacccgt ctttatgttt    22740
tgtttgaagt ctttgacgtg gtccgtgtgc accggccgca ccgcggcgtc atcgaaaccg    22800
tgtacctgcg cacgcccttc tcggccggca acgccacaac ataaagaagc aagcaacatc    22860
aacaacagct gccgccatgg gctccagtga gcaggaactg aaagccattg tcaaagatct    22920
tggttgtggg ccatatttt tgggcaccta tgacaagcgc tttccaggct ttgtttctcc    22980
```

```
acacaagctc gcctgcgcca tagtcaatac ggccggtcgc gagactgggg gcgtacactg    23040
gatggccttt gcctggaacc cgcactcaaa aacatgctac ctctttgagc cctttggctt    23100
ttctgaccag cgactcaagc aggtttacca gtttgagtac gagtcactcc tgcgccgtag    23160
cgccattgct tcttcccccg accgctgtat aacgctggaa aagtccaccc aaagcgtaca    23220
ggggcccaac tcggccgcct gtggactatt ctgctgcatg tttctccacg cctttgccaa    23280 ctggcccaa actcccatgg atcacaaccc caccatgaac cttattaccg gggtacccaa     23340
ctccatgctc aacagtcccc aggtacagcc caccctgcgt cgcaaccagg aacagctcta    23400
cagcttcctg gagcgccact cgccctactt ccgcagccac agtgcgcaga ttaggagcgc    23460
cacttctttt tgtcacttga aaaacatgta aaataatgt actagagaca ctttcaataa     23520
aggcaaatgc ttttatttgt acactctcgg gtgattattt accccaccc ttgccgtctg     23580 cgccgtttaa aaatcaaagg ggttctgccg cgcatcgcta tgcgccactg gcagggacac    23640
gttgcgatac tggtgtttag tgctccactt aaactcaggc acaaccatcc gcggcagctc    23700
ggtgaagttt tcactccaca ggctgcgcac catcaccaac gcgtttagca ggtcgggcgc    23760
cgatatcttg aagtcgcagt tgggcctcc gccctgcgcg cgcgagttgc gatacacagg     23820
gttgcagcac tggaacacta tcagcgccgg gtggtgcacg ctggccagca cgctcttgtc    23880
ggagatcaga tccgcgtcca ggtcctccgc gttgctcagg gcgaacggag tcaactttgg    23940
tagctgcctt cccaaaaagg gcgcgtgccc aggctttgag ttgcactcgc accgtagtgg    24000
catcaaaagg tgaccgtgcc cggtctgggc gttaggatac agcgcctgca taaaagcctt    24060
gatctgctta aaagccacct gagcctttgc gccttcagag aagaacatgc cgcaagactt    24120
gccggaaaac tgattggccg gacaggccgc gtcgtgcacg cagcaccttg cgtcggtgtt    24180
ggagatctgc accacatttc ggccccaccg gttcttcacg atcttggcct tgctagactg    24240
ctccttcagc gcgcgctgcc cgttttcgct cgtcacatcc atttcaatca cgtgctcctt    24300
atttatcata atgcttccgt gtagacactt aagctcgcct tcgatctcag cgcagcggtg    24360
cagccacaac gcgcagcccg tgggctcgtg atgcttgtag gtcacctctg caaacgactg    24420
caggtacgcc tgcaggaatc gccccatcat cgtcacaaag gtcttgttgc tggtgaaggt    24480
cagctgcaac ccgcggtgct cctcgttcag ccaggtcttg catacggccg ccagagcttc    24540
cacttggtca ggcagtagtt tgaagttcgc ctttagatct ttatccacgt ggtacttgtc    24600
catcagcgcg cgcgcagcct ccatgcccct ctcccacgca gacacgatcg gcacactcag    24660
cgggttcatc accgtaattt cactttccgc ttcgctgggc tcttcctctt cctcttgcgt    24720
ccgcatacca cgcgccactg ggtcgtcttc attcagccgc cgcactgtgc gcttacctcc    24780
tttgccatgc ttgattagca ccggtgggtt gctgaaaccc accatttgta gcgccacatc    24840
ttctctttct tcctcgctgt ccacgattac ctctggtgat ggcgggcgct cgggcttggg    24900
agaagggcgc ttcttttct tcttgggcgc aatggccaaa tccgccgccg aggtcgatgg     24960
ccgcgggctg ggtgtgcgcg gcaccagcgc gtcttgtgat gagtcttcct cgtcctcgga    25020
ctcgatacgc cgcctcatcc gcttttttgg gggcgcccgg ggaggcggcg gcgacgggga    25080
cggggacgac acgtcctcca tggttggggg acgtcgcgcc gcaccgcgtc gcgcgctcgg    25140
ggtggtttcg cgctgctcct cttcccgact ggccatttcc ttctcctata ggcagaaaaa    25200
gatcatggag tcagtcgaga agaaggacag cctaaccgcc ccctctgagt tcgccaccac    25260
cgcctccacc gatgccgcca acgcgcctac caccttcccc gtcgaggcac cccgcttga    25320 ggaggaggaa gtgattatcg agcaggaccc aggttttgta agcgaagacg acgaggaccg    25380
```

```
ctcagtacca acagaggata aaaagcaaga ccaggacaac gcagaggcaa acgaggaaca    25440
agtcgggcgg ggggacgaaa ggcatggcga ctacctagat gtgggagacg acgtgctgtt    25500
gaagcatctg cagcgccagt gcgccattat ctgcgacgcg ttgcaagagc gcagcgatgt    25560
gcccctcgcc atagcggatg tcagccttgc ctacgaacgc cacctattct caccgcgcgt    25620
accccccaaa cgccaagaaa acggcacatg cgagcccaac ccgcgcctca acttctaccc    25680
cgtatttgcc gtgccagagg tgcttgccac ctatcacatc tttttccaaa actgcaagat    25740 accccctatcc tgccgtgcca accgcagccg agcggacaag cagctggcct tgcggcaggg    25800
cgctgtcata cctgatatcg cctcgctcaa cgaagtgcca aaaatctttg agggtcttgg    25860
acgcgacgag aagcgcgcgg caaacgctct gcaacaggaa acagcgaaa atgaaagtca    25920 ctctggagtg ttggtggaac tcgagggtga caacgcgcgc ctagccgtac taaaacgcag    25980
catcgaggtc acccactttg cctacccggc acttaaccta ccccccaagg tcatgagcac    26040
agtcatgagt gagctgatcg tgcgccgtgc gcagcccctg gagagggatg caaatttgca    26100
agaacaaaca gaggagggcc taccccgcagt tggcgacgag cagctagcgc gctggcttca    26160
aacgcgcgag cctgccgact tggaggagcg acgcaaacta atgatggccg cagtgctcgt    26220
taccgtggag cttgagtgca tgcagcggtt ctttgctgac ccggagatgc agcgcaagct    26280
agaggaaaca ttgcactaca cctttcgaca gggctacgta cgccaggcct gcaagatctc    26340
caacgtggag ctctgcaacc tggtctccta ccttggaatt ttgcacgaaa accgccttgg    26400
gcaaaacgtg cttcattcca cgctcaaggg cgaggcgcgc cgcgactacg tccgcgactg    26460
cgtttactta tttctatgct acacctggca gacggccatg ggcgtttggc agcagtgctt    26520
ggaggagtgc aacctcaagg agctgcagaa actgctaaag caaaacttga aggacctatg    26580
gacggccttc aacgagcgct ccgtggccgc gcacctggcg gacatcattt tccccgaacg    26640
cctgcttaaa accctgcaac agggtctgcc agacttcacc agtcaaagca tgttgcagaa    26700
ctttaggaac tttatcctag agcgctcagg aatcttgccc gccacctgct gtgcacttcc    26760
tagcgacttt gtgcccatta agtaccgcga atgccctccg ccgctttggg gccactgcta    26820
ccttctgcag ctagccaact accttgccta ccactctgac ataatggaag acgtgagcgg    26880
tgacggtcta ctggagtgtc actgtcgctg caacctatgc accccgcacc gctccctggt    26940
ttgcaattcg cagctgctta acgaaagtca aattatcggt acctttgagc tgcagggtcc    27000
ctcgcctgac gaaaagtccg cggctccggg gttgaaactc actccggggc tgtggacgtc    27060
ggcttacctt cgcaaatttg tacctgagga ctaccacgcc cacgagatta ggttctacga    27120
agaccaatcc cgcccgccaa atgcggagct taccgcctgc gtcattaccc agggccacat    27180
tcttggccaa ttgcaagcca tcaacaaagc ccgccaagag tttctgctac gaaagggacg    27240
gggggtttac ttggaccccc agtccggcga ggagctcaac ccaatccccc cgccgccgca    27300
gccctatcag cagcagccgc gggcccttgc ttcccaggat ggcacccaaa aagaagctgc    27360
agctgccgcc gccacccacg acgaggagg aatactggga cagtcaggca gaggaggttt    27420
tggacgagga ggaggaggac atgatggaag actgggagag cctagacgag gaagcttccg    27480
aggtcgaaga ggtgtcagac gaaacaccgt caccctcggt cgcattcccc tcgccggcgc    27540
cccagaaatc ggcaaccggt tccagcatgg ctacaacctc cgctcctcag gcgccgccgg    27600
cactgcccgt tcgccgaccc aaccgtagat gggacaccac tggaaccagg gccggtaagt    27660
ccaagcagcc gccgccgtta gcccaagagc aacaacagcg ccaaggctac cgctcatggc    27720
```

```
gcgggcacaa gaacgccata gttgcttgct tgcaagactg tgggggcaac atctccttcg    27780
cccgccgctt tcttctctac catcacggcg tggccttccc ccgtaacatc ctgcattact    27840
accgtcatct ctacagccca tactgcaccg gcggcagcgg cagcggcagc aacagcagcg    27900
gccacacaga agcaaaggcg accggatagc aagactctga caaagcccaa gaaatccaca    27960
gcggcggcag cagcaggagg aggagcgctg cgtctggcgc ccaacgaacc cgtatcgacc    28020
cgcgagctta gaaacaggat ttttcccact ctgtatgcta tatttcaaca gagcaggggc    28080
caagaacaag agctgaaaat aaaaaacagg tctctgcgat ccctcacccg cagctgcctg    28140
tatcacaaaa gcgaagatca gcttcggcgc acgctggaag acgcggaggc tctcttcagt    28200
aaatactgcg cgctgactct taaggactag tttcgcgccc tttctcaaat ttaagcgcga    28260
aaactacgtc atctccagcg gccacacccg gcgccagcac ctgtcgtcag cgccattatg    28320
agcaaggaaa ttcccacgcc ctacatgtgg agttaccagc cacaaatggg acttgcggct    28380
ggagctgccc aagactactc aacccgaata aactacatga gcgcgggacc ccacatgata    28440
tcccgggtca acggaatccg cgcccaccga aaccgaattc tcttggaaca ggcggctatt    28500
accaccacac ctcgtaataa ccttaatccc cgtagttggc ccgctgccct ggtgtaccag    28560
gaaagtcccg ctcccaccac tgtggtactt cccagagacg cccaggccga agttcagatg    28620
actaactcag gggcgcagct tgcgggcggc tttcgtcaca gggtgcggtc gcccgggcag    28680
ggtataactc acctgacaat cagagggcga ggtattcagc tcaacgacga gtcggtgagc    28740
tcctcgcttg gtctccgtcc ggacgggaca tttcagatcg gcggcgccgg ccgtccttca    28800
ttcacgcctc gtcaggcaat cctaactctg cagacctcgt cctctgagcc gcgctctgga    28860
ggcattggaa ctctgcaatt tattgaggag tttgtgccat cggtctactt taacccctttc   28920 tcgggacctc ccggccacta tccggatcaa tttattccta actttgacgc ggtaaaggac    28980
tcggcggacg gctacgactg aatgttaagt ggagaggcag agcaactgcg cctgaaacac    29040
ctggtccact gtcgccgcca caagtgcttt gcccgcgact ccggtgagtt ttgctacttt    29100
gaattgcccg aggatcatat cgagggcccg gcgcacggcg tccggcttac cgcccaggga    29160
gagcttgccc gtagcctgat tcgggagttt acccagcgcc cctgctagt tgagcgggac     29220 aggggaccct gtgttctcac tgtgatttgc aactgtccta accttggatt acatcaagat    29280
ttaattaatt gccacatcct cttacacttt ttcatacatt gcccaagaat aaagaatcgt    29340
ttgtgttatg tttcaacgtg tttattttc aattgcagaa aatttcaagt cattttttcat    29400 tcagtagtat agccccacca ccacatagct tatacagatc accgtacctt aatcaaactc    29460
acagaaccct agtattcaac ctgccacctc cctcccaaca cacagagtac acagtccttt    29520
ctccccggct ggccttaaaa agcatcatat catgggtaac agacatattc ttaggtgtta    29580
tattccacac ggtttcctgt cgagccaaac gctcatcagt gatattaata aactccccgg    29640
gcagctcact taagttcatg tcgctgtcca gctgctgagc cacaggctgc tgtccaactt    29700
gcggttgctt aacgggcggc gaaggagaag tccacgccta catgggggta gagtcataat    29760
cgtgcatcag atagggcgg tggtgctgca gcagcgcgcg aataaactgc tgccgccgcc    29820
gctccgtcct gcaggaatac aacatggcag tggtctcctc agcgatgatt cgcaccgccc    29880
gcagcataag gcgccttgtc ctccgggcac agcagcgcac cctgatctca cttaaatcag    29940
cacagtaact gcagcacagc accacaatat tgttcaaaat cccacagtgc aaggcgctgt    30000
atccaaagct catggcgggg accacagaac ccacgtggcc atcataccac aagcgcaggt    30060
agattaagtg gcgacccctc ataaacacgc tggacataaa cattacctct tttggcatgt    30120
```

```
tgtaattcac cacctcccgg taccatataa acctctgatt aaacatggcg ccatccacca    30180
ccatcctaaa ccagctggcc aaaacctgcc cgccggctat acactgcagg gaaccgggac    30240
tggaacaatg acagtggaga gcccaggact cgtaaccatg gatcatcatg ctcgtcatga    30300
tatcaatgtt ggcacaacac aggcacacgt gcatacactt cctcaggatt acaagctcct    30360
cccgcgttag aaccatatcc cagggaacaa cccattcctg aatcagcgta atcccacac     30420 tgcagggaag acctcgcacg taactcacgt tgtgcattgt caaagtgtta cattcgggca    30480
gcagcggatg atcctccagt atggtagcgc gggtttctgt ctcaaaagga ggtagacgat    30540
ccctactgta cggagtgcgc cgagacaacc gagatcgtgt tggtcgtagt gtcatgccaa    30600
atggaacgcc ggacgtagtc atatttcctg aagcaaaacc aggtgcgggc gtgacaaaca    30660
gatctgcgtc tccggtctcg ccgcttagat cgctctgtgt agtagttgta gtatatccac    30720
tctctcaaag catccaggcg cccctggct tcgggttcta tgtaaactcc ttcatgcgcc     30780
gctgccctga taacatccac caccgcagaa taagccacac ccagccaacc tacacattcg    30840
ttctgcgagt cacacacggg aggagcggga agagctggaa gaaccatgtt ttttttttta    30900
ttccaaaaga ttatccaaaa cctcaaaatg aagatctatt aagtgaacgc gctcccctcc    30960
ggtggcgtgg tcaaactcta cagccaaaga acagataatg gcatttgtaa gatgttgcac    31020
aatggcttcc aaaaggcaaa cggccctcac gtccaagtgg acgtaaaggc taaacccttc    31080
agggtgaatc tcctctataa acattccagc accttcaacc atgcccaaat aattctcatc    31140
tcgccacctt ctcaatatat ctctaagcaa atcccgaata ttaagtccgg ccattgtaaa    31200
aatctgctcc agagcgccct ccaccttcag cctcaagcag cgaatcatga ttgcaaaaat    31260
tcaggttcct cacagacctg tataagattc aaaagcggaa cattaacaaa ataccgcga     31320 tcccgtaggt cccttcgcag ggccagctga acataatcgt gcaggtctgc acggaccagc    31380
gcggccactt ccccgccagg aaccttgaca aaagaaccca cactgattat gacacgcata    31440
ctcggagcta tgctaaccag cgtagccccg atgtaagctt tgttgcatgg gcggcgatat    31500
aaaatgcaag gtgctgctca aaaatcagg caaagcctcg cgcaaaaaag aaagcacatc     31560
gtagtcatgc tcatgcagat aaaggcaggt aagctccgga accaccacag aaaaagacac    31620 cattttctc tcaaacatgt ctgcgggttt ctgcataaac acaaaataaa ataacaaaaa     31680
aacatttaaa cattagaagc ctgtcttaca acaggaaaaa caacccttat aagcataaga    31740
cggactacgg ccatgccggc gtgaccgtaa aaaaactggt caccgtgatt aaaaagcacc    31800
accgacagct cctcggtcat gtccggagtc ataatgtaag actcggtaaa cacatcaggt    31860
tgattcatcg gtcagtgcta aaagcgacc gaaatagccc ggggaatac ataccccgcag     31920 gcgtagagac aacattacag cccccatagg aggtataaca aaattaatag gagagaaaaa    31980
cacataaaca cctgaaaaac cctcctgcct aggcaaaata gcaccctccc gctccagaac    32040
aacatacagc gcttcacagc ggcagcctaa cagtcagcct taccagtaaa aagaaaaacc    32100
tattaaaaaa acaccactcg acacggcacc agctcaatca gtcacagtgt aaaaaagggc    32160
caagtgcaga gcgagtatat ataggactaa aaaatgacgt aacggttaaa gtccacaaaa    32220
aacacccaga aaaccgcacg cgaacctacg cccagaaacg aaagccaaaa aacccacaac    32280
ttcctcaaat cgtcacttcc gttttcccac gttacgtaac ttcccatttt aagaaaacta    32340
caattcccaa cacatacaag ttactccgcc ctaaaaccta cgtcaccgc ccgttccca      32400 cgccccgcgc cacgtcacaa actccacccc ctcattatca tattggcttc aatccaaaat    32460
```

```
                                                     -continued aaggtatatt attgatgatg                                                  32480

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 28
ctcaacaatt gtggatccgt actcc                                               25

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 29
gtgctcagca gatcttgcga ctgtg                                               25

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 30
ggcgcgttcg gatccactct cttcc                                               25

<210> SEQ ID NO 31
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 31
ctacatgcta ggcagatctc gttcggag                                            28

<210> SEQ ID NO 32
<211> LENGTH: 1240
<212> TYPE: DNA
<213> ORGANISM: adenovirus

<400> SEQUENCE: 32
ggatccactc tcttccgcat cgctgtctgc gagggccagc tgttggggtg agtactccct         60
ctgaaaagcg ggcatgactt ctgcgctaag attgtcagtt ccaaaaacg aggaggattt        120 gatattcacc tggcccgcgg tgatgccttt gagggtggcc gcatccatct ggtcagaaaa       180
gacaatcttt ttgttgtcaa gcttggtggc aaacgacccg tagagggcgt tggacagcaa       240
cttggcgatg gagcgcaggg tttggttttt gtcgcgatcg gcgcgctcct tggccgcgat       300
gtttagctgc acgtattcgc gcgcaacgca ccgccattcg ggaaagacgg tggtgcgctc       360
gtcgggcacc aggtgcacgc gccaaccgcg gttgtgcagg gtgacaaggt caacgctggt       420
ggctacctct ccgcgtaggc gctcgttggt ccagcagagg cggccgccct tgcgcgagca       480
gaatggcggt agggggtcta gctgcgtctc gtccggggggg tctgcgtcca cggtaaagac      540
cccgggcagc aggcgcgcgt cgaagtagtc tatcttgcat ccttgcaagt ctagcgcctg       600
ctgccatgcg cgggcggcaa gcgcgcgctc gtatgggttg agtgggggac cccatggcat       660
```

-continued

```
ggggtgggtg agcgcggagg cgtacatgcc gcaaatgtcg taaacgtaga ggggctctct    720
gagtattcca agatatgtag ggtagcatct tccaccgcgg atgctggcgc gcacgtaatc    780
gtatagttcg tgcgagggag cgaggaggtc gggaccgagg ttgctacggg cgggctgctc    840
tgctcggaag actatctgcc tgaagatggc atgtgagttg gatgatatgg ttggacgctg    900
gaagacgttg aagctggcgt ctgtgagacc taccgcgtca cgcacgaagg aggcgtagga    960
gtcgcgcagc ttgttgacca gctcggcggt gacctgcacg tctagggcgc agtagtccag   1020
ggtttccttg atgatgtcat acttatcctg tccctttttt ttccacagct cgcggttgag   1080
gacaaactct tcgcggtctt tccagtactc ttggatcgga aacccgtcgg cctccgaacg   1140
agatccgtac tccgccgccg agggacctga gcgagtccgc atcgaccgga tcggaaaacc   1200
tctcgagaaa ggcgtctaac cagtcacagt cgcaagatct                         1240
```

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 33
ggcgcgttcg gatccactct cttcc                                            25

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 34
gggagtagat ctcccaacag                                                  20

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 35
cccttttttt tggatccctc gcgg                                             24

<210> SEQ ID NO 36
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 36
ctacatgcta ggcagatctc gttcggag                                         28

<210> SEQ ID NO 37
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 37

-continued ctcaacaatt gttggatccg tactcc                                                  26

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 38
gtgctcagca gatcttgcga ctgtg                                                   25

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 39
ggcgcgttcg gatccactct cttcc                                                   25

<210> SEQ ID NO 40
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 40
ctacatgcta ggcagatctc gttcggag                                                28

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 41
cccttttttt tggatccctc gcgg                                                    24

<210> SEQ ID NO 42
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 42
gtgctcagca gatcttgcga ctgtg                                                   25

<210> SEQ ID NO 43
<211> LENGTH: 8383
<212> TYPE: DNA
<213> ORGANISM: Artificial Sequence
<220> FEATURE:
<223> OTHER INFORMATION: Description of Artificial Sequence: plasmid

<400> SEQUENCE: 43
gacggatcgg gagatctccc gatcccctat ggtcgactct cagtacaatc tgctctgatg        60
ccgcatagtt aagccagtat ctgctccctg cttgtgtgtt ggaggtcgct gagtagtgcg       120
cgagcaaaat ttaagctaca acaaggcaag gcttgaccga caattgcatg aagaatctgc       180
ttagggttag gcgttttgcg ctgcttcgcg atgtacgggc cagatatacg cgttgacatt       240

-continued

| | |
|---|---|
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggac tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccaccccca ttgacgtcaa tgggagtttg ttttggcacc | 720 |
| aaaatcaacg ggactttcca aaatgtcgta acaactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gcttggtacc | 900 |
| gagctcggat ccactctctt ccgcatcgct gtctgcgagg gccagctgtt ggggtgagta | 960 |
| ctccctctga aaagcgggca tgacttctgc gctaagattg tcagtttcca aaaacgagga | 1020 |
| ggatttgata ttcacctggc ccgcggtgat gcctttgagg gtggccgcat ccatctggtc | 1080 |
| agaaaagaca atcttttttgt tgtcaagctt ggtggcaaac gacccgtaga gggcgttgga | 1140 |
| cagcaacttg gcgatggagc gcagggtttg gtttttgtcg cgatcggcgc gctccttggc | 1200 |
| cgcgatgttt agctgcacgt attcgcgcgc aacgcaccgc cattcgggaa agacggtggt | 1260 |
| gcgctcgtcg ggcaccaggt gcacgcgcca accgcggttg tgcagggtga caaggtcaac | 1320 |
| gctggtggct acctctccgc gtaggcgctc gttggtccag cagaggcggc cgcccttgcg | 1380 |
| cgagcagaat ggcggtaggg ggtctagctg cgtctcgtcc gggggggtctg cgtccacggt | 1440 |
| aaagaccccg ggcagcaggc gcgcgtcgaa gtagtctatc ttgcatcctt gcaagtctag | 1500 |
| cgcctgctgc catgcgcggg cggcaagcgc gcgctcgtat gggttgagtg ggggacccca | 1560 |
| tggcatgggg tgggtgagcg cggaggcgta catgccgcaa atgtcgtaaa cgtagagggg | 1620 |
| ctctctgagt attccaagat atgtagggta gcatcttcca ccgcggatgc tggcgcgcac | 1680 |
| gtaatcgtat agttcgtgcg agggagcgag gaggtcggga ccgaggttgc tacgggcggg | 1740 |
| ctgctctgct cggaagacta tctgcctgaa gatggcatgt gagttggatg atatggttgg | 1800 |
| acgctggaag acgttgaagc tggcgtctgt gagacctacc gcgtcacgca cgaaggaggc | 1860 |
| gtaggagtcg cgcagcttgt tgaccagctc ggcggtgacc tgcacgtcta gggcgcagta | 1920 |
| gtccagggtt tccttgatga tgtcatactt atcctgtccc tttttttttcc acagctcgcg | 1980 |
| gttgaggaca aactcttcgc ggtctttcca gtactcttgg atcggaaacc cgtcggcctc | 2040 |
| cgaacgagat ccgtactccg ccgccgaggg acctgagcga gtccgcatcg accggatcgg | 2100 |
| aaaacctctc gagaaaggcg tctaaccagt cacagtcgca agatccaaga tgaagcgcgc | 2160 |
| aagaccgtct gaagatacct tcaaccccgt gtatccatat gacacggaaa ccggtcctcc | 2220 |
| aactgtgcct tttcttactc ctcccttttgt atccccccaat gggtttcaag agagtccccc | 2280 |
| tggggtactc tctttgcgcc tatccgaacc tctagttacc tccaatggca tgcttgcgct | 2340 |
| caaaatgggc aacggcctct ctctggacga ggccggcaac cttacctccc aaaatgtaac | 2400 |
| cactgtgagc ccacctctca aaaaaaccaa gtcaaacata aacctggaaa tatctgcacc | 2460 |
| cctcacagtt acctcagaag ccctaactgt ggctgccgcc gcacctctaa tggtcgcggg | 2520 |
| caacacactc accatgcaat cacaggcccc gctaaccgtg cacgactcca aacttagcat | 2580 |

-continued

```
tgccacccaa ggacccctca cagtgtcaga aggaaagcta gccctgcaaa catcaggccc    2640
cctcaccacc accgatagca gtaccttac  tatcactgcc tcacccctc  taactactgc    2700 cactggtagc ttgggcattg acttgaaaga gcccatttat acacaaaatg gaaaactagg    2760
actaaagtac ggggctcctt tgcatgtaac agacgaccta aacactttga ccgtagcaac    2820
tggtccaggt gtgactatta ataatacttc cttgcaaact aaagttactg gagccttggg    2880
ttttgattca caaggcaata tgcaacttaa tgtagcagga ggactaagga ttgattctca    2940
aaacagacgc cttatacttg atgttagtta tccgtttgat gctcaaaacc aactaaatct    3000
aagactagga cagggccctc tttttataaa ctcagcccac aacttggata ttaactacaa    3060
caaaggcctt tacttgttta cagcttcaaa caattccaaa aagcttgagg ttaacctaag    3120
cactgccaag gggttgatgt tgacgctac  agccatagcc attaatgcag gagatgggct    3180
tgaatttggt tcacctaatg caccaaacac aaatcccctc aaaacaaaaa ttggccatgg    3240
cctagaattt gattcaaaca aggctatggt tcctaaacta ggaactggcc ttagttttga    3300
cagcacaggt gccattacag taggaaacaa aaataatgat aagctaactt tgtggaccac    3360
accagctcca tctcctaact gtagactaaa tgcagagaaa gatgctaaac tcactttggt    3420
cttaacaaaa tgtggcagtc aaatacttgc tacagtttca gttttggctg ttaaaggcag    3480
tttggctcca atatctggaa cagttcaaag tgctcatctt attataagat ttgacgaaaa    3540
tggagtgcta ctaaacaatt ccttcctgga cccagaatat tggaacttta gaaatggaga    3600
tcttactgaa ggcacagcct atacaaacgc tgttggattt atgcctaacc tatcagctta    3660
tccaaaatct cacggtaaaa ctgccaaaag taacattgtc agtcaagttt acttaaacgg    3720
agacaaaact aaacctgtaa cactaaccat tacactaaac ggtacacagg aaacaggaga    3780
cacaactcca agtgcatact ctatgtcatt ttcatgggac tggtctggcc acaactacat    3840
taatgaaata tttgccacat cctcttacac tttttcatac attgcccaag aataaaagaa    3900
gcggccgctc gagcatgcat ctagagggcc ctattctata gtgtcaccta aatgctagag    3960
ctcgctgatc agcctcgact gtgccttcta gttgccagcc atctgttgtt tgcccctccc    4020
ccgtgccttc cttgaccctg gaaggtgcca ctcccactgt cctttcctaa taaaatgagg    4080
aaattgcatc gcattgtctg agtaggtgtc attctattct ggggggtggg gtggggcagg    4140
acagcaaggg ggaggattgg gaagacaata gcaggcatgc tggggatgcg gtgggctcta    4200
tggcttctga ggcggaaaga accagctggg gctctagggg gtatcccac  gcgcccgta    4260 gcggcgcatt aagcgcggcg ggtgtggtgg ttacgcgcag cgtgaccgct acacttgcca    4320
gcgccctagc gcccgctcct ttcgctttct tcccttcctt tctcgccacg ttcgccggct    4380
ttccccgtca gctctaaat  cggggcatcc ctttagggtt ccgatttagt gctttacggc    4440
acctcgaccc caaaaaactt gattagggtg atggttcacg tagtgggcca tcgccctgat    4500
agacggtttt tcgccctttg acgttggagt ccacgttctt taatagtgga ctcttgttcc    4560
aaactggaac aacactcaac cctatctcgg tctattcttt tgatttataa gggattttgg    4620
ggatttcggc ctattggtta aaaaatgagc tgatttaaca aaaatttaac gcgaattaat    4680
tctgtggaat gtgtgtcagt tagggtgtgg aaagtcccca ggctcccag  gcaggcagaa    4740 gtatgcaaag catgcatctc aattagtcag caaccaggtg tggaaagtcc caggctccc     4800 cagcaggcag aagtatgcaa agcatgcatc tcaattagtc agcaaccata gtcccgcccc    4860
taactccgcc catcccgccc ctaactccgc ccagttccgc ccattctccg ccccatggct    4920
gactaatttt ttttatttat gcagaggccg aggccgcctc tgcctctgag ctattccaga    4980
```

```
agtagtgagg aggctttttt ggaggcctag gcttttgcaa aaagctcccg ggagcttgta      5040
tatccatttt cggatctgat caagagacag gatgaggatc gtttcgcatg attgaacaag      5100
atggattgca cgcaggttct ccggccgctt ggtggagag gctattcggc tatgactggg      5160
cacaacagac aatcggctgc tctgatgccg ccgtgttccg gctgtcagcg caggggcgcc      5220
cggttctttt tgtcaagacc gacctgtccg gtgccctgaa tgaactgcag gacgaggcag      5280
cgcggctatc gtggctggcc acgacgggcg ttccttgcgc agctgtgctc gacgttgtca      5340
ctgaagcggg aagggactgg ctgctattgg gcgaagtgcc ggggcaggat ctcctgtcat      5400
ctcaccttgc tcctgccgag aaagtatcca tcatggctga tgcaatgcgg cggctgcata      5460
cgcttgatcc ggctacctgc ccattcgacc accaagcgaa acatcgcatc gagcgagcac      5520
gtactcggat ggaagccggt cttgtcgatc aggatgatct ggacgaagag catcaggggc      5580
tcgcgccagc cgaactgttc gccaggctca aggcgcgcat gcccgacggc gaggatctcg      5640
tcgtgaccca tggcgatgcc tgcttgccga atatcatggt ggaaaatggc cgcttttctg      5700
gattcatcga ctgtggccgg ctgggtgtgg cggaccgcta tcaggacata gcgttggcta      5760
cccgtgatat tgctgaagag cttggcggcg aatgggctga ccgcttcctc gtgctttacg      5820
gtatcgccgc tcccgattcg cagcgcatcg ccttctatcg ccttcttgac gagttcttct      5880
gagcgggact ctggggttcg aaatgaccga ccaagcgacg cccaacctgc catcacgaga      5940
tttcgattcc accgccgcct tctatgaaag gttgggcttc ggaatcgttt tccgggacgc      6000
cggctggatg atcctccagc gcggggatct catgctggag ttcttcgccc accccaactt      6060
gtttattgca gcttataatg gttacaaata aagcaatagc atcacaaatt tcacaaataa      6120
agcatttttt tcactgcatt ctagttgtgg tttgtccaaa ctcatcaatg tatcttatca      6180
tgtctgtata ccgtcgacct ctagctagag cttggcgtaa tcatggtcat agctgtttcc      6240
tgtgtgaaat tgttatccgc tcacaattcc acacaacata cgagccggaa gcataaagtg      6300
taaagcctgg ggtgcctaat gagtgagcta actcacatta attgcgttgc gctcactgcc      6360
cgctttccag tcgggaaacc tgtcgtgcca gctgcattaa tgaatcggcc aacgcgcggg      6420
gagaggcggt ttgcgtattg ggcgctcttc cgcttcctcg ctcactgact cgctgcgctc      6480
ggtcgttcgg ctgcggcgag cggtatcagc tcactcaaag gcggtaatac ggttatccac      6540
agaatcaggg gataacgcag gaaagaacat gtgagcaaaa ggccagcaaa aggccaggaa      6600
ccgtaaaaag gccgcgttgc tggcgttttt ccataggctc cgcccccctg acgagcatca      6660
caaaaatcga cgctcaagtc agaggtggcg aaacccgaca ggactataaa gataccaggc      6720
gtttccccct ggaagctccc tcgtgcgctc tcctgttccg accctgccgc ttaccggata      6780
cctgtccgcc tttctccctt cgggaagcgt ggcgctttct caatgctcac gctgtaggta      6840
tctcagttcg gtgtaggtcg ttcgctccaa gctgggctgt gtgcacgaac cccccgttca      6900
gcccgaccgc tgcgccttat ccggtaacta tcgtcttgag tccaacccgg taagacacga      6960
cttatcgcca ctggcagcag ccactggtaa caggattagc agagcgaggt atgtaggcgg      7020
tgctacagag ttcttgaagt ggtggcctaa ctacggctac actagaagga cagtatttgg      7080
tatctgcgct ctgctgaagc cagttacctt cggaaaaaga gttggtagct cttgatccgg      7140
caaacaaacc accgctggta gcggtggttt ttttgtttgc aagcagcaga ttacgcgcag      7200
aaaaaaagga tctcaagaag atcctttgat cttttctacg gggtctgacg ctcagtggaa      7260
cgaaaactca cgttaaggga ttttggtcat gagattatca aaaaggatct tcacctagat      7320
```

```
cctttttaaat taaaaatgaa gttttaaatc aatctaaagt atatatgagt aaacttggtc    7380
tgacagttac caatgcttaa tcagtgaggc acctatctca gcgatctgtc tatttcgttc    7440
atccatagtt gcctgactcc ccgtcgtgta gataactacg atacgggagg gcttaccatc    7500
tggccccagt gctgcaatga taccgcgaga cccacgctca ccggctccag atttatcagc    7560
aataaaccag ccagccggaa gggccgagcg cagaagtggt cctgcaactt tatccgcctc    7620
catccagtct attaattgtt gccgggaagc tagagtaagt agttcgccag ttaatagttt    7680
gcgcaacgtt gttgccattg ctacaggcat cgtggtgtca cgctcgtcgt ttggtatggc    7740
ttcattcagc tccggttccc aacgatcaag gcgagttaca tgatccccca tgttgtgcaa    7800
aaaagcggtt agctccttcg gtcctccgat cgttgtcaga agtaagttgg ccgcagtgtt    7860
atcactcatg gttatggcag cactgcataa ttctcttact gtcatgccat ccgtaagatg    7920
cttttctgtg actggtgagt actcaaccaa gtcattctga aatagtgta tgcggcgacc    7980
gagttgctct tgcccggcgt caatacggga taataccgcg ccacatagca gaactttaaa    8040
agtgctcatc attggaaaac gttcttcggg gcgaaaactc tcaaggatct taccgctgtt    8100
gagatccagt tcgatgtaac ccactcgtgc acccaactga tcttcagcat cttttacttt    8160
caccagcgtt tctgggtgag caaaaacagg aaggcaaaat gccgcaaaaa agggaataag    8220
ggcgacacgg aaatgttgaa tactcatact cttcctttttt caatattatt gaagcattta    8280
tcagggttat tgtctcatga gcggatacat atttgaatgt atttagaaaa ataaacaaat    8340
agggggttccg cgcacatttc cccgaaaagt gccacctgac gtc                     8383

<210> SEQ ID NO 44
<211> LENGTH: 7960
<212> TYPE: DNA
<213> ORGANISM: Artificial Sequence
<220> FEATURE:
<223> OTHER INFORMATION: Description of Artificial Sequence: plasmid

<400> SEQUENCE: 44
gacggatcgg gagatctccc gatcccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggac tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctagc     900
gtttaaactt aagcttggta ccgagctcgg atccactctc ttccgcatcg ctgtctgcga     960
gggccagctg ttggggtgag tactccctct gaaaagcggg catgacttct gcgctaagat    1020
```

-continued

```
tgtcagtttc caaaaacgag gaggatttga tattcacctg gcccgcggtg atgcctttga   1080
gggtggccgc atccatctgg tcagaaaaga caatctttt gttgtcaagc ttggtggcaa    1140
acgacccgta gagggcgttg dacagcaact tggcgatgga gcgcagggtt tggttttgt     1200 cgcgatcggc gcgctccttg gccgcgatgt ttagctgcac gtattcgcgc gcaacgcacc   1260
gccattcggg aaagacggtg gtgcgctcgt cgggcaccag gtgcacgcgc caaccgcggt   1320
tgtgcagggt gacaaggtca acgctggtgg ctacctctcc gcgtaggcgc tcgttggtcc    1380
agcagaggcg gccgcccttg cgcgagcaga atggcggtag ggggtctagc tgcgtctcgt     1440 ccgggggtc tgcgtccacg gtaaagaccc cgggcagcag gcgcgcgtcg aagtagtcta     1500
tcttgcatcc ttgcaagtct agcgcctgct gccatgcgcg ggcggcaagc gcgcgctcgt   1560
atgggttgag tgggggaccc catggcatgg ggtgggtgag cgcggaggcg tacatgccgc   1620
aaatgtcgta aacgtagagg ggctctctga gtattccaag atatgtaggg tagcatcttc     1680
caccgcggat gctggcgcgc acgtaatcgt atagttcgtg cgagggagcg aggaggtcgg   1740
gaccgaggtt gctacgggcg ggctgctctg ctcggaagac tatctgcctg aagatggcat   1800
gtgagttgga tgatatggtt ggacgctgga agacgttgaa gctggcgtct gtgagaccta   1860
ccgcgtcacg cacgaaggag gcgtaggagt cgcgcagctt gttgaccagc tcggcggtga   1920
cctgcacgtc tagggcgcag tagtccaggg tttccttgat gatgtcatac ttatcctgtc    1980 ccttttttt ccacagctcg cggttgagga caaactcttc gcggtctttc cagtactctt     2040
ggatcggaaa cccgtcggcc tccgaacgag atccgtactc cgccgccgag ggacctgagc   2100
gagtccgcat cgaccggatc ggaaaacctc tcgagaaagg cgtctaacca gtcacagtcg   2160
caagatccaa gatgaagcgc gcaagaccgt ctgaagatac cttcaacccc gtgtatccat    2220
atgacacgga aaccggtcct ccaactgtgc cttttcttac tcctcccttt gtatcccca    2280 atgggtttca agagagtccc cctggggtac tctctttgcg cctatccgaa cctctagtta   2340
cctccaatgg catgcttgcg ctcaaaatgg gcaacggcct ctctctggac gaggccggca   2400
accttacctc ccaaaatgta accactgtga gcccacctct caaaaaaacc aagtcaaaca   2460
taaacctgga aatatctgca cccctcacag ttacctcaga agccctaact gtggctgccg   2520
ccgcacctct aatggtcgcg ggcaacacac tcaccatgca atcacaggcc ccgctaaccg   2580
tgcacgactc caaacttagc attgccaccc aaggacccct cacagtgtca gaaggaaagc   2640
tagccctgca aacatcaggc cccctcacca ccaccgatag cagtacccct actatcactg   2700
cctcaccccc tctaactact gccactggta gcttgggcat tgacttgaaa gagcccattt    2760
atacacaaaa tggaaaacta ggactaaagt acggggctcc tttgcatgta acagacgacc   2820
taaacacttt gaccgtagca actggtccag gtgtgactat taataatact tccttgcaaa   2880
ctaaagttac tggagccttg ggttttgatt cacaaggcaa tatgcaactt aatgtagcag   2940
gaggactaag gattgattct caaaacagac gccttatact tgatgttagt tatccgtttg    3000
atgctcaaaa ccaactaaat ctaagactag acagggccc tctttttata aactcagccc    3060
acaacttgga tattaactac aacaaaggcc tttacttgtt tacagcttca aacaattcca   3120
aaaagcttga ggttaaccta agcactgcca aggggttgat gtttgacgct acagccatag   3180
ccattaatgc aggagatggg cttgaatttg gttcacctaa tgcaccaaac acaaatcccc   3240
tcaaaacaaa aattggccat ggcctagaat ttgattcaaa caaggctatg gttcctaaac   3300
taggaactgg ccttagtttt gacagcacag gtgccattac agtaggaaac aaaaataatg   3360
```

```
ataagctaac tttgtggacc acaccagctc catctcctaa ctgtagacta aatgcagaga    3420
aagatgctaa actcactttg gtcttaacaa aatgtggcag tcaaatactt gctacagttt    3480
cagttttggc tgttaaaggc agtttggctc caatatctgg aacagttcaa agtgctcatc    3540
ttattataag atttgacgaa aatggagtgc tactaaacaa ttccttcctg gacccagaat    3600
attggaactt tagaaatgga gatcttactg aaggcacagc ctatacaaac gctgttggat    3660
ttatgcctaa cctatcagct tatccaaaat ctcacgtaa aactgccaaa agtaacattg     3720
tcagtcaagt ttacttaaac ggagacaaaa ctaaacctgt aacactaacc attacactaa    3780
acggtacaca ggaaacagga gacacaactc caagtgcata ctctatgtca ttttcatggg    3840
actggtctgg ccacaactac attaatgaaa tatttgccac atcctcttac actttttcat    3900
acattgccca agaataaaag aagcggccgc tcgagtctag agggcccgtt taaacccgct    3960
gatcagcctc gactgtgcct tctagttgcc agccatctgt tgtttgcccc tcccccgtgc    4020
cttccttgac cctggaaggt gccactccca ctgtcctttc ctaataaaat gaggaaattg    4080
catcgcattg tctgagtagg tgtcattcta ttctgggggg tggggtgggg caggacagca    4140
agggggagga ttgggaagac aatagcaggc atgctgggga tgcggtgggc tctatggctt    4200
ctgaggcgga agaaccagc tggggctcta ggggtatcc ccacgcgccc tgtagcggcg      4260
cattaagcgc ggcgggtgtg gtggttacgc gcagcgtgac cgctacactt gccagcgccc    4320
tagcgcccgc tcctttcgct ttcttccctt cctttctcgc cacgttcgcc ggctttcccc    4380
gtcaagctct aaatcgggc atcccttag ggttccgatt tagtgcttta cggcacctcg      4440
accccaaaaa acttgattag ggtgatggtt cacgtagtgg gccatcgccc tgatagacgg    4500
tttttcgccc tttgacgttg gagtccacgt tctttaatag tggactcttg ttccaaactg    4560
gaacaacact caaccctatc tcggtctatt cttttgattt ataagggatt ttgggg attt   4620 cggcctattg gttaaaaaat gagctgattt aacaaaaatt taacgcgaat taattctgtg    4680
gaatgtgtgt cagttagggt gtggaaagtc cccaggctcc ccaggcaggc agaagtatgc    4740
aaagcatgca tctcaattag tcagcaacca ggtgtggaaa gtccccaggc tccccagcag    4800
gcagaagtat gcaaagcatg catctcaatt agtcagcaac catagtcccg cccctaactc    4860
cgcccatccc gcccctaact ccgcccagtt ccgcccattc tccgcccat ggctgactaa     4920 ttttttttat ttatgcagag gccgaggccg cctctgcctc tgagctattc cagaagtagt    4980
gaggaggctt ttttggaggc ctaggctttt gcaaaaagct cccgggagct tgtatatcca    5040
ttttcggatc tgatcagcac gtgttgacaa ttaatcatcg gcatagtata tcggcatagt    5100
ataatacgac aaggtgagga actaaaccat ggccaagttg accagtgccg ttccggtgct    5160
caccgcgcgc gacgtcgccg gagcggtcga gttctgacc gaccggctcg ggttctcccg     5220
ggacttcgtg gaggacgact tcgccggtgt ggtccgggac gacgtgaccc tgttcatcag    5280
cgcggtccag gaccaggtgg tgccggacaa caccctggcc tgggtgtggg tgcgcggcct    5340
ggacgagctg tacgccgagt ggtcggaggt cgtgtccacg aacttccggg acgcctccgg    5400
gccggccatg accgagatcg cgagcagcc gtggggggcgg gagttcgccc tgcgcgaccc    5460
ggccggcaac tgcgtgcact tcgtggccga ggagcaggac tgacacgtgc tacgagattt    5520
cgattccacc gccgccttct atgaaaggtt gggcttcgga atcgttttcc gggacgccgg    5580
ctggatgatc ctccagcgcg gggatctcat gctggagttc ttcgcccacc ccaacttgtt    5640
tattgcagct tataatggtt acaaataaag caatagcatc acaaatttca caaataaagc    5700
atttttttca ctgcattcta gttgtggttt gtccaaactc atcaatgtat cttatcatgt    5760
```

-continued

```
ctgtataccg tcgacctcta gctagagctt ggcgtaatca tggtcatagc tgtttcctgt    5820
gtgaaattgt tatccgctca caattccaca acatacga gccggaagca taaagtgtaa      5880
agcctggggt gcctaatgag tgagctaact cacattaatt gcgttgcgct cactgcccgc    5940
tttccagtcg ggaaacctgt cgtgccagct gcattaatga atcggccaac gcgcggggag    6000
aggcggtttg cgtattgggc gctcttccgc ttcctcgctc actgactcgc tgcgctcggt    6060
cgttcggctg cggcgagcgg tatcagctca ctcaaaggcg gtaatacggt tatccacaga    6120
atcaggggat aacgcaggaa agaacatgtg agcaaaaggc cagcaaaagg ccaggaaccg    6180
taaaaaggcc gcgttgctgg cgttttccca taggctccgc ccccctgacg agcatcacaa    6240
aaatcgacgc tcaagtcaga ggtggcgaaa cccgacagga ctataaagat accaggcgtt    6300
tccccctgga agctccctcg tgcgctctcc tgttccgacc ctgccgctta ccggatacct    6360
gtccgccttt ctcccttcgg gaagcgtggc gctttctcaa tgctcacgct gtaggtatct    6420
cagttcggtg taggtcgttc gctccaagct gggctgtgtg cacgaacccc ccgttcagcc    6480
cgaccgctgc gccttatccg gtaactatcg tcttgagtcc aacccggtaa gacacgactt    6540
atcgccactg gcagcagcca ctggtaacag gattagcaga gcgaggtatg taggcggtgc    6600
tacagagttc ttgaagtggt ggcctaacta cggctacact agaaggacag tatttggtat    6660
ctgcgctctg ctgaagccag ttaccttcgg aaaaagagtt ggtagctctt gatccggcaa    6720
acaaaccacc gctggtagcg tggtttttt tgtttgcaag cagcagatta cgcgcagaaa    6780
aaaaggatct caagaagatc ctttgatctt ttctacgggg tctgacgctc agtggaacga    6840
aaactcacgt taagggattt tggtcatgag attatcaaaa aggatcttca cctagatcct    6900
tttaaattaa aaatgaagtt ttaaatcaat ctaaagtata tatgagtaaa cttggtctga    6960
cagttaccaa tgcttaatca gtgaggcacc tatctcagcg atctgtctat ttcgttcatc    7020
catagttgcc tgactccccg tcgtgtagat aactacgata cgggagggct taccatctgg    7080
ccccagtgct gcaatgatac cgcgagaccc acgctcaccg gctccagatt tatcagcaat    7140
aaaccagcca gccggaaggg ccgagcgcag aagtggtcct gcaactttat ccgcctccat    7200
ccagtctatt aattgttgcc gggaagctag agtaagtagt tcgccagtta atagtttgcg    7260
caacgttgtt gccattgcta caggcatcgt ggtgtcacgc tcgtcgtttg gtatggcttc    7320
attcagctcc ggttcccaac gatcaaggcg agttacatga tcccccatgt tgtgcaaaaa    7380
agcggttagc tccttcggtc ctccgatcgt tgtcagaagt aagttggccg cagtgttatc    7440
actcatggtt atggcagcac tgcataattc tcttactgtc atgccatccg taagatgctt    7500
ttctgtgact ggtgagtact caaccaagtc attctgagaa tagtgtatgc ggcgaccgag    7560
ttgctcttgc ccggcgtcaa tacgggataa taccgcgcca catagcagaa ctttaaaagt    7620
gctcatcatt ggaaaacgtt cttcggggcg aaaactctca aggatcttac cgctgttgag    7680
atccagttcg atgtaaccca ctcgtgcacc caactgatct tcagcatctt ttactttcac    7740
cagcgtttct gggtgagcaa aaacaggaag gcaaaatgcc gcaaaaaagg gaataagggc    7800
gacacggaaa tgttgaatac tcatactctt cctttttcaa tattattgaa gcatttatca    7860
gggttattgt ctcatgagcg gatacatatt tgaatgtatt tagaaaaata aacaaatagg    7920
ggttccgcgc acatttcccc gaaaagtgcc acctgacgtc                          7960
```

<210> SEQ ID NO 45
<211> LENGTH: 30
<212> TYPE: DNA

```
<213> ORGANISM: Artificial Sequence
<220> FEATURE:
<223> OTHER INFORMATION: Description of Artificial Sequence: primer

<400> SEQUENCE: 45
atgggatcca agatgaagcg cgcaagaccg                                    30

<210> SEQ ID NO 46
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 46
cactatagcg gccgcattct cagtcatctt                                    30

<210> SEQ ID NO 47
<211> LENGTH: 7989
<212> TYPE: DNA
<213> ORGANISM: Artificial Sequence
<220> FEATURE:
<223> OTHER INFORMATION: Description of Artificial Sequence: plasmid

<400> SEQUENCE: 47
gacggatcgg gagatctccc gatccctat  ggtcgactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta caactccgc  cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgagctcgg atccactctc ttccgcatcg ctgtctgcga    960
gggccagctg ttggggtgag tactccctct gaaaagcggg catgacttct gcgctaagat   1020
tgtcagtttc caaaaacgag gaggatttga tattcacctg gcccgcggtg atgcctttga   1080
gggtggccgc atccatctgg tcagaaaaga caatcttttt gttgtcaagc ttggtggcaa   1140
acgacccgta gagggcgttg gacagcaact ggcgatgga  gcgcagggtt tggttttgt    1200 cgcgatcggc gcgctccttg gccgcgatgt ttagctgcac gtattcgcgc gcaacgcacc   1260
gccattcggg aaagacggtg gtgcgctcgt cgggcaccag gtgcacgcgc caaccgcggt   1320
tgtgcagggt gacaaggtca acgctggtgg ctacctctcc gcgtaggcgc tcgttggtcc   1380
agcagaggcg gccgcccttg cgcgagcaga atggcggtag ggggtctagc tgcgtctcgt   1440 ccgggggtc  tgcgtccacg gtaaagaccc cgggcagcag gcgcgcgtcg aagtagtcta   1500
```

```
tcttgcatcc ttgcaagtct agcgcctgct gccatgcgcg ggcggcaagc gcgcgctcgt    1560
atgggttgag tgggggaccc catggcatgg ggtgggtgag cgcggaggcg tacatgccgc    1620
aaatgtcgta aacgtagagg ggctctctga gtattccaag atatgtaggg tagcatcttc    1680
caccgcggat gctggcgcgc acgtaatcgt atagttcgtg cgagggagcg aggaggtcgg    1740
gaccgaggtt gctacgggcg ggctgctctg ctcggaagac tatctgcctg aagatggcat    1800
gtgagttgga tgatatggtt ggacgctgga agacgttgaa gctggcgtct gtgagaccta    1860
ccgcgtcacg cacgaaggag gcgtaggagt cgcgcagctt gttgaccagc tcggcggtga    1920
cctgcacgtc tagggcgcag tagtccaggg tttccttgat gatgtcatac ttatcctgtc    1980
cctttttttt ccacagctcg cggttgagga caaactcttc gcggtctttc cagtactctt    2040
ggatcggaaa cccgtcggcc tccgaacgag atccgtactc cgccgccgag ggacctgagc    2100
gagtccgcat cgaccggatc ggaaaacctc tcgagaaagg cgtctaacca gtcacagtcg    2160
caagatccaa gatgaagcgc gcaagaccgt ctgaagatac cttcaacccc gtgtatccat    2220
atgacacgga aaccggtcct ccaactgtgc cttttcttac tcctcccttt gtatccccca    2280
atgggtttca agagagtccc cctggggtac tctctttgcg cctatccgaa cctctagtta    2340
cctccaatgg catgcttgcg ctcaaaatgg gcaacggcct ctctctggac gaggccggca    2400
accttacctc ccaaaatgta accactgtga gcccacctct caaaaaaacc aagtcaaaca    2460
taaacctgga aatatctgca cccctcacag ttacctcaga agccctaact gtggctgccg    2520
ccgcacctct aatggtcgcg ggcaacacac tcaccatgca atcacaggcc ccgctaaccg    2580
tgcacgactc caaacttagc attgccaccc aaggaccect cacagtgtca gaaggaaagc    2640
tagccctgca aacatcaggc cccctcacca ccaccgatag cagtacccct actatcactg    2700
cctcaccccc tctaactact gccactggta gcttgggcat tgacttgaaa gagcccattt    2760
atacacaaaa tggaaaacta ggactaaagt acggggctcc tttgcatgta acagacgacc    2820
taaacacttt gaccgtagca actggtccag gtgtgactat taataatact tccttgcaaa    2880
ctaaagttac tggagccttg ggttttgatt cacaaggcaa tatgcaactt aatgtagcag    2940
gaggactaag gattgattct caaaacagac gccttatact tgatgttagt tatccgtttg    3000
atgctcaaaa ccaactaaat ctaagactag gacagggccc tcttttttata aactcagccc    3060 acaacttgga tattaactac aacaaaggcc tttacttgtt tacagcttca aacaattcca    3120
aaaagcttga ggttaaccta agcactgcca aggggttgat gtttgacgct acagccatag    3180
ccattaatgc aggagatggg cttgaatttg gttcacctaa tgcaccaaac acaaatcccc    3240
tcaaaacaaa aattggccat ggcctagaat ttgattcaaa caaggctatg gttcctaaac    3300
taggaactgg ccttagtttt gacagcacag gtgccattac agtaggaaac aaaaataatg    3360
ataagctaac tttgtggacc ggtccaaaac cagaagccaa ctgcataatt gaatacggga    3420
aacaaaaccc agatagcaaa ctaactttaa tccttgtaaa aaatggagga attgttaatg    3480
gatatgtaac gctaatggga gcctcagact acgttaacac cttatttaaa aacaaaaatg    3540
tctccattaa tgtagaacta ctttgatg ccactggtca tatattacca gactcatctt    3600
ctcttaaaac agatctagaa ctaaaataca agcaaaccgc tgactttagt gcaagaggtt    3660
ttatgccaag tactacagcg tatccatttg tccttcctaa tgcgggaaca cataatgaaa    3720
attatatttt tggtcaatgc tactacaaag caagcgatgg tgcccttttt ccgttggaag    3780
ttactgttat gcttaataaa cgcctgccag atagtcgcac atcctatgtt atgactttt    3840
```

-continued

```
tatggtccctt gaatgctggt ctagctccag aaactactca ggcaaccctc ataacctccc    3900
catttacctt ttcctatatt agagaagatg actgattttt aagaagcggc cgctcgagtc    3960
tagagggccc gtttaaaccc gctgatcagc ctcgactgtg ccttctagtt gccagccatc    4020
tgttgtttgc ccctccccg tgccttcctt gaccctggaa ggtgccactc ccactgtcct    4080
ttcctaataa aatgaggaaa ttgcatcgca ttgtctgagt aggtgtcatt ctattctggg    4140
gggtggggtg gggcaggaca gcaaggggga ggattgggaa gacaatagca ggcatgctgg    4200
ggatgcggtg ggctctatgg cttctgaggc ggaaagaacc snccntagct ggggctctag    4260
ggggtatccc cacgcgccct gtagcggcgc attaagcgcg gcgggtgtgg tggttacgcg    4320
cagcgtgacc gctacacttg ccagcgccct agcgcccgct cctttcgctt tcttcccttc    4380
ctttctcgcc acgttcgccg gctttccccg tcaagctcta atcgggcca tccctttagg    4440 gttccgattt agtgctttac ggcacctcga ccccaaaaaa cttgattagg gtgatggttc    4500
acgtagtggg ccatcgccct gatagacggt ttttcgccct tgacgttgg agtccacgtt    4560 ctttaatagt ggactcttgt tccaaactgg aacaacactc aaccctatct cggtctattc    4620
ttttgattta tagggatttt tggggattc ggcctattgg ttaaaaaatg agctgattta    4680
acaaaaattt aacgcgaatt aattctgtgg aatgtgtgtc agttagggtg tggaaagtcc    4740
ccaggctccc caggcaggca gaagtatgca aagcatgcat ctcaattagt cagcaaccag    4800
gtgtggaaag tccccaggct ccccagcagg cagaagtatg caaagcatgc atctcaatta    4860
gtcagcaacc atagtcccgc ccctaactcc gcccatcccg cccctaactc cgcccagttc    4920
cgcccattct ccgccccatg gctgactaat ttttttttatt tatgcagagg ccgaggccgc    4980
ctctgcctct gagctattcc agaagtagtg aggaggcttt tttggaggcc taggcttttg    5040
caaaaagctc ccgggagctt gtatatccat tttcggatct gatcagcacg tgttgacaat    5100
taatcatcgg catagtatat cggcatagta taatacgaca aggtgaggaa ctaaaccatg    5160
gccaagttga ccagtgccgt tccggtgctc accgcgcgcg acgtcgccgg agcggtcgag    5220
ttctggaccg accggctcgg gttctcccgg gacttcgtgg aggacgactt cgccggtgtg    5280
gtccgggacg acgtgaccct gttcatcagc gcggtccagg accaggtggt gccggacaac    5340
accctggcct gggtgtgggt gcgcggcctg gacgagctgt acgccgagtg gtcggaggtc    5400
gtgtccacga acttccggga cgcctccggg ccggccatga ccgagatcgg cgagcagccg    5460
tgggggcggg agttcgccct gcgcgacccg gccggcaact gcgtgcactt cgtggccgag    5520
gagcaggact gacacgtgct acgagatttc gattccaccg ccgccttcta tgaaaggttg    5580
ggcttcggaa tcgttttccg gacgccggc tggatgatcc tccagcgcgg ggatctcatg    5640
ctggagttct tcgcccaccc caacttgttt attgcagctt ataatggtta caaataaagc    5700
aatagcatca caaatttcac aaataaagca tttttttcac tgcattctag ttgtggtttg    5760
tccaaactca tcaatgtatc ttatcatgtc tgtataccgt cgacctctag ctagagcttg    5820
gcgtaatcat ggtcatagct gtttcctgtg tgaaattgtt atccgctcac aattccacac    5880
aacatacgag ccggaagcat aaagtgtaaa gcctggggtg cctaatgagt gagctaactc    5940
acattaattg cgttgcgctc actgcccgct ttccagtcgg gaaacctgtc gtgccagctg    6000
cattaatgaa tcggccaacg cgcggggaga ggcggtttgc gtattgggcg ctcttccgct    6060
tcctcgctca ctgactcgct gcgctcggtc gttcggctgc ggcgagcggt atcagctcac    6120
tcaaaggcgg taatacggtt atccacagaa tcaggggata acgcaggaaa gaacatgtga    6180
gcaaaaggcc agcaaaaggc caggaaccgt aaaaaggccg cgttgctggc gtttttccat    6240
```

-continued

```
aggctccgcc ccccctgacga gcatcacaaa aatcgacgct caagtcagag gtggcgaaac    6300
ccgacaggac tataaagata ccaggcgttt ccccctggaa gctccctcgt gcgctctcct    6360
gttccgaccc tgccgcttac cggatacctg tccgcctttc tcccttcggg aagcgtggcg    6420
ctttctcaat gctcacgctg taggtatctc agttcggtgt aggtcgttcg ctccaagctg    6480
ggctgtgtgc acgaaccccc cgttcagccc gaccgctgcg ccttatccgg taactatcgt    6540
cttgagtcca acccggtaag acacgactta tcgccactgg cagcagccac tggtaacagg    6600
attagcagag cgaggtatgt aggcggtgct acagagttct tgaagtggtg cctaactac     6660 ggctacacta aaggacagt atttggtatc tgcgctctgc tgaagccagt taccttcgga    6720
aaaagagttg gtagctcttg atccggcaaa caaaccaccg ctggtagcgg tggtttttt    6780 gtttgcaagc agcagattac gcgcagaaaa aaggatctc aagaagatcc tttgatcttt    6840 tctacgggt ctgacgctca gtggaacgaa aactcacgtt aagggatttt ggtcatgaga    6900
ttatcaaaaa ggatcttcac ctagatcctt ttaaattaaa aatgaagttt taaatcaatc    6960
taaagtatat atgagtaaac ttggtctgac agttaccaat gcttaatcag tgaggcacct    7020
atctcagcga tctgtctatt tcgttcatcc atagttgcct gactccccgt cgtgtagata    7080
actacgatac gggagggctt accatctggc cccagtgctg caatgatacc gcgagaccca    7140
cgctcaccgg ctccagattt atcagcaata aaccagccag ccggaagggc cgagcgcaga    7200
agtggtcctg caactttatc cgcctccatc cagtctatta attgttgccg ggaagctaga    7260
gtaagtagtt cgccagttaa tagtttgcgc aacgttgttg ccattgctac aggcatcgtg    7320
gtgtcacgct cgtcgtttgg tatggcttca ttcagctccg gttcccaacg atcaaggcga    7380
gttacatgat cccccatgtt gtgcaaaaaa gcggttagct ccttcggtcc tccgatcgtt    7440
gtcagaagta agttggccgc agtgttatca ctcatggtta tggcagcact gcataattct    7500
cttactgtca tgccatccgt aagatgcttt tctgtgactg gtgagtactc aaccaagtca    7560
ttctgagaat agtgtatgcg gcgaccgagt tgctcttgcc cggcgtcaat acgggataat    7620
accgcgccac atagcagaac tttaaaagtg ctcatcattg gaaaacgttc ttcggggcga    7680
aaactctcaa ggatcttacc gctgttgaga tccagttcga tgtaacccac tcgtgcaccc    7740
aactgatctt cagcatcttt tactttcacc agcgtttctg ggtgagcaaa aacaggaagg    7800
caaaatgccg caaaaaaggg aataagggcg acacggaaat gttgaatact catactcttc    7860 cttttcaat attattgaag catttatcag ggttattgtc tcatgagcgg atacatattt    7920
gaatgtattt agaaaaataa acaaataggg gttccgcgca catttccccg aaaagtgcca    7980
cctgacgtc                                                           7989
```

<210> SEQ ID NO 48
<211> LENGTH: 7607
<212> TYPE: DNA
<213> ORGANISM: Artificial Sequence
<220> FEATURE:
<223> OTHER INFORMATION: Description of Artificial Sequence: plasmid

<400> SEQUENCE: 48

```
tctagaagat ccgctgtaca ggatgttcta gctactttat tagatccgct gtacaggatg     60
ttctagctac tttattagat ccgctgtaca ggatgttcta gctactttat tagatccgct    120
gtacaggatg ttctagctac tttattagat ccgtgtacag gatgttctag ctactttatt    180
agatcgatct cctggccgtt cggggtcaaa accaggtttt ggctataaaa ggggtgggg    240 gcgcgttcgt cctcactctc ttccgcatcg ctgtctgcga gggccaggat cgatcctgag    300
```

```
aacttcaggg tgagtttggg gacccttgat tgttctttct ttttcgctat tgtaaaattc    360
atgttatatg gaggggcaa agttttcagg gtgttgttta gaatgggaag atgtcccttg    420
tatcaccatg gaccctcatg ataattttgt ttctttcact ttctactctg ttgacaacca    480
ttgtctcctc ttatttcctt ttcattttct gtaacttttt cgttaaactt tagcttgcat    540
ttgtaacgaa tttttaaatt cactttgtt tatttgtcag attgtaagta ctttctctaa    600 tcacttttt ttcaaggcaa tcagggtata ttatattgta cttcagcaca gttttagaga    660
acaattgtta taattaaatg ataaggtaga atatttctgc atataaattc tggctggcgt    720
ggaaatattc ttattggtag aaacaactac atcctggtca tcatcctgcc tttctcttta    780
tggttacaat gatatacact gtttgagatg aggataaaat actctgagtc caaaccgggc    840
ccctctgcta accatgttca tgccttcttc ttttcctac agctcctggg caacgtgctg    900
gttattgtgc tgtctcatca ttttggcaaa gaattagatc taagcttctg cagctcgagg    960
actcggtcga ctgaaaatga gacatattat ctgccacgga ggtgttatta ccgaagaaat   1020
ggccgccagt cttttggacc agctgatcga agaggtactg gctgataatc ttccacctcc   1080
tagccatttt gaaccaccta ccctttcacga actgtatgat ttagacgtga cggccccga   1140 agatcccaac gaggaggcgg tttcgcagat ttttcccgac tctgtaatgt tggcggtgca   1200
ggaagggatt gacttactca cttttccgcc ggcgcccggt tctccggagc cgcctcacct   1260
ttcccggcag cccgagcagc cggagcagag agccttgggt ccggtttcta tgccaaacct   1320 tgtaccgag gtgatcgatc ttacctgcca cgaggctggc tttccaccca gtgacgacga   1380
ggatgaagag ggtgaggagt ttgtgttaga ttatgtggag caccccgggc acggttgcag   1440
gtcttgtcat tatcaccgga ggaatacggg ggacccagat attatgtgtt cgcttttgcta  1500 tatgaggacc tgtggcatgt ttgtctacag taagtgaaaa ttatgggcag tgggtgatag   1560
agtggtgggt ttgtgtggt aattttttt ttaatttta cagttttgtg gtttaaagaa     1620
ttttgtattg tgatttttt aaaaggtcct gtgtctgaac ctgagcctga gcccgagcca   1680
gaaccggagc ctgcaagacc tacccgccgt cctaaaatgg cgcctgctat cctgagacgc   1740
ccgacatcac ctgtgtctag agaatgcaat agtagtacgg atagctgtga ctccggtcct   1800
tctaacacac ctcctgagat acaccgggtg gtcccgctgt gccccattaa accagttgcc   1860
gtgagagttg gtgggcgtcg ccaggctgtg gaatgtatcg aggacttgct taacgagcct   1920
gggcaacctt tggacttgag ctgtaaacgc cccaggccat aaggtgtaaa cctgtgattg   1980
cgtgtgtggt taacgccttt gttgtgctgaa tgagttgatg taagtttaat aaagggtgag   2040
ataatgttta acttgcatgg cgtgttaaat ggggcgggc ttaaagggta tataatgcgc    2100
cgtgggctaa tcttggttac atctgacctc atggaggctt gggagtgttt ggaagatttt   2160
tctgctgtgc gtaacttgct ggaacagagc tctaacagta cctcttggtt ttggaggttt    2220
ctgtggggct catcccaggc aaagttagtc tgcagaatta aggaggatta caagtgggaa   2280
tttgaagagc ttttgaaatc ctgtggtgag ctgtttgatt ctttgaatct gggtcaccag   2340
gcgcttttcc aagagaaggt catcaagact ttggattttt ccacaccggg gcgcgctgcg   2400
gctgctgttg ctttttttgag ttttataaag gataaatgga gcgaagaaac ccatctgagc   2460 gggggtacc tgctggattt tctggccatg catctgtgga gagcggttgt gagacacaag   2520
aatcgcctgc tactgttgtc ttccgtccgc ccggcgataa taccgacgga ggagcagcag   2580
cagcagcagg aggaagccag gcggcggcgg caggagcaga gcccatggaa cccgagagcc   2640
```

```
ggcctggacc ctcgggaatg aatgttgtac aggtggctga actgtatcca gaactgagac   2700
gcattttgac aattacagag gatgggcagg ggctaaaggg ggtaaagagg gagcggggggg   2760 cttgtgaggc tacagaggag gctaggaatc tagcttttag cttaatgacc agacaccgtc   2820
ctgagtgtat tactttcaa cagatcaagg ataattgcgc taatgagctt gatctgctgg    2880
cgcagaagta ttccatagag cagctgacca cttactggct gcagccaggg gatgattttg   2940
aggaggctat tagggtatat gcaaaggtgg cacttaggcc agattgcaag tacaagatca   3000
gcaaacttgt aaatatcagg aattgttgct acatttctgg gaacggggcc gaggtggaga   3060
tagatacgga ggataggggtg gcctttagat gtagcatgaa aaatatgtgg ccgggggtgc   3120
ttggcatgga cggggtggtt attatgaatg taaggtttac tggccccaat tttagcggta   3180
cggttttcct ggccaatacc aaccttatcc tacacggtgt aagcttctat gggtttaaca   3240
atacctgtgt ggaagcctgg accgatgtaa gggttcgggg ctgtgccttt tactgctgct   3300
ggaagggggt ggtgtgtcgc cccaaaagca gggcttcaat taagaaatgc ctctttgaaa   3360
ggtgtacctt gggtatcctg tctgagggta actccagggt gcgccacaat gtggcctccg   3420
actgtggttg cttcatgcta gtgaaaagcg tggctgtgat taagcataac atggtatgtg   3480
gcaactgcga ggacagggcc tctcagatgc tgacctgctc ggacggcaac tgtcacctgc   3540
tgaagaccat tcacgtagcc agccactctc gcaaggcctg gccagtgttt gagcataaca   3600
tactgacccg ctgttccttg catttgggta acaggagggg ggtgttccta ccttaccaat   3660
gcaatttgag tcacactaag atattgcttg agcccgagag catgtccaag gtgaacctga   3720
acggggtgtt tgacatgacc atgaagatct ggaaggtgct gaggtacgat gagacccgca   3780
ccaggtgcag accctgcgag tgtggcggta acatattag gaaccagcct gtgatgctgg   3840
atgtgaccga ggagctgagg cccgatcact tggtgctggc ctgcacccgc gctgagtttg   3900
gctctagcga tgaagataca gattgaggta ctgaaatgtg tgggcgtggc ttaagggtgg   3960
gaaagaatat ataaggtggg ggtcttatgt agttttgtat ctgttttgca gcagccgccg   4020
ccgccatgag caccaactcg tttgatggaa gcattgtgag ctcatatttg acaacgcgca   4080
tgcccccatg ggccggggtg cgtcagaatg tgatgggctc cagcattgat ggtcgccccg   4140
tcctgcccgc aaactctact accttgacct acgagaccgt gtctggaacg ccgttggaga   4200
ctgcagcctc cgccgccgct tcagccgctg cagccaccgc ccgcgggatt gtgactgact   4260
ttgctttcct gagcccgctt gcaagcagtg cagcttcccg ttcatccgcc cgcgatgaca   4320
agttgacggc tcttttggca caattggatt cttttgacccg ggaacttaat gtcgtttctc   4380
agcagctgtt ggatctgcgc cagcaggttt ctgccctgaa ggcttcctcc cctcccaatg   4440
cggtttaaaa cataaataaa aaaccagact ctgtttggat ttggatcaag caagtgtctt   4500
gctgtctcag ctgactgctt aagtcgcaag ccgaattgga tccaattcgg atcgatctta   4560
ttaaagcaga acttgtttat tgcagcttat aatggttaca aataaagcaa tagcatcaca   4620
aatttcacaa ataaagcatt ttttcactg cattctagtt gtggtttgtc caaactcatc    4680
aatgtatctt atcatgtctg gtcgactcta gactcttccg cttcctcgct cactgactcg   4740
ctgcgctcgg tcgttcggct gcggcgagcg gtatcagctc actcaaaggc ggtaatacgg   4800
ttatccacac aatcagggga taacgcagga agaacatgt gagcaaaagg ccagcaaaag    4860
gccaggaacc gtaaaaaggc cgcgttgctg gcgtttttcc ataggctccg ccccctgac    4920 gagcatcaca aaaatcgacg ctcaagtcag aggtggcgaa acccgacagg actataaaga   4980
taccaggcgt ttcccctgg aagctccctc gtgcgctctc ctgttccgac cctgccgctt   5040
```

-continued

| | |
|---|---|
| accggatacc tgtccgcctt tctcccttcg ggaagcgtgg cgctttctca tagctcacgc | 5100 |
| tgtaggtatc tcagttcggt gtaggtcgtt cgctccaagc tgggctgtgt gcacgaaccc | 5160 |
| cccgttcagc ccgaccgctg cgccttatcc ggtaactatc gtcttgagtc caacccggta | 5220 |
| agacacgact tatcgccact ggcagcagcc actggtaaca ggattagcag agcgaggtat | 5280 |
| gtaggcggtg ctacagagtt cttgaagtgg tggcctaact acggctacac tagaaggaca | 5340 |
| gtatttggta tctgcgctct gctgaagcca gttaccttcg aaaaagagt tggtagctct | 5400 |
| tgatccggca aacaaaccac cgctggtagc ggtggttttt tgtttgcaa gcagcagatt | 5460 |
| acgcgcagaa aaaaggatc tcaagaagat cctttgatct tttctacggg gtctgacgct | 5520 |
| cagtggaacg aaaactcacg ttaagggatt ttggtcatga gattatcaaa aaggatcttc | 5580 |
| acctagatcc ttttaaatta aaaatgaagt tttaaatcaa tctaaagtat atatgagtaa | 5640 |
| acttggtctg acagttacca atgcttaatc agtgaggcac ctatctcagc gatctgtcta | 5700 |
| tttcgttcat ccatagttgc ctgactcccc gtcgtgtaga taactacgat acgggagggc | 5760 |
| ttaccatctg gccccagtgc tgcaatgata ccgcgagacc cacgctcacc ggctccagat | 5820 |
| ttatcagcaa taaaccagcc agccggaagg gccgagcgca gaagtggtcc tgcaacttta | 5880 |
| tccgcctcca tccagtctat taattgttgc cgggaagcta gagtaagtag ttcgccagtt | 5940 |
| aatagtttgc gcaacgttgt tgccattgct acaggcatcg tggtgtcacg ctcgtcgttt | 6000 |
| ggtatggctt cattcagctc cggttcccaa cgatcaaggc gagttacatg atcccccatg | 6060 |
| ttgtgcaaaa aagcggttag ctccttcggt cctccgatcg ttgtcagaag taagttggcc | 6120 |
| gcagtgttat cactcatggt tatggcagca ctgcataatt ctcttactgt catgccatcc | 6180 |
| gtaagatgct tttctgtgac tggtgagtac tcaaccaagt cattctgaga atagtgtatg | 6240 |
| cggcgaccga gttgctcttg cccggcgtca atacgggata ataccgcgcc acatagcaga | 6300 |
| actttaaaag tgctcatcat tggaaaacgt tcttcgggc gaaaactctc aaggatctta | 6360 |
| ccgctgttga gatccagttc gatgtaaccc actcgtgcac ccaactgatc ttcagcatct | 6420 |
| tttactttca ccagcgtttc tgggtgagca aaaacaggaa ggcaaaatgc cgcaaaaaag | 6480 |
| ggaataaggg cgacacggaa atgttgaata ctcatactct tccttttca atattattga | 6540 |
| agcatttatc agggttattg tctcatgagc ggatacatat ttgaatgtat ttagaaaaat | 6600 |
| aaacaaatag gggttccgcg cacatttccc cgaaaagtgc cacctgacgt ctaagaaacc | 6660 |
| attattatca tgacattaac ctataaaaat aggcgtatca cgaggcccct ttcgtctcgc | 6720 |
| gcgtttcggt gatgacggtg aaaacctctg acacatgcag ctcccggaga cggtcacagc | 6780 |
| ttgtctgtaa gcggatgccg ggagcagaca agcccgtcag ggcgcgtcag cgggtgttgg | 6840 |
| cgggtgtcgg ggctggctta actatgcggc atcagagcag attgtactga gagtgcacca | 6900 |
| tatgcggtgt gaaataccgc acagatgcgt aaggagaaaa taccgcatca ggaaattgta | 6960 |
| agcgttaata ttttgttaaa attcgcgtta aattttgtt aaatcagctc attttttaac | 7020 |
| caataggccg aaatcggcaa aatcccttat aaatcaaaag aatagaccga gatagggttg | 7080 |
| agtgttgttc cagtttggaa caagagtcca ctattaaaga acgtggactc caacgtcaaa | 7140 |
| gggcgaaaaa ccgtctatca gggcgatggc ccactacgtg aaccatcacc ctaatcaagt | 7200 |
| tttttgggt cgaggtgccg taaagcacta atcggaacc ctaaagggag cccccgattt | 7260 |
| agagcttgac ggggaaagcc ggcgaacgtg cgagaaagg aagggaagaa agcgaaagga | 7320 |
| gcgggcgcta gggcgctggc aagtgtagcg gtcacgctgc gcgtaaccac cacacccgcc | 7380 |

```
gcgcttaatg cgccgctaca gggcgcgtcc cattcgccat tcaggctgcg caactgttgg      7440
gaagggcgat cggtgcgggc ctcttcgcta ttacgccagc tggcgaaagg gggatgtgct      7500
gcaaggcgat taagttgggt aacgccaggg ttttcccagt cacgacgttg taaaacgacg      7560
gccagtgaat tgtaatacga ctcactatag ggcgaattaa ttcgggg                    7607
```

<210> SEQ ID NO 49
<211> LENGTH: 11600
<212> TYPE: DNA
<213> ORGANISM: Artificial Sequence
<220> FEATURE:
<223> OTHER INFORMATION: Description of Artificial Sequence: plasmid

<400> SEQUENCE: 49

```
gaattccgca ttgcagagat attgtattta agtgcctagc tcgatacaat aaacgccatt       60
tgaccattca ccacattggt gtgcacctcc aagcttgggc agaaatggtt gaactcccga      120
gagtgtccta cacctagggg agaagcagcc aaggggttgt ttcccaccaa ggacgacccg      180
tctgcgcaca aacggatgag cccatcagac aaagacatat tcattctctg ctgcaaactt      240
ggcatagctc tgctttgcct ggggctattg ggggaagttg cggttcgtgc tcgcagggct      300
ctcacccttg actcttttaa tagctcttct gtgcaagatt acaatctaaa caattcggag      360
aactcgacct tcctcctgag gcaaggacca cagccaactt cctcttacaa gccgcatcga      420
ttttgtcctt cagaaataga aataagaatg cttgctaaaa attatatttt taccaataag      480
accaatccaa taggtagatt attagttact atgttaagaa atgaatcatt atcttttagt      540 actatttta ctcaaattca gaagttagaa atgggaatag aaaatagaaa gagacgctca      600
acctcaattg aagaacaggt gcaaggacta ttgaccacag gcctagaagt aaaaaaggga      660
aaaaagagtg tttttgtcaa aataggagac aggtggtggc aaccagggac ttataggga      720 ccttacatct acagaccaac agatgccccc ttaccatata caggaagata tgacttaaat      780
tgggataggt gggttacagt caatggctat aaagtgttat atagatccct cccttttcgt      840
gaaagactcg ccagagctag acctccttgg tgtatgttgt ctcaagaaga aaaagacgac      900
atgaaacaac aggtacatga ttatatttat ctaggaacag gaatgcactt ttggggaaag      960
attttccata ccaaggaggg gacagtggct ggactaatag aacattattc tgcaaaaact     1020
catggcatga gttattatga atagccttta ttggcccaac cttgcggttc ccagggctta     1080
agtaagtttt tggttacaaa ctgttcttaa aacgaggatg tgagacaagt ggtttcctga     1140
cttggtttgg tatcaaaggt tctgatctga gctctgagtg ttctattttc ctatgttctt     1200
ttggaattta tccaaatctt atgtaaatgc ttatgtaaac caagatataa aagagtgctg     1260 atttttgag taaacttgca acagtcctaa cattcacctc ttgtgtgttt gtgtctgttc     1320
gccatcccgt ctccgctcgt cacttatcct tcactttcca gagggtcccc ccgcagaccc     1380
cggcgaccct caggtcggcc gactgcggca gctggcgccc gaacagggac cctcggataa     1440 gtgaccttg tctctatttc tactatttgg tgtttgtctt gtattgtctc tttcttgtct     1500
ggctatcatc acaagagcgg aacggactca ccatagggac caagctagcg cttctcgtcg     1560
cgtccaagac cctcaaagat ttttggcact tcgttgagcg aggcgatatc aggtatgaca     1620
gcgccctgcc gcaaggccag ctgcttgtcc gctcggctgc ggttggcacg gcaggatagg     1680
ggtatcttgc agttttggaa aaagatgtga taggtggcaa gcacctctgg cacggcaaat     1740
acggggtaga agttgaggcg cgggttgggc tcgcatgtgc cgttttcttg gcgtttgggg     1800
ggtacgcgcg gtgagaatag gtggcgttcg taggcaaggc tgacatccgc tatggcgagg     1860
```

```
ggcacatcgc tgcgctcttg caacgcgtcg cagataatgg cgcactggcg ctgcagatgc    1920
ttcaacagca cgtcgtctcc cacatctagg tagtcgccat gcctttcgtc ccccgcccg     1980 acttgttcct cgtttgcctc tgcgttgtcc tggtcttgct ttttatcctc tgttggtact    2040
gagcggtcct cgtcgtcttc gcttacaaaa cctgggtcct gctcgataat cacttcctcc    2100
tcctcaagcg ggggtgcctc gacggggaag gtggtaggcg cgttggcggc atcggtggag    2160
gcggtggtgg cgaactcaga gggggcggtt aggctgtcct tcttctcgac tgactccatg    2220
atcttttcct gcctatagga gaaggaaatg gccagtcggg aagaggagca gcgcgaaacc    2280
acccccgagc gcggacgcgg tgcggcgcga cgtcccccaa ccatggagga cgtgtcgtcc    2340
ccgtccccgt cgccgccgcc tcccggggcg cccccaaaaa agcggatgag gcggcgtatc    2400
gagtccgagg acgaggaaga ctcatcacaa gacgcgctgg tgccgcgcac acccagcccg    2460
cggccatcga cctcggcggc ggatttggcc attgcgccca agaagaaaaa gaagcgccct    2520
tctcccaagc ccgagcgccc gccatcacca gaggtaatcg tggacagcga ggaagaaaga    2580
gaagatgtgg cgctacaaat ggtgggtttc agcaacccac cggtgctaat caagcatggc    2640
aaaggaggta agcgcacagt gcggcggctg aatgaagacg acccagtggc gcgtggtatg    2700
cggacgcaag aggaagagga agagcccagc gaagcggaaa gtgaaattac ggtgatgaac    2760
ccgctgagtg tgccgatcgt gtctgcgtgg gagaagggca tggaggctgc gcgcgcgctg    2820
atggacaagt accacgtgga taacgatcta aaggcgaact tcaaactact gcctgaccaa    2880
gtggaagctc tggcggccgt atgcaagacc tggctgaacg aggagcaccg cgggttgcag    2940
ctgaccttca ccagcaacaa gacctttgtg acgatgatgg ggcgattcct gcaggcgtac    3000
ctgcagtcgt tgcagaggt gacctacaag catcacgagc ccacgggctg cgcgttgtgg    3060
ctgcaccgct gcgctgagat cgaaggcgag cttaagtgtc tacacggaag cattatgata    3120
aataaggagc acgtgattga aatggatgtg acgagcgaaa acgggcagcg cgcgctgaag    3180
gagcagtcta gcaaggccaa gatcgtgaag aaccggtggg gccgaaatgt ggtgcagatc    3240
tccaacaccg acgcaaggtg ctgcgtgcac gacgcggcct gtccggccaa tcagttttcc    3300
ggcaagtctt gcggcatgtt cttctctgaa ggcgcaaagg ctcaggtggc ttttaagcag    3360
atcaaggctt ttatgcaggc gctgtatcct aacgcccaga ccgggcacgg tcaccttttg    3420
atgccactac ggtgcgagtg caactcaaag cctgggcacg cgcccttttt gggaaggcag    3480
ctaccaaagt tgactccgtt cgccctgagc aacgcggagg acctggacgc ggatctgatc    3540
tccgacaaga gcgtgctggc cagcgtgcac caccccggcgc tgatagtgtt ccagtgctgc    3600
aaccctgtgt atcgcaactc gcgcgcgcag ggcggaggcc ccaactgcga cttcaagata    3660
tcggcgcccg acctgctaaa cgcgttggtg atggtgcgca gcctgtggag tgaaaacttc    3720
accgagctgc cgcggatggt tgtgcctgag tttaagtgga gcactaaaca ccagtatcgc    3780
aacgtgtccc tgccagtggc gcatagcgat gcgcggcaga ccccctttga tttttaaacg    3840
gcgcagacgg caagggtggg ggtaaataat cacccgagag tgtacaaata aaagcatttg    3900
cctttattga aagtgtctct agtacattat ttttacatgt ttttcaagtg acaaaaagaa    3960
gtggcgctcc taatctgcgc actgtggctg cggaagtagg gcgagtggcg ctccaggaag    4020
ctgtagagct gttcctggtt gcgacgcagg gtgggctgta cctggggact gttgagcatg    4080
gagttgggta ccccgtaat aaggttcatg gtgggttgt gatccatggg agtttggggc     4140
cagttggcaa aggcgtggag aaacatgcag cagaatagtc cacaggcggc cgagttgggc    4200
```

-continued

```
ccctgtacgc tttgggtgga cttttccagc gttatacagc ggtcggggga agaagcaatg    4260
gcgctacggc gcaggagtga ctcgtactca aactggtaaa cctgcttgag tcgctggtca    4320
gaaaagccaa agggctcaaa gaggtagcat gttttttgagt gcgggttcca ggcaaaggcc    4380
atccagtgta cgcccccagt ctcgcgaccg gccgtattga ctatgcgca ggcgagcttg     4440 tgtggagaaa caaagcctgg aaagcgcttg tcataggtgc ccaaaaaata tggcccacaa    4500
ccaagatctt tgacaatggc tttcagttcc tgctcactgg agcccatggc ggcagctgtt    4560
gttgatgttg cttgcttctt tatgttgtgg cgttgccggc cgagaagggc gtgcgcaggt    4620
acacggtttc gatgacgccg cggtgcggcc ggtgcacacg gaccacgtca aagacttcaa    4680
acaaaacata aagaagggtg ggctcgtcca tgggatccat atatagggcc cgggttataa    4740
ttacctcagg tcgacctcga gggatctttg tgaaggaacc ttacttctgt ggtgtgacat    4800
aattggacaa actacctaca gagatttaaa gctctaaggt aaatataaaa tttttaagtg    4860
tataatgtgt taaactactg attctaattg tttgtgtatt ttagattcca acctatggaa    4920
ctgatgaatg ggagcagtgg tggaatgcct ttaatgagga aaacctgttt tgctcagaag    4980
aaatgccatc tagtgatgat gaggctactg ctgactctca acattctact cctccaaaaa    5040
agaagagaaa ggtagaagac cccaaggact ttccttcaga attgctaagt tttttgagtc    5100
atgctgtgtt tagtaataga actcttgctt gctttgctat ttacaccaca aaggaaaaag    5160
ctgcactgct atacaagaaa attatggaaa atattctgt aacctttata gtaggcata     5220 acagttataa tcataacata ctgttttttc ttactccaca caggcataga gtgtctgcta    5280
ttaataacta tgctcaaaaa ttgtgtacct ttagctttttt aatttgtaaa ggggttaata   5340
aggaatattt gatgtatagt gccttgacta gagatcataa tcagccatac cacatttgta    5400
gaggttttac ttgctttaaa aaacctccca cacctcccc tgaacctgaa acataaaatg     5460
aatgcaattg ttgttgttaa cttgtttatt gcagcttata atggttacaa ataaagcaat    5520
agcatcacaa atttcacaaa taaagcattt ttttcactgc attctagttg tggtttgtcc    5580
aaactcatca atgtatctta tcatgtctgg atccggctgt ggaatgtgtg tcagttaggg    5640
tgtggaaagt ccccaggctc cccagcaggc agaagtatgc aaagcatgca tctcaattag    5700
tcagcaacca ggtgtggaaa gtccccaggc tccccagcag gcagaagtat gcaaagcatg    5760
catctcaatt agtcagcaac catagtcccg cccctaactc cgcccatccc gcccctaact    5820
ccgcccagtt ccgcccattc tccgcccccat ggctgactaa ttttttttat ttatgcagag    5880
gccgaggccg cctcggcctc tgagctattc cagaagtagt gaggaggctt ttttggaggc    5940
ctaggctttt gcaaaaagct tcacgctgcc gcaagcactc agggcgcaag ggctgctaaa    6000
ggaagcggaa cacgtagaaa gccagtccgc agaaacggtg ctgaccccgg atgaatgtca    6060
gctactgggc tatctggaca agggaaaacg caagcgcaaa gagaaagcag gtagcttgca    6120
gtgggcttac atggcgatag ctagactggg cggttttatg gacagcaagc gaaccggaat    6180
tgccagctgg ggcgccctct ggtaaggttg ggaagccctg caaagtaaac tggatggctt    6240
tcttgccgcc aaggatctga tggcgcaggg gatcaagatc tgatcaagag acaggatgag    6300
gatcgtttcg catgattgaa caagatggat tgcacgcagg ttctccggcc gcttgggtgg    6360
agaggctatt cggctatgac tgggcacaac agacaatcgg ctgctctgat gccgccgtgt    6420
tccggctgtc agcgcagggg cgcccggttc ttttttgtcaa gaccgacctg tccggtgccc    6480
tgaatgaact gcaggacgag gcagcgcggc tatcgtggct ggccacgacg ggcgttcctt    6540
gcgcagctgt gctcgacgtt gtcactgaag cgggaaggga ctggctgcta ttgggcgaag    6600
```

```
tgccggggca ggatctcctg tcatctcacc ttgctcctgc cgagaaagta tccatcatgg    6660
ctgatgcaat gcggcggctg catacgcttg atccggctac ctgcccattc gaccaccaag    6720
cgaaacatcg catcgagcga gcacgtactc ggatggaagc cggtcttgtc gatcaggatg    6780
atctggacga agagcatcag gggctcgcgc cagccgaact gttcgccagg ctcaaggcgc    6840
gcatgcccga cggcgaggat ctcgtcgtga cccatggcga tgcctgcttg ccgaatatca    6900
tggtggaaaa tggccgcttt tctggattca tcgactgtgg ccggctgggt gtggcggacc    6960
gctatcagga catagcgttg gctacccgtg atattgctga agagcttggc ggcgaatggg    7020
ctgaccgctt cctcgtgctt tacggtatcg ccgctcccga ttcgcagcgc atcgccttct    7080
atcgccttct tgacgagttc ttctgagcgg gactctgggg ttcgaaatga ccgaccaagc    7140
gacgcccaac ctgccatcac gagatttcga ttccaccgcc gccttctatg aaaggttggg    7200
cttcggaatc gttttccggg acgccggctg gatgatcctc cagcgcgggg atctcatgct    7260
ggagttcttc gcccacccccg ggctcgatcc cctcgcgagt tggttcagct gctgcctgag    7320
gctggacgac ctcgcggagt tctaccggca gtgcaaatcc gtcggcatcc aggaaaccag    7380
cagcggctat ccgcgcatcc atgccccccga actgcaggag tggggaggca cgatggccgc    7440
tttggtcccg gatctttgtg aaggaacctt acttctgtgg tgtgacataa ttggacaaac    7500
tacctacaga gatttaaagc tctaaggtaa atataaaatt tttaagtgta taatgtgtta    7560
aactactgat tctaattgtt tgtgtatttt agattccaac ctatggaact gatgaatggg    7620
agcagtggtg gaatgccttt aatgaggaaa acctgttttg ctcagaagaa atgccatcta    7680
gtgatgatga ggctactgct gactctcaac attctactcc tccaaaaaag aagagaaagg    7740
tagaagaccc caaggacttt ccttcagaat tgctaagttt tttgagtcat gctgtgttta    7800
gtaatagaac tcttgcttgc tttgctattt acaccacaaa ggaaaaagct gcactgctat    7860
acaagaaaat tatggaaaaa tattctgtaa cctttataag taggcataac agttataatc    7920
ataacatact gttttttctt actccacaca ggcatagagt gtctgctatt aataactatg    7980
ctcaaaaatt gtgtaccttt agcttttttaa tttgtaaagg ggttaataag gaatatttga    8040
tgtatagtgc cttgactaga gatcataatc agccatacca catttgtaga ggttttactt    8100
gctttaaaaa acctcccaca cctcccccctg aacctgaaac ataaaatgaa tgcaattgtt    8160
gttgttaact tgtttattgc agcttataat ggttacaaat aaagcaatag catcacaaat    8220
ttcacaaata aagcattttt ttcactgcat tctagttgtg gtttgtccaa actcatcaat    8280
gtatcttatc atgtctggat ccccaggaag ctcctctgtg tcctcataaa ccctaacctc    8340
ctctacttga gaggacattc caatcatagg ctgcccatcc accctctgtg tcctcctgtt    8400
aattaggtca cttaacaaaa aggaaattgg gtaggggttt ttcacagacc gctttctaag    8460
ggtaatttta aaatatctgg gaagtcccctt ccactgctgt gttccagaag tgttggtaaa    8520
cagcccacaa atgtcaacag cagaaacata caagctgtca gctttgcaca agggcccaac    8580
accctgctca tcaagaagca ctgtggttgc tgtgttagta atgtgcaaaa caggaggcac    8640 atttttcccca cctgtgtagg ttccaaaata tctagtgttt tcatttttac ttggatcagg    8700
aacccagcac tccactggat aagcattatc cttatccaaa acagccttgt ggtcagtgtt    8760
catctgctga ctgtcaactg tagcattttt tggggttaca gtttgagcag atatttggt    8820 cctgtagttt gctaacacac cctgcagctc caaaggttcc ccaccaacag caaaaaaatg    8880
aaaatttgac ccttgaatgg gttttccagc accattttca tgagtttttt gtgtccctga    8940
```

```
atgcaagttt aacatagcag ttaccccaat aacctcagtt ttaacagtaa cagcttccca    9000
catcaaaata tttccacagg ttaagtcctc atttaaatta ggcaaaggaa ttcttgaaga    9060
cgaaagggcc tcgtgatacg cctattttta taggttaatg tcatgataat aatggtttct    9120
tagacgtcag gtggcacttt tcggggaaat gtgcgcggaa ccctatttg tttattttc     9180 taaatacatt caaatatgta tccgctcatg agacaataac cctgataaat gcttcaataa    9240
tattgaaaaa ggaagagtat gagtattcaa catttccgtg tcgcccttat ccctttttt    9300 gcggcatttt gccttcctgt ttttgctcac ccagaaacgc tggtgaaagt aaaagatgct    9360
gaagatcagt tgggtgcacg agtgggttac atcgaactgg atctcaacag cggtaagatc    9420
cttgagagtt ttcgccccga agaacgtttt ccaatgatga gcacttttaa agttctgcta    9480
tgtggcgcgg tattatcccg tgttgacgcc gggcaagagc aactcggtcg ccgcatacac    9540
tattctcaga atgacttggt tgagtactca ccagtcacag aaaagcatct tacggatggc    9600
atgacagtaa gagaattatg cagtgctgcc ataaccatga gtgataacac tgcggccaac    9660
ttacttctga caacgatcgg aggaccgaag gagctaaccg cttttttgca acatggggg     9720 gatcatgtaa ctcgccttga tcgttgggaa ccggagctga atgaagccat accaaacgac    9780
gagcgtgaca ccacgatgcc tgcagcaatg gcaacaacgt tgcgcaaact attaactggc    9840
gaactactta ctctagcttc ccggcaacaa ttaatagact ggatggaggc ggataaagtt    9900
gcaggaccac ttctgcgctc ggcccttccg gctggctggt ttattgctga taaatctgga    9960
gccggtgagc gtgggtctcg cggtatcatt gcagcactgg ggccagatgg taagccctcc    10020
cgtatcgtag ttatctacac gacggggagt caggcaacta tggatgaacg aaatagacag    10080
atcgctgaga taggtgcctc actgattaag cattggtaac tgtcagacca agtttactca    10140
tatatacttt agattgattt aaaacttcat ttttaattta aaaggatcta ggtgaagatc    10200
ctttttgata atctcatgac caaaatccct taacgtgagt tttcgttcca ctgagcgtca    10260
gaccccgtag aaaagatcaa aggatcttct tgagatcctt ttttttctgcg cgtaatctgc    10320 tgcttgcaaa caaaaaaacc accgctacca gcggtggttt gtttgccgga tcaagagcta    10380
ccaactcttt ttccgaaggt aactggcttc agcagagcgc agataccaaa tactgtcctt    10440
ctagtgtagc cgtagttagg ccaccacttc aagaactctg tagcaccgcc tacatacctc    10500
gctctgctaa tcctgttacc agtggctgct gccagtggcg ataagtcgtg tcttaccggg    10560
ttggactcaa gacgatagtt accggataag gcgcagcggt cgggctgaac ggggggttcg    10620
tgcacacagc ccagcttgga gcgaacgacc tacaccgaac tgagatacct acagcgtgag    10680
ctatgagaaa gcgccacgct tcccgaaggg agaaaggcgg acaggtatcc ggtaagcggc    10740
agggtcggaa caggagagcg cacgagggag cttccagggg gaaacgcctg gtatctttat    10800
agtcctgtcg ggtttcgcca cctctgactt gagcgtcgat ttttgtgatg ctcgtcaggg    10860
gggcggagcc tatggaaaaa cgccagcaac gcggcctttt tacggttcct ggccttttgc    10920
tggccttttg ctcacatgtt ctttcctgcg ttatcccctg attctgtgga taaccgtatt    10980
accgcctttg agtgagctga taccgctcgc cgcagccgaa cgaccgagcg cagcgagtca    11040
gtgagcgagg aagcggaaga gcgcctgatg cggtattttc tccttacgca tctgtgcggt    11100
atttcacacc gcatatggtg cactctcagt acaatctgct ctgatgccgc atagttaagc    11160
cagtatctgc tccctgcttg tgtgttggag gtcgctgagt agtgcgcgag caaaatttaa    11220
gctacaacaa ggcaaggctt gaccgacaat tgcatgaaga atctgcttag ggttaggcgt    11280
tttgcgctgc ttcgcgatgt acgggccaga tatacgcgta tctgagggga ctagggtgtg    11340
```

-continued

```
tttaggcgaa aagcgggget tcggttgtac gcggttagga gtccctcag gatatagtag    11400 tttcgctttt gcataggag ggggaaatgt agtcttatgc aatacacttg tagtcttgca    11460
acatggtaac gatgagttag caacatgcct tacaaggaga gaaaaagcac cgtgcatgcc    11520
gattggtgga agtaaggtgg tacgatcgtg ccttattagg aaggcaacag acgggtctga   11580
catggattgg acgaaccact                                               11600
```

<210> SEQ ID NO 50
<211> LENGTH: 8238
<212> TYPE: DNA
<213> ORGANISM: Artificial Sequence
<220> FEATURE:
<223> OTHER INFORMATION: Description of Artificial Sequence: plasmid

<400> SEQUENCE: 50

```
gcggccgcca tcatcaataa tataccttat tttggattga agccaatatg ataatgaggg     60
ggtggagttt gtgacgtggc gcggggcgtg ggaacggggc gggtgacgta gtagtgtggc    120
ggaagtgtga tgttgcaagt gtggcggaac acatgtaagc gacggatgtg gcaaaagtga    180 cgttttttggt gtgcgccggt gtacacagga agtgacaatt tcgcgcggt tttaggcgga    240 tgttgtagta aatttgggcg taaccgagta agatttggcc attttcgcgg gaaaactgaa    300
taagaggaag tgaaatctga ataattttgt gttactcata gcgcgtaata tttgtctagg    360
gccgcgggga ctttgaccgt ttacgtggag actcgcccag ggcgcgcccc gatgtacggg    420
ccagatatac gcgtatctga ggggactagg gtgtgtttag gcgaaaagcg gggcttcggt    480
tgtacgcggt taggagtccc ctcaggatat agtagtttcg cttttgcata gggagggggga   540 aatgtagtct tatgcaatac tcttgtagtc ttgcaacatg gtaacgatga gttagcaaca    600
tgccttacaa ggagagaaaa agcaccgtgc atgccgattg gtggaagtaa ggtggtacga    660
tcgtgcctta ttaggaaggc aacagacggg tctgacatgg attggacgaa ccactgaatt    720
ccgcattgca gagatattgt atttaagtgc ctagctcgat acaataaacg ccatttgacc    780
attcaccaca ttggtgtgca cctccggccc atatggccac tctcttccgc atcgctgtct    840
gcggggccca gctgttgggc tcgcggttga ggacaaactc ttcgcggtct ttccagtact    900
cttggatcgg aaaccgtcg gcctccgaac ggtactccgc cgccgaggga cctgagcgag    960
tccgcatcga ccggatcgga aaacctctcg agaaaggcgt gtaaccagtc acagtcgctc   1020
tagaactagt ggatcccccg ggctgcagga attcgatgat cttggtggcg tgaaactccc   1080
gcacctcttt ggcaagcgcc ttgtagaagc gcgtatggct tcgtacccct gccatcaaca   1140
cgcgtctgcg ttcgaccagg ctgcgcgttc tcgcggccat agcaaccgac gtacggcgtt   1200
gcgccctcgc cggcagcaag aagccacgga agtccgcctg gagcagaaaa tgcccacgct   1260
actgcgggtt tatatagacg gtcctcacgg gatgggaaa accaccacca cgcaactgct   1320
ggtggccctg ggttcgcgcg acgatatcgt ctacgtaccc gagccgatga cttactggca   1380
ggtgctgggg gcttccgaga caatcgcgaa catctacacc acacaacacc gcctcgacca   1440
gggtgagata tcggccggg acgcggcggt ggtaatgaca agcgcccaga taacaatggg   1500
catgccttat gccgtgaccg acgccgttct ggctcctcat gtcggggggg aggctgggag   1560
ttcacatgcc ccgccccgg ccctcaccct catcttcgac cgccatccca tcgccgccct   1620
cctgtgctac ccggccgcgc gataccttat gggcagcatg accccccagg ccgtgctggc   1680
gttcgtggcc ctcatcccgc cgaccttgcc cggcacaaac atcgtgttgg gggcccttcc   1740
```

```
ggaggacaga cacatcgacc gcctggccaa acgccagcgc cccggcgagc ggcttgacct    1800
ggctatgctg gccgcgattc gccgcgttta cgggctgctt gccaatacgg tgcggtatct    1860
gcagggcggc gggtcgtggt gggaggattg gggacagctt tcggggacgg ccgtgccgcc    1920
ccagggtgcc gagccccaga gcaacgcggg cccacgaccc catatcgggg acacgttatt    1980
taccctgttt cgggccccg agttgctggc ccccaacggc gacctgtata acgtgttttgc    2040
ctgggccttg gacgtcttgg ccaaacgcct ccgtcccatg cacgtcttta tcctggatta    2100
cgaccaatcg cccgccggct gccgggacgc cctgctgcaa cttacctccg ggatggtcca    2160
gacccacgtc accaccccag gctccatacc gacgatctgc gacctggcgc gcacgtttgc    2220
ccgggagatg ggggaggcta actgactcga gaagcttggg cccatcgatc aagcttatcg    2280
ataccgtcga aacttgttta ttgcagctta taatggttac aaataaagca atagcatcac    2340
aaatttcaca aataaagcat ttttttcact gcattctagt tgtggtttgt ccaaactcat    2400
caatgtatct tatcatgtct ggatccgacc tcggatctgg aaggtgctga ggtacgatga    2460
gacccgcacc aggtgcagac cctgcgagtg tggcggtaaa catattagga accagcctgt    2520
gatgctggat gtgaccgagg agctgaggcc cgatcacttg gtgctggcct gcacccgcgc    2580
tgagtttggc tctagcgatg aagatacaga ttgaggtact gaaatgtgtg ggcgtggctt    2640
aagggtggga aagaatatat aaggtggggg tcttatgtag ttttgtatct gttttgcagc    2700
agccgccgcc gccatgagca ccaactcgtt tgatggaagc attgtgagct catatttgac    2760
aacgcgcatg cccccatggg ccggggtgcg tcagaatgtg atgggctcca gcattgatgg    2820
tcgcccccgtc ctgcccgcaa actctactac cttgacctac gagaccgtgt ctggaacgcc    2880
gttggagact gcagcctccg ccgccgcttc agccgctgca gccaccgccc gcgggattgt    2940
gactgacttt gctttcctga gccgcttgc aagcagtgca gcttcccgtt catccgcccg    3000
cgatgacaag ttgacggctc ttttggcaca attggattct ttgacccggg aacttaatgt    3060
cgtttctcag cagctgttgg atctgcgcca gcaggtttct gccctgaagg cttcctcccc    3120
tcccaatgcg gtttaaaaca taaataaaaa accagactct gtttggattt ggatcaagca    3180
agtgtcttgc tgtctttatt tagggttttt gcgcgcgcgg taggcccggg accagcggtc    3240
tcggtcgttg agggtcctgt gtattttttc caggacgtgg taaaggtgac tctgatgtt    3300
cagatacatg ggcataagcc cgtctctggg gtggaggtag caccactgca gagcttcatg    3360
ctgcggggtg gtgttgtaga tgatccagtc gtagcaggag cgctgggcgt ggtgcctaaa    3420
aatgtctttc agtagcaagc tgattgccag gggcaggccc ttggtgtaag tgtttacaaa    3480
gcggttaagc tgggatgggt gcatacgtgg ggatatgaga tgcatcttgg actgtatttt    3540
taggttggct atgttcccag ccatatccct ccggggattc atgttgtgca gaaccaccag    3600
cacagtgtat ccggtgcact tgggaaattt gtcatgtagc ttagaaggaa atgcgtggaa    3660
gaacttggag acgcccttgt gacctccaag attttccatg cattcgtcca taatgatggc    3720
aatgggccca cgggcggcgg cctgggcgaa gatatttctg ggatcactaa cgtcatagtt    3780
gtgttccagg atgagatcgt cataggccat ttttacaaag cgcggcgga gggtgccaga    3840
ctgcggtata atggttccat ccgcccagg ggcgtagtta ccctcacaga tttgcatttc    3900
ccacgctttg agttcagatg ggggatcat gtctacctgc ggggcgatga agaaaacggt    3960
ttccggggta ggggagatca gctgggaaga aagcaggttc ctgagcagct gcgacttacc    4020
gcagccggtg ggcccgtaaa tcacacctat taccggctgc aactggtagt taagagagct    4080
gcagctgccg tcatccctga gcagggggc cacttcgtta agcatgtccc tgactcgcat    4140
```

```
gttttccctg accaaatccg ccagaaggcg ctcgccgccc agcgatagca gttcttgcaa   4200
ggaagcaaag ttttcaacg gtttgagacc gtccgccgta ggcatgcttt tgagcgtttg    4260
accaagcagt tccaggcggt cccacagctc ggtcacctgc tctacggcat ctcgatccag   4320
catatctcct cgtttcgcgg gttggggcgg ctttcgctgt acggcagtag tcggtgctcg   4380
tccagacggg ccaggtcat gtctttccac gggcgcaggg tcctcgtcag cgtagtctgg    4440
gtcacggtga agggtgcgc tccgggctgc gcgctggcca gggtgcgctt gaggctggtc    4500
ctgctggtgc tgaagcgctg ccggtcttcg ccctgcgcgt cggccaggta gcatttgacc   4560
atggtgtcat agtccagccc ctccgcggcg tggcccttgg cgcgcagctt gcccttggag   4620
gaggcgccgc acgaggggca gtgcagactt tgagggcgt agagcttggg cgcgagaaat    4680
accgattccg gggagtaggc atccgcgccg caggccccgc agacggtctc gcattccacg   4740
agccaggtga gctctggccg ttcggggtca aaaaccaggt ttcccccatg cttttgatg    4800
cgtttcttac ctctggtttc catgagccgg tgtccacgct cggtgacgaa aaggctgtcc   4860
gtgtccccgt atacagactt gagaggcctg tcctcgagcg gtgttccgcg gtcctcctcg   4920
tatagaaact cggaccactc tgagacaaag gctcgcgtcc aggccagcac gaaggaggct   4980
aagtgggagg gtagcggtc gttgtccact aggggtcca ctcgctccag ggtgtgaaga     5040
cacatgtcgc cctcttcggc atcaaggaag gtgattggtt tgtaggtgta ggccacgtga   5100
ccgggtgttc ctgaagggg gctataaaaa ggggtggggg cgcgttcgtc ctcactctct    5160
tccgcatcgc tgtctgcgag ggccagctgt tggggtgagt actccctctg aaaagcgggc   5220
atgacttctg cgctaagatt gtcagttccc aaaaacgagg aggatttgat attcacctgg   5280
cccgcggtga tgccttgag ggtggccgca tccatctggt cagaaaagac aatcttttg     5340
ttgtcaagct cgaggggg gcccggtacc cagcttttgt tcccttagt gagggttaat      5400
tgcgcgcttg gcgtaatcat ggtcatagct gtttcctgtg tgaaattgtt atccgctcac   5460
aattccacac aacatacgag ccggaagcat aaagtgtaaa gcctggggtg cctaatgagt   5520
gagctaactc acattaattg cgttgcgctc actgcccgct ttccagtcgg gaaacctgtc   5580
gtgccagctg cattaatgaa tcggccaacg cgcggggaga ggcggtttgc gtattgggcg   5640
ctcttccgct tcctcgctca ctgactcgct gcgctcggtc gttcggctgc ggcgagcggt   5700
atcagctcac tcaaaggcgg taatacggtt atccacagaa tcaggggata acgcaggaaa   5760
gaacatgtga gcaaaaggcc agcaaaaggc caggaaccgt aaaaaggccg cgttgctggc   5820
gttttccat aggctccgcc cccctgacga gcatcacaaa aatcgacgct caagtcagag    5880
gtggcgaaac ccgacaggac tataaagata ccaggcgttt ccccctggaa gctccctcgt   5940
gcgctctcct gttccgaccc tgccgcttac cggatacctg tccgccttc tcccttcggg    6000
aagcgtggcg ctttctcata gctcacgctg taggtatctc agttcggtgt aggtcgttcg   6060
ctccaagctg ggctgtgtgc acgaaccccc cgttcagccc gaccgctgcg ccttatccgg   6120
taactatcgt cttgagtcca acccggtaag acacgactta tcgccactgg cagcagccac   6180
tggtaacagg attagcagag cgaggtatgt aggcggtgct acagagttct tgaagtggtg   6240
gcctaactac ggctacacta aaggacagt atttggtatc tgcgctctgc tgaagccagt    6300
taccttcgga aaagagttg gtagctcttg atccggcaaa caaaccaccg ctggtagcgg    6360
tggtttttt gtttgcaagc agcagattac gcgcagaaaa aaggatctc aagaagatcc     6420
tttgatcttt tctacgggt ctgacgctca gtggaacgaa aactcacgtt aagggatttt    6480
```

-continued

```
ggtcatgaga ttatcaaaaa ggatcttcac ctagatcctt ttaaattaaa aatgaagttt    6540
taaatcaatc taaagtatat atgagtaaac ttggtctgac agttaccaat gcttaatcag    6600
tgaggcacct atctcagcga tctgtctatt tcgttcatcc atagttgcct gactcccgt     6660 cgtgtagata actacgatac gggagggctt accatctggc cccagtgctg caatgatacc    6720
gcgagaccca cgctcaccgg ctccagattt atcagcaata accagccag ccggaagggc     6780 cgagcgcaga agtggtcctg caactttatc cgcctccatc cagtctatta attgttgccg    6840
ggaagctaga gtaagtagtt cgccagttaa tagtttgcgc aacgttgttg ccattgctac    6900
aggcatcgtg gtgtcacgct cgtcgtttgg tatggcttca ttcagctccg gttcccaacg    6960
atcaaggcga gttacatgat cccccatgtt gtgcaaaaaa gcggttagct ccttcggtcc    7020
tccgatcgtt gtcagaagta agttggccgc agtgttatca ctcatggtta tggcagcact    7080
gcataattct cttactgtca tgccatccgt aagatgcttt tctgtgactg gtgagtactc    7140
aaccaagtca ttctgagaat agtgtatgcg gcgaccgagt tgctcttgcc cggcgtcaat    7200
acgggataat accgcgccac atagcagaac tttaaaagtg ctcatcattg gaaaacgttc    7260
ttcggggcga aaactctcaa ggatcttacc gctgttgaga tccagttcga tgtaacccac    7320
tcgtgcaccc aactgatctt cagcatcttt tactttcacc agcgtttctg ggtgagcaaa    7380
aacaggaagg caaaatgccg caaaaaaggg aataagggcg acacggaaat gttgaatact    7440
catactcttc ctttttcaat attattgaag catttatcag ggttattgtc tcatgagcgg    7500
atacatattt gaatgtattt agaaaaataa acaaataggg gttccgcgca catttccccg    7560
aaaagtgcca cctgacgcgc cctgtagcgg cgcattaagc gcggcgggtg tggtggttac    7620
gcgcagcgtg accgctacac ttgccagcgc cctagcgccc gctcctttcg ctttcttccc    7680
ttcctttctc gccacgttcg ccggctttcc ccgtcaagct ctaaatcggg ggctcccttt    7740
agggttccga tttagtgctt tacgcaccct cgaccccaaa aaacttgatt agggtgatgg    7800
ttcacgtagt gggccatcgc cctgatagac ggttttttcgc cctttgacgt tggagtccac    7860
gttctttaat agtggactct tgttccaaac tggaacaaca ctcaaccccta tctcggtcta    7920 ttctttttgat ttataaggga ttttgcgatt tcggcctatt ggttaaaaaa tgagctgatt   7980
taacaaaaat ttaacgcgaa ttttaacaaa atattaacgc ttacaatttc cattcgccat    8040
tcaggctgcg caactgttgg gaagggcgat cggtgcgggc ctcttcgcta ttacgccagc    8100
tggcgaaagg gggatgtgct gcaaggcgat taagttgggt aacgccaggg ttttcccagt    8160
cacgacgttg taaaacgacg gccagtgagc gcgcgtaata cgactcacta tagggcgaat    8220
tggagctcca ccgcggtg                                                   8238
```

<210> SEQ ID NO 51
<211> LENGTH: 11
<212> TYPE: DNA
<213> ORGANISM: adenovirus

<400> SEQUENCE: 51
cgcggatccc g                                                          11

<210> SEQ ID NO 52
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 52
ctgacaaact cagatcttgt ttattg                                            26

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 53
gtcgactcta gaggatccag a                                                 21

<210> SEQ ID NO 54
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 54
ccggactcta gatggcaacc atggcgctac                                        30

<210> SEQ ID NO 55
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 55 ggagggaag cttggccctc agccagcctc t                                       31

<210> SEQ ID NO 56
<211> LENGTH: 48
<212> TYPE: DNA
<213> ORGANISM: Artificial Sequence
<220> FEATURE:
<223> OTHER INFORMATION: Description of Artificial Sequence: primer

<400> SEQUENCE: 56
tgtcttggat ccaagatgaa gcgcgcccgc cccagcgaag atgacttc                    48

<210> SEQ ID NO 57
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 57
aaacacggcg gccgctcttt cattcttg                                          28

<210> SEQ ID NO 58
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 58
cgcgctgact cttaggacta gtttc                                             25

<210> SEQ ID NO 59
<211> LENGTH: 37
<212> TYPE: DNA

```
<213> ORGANISM: Artificial Sequence
<220> FEATURE:
<223> OTHER INFORMATION: Description of Artificial Sequence: primer

<400> SEQUENCE: 59
gcgcttaatt aacatcatca ataatatacc ttattttt                              37

<210> SEQ ID NO 60
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 60
tgaagcgcgc aagaccgtct gaag                                             24

<210> SEQ ID NO 61
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 61
cataacactg cagattcttt attcttgg                                         28

<210> SEQ ID NO 62
<211> LENGTH: 47
<212> TYPE: DNA
<213> ORGANISM: Artificial Sequence
<220> FEATURE:
<223> OTHER INFORMATION: Description of Artificial Sequence: primer

<400> SEQUENCE: 62
ggtacacagg aaacaggagg ttccggaggt ggaggagaca caactcc                    47

<210> SEQ ID NO 63
<211> LENGTH: 6
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 63

Gly Gly Ser Gly Gly Gly
  1               5

<210> SEQ ID NO 64
<211> LENGTH: 7231
<212> TYPE: DNA
<213> ORGANISM: Artificial Sequence
<220> FEATURE:
<223> OTHER INFORMATION: Description of Artificial Sequence: plasmid

<400> SEQUENCE: 64
ctgctccctg cttgtgtgtt ggaggtcgct gagtagtgcg cgagcaaaat ttaagctaca      60
acaaggcaag gcttgaccga caattgcatg aagaatctgc ttagggttag gcgttttgcg     120
ctgcttcgcg atgtacgggc cagatatacg cgttgacatt gattattgac tagttattaa    180
tagtaatcaa ttacggggtc attagttcat agcccatata tggagttccg cgttacataa    240
cttacggtaa atggcccgcc tggctgaccg cccaacgacc cccgcccatt gacgtcaata    300
atgacgtatg ttcccatagt aacgccaata gggactttcc attgacgtca atgggtggac    360
```

-continued

```
tatttacggt aaactgccca cttggcagta catcaagtgt atcatatgcc aagtacgccc      420
cctattgacg tcaatgacgg taaatggccc gcctggcatt atgcccagta catgacctta      480
tgggactttc ctacttggca gtacatctac gtattagtca tcgctattac catggtgatg      540
cggttttggc agtacatcaa tgggcgtgga tagcggtttg actcacgggg atttccaagt      600
ctccacccca ttgacgtcaa tgggagtttg ttttggcacc aaaatcaacg ggactttcca      660
aaatgtcgta caactccgcc ccattgacg caaatgggcg gtaggcgtgt acggtgggag       720
gtctatataa gcagagctct ctggctaact agagaaccca ctgcttactg gcttatcgaa      780
attaatacga ctcactatag ggagacccaa gctggctagc gtttaaactt aagcttggta      840
ccgagctcgg atccactctc ttccgcatcg ctgtctgcga gggccagctg ttggggtgag      900
tactccctct gaaaagcggg catgacttct gcgctaagat tgtcagtttc caaaaacgag      960
gaggatttga tattcacctg gcccgcggtg atgcctttga gggtggccgc atccatctgg     1020
tcagaaaaga caatcttttt gttgtcaagc ttggtggcaa acgacccgta gagggcgttg     1080
gacagcaact ggcgatgga gcgcagggtt tggttttgt cgcgatcggc gcgtccttg        1140
gccgcgatgt ttagctgcac gtattcgcgc gcaacgcacc gccattcggg aaagacggtg     1200
gtgcgctcgt cgggcaccag gtgcacgcgc aacccgcggt tgtgcagggt gacaaggtca     1260
acgctggtgg ctacctctcc gcgtaggcgc tcgttggtcc agcagaggcg gccgcccttg     1320
cgcgagcaga atggcggtag ggggtctagc tgcgtctcgt ccgggggggtc tgcgtccacg    1380
gtaaagaccc cgggcagcag gcgcgcgtcg aagtagtcta tcttgcatcc ttgcaagtct     1440
agcgcctgct gccatgcgcg ggcggcaagc gcgcgctcgt atgggttgag tgggggaccc     1500
catggcatgg ggtgggtgag cgcggaggcg tacatgccgc aaatgtcgta aacgtagagg     1560
ggctctctga gtattccaag atatgtaggg tagcatcttc caccgcggat gctggcgcgc     1620
acgtaatcgt atagttcgtg cgagggagcg aggaggtcgg gaccgaggtt gctacgggcg     1680
ggctgctctg ctcggaagac tatctgcctg aagatggcat gtgagttgga tgatatggtt     1740
ggacgctgga agacgttgaa gctggcgtct gtgagaccta ccgcgtcacg cacgaaggag     1800
gcgtaggagt cgcgcagctt gttgaccagc tcggcggtga cctgcacgtc tagggcgcag     1860
tagtccaggg tttccttgat gatgtcatac ttatcctgtc cctttttttt ccacagctcg     1920
cggttgagga caaactcttc gcggtctttc cagtactctt ggatcggaaa cccgtcggcc     1980
tccgaacaga atccgtactc cgccgccgag ggacctgagc gagtccgcat cgaccggatc     2040
ggaaaacctc tcgagaaagg cgtctaacca gtcacagtcg caagatccaa gatgaagcgc     2100
gcccgcccca gcgaagatga cttcaacccc gtctacccct atggctacgc gcggaatcag     2160
aatatcccct tcctcactcc cccctttgtc tcctccgatg gattcaaaaa cttcccccct     2220
ggggtactgt cactcaaact ggctgatcca atcaccatta ccaatgggga tgtatccctc     2280
aaggtgggag gtggtctcac tttgcaagat ggaagcctaa ctgtaaaccc taaggctcca     2340
ctgcaagtta atactgataa aaacttgag cttgcatatg ataatccatt tgaaagtagt      2400
gctaataaac ttagtttaaa agtaggacat ggattaaaag tattagatga aaaagtgct     2460
gcggggttaa aagatttaat tgcaaactt gtggttttaa caggaaaagg aataggcact     2520
gaaaatttag aaaatacaga tggtagcagc agaggaattg tataaatgt aagagcaaga     2580
gaagggttga catttgacaa tgatggatac ttggtagcat ggaacccaaa gtatgacacg     2640
cgcacacttt ggacaacacc agacacatct ccaaactgca caattgctca agataaggac     2700
```

```
tctaaactca ctttggtact tacaaagtgt ggaagtcaaa tattagctaa tgtgtctttg      2760
attgtggtcg caggaaagta ccacatcata aataataaga caaatccaaa aataaaaagt      2820
tttactatta aactgctatt taataagaac ggagtgcttt tagacaactc aaatcttgga      2880
aaagcttatt ggaactttag aagtggaaat tccaatgttt cgacagctta tgaaaaagca      2940
attggtttta tgcctaattt ggtagcgtat ccaaaaccca gtaattctaa aaatatgca       3000 agagacatag tttatggaac tatatatctt ggtggaaaac ctgatcagcc agcagtcatt      3060
aaaactacct ttaaccaaga aactggatgt gaatactcta tcacatttaa ctttagttgg      3120
tccaaaacct atgaaaatgt tgaatttgaa accacctctt ttaccttctc ctatattgcc      3180
caagaatgaa agagcggccg ctcgagtcta gagggcccgt ttaaacccgc tgatcagcct      3240
cgactgtgcc ttctagttgc cagccatctg ttgtttgccc ctcccccgtg ccttccttga      3300
ccctggaagg tgccactccc actgtccttt cctaataaaa tgaggaaatt gcatcgcatt      3360
gtctgagtag gtgtcattct attctggggg gtggggtggg caggacagc aaggggggagg      3420 attgggaaga caatagcagg catgctgggg atgcggtggg ctctatggct tctgaggcgg      3480
aaagaaccag ctggggctct aggggtatc cccacgcgcc ctgtagcggc gcattaagcg       3540
cggcgggtgt ggtggttacg cgcagcgtga ccgctacact tgccagcgcc ctagcgcccg      3600
ctcctttcgc tttcttccct tcctttctcg ccacgttcgc cggctttccc cgtcaagctc      3660
taaatcgggg catcccttta gggttccgat ttagtgcttt acggcacctc gaccccaaaa      3720
aacttgatta gggtgatggt tcacgtagtg gccatcgcc ctgatagacg ttttttcgcc        3780
ctttgacgtt ggagtccacg ttctttaata gtggactctt gttccaaact ggaacaacac      3840
tcaaccctat ctcggtctat tcttttgatt tataagggat tttggggatt tcggcctatt      3900
ggttaaaaaa tgagctgatt taacaaaaat ttaacgcgaa ttaattctgt ggaatgtgtg      3960
tcagttaggg tgtggaaagt ccccaggctc cccaggcagg cagaagtatg caaagcatgc      4020
atctcaatta gtcagcaacc aggtgtggaa agtccccagg ctccccagca ggcagaagta      4080
tgcaaagcat gcatctcaat tagtcagcaa ccatagtccc gccccctaact ccgcccatcc      4140 cgcccctaac tccgcccagt tccgcccatt ctccgcccca tggctgacta atttttttta      4200
tttatgcaga ggccgaggcc gcctctgcct ctgagctatt ccagaagtag tgaggaggct      4260 ttttttggagg cctaggcttt tgcaaaaagc tcccgggagc ttgtatatcc attttcggat      4320
ctgatcagca cgtgttgaca attaatcatc ggcatagtat atcggcatag tataatacga      4380
caaggtgagg aactaaacca tggccaagtt gaccagtgcc gttccggtgc tcaccgcgcg      4440
cgacgtcgcc ggagcggtcg agttctggac cgaccggctc gggttctccc gggacttcgt      4500
ggaggacgac ttcgccggtg tggtccggga cgacgtgacc ctgttcatca gcgcggtcca      4560
ggaccaggtg gtgccggaca cacacctggc ctgggtgtgg gtgcgcggcc tggacgagct      4620
gtacgccgag tggtcggagg tcgtgtccac gaacttccgg gacgcctccg gccggccat       4680 gaccgagatc ggcgagcagc cgtggggggcg ggagttcgcc ctgcgcgacc cggccggcaa      4740
ctgcgtgcac ttcgtggccg aggagcagga ctgacacgtg ctacgagatt tcgattccac      4800
cgccgccttc tatgaaaggt tgggcttcgg aatcgttttc cgggacgccg gctggatgat      4860
cctccagcgc ggggatctca tgctggagtt cttcgcccac cccaacttgt ttattgcagc      4920
ttataatggt tacaaataaa gcaatagcat cacaaatttc acaaataaag cattttttc        4980 actgcattct agttgtggtt tgtccaaact catcaatgta tcttatcatg tctgtatacc      5040
gtcgacctct agctagagct tggcgtaatc atggtcatag ctgtttcctg tgtgaaattg      5100
```

-continued

```
ttatccgctc acaattccac acaacatacg agccggaagc ataaagtgta aagcctgggg    5160
tgcctaatga gtgagctaac tcacattaat tgcgttgcgc tcactgcccg ctttccagtc    5220
gggaaacctg tcgtgccagc tgcattaatg aatcggccaa cgcgcgggga gaggcggttt    5280
gcgtattggg cgctcttccg cttcctcgct cactgactcg ctgcgctcgg tcgttcggct    5340
gcggcgagcg gtatcagctc actcaaaggc ggtaatacgg ttatccacag aatcagggga    5400
taacgcagga agaacatgt gagcaaaagg ccagcaaaag gccaggaacc gtaaaaaggc    5460
cgcgttgctg gcgtttttcc ataggctccg ccccctgac gagcatcaca aaaatcgacg    5520
ctcaagtcag aggtggcgaa acccgacagg actataaaga taccaggcgt ttcccctgg    5580
aagctccctc gtgcgctctc ctgttccgac cctgccgctt accggatacc tgtccgcctt    5640
tctcccttcg ggaagcgtgg cgctttctca atgctcacgc tgtaggtatc tcagttcggt    5700
gtaggtcgtt cgctccaagc tgggctgtgt gcacgaaccc cccgttcagc ccgaccgctg    5760
cgccttatcc ggtaactatc gtcttgagtc caacccggta agacacgact tatcgccact    5820
ggcagcagcc actggtaaca ggattagcag agcgaggtat gtaggcggtg ctacagagtt    5880
cttgaagtgg tggcctaact acggctacac tagaaggaca gtatttggta tctgcgctct    5940
gctgaagcca gttaccttcg aaaaagagt tggtagctct tgatccggca acaaaccac    6000
cgctggtagc ggtggttttt tgtttgcaa gcagcagatt acgcgcagaa aaaaaggatc    6060
tcaagaagat cctttgatct tttctacggg gtctgacgct cagtggaacg aaaactcacg    6120
ttaagggatt ttggtcatga gattatcaaa aaggatcttc acctagatcc ttttaaatta    6180
aaaatgaagt tttaaatcaa tctaaagtat atatgagtaa acttggtctg acagttacca    6240
atgcttaatc agtgaggcac ctatctcagc gatctgtcta tttcgttcat ccatagttgc    6300
ctgactcccc gtcgtgtaga taactacgat acgggagggc ttaccatctg gccccagtgc    6360
tgcaatgata ccgcgagacc cacgctcacc ggctccagat ttatcagcaa taaaccagcc    6420
agccggaagg gccgagcgca gaagtggtcc tgcaacttta tccgcctcca tccagtctat    6480
taattgttgc cgggaagcta gagtaagtag ttcgccagtt aatagtttgc gcaacgttgt    6540
tgccattgct acaggcatcg tggtgtcacg ctcgtcgttt ggtatggctt cattcagctc    6600
cggttcccaa cgatcaaggc gagttacatg atccccatg ttgtgcaaaa aagcggttag    6660
ctccttcggt cctccgatcg ttgtcagaag taagttggcc gcagtgttat cactcatggt    6720
tatggcagca ctgcataatt ctcttactgt catgccatcc gtaagatgct tttctgtgac    6780
tggtgagtac tcaaccaagt cattctgaga atagtgtatg cggcgaccga gttgctcttg    6840
cccggcgtca atacgggata ataccgcgcc acatagcaga actttaaaag tgctcatcat    6900
tggaaaacgt tcttcggggc gaaaactctc aaggatctta ccgctgttga tccagttc    6960
gatgtaaccc actcgtgcac ccaactgatc ttcagcatct tttactttca ccagcgtttc    7020
tgggtgagca aaaacaggaa ggcaaaatgc cgcaaaaaag gaataagggc gacacggaa    7080
atgttgaata ctcatactct tcctttttca atattattga agcatttatc agggttattg    7140
tctcatgagc ggatacatat ttgaatgtat ttagaaaaat aaacaaatag gggttccgcg    7200
cacatttccc cgaaaagtgc cacctgacgt c                                    7231
```

<210> SEQ ID NO 65
<211> LENGTH: 8484
<212> TYPE: DNA
<213> ORGANISM: Artificial Sequence
<220> FEATURE:

<223> OTHER INFORMATION: Description of Artificial Sequence: plasmid

<400> SEQUENCE: 65

```
ctgctccctg cttgtgtgtt ggaggtcgct gagtagtgcg cgagcaaaat ttaagctaca      60
acaaggcaag gcttgaccga caattgcatg aagaatctgc ttagggttag gcgttttgcg     120
ctgcttcgcg atgtacgggc cagatatacg cgttgacatt gattattgac tagttattaa     180
tagtaatcaa ttacggggtc attagttcat agcccatata tggagttccg cgttacataa     240
cttacggtaa atggcccgcc tggctgaccg cccaacgacc cccgcccatt gacgtcaata     300
atgacgtatg ttcccatagt aacgccaata gggactttcc attgacgtca atgggtggac     360
tatttacggt aaactgccca cttggcagta catcaagtgt atcatatgcc aagtacgccc     420
cctattgacg tcaatgacgg taaatggccc gcctggcatt atgcccagta catgacctta     480
tgggactttc ctacttggca gtacatctac gtattagtca tcgctattac catggtgatg     540
cggttttggc agtacatcaa tgggcgtgga tagcggtttg actcacgggg atttccaagt     600
ctccacccca ttgacgtcaa tgggagtttg ttttggcacc aaaatcaacg ggactttcca     660
aaatgtcgta acaactccgc cccattgacg caaatgggcg gtaggcgtgt acggtgggag     720
gtctatataa gcagagctct ctggctaact agagaaccca ctgcttactg gcttatcgaa     780
attaatacga ctcactatag ggagacccaa gctggctagc gtttaaactt aagcttggta     840
ccgagctcgg atccactctc ttccgcatcg ctgtctgcga gggccagctg ttggggtgag     900
tactccctct gaaaagcggg catgacttct gcgctaagat tgtcagtttc caaaaacgag     960
gaggatttga tattcacctg gcccgcggtg atgcctttga gggtggccgc atccatctgg    1020
tcagaaaaga caatctttt gttgtcaagc ttggtggcaa acgacccgta gagggcgttg    1080
gacagcaact tggcgatgga gcgcagggtt tggttttgt cgcgatcggc gcgctccttg    1140
gccgcgatgt ttagctgcac gtattcgcgc gcaacgcacc gccattcggg aaagacggtg    1200
gtgcgctcgt cgggcaccag gtgcacgcgc caaccgcggt tgtgcagggt gacaaggtca    1260
acgctggtgg ctacctctcc gcgtaggcgc tcgttggtcc agcagaggcg gccgcccttg    1320
cgcgagcaga atggcggtag ggggtctagc tgcgtctcgt ccgggggtc tgcgtccacg    1380
gtaaagaccc cggcagcag gcgcgcgtcg aagtagtcta tcttgcatcc ttgcaagtct    1440
agcgcctgct gccatgcgcg ggcggcaagc gcgcgctcgt atgggttgag tgggggaccc    1500
catggcatgg ggtgggtgag cgcggaggcg tacatgccgc aaatgtcgta aacgtagagg    1560
ggctctctga gtattccaag atatgtaggg tagcatcttc caccgcggat gctggcgcgc    1620
acgtaatcgt atagttcgtg cgagggagcg aggaggtcgg gaccgaggtt gctacgggcg    1680
ggctgctctg ctcggaagac tatctgcctg aagatggcat gtgagttgga tgatatggtt    1740
ggacgctgga agacgttgaa gctggcgtct gtgagaccta ccgcgtcacg cacgaaggag    1800
gcgtaggagt cgcgcagctt gttgaccagc tcggcggtga cctgcacgtc tagggcgcag    1860
tagtccaggg tttccttgat gatgtcatac ttatcctgtc cttttttt ccacagctcg    1920
cggttgagga caaactcttc gcggtctttc cagtactctt ggatcggaaa cccgtcggcc    1980
tccgaacgag atccgtactc cgccgccgag ggacctgagc gagtccgcat cgaccggatc    2040
ggaaaacctc tcgagaaagg cgtctaacca gtcacagtcg caagatccaa gatgaagcgc    2100
gcaagaccgt ctgaagatac cttcaacccc gtgtatccat atgacacgga aaccggtcct    2160
ccaactgtgc cttttcttac tcctcccttt gtatccccca atgggtttca agagagtccc    2220
cctggggtac tctctttgcg cctatccgaa cctctagtta cctccaatgg catgcttgcg    2280
```

-continued

```
ctcaaaatgg gcaacggcct ctctctggac gaggccggca accttacctc ccaaaatgta    2340
accactgtga gcccacctct caaaaaaacc aagtcaaaca taaacctgga aatatctgca    2400
cccctcacag ttacctcaga agccctaact gtggctgccg ccgcacctct aatggtcgcg    2460
ggcaacacac tcaccatgca atcacaggcc ccgctaaccg tgcacgactc caaacttagc    2520
attgccaccc aaggacccct cacagtgtca aaggaaagc tagccctgca acatcaggc    2580 cccctcacca ccaccgatag cagtacccct actatcactg cctcaccccc tctaactact    2640
gccactggta gcttgggcat tgacttgaaa gagcccattt atacacaaaa tggaaaacta    2700
ggactaaagt acgggctcc tttgcatgta acagacgacc taaacacttt gaccgtagca    2760
actggtccag gtgtgactat taataatact tccttgcaaa ctaaagttac tggagccttg    2820
ggttttgatt cacaaggcaa tatgcaactt aatgtagcag gaggactaag gattgattct    2880
caaaacagac gccttatact tgatgttagt tatccgtttg atgctcaaaa ccaactaaat    2940
ctaagactag gacagggccc tctttttata aactcagccc acaacttgga tattaactac    3000
aacaaaggcc tttacttgtt tacagcttca acaattccaa aaaagcttga ggttaaccta    3060
agcactgcca aggggttgat gtttgacgct acagccatag ccattaatgc aggagatggg    3120 cttgaattig gttcacctaa tgccaaac acaaatcccc tcaaaacaaa aattggccat    3180
ggcctagaat ttgattcaaa caaggctatg gttcctaaac taggaactgg ccttagtttt    3240
gacagcacag gtgccattac agtaggaaac aaaaataatg ataagctaac tttgtggacc    3300
acaccagctc catctcctaa ctgtagacta aatgcagaga aagatgctaa actcactttg    3360
gtcttaacaa aatgtggcag tcaaatactt gctacagttt cagttttggc tgttaaaggc    3420
agtttggctc caatatctgg aacagttcaa agtgctcatc ttattataag atttgacgaa    3480
aatggagtgc tactaaacaa ttccttcctg gacccagaat attggaactt tagaaatgga    3540
gatcttactg aaggcacagc ctatacaaac gctgttggat ttatgcctaa cctatcagct    3600
tatccaaaat ctcacggtaa aactgccaaa agtaacattg tcagtcaagt ttacttaaac    3660
ggagacaaaa ctaaacctgt aacactaacc attacactaa acggtacaca ggaaacagga    3720
gacacaactc caagtgcata ctctatgtca ttttcatggg actggtctgg ccacaactac    3780
attaatgaaa tatttgccac atcctcttac actttttcat acattgccca agaataaaag    3840
aagcggccgc tcgagtctag cgataatcaa cctctggatt acaaaatttg tgaaagattg    3900
actggtattc ttaactatgt tgctcctttt acgctatgtg gatacgctgc tttaatgcct    3960
ttgtatcatg ctattgcttc ccgtatggct ttcattttct cctccttgta taaatcctgg    4020
ttgctgtctc tttatgagga gttgtggccc gttgtcaggc aacgtggcgt ggtgtgcact    4080
gtgtttgctg acgcaacccc cactggttgg ggcattgcca ccacctgtca gctcctttcc    4140
gggactttcg ctttccccct ccctattgcc acggcggaac tcatcgccgc ctgccttgcc    4200
cgctgctgga caggggctcg gctgttgggc actgacaatt ccgtggtgtt gtcggggaag    4260
ctgacgtcct ttccatggct gctcgcctgt gttgccacct ggattctgcg cgggacgtcc    4320
ttctgctacg tcccttcggc cctcaatcca gcggaccttc cttcccgcgg cctgctgccg    4380
gctctgcggc ctcttccgcg tcttcgcctt cgccctcaga cgagtcggat ctccctttgg    4440
gccgcctccc cgcctgatcg ctagagggcc cgtttaaacc cgctgatcag cctcgactgt    4500
gccttctagt tgccagccat ctgttgtttg ccctccccc gtgccttcct tgaccctgga    4560
aggtgccact cccactgtcc tttcctaata aaatgaggaa attgcatcgc attgtctgag    4620
```

```
taggtgtcat tctattctgg ggggtggggt ggggcaggac agcaaggggg aggattggga    4680
agacaatagc aggcatgctg gggatgcggt gggctctatg gcttctgagg cggaaagaac    4740
cagctgggc tctaggggt atccccacgc gccctgtagc ggcgcattaa gcgcggcggg     4800
tgtggtggtt acgcgcagcg tgaccgctac acttgccagc gccctagcgc ccgctccttt    4860
cgctttcttc ccttccttc tcgccacgtt cgccggcttt cccgtcaag ctctaaatcg     4920
gggcatccct ttaggttcc gatttagtgc tttacggcac ctcgacccca aaaacttga     4980
ttagggtgat ggttcacgta gtgggccatc gccctgatag acggttttc gcccttgac     5040
gttggagtcc acgttcttta atagtggact cttgttccaa actggaacaa cactcaaccc    5100
tatctcggtc tattcttttg atttataagg gatttgggg atttcggcct attggttaaa    5160
aaatgagctg atttaacaaa aatttaacgc gaattaattc tgtggaatgt gtgtcagtta    5220
gggtgtggaa agtccccagg ctccccaggc aggcagaagt atgcaaagca tgcatctcaa    5280
ttagtcagca accaggtgtg gaaagtcccc aggctcccca gcaggcagaa gtatgcaaag    5340
catgcatctc aattagtcag caaccatagt cccgccccta actccgccca tcccgcccct    5400
aactccgccc agttccgccc attctccgcc ccatggctga ctaatttttt ttatttatgc    5460
agaggccgag gccgcctctg cctctgagct attccagaag tagtgaggag cttttttgg    5520
aggcctaggc ttttgcaaaa agctcccggg agcttgtata tccattttcg gatctgatca    5580
gcacgtgttg acaattaatc atcggcatag tatatcggca tagtataata cgacaaggtg    5640
aggaactaaa ccatggccaa gttgaccagt gccgttccgg tgctcaccgc gcgcgacgtc    5700
gccggagcgg tcgagttctg gaccgaccgg ctcgggttct cccgggactt cgtggaggac    5760
gacttcgccg gtgtggtccg ggacgacgtg accctgttca tcagcgcggt ccaggaccag    5820
gtggtgccgg acaacaccct ggcctgggtg tgggtgcgcg gcctggacga gctgtacgcc    5880
gagtggtcgg aggtcgtgtc cacgaacttc cgggacgcct ccgggccggc catgaccgag    5940
atcggcgagc agccgtgggg gcgggagttc gccctgcgcg accggccgg caactgcgtg    6000
cacttcgtgg ccgaggagca ggactgacac gtgctacgag atttcgattc caccgccgcc    6060
ttctatgaaa ggttgggctt cggaatcgtt ttccgggacg ccggctggat gatcctccag    6120
cgcgggatc tcatgctgga gttcttcgcc cacccccaact tgtttattgc agcttataat    6180
ggttacaaat aaagcaatag catcacaaat ttcacaaata aagcattttt ttcactgcat    6240
tctagttgtg gtttgtccaa actcatcaat gtatcttatc atgtctgtat accgtcgacc    6300
tctagctaga gcttggcgta atcatggtca tagctgtttc ctgtgtgaaa ttgttatccg    6360
ctcacaattc cacacaacat acgagccgga agcataaagt gtaaagcctg gggtgcctaa    6420
tgagtgagct aactcacatt aattgcgttg cgctcactgc ccgctttcca gtcgggaaac    6480
ctgtcgtgcc agctgcatta atgaatcggc caacgcgcgg ggagaggcgg tttgcgtatt    6540
gggcgctctt ccgcttcctc gctcactgac tcgctgcgct cggtcgttcg gctgcggcga    6600
gcggtatcag ctcactcaaa ggcggtaata cggttatcca cagaatcagg ggataacgca    6660
ggaaagaaca tgtgagcaaa aggccagcaa aaggccagga accgtaaaaa ggccgcgttg    6720
ctggcgtttt tccataggct ccgcccccct gacgagcatc acaaaaatcg acgctcaagt    6780
cagaggtggc gaaacccgac aggactataa agataccagg cgtttccccc tggaagctcc    6840
ctcgtgcgct ctcctgttcc gaccctgccg cttaccggat acctgtccgc ctttctccct    6900
tcgggaagcg tggcgctttc tcaatgctca cgctgtaggt atctcagttc ggtgtaggtc    6960
gttcgctcca agctgggctg tgtgcacgaa ccccccgttc agcccgaccg ctgcgcctta    7020
```

```
tccggtaact atcgtcttga gtccaacccg gtaagacacg acttatcgcc actggcagca      7080
gccactggta acaggattag cagagcgagg tatgtaggcg gtgctacaga gttcttgaag      7140
tggtggccta actacggcta cactagaagg acagtatttg gtatctgcgc tctgctgaag      7200
ccagttacct tcggaaaaag agttggtagc tcttgatccg gcaaacaaac caccgctggt      7260
agcggtggtt ttttgtttg caagcagcag attacgcgca gaaaaaaagg atctcaagaa      7320
gatcctttga tcttttctac ggggtctgac gctcagtgga acgaaaactc acgttaaggg      7380
attttggtca tgagattatc aaaaaggatc ttcacctaga tccttttaaa ttaaaaatga      7440
agttttaaat caatctaaag tatatatgag taaacttggt ctgacagtta ccaatgctta      7500
atcagtgagg cacctatctc agcgatctgt ctatttcgtt catccatagt tgcctgactc      7560
cccgtcgtgt agataactac gatacgggag ggcttaccat ctggccccag tgctgcaatg      7620
ataccgcgag acccacgctc accggctcca gatttatcag caataaacca gccagccgga      7680
agggccgagc gcagaagtgg tcctgcaact ttatccgcct ccatccagtc tattaattgt      7740
tgccgggaag ctagagtaag tagttcgcca gttaatagtt tgcgcaacgt tgttgccatt      7800
gctacaggca tcgtggtgtc acgctcgtcg tttggtatgg cttcattcag ctccggttcc      7860
caacgatcaa ggcgagttac atgatccccc atgttgtgca aaaaagcggt tagctccttc      7920
ggtcctccga tcgttgtcag aagtaagttg gccgcagtgt tatcactcat ggttatggca      7980
gcactgcata attctcttac tgtcatgcca tccgtaagat gcttttctgt gactggtgag      8040
tactcaacca agtcattctg agaatagtgt atgcggcgac cgagttgctc ttgcccggcg      8100
tcaatacggg ataataccgc gccacatagc agaactttaa aagtgctcat cattggaaaa      8160
cgttcttcgg ggcgaaaact ctcaaggatc ttaccgctgt tgagatccag ttcgatgtaa      8220
cccactcgtg cacccaactg atcttcagca tcttttactt tcaccagcgt ttctgggtga      8280
gcaaaaacag gaaggcaaaa tgccgcaaaa aagggaataa gggcgacacg gaaatgttga      8340
atactcatac tcttcctttt tcaatattat tgaagcattt atcagggtta ttgtctcatg      8400
agcggataca tatttgaatg tatttagaaa aataaacaaa tagggggttcc gcgcacattt      8460 ccccgaaaag tgccacctga cgtc                                           8484
```

```
<210> SEQ ID NO 66
<211> LENGTH: 53
<212> TYPE: DNA
<213> ORGANISM: Artificial Sequence
<220> FEATURE:
<223> OTHER INFORMATION: Description of Artificial Sequence: primer

<400> SEQUENCE: 66
gtcactcgag gactcggtcg actgaaaatg agacatatta tctgccacgg acc            53

<210> SEQ ID NO 67
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 67
cgagatcgat cacctccggt acaaggtttg gcatag                               36

<210> SEQ ID NO 68
<211> LENGTH: 37
<212> TYPE: DNA
```

<213> ORGANISM: Artificial Sequence
<220> FEATURE:
<223> OTHER INFORMATION: Description of Artificial Sequence: primer

<400> SEQUENCE: 68
catgaagatc tggaaggtgc tgaggtacga tgagacc         37

<210> SEQ ID NO 69
<211> LENGTH: 51
<212> TYPE: DNA
<213> ORGANISM: Artificial Sequence
<220> FEATURE:
<223> OTHER INFORMATION: Description of Artificial Sequence: primer

<400> SEQUENCE: 69
gcgacttaag cagtcagctg agacagcaag acacttgctt gatccaaatc c         51

<210> SEQ ID NO 70
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 70
cacgaattcg tcagcgcttc tcgtcgcgtc caagaccc         38

<210> SEQ ID NO 71
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 71
caccccgggg aggcggcggc gacggggacg gg         32

<210> SEQ ID NO 72
<211> LENGTH: 30
<212> TYPE: DNA
<213> ORGANISM: Artificial Sequence
<220> FEATURE:
<223> OTHER INFORMATION: Description of Artificial Sequence:
    oligonucleotide

<400> SEQUENCE: 72
atgggatcca agatgaagcg cgcaagaccg         30

<210> SEQ ID NO 73
<211> LENGTH: 30
<212> TYPE: DNA
<213> ORGANISM: Artificial Sequence
<220> FEATURE:
<223> OTHER INFORMATION: Description of Artificial Sequence:
    oligonucleotide

<400> SEQUENCE: 73
cataacctgc aggattcttt attcttgggc         30

<210> SEQ ID NO 74
<211> LENGTH: 47
<212> TYPE: DNA
<213> ORGANISM: Artificial Sequence
<220> FEATURE:
<223> OTHER INFORMATION: Description of Artificial Sequence:
    oligonucleotide

```
-continued

<400> SEQUENCE: 74
ggtacacagg aaacaggagg ttccggaggt ggaggagaca caactcc              47

<210> SEQ ID NO 75
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 75
atgggatcca agatgaagcg cgcaagaccg                                30

<210> SEQ ID NO 76
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 76
cactatagcg gccgcattct cagtcatctt                                30
```